US012740317B2

(12) United States Patent
Yoo et al.

(10) Patent No.: US 12,740,317 B2
(45) Date of Patent: Sep. 15, 2026

(54) ORGANIC LIGHT EMITTING ELEMENT

(71) Applicant: LG DISPLAY CO., LTD., Seoul (KR)

(72) Inventors: Seonkeun Yoo, Paju-si (KR); Youngjun Yu, Paju-si (KR); SangBeom Kim, Paju-si (KR)

(73) Assignee: LG Display Co., Ltd., Seoul (KR)

( * ) Notice: Subject to any disclaimer, the term of this patent is extended or adjusted under 35 U.S.C. 154(b) by 908 days.

(21) Appl. No.: 17/978,083

(22) Filed: Oct. 31, 2022

(65) Prior Publication Data

US 2023/0142329 A1 May 11, 2023

(30) Foreign Application Priority Data

Nov. 10, 2021 (KR) ........................ 10-2021-0154313

(51) Int. Cl.

| | |
|---|---|
| ***H01L 51/50*** | (2006.01) |
| ***C07D 263/57*** | (2006.01) |
| ***C07D 277/66*** | (2006.01) |
| ***C07D 413/12*** | (2006.01) |
| ***C07D 417/12*** | (2006.01) |
| ***C09K 11/06*** | (2006.01) |
| ***H10K 85/60*** | (2023.01) |
| *H10K 50/13* | (2023.01) |
| *H10K 101/00* | (2023.01) |

(52) U.S. Cl.

CPC ......... *H10K 85/636* (2023.02); *C07D 263/57* (2013.01); *C07D 277/66* (2013.01); *C07D 413/12* (2013.01); *C07D 417/12* (2013.01); *C09K 11/06* (2013.01); *H10K 85/633* (2023.02); *C09K 2211/1018* (2013.01); *H10K 50/131* (2023.02); *H10K 85/615* (2023.02); *H10K 85/624* (2023.02); *H10K 85/626* (2023.02); *H10K 85/657* (2023.02); *H10K 85/6574* (2023.02); *H10K 85/6576* (2023.02); *H10K 2101/90* (2023.02)

(58) Field of Classification Search

None

See application file for complete search history.

(56) References Cited

U.S. PATENT DOCUMENTS

2003/0170491 A1* 9/2003 Liao et al. ............. H05B 33/00

FOREIGN PATENT DOCUMENTS

| | | | | |
|---|---|---|---|---|
| CN | 111808042 A | * 11/2020 | | H01L 51/54 |
| CN | 111892586 A | 11/2020 | | |
| CN | 112341449 A | 2/2021 | | |

(Continued)

OTHER PUBLICATIONS

Office Action issued on Aug. 22, 2025 for counterpart German Patent Application No. 102022129485.4 (Note: CN 112341449 A cited in this DE Office Action has already been cited in a prior IDS.).

(Continued)

*Primary Examiner* — Gregory D Clark

(74) *Attorney, Agent, or Firm* — Morgan, Lewis & Bockius LLP

(57) ABSTRACT

Embodiments of the disclosure relate to an organic light emitting element. Specifically, there may be provided an organic light emitting element having high efficiency or long lifespan by including a first electrode, a second electrode, and an organic material layer positioned therebetween wherein the organic material layer includes a specific compound.

8 Claims, 4 Drawing Sheets

100

(56) References Cited

FOREIGN PATENT DOCUMENTS

| | | | |
|---|---|---|---|
| CN | 113620917 | A | 11/2021 |
| CN | 113816863 | A | 12/2021 |

OTHER PUBLICATIONS

United Kingdom Search and Examination Report dated May 26, 2023, issued in corresponding United Kingdom Patent Application No. GB2215823.2.

* cited by examiner

ORGANIC LIGHT EMITTING ELEMENT

CROSS-REFERENCE TO RELATED APPLICATION

This application claims priority from Korean Patent Application No. 10-2021-0154313, filed on Nov. 10, 2021, which is hereby incorporated by reference for all purposes as if fully set forth herein.

BACKGROUND

Technical Field

Embodiments of the disclosure relate to an organic light emitting element.

Discussion of the Related Art

In general, organic light emission refers to a phenomenon in which electric energy is converted into light energy by an organic material. The organic light emitting element refers to a light emitting element using the organic light emission phenomenon. The organic light emitting element has a structure including an anode, a cathode, and an organic material layer disposed therebetween.

The organic material layer may have a multilayer structure composed of different materials to increase the efficiency and stability of the organic light emitting element and may include a light emitting layer (also referred to as an emission material layer (EML)).

The lifespan and efficiency are the most important issues with organic light emitting elements. The efficiency, lifespan, and driving voltage are related to each other. If the efficiency is increased, the driving voltage is relatively decreased, so that the crystallization of the organic material by the Joule heating during driving is reduced, leading to an increase in lifespan.

The role of the light emitting layer EML is important to enhance the light emitting properties of the organic light emitting element and increase the lifespan. In particular, to have high-efficiency characteristics, the host material of the light emitting layer is required to have a high triplet level, and the stability of the material is needed.

SUMMARY

Accordingly, embodiments of the present disclosure are directed to an organic light emitting element that substantially obviates one or more of the problems due to limitations and disadvantages of the related art.

In order for the organic light emitting element to sufficiently exhibit its excellent characteristics, the materials constituting the organic material layer should be stable and have excellent efficiency. Since the phosphorescent organic light emitting element has a greater hole mobility than electron mobility in the light emitting layer and a long triplet state lifespan, excitons formed in the light emitting layer are distributed over a wide area, so that the light emission may be reduced. Accordingly, the inventors of the disclosure have invented an organic light emitting element that may have excellent efficiency or long lifespan.

An aspect of the present disclosure is to provide an organic light emitting element having high efficiency or long lifespan.

Additional features and aspects will be set forth in the description that follows, and in part will be apparent from the description, or may be learned by practice of the inventive concepts provided herein. Other features and aspects of the inventive concepts may be realized and attained by the structure particularly pointed out in the written description, or derivable therefrom, and the claims hereof as well as the appended drawings.

To achieve these and other aspects of the inventive concepts, as embodied and broadly described herein, an organic light emitting element comprises a first electrode, a second electrode, and an organic material layer positioned between the first electrode and the second electrode.

The organic material layer includes a compound represented by chemical formula 1 below:

[Chemical formula 1]

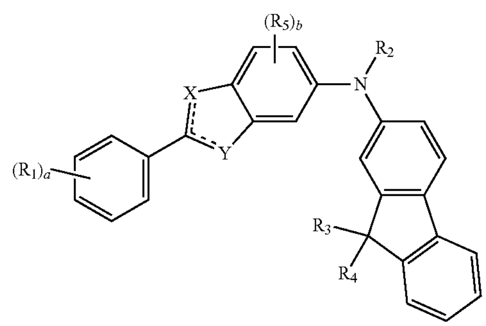

According to embodiments of the disclosure, there may be provided an organic light emitting element having high efficiency or long lifespan.

BRIEF DESCRIPTION OF DRAWINGS

The accompanying drawings, which are included to provide a further understanding of the disclosure and are incorporated in and constitute a part of this application, illustrate embodiments of the disclosure and together with the description serve to explain various principles. In the drawings.

DETAILED DESCRIPTION

Figure 1:
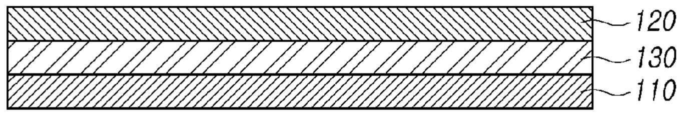
FIGS. 1 and 2 are views schematically illustrating an organic light emitting element according to embodiments of the disclosure.

In the following description of examples or embodiments of the disclosure, reference will be made to the accompanying drawings in which it is shown by way of illustration specific examples or embodiments that can be implemented, and in which the same reference numerals and signs can be used to designate the same or like components even when they are shown in different accompanying drawings from one another. Further, in the following description of examples or embodiments of the disclosure, detailed descriptions of well-known functions and components incorporated herein will be omitted when it is determined that the description may make the subject matter in some embodiments of the disclosure rather unclear. The terms such as "including", "having", "containing", "constituting" "make up of", and "formed of" used herein are generally intended to allow other components to be added unless the terms are used with the term "only". As used herein, singular forms are intended to include plural forms unless the context clearly indicates otherwise.

Terms, such as "first", "second", "A", "B", "(A)", or "(B)" may be used herein to describe elements of the disclosure. Each of these terms is not used to define essence, order, sequence, or number of elements etc., but is used merely to distinguish the corresponding element from other elements.

When it is mentioned that a first element "is connected or coupled to", "contacts or overlaps" etc. a second element, it should be interpreted that, not only can the first element "be directly connected or coupled to" or "directly contact or overlap" the second element, but a third element can also be "interposed" between the first and second elements, or the first and second elements can "be connected or coupled to", "contact or overlap", etc. each other via a fourth element. Here, the second element may be included in at least one of two or more elements that "are connected or coupled to", "contact or overlap", etc. each other.

When time relative terms, such as "after," "subsequent to," "next," "before," and the like, are used to describe processes or operations of elements or configurations, or flows or steps in operating, processing, manufacturing methods, these terms may be used to describe non-consecutive or non-sequential processes or operations unless the term "directly" or "immediately" is used together.

In addition, when any dimensions, relative sizes etc. are mentioned, it should be considered that numerical values for an elements or features, or corresponding information (e.g., level, range, etc.) include a tolerance or error range that may be caused by various factors (e.g., process factors, internal or external impact, noise, etc.) even when a relevant description is not specified. Further, the term "may" fully encompasses all the meanings of the term "can".

Hereinafter, various embodiments of the disclosure are described in detail with reference to the accompanying drawings.

As used herein, the term "halo" or "halogen" includes fluorine (F), chlorine (Cl), bromine (Br), and iodine (I), and the like, unless otherwise specified.

As used herein, the term "alkyl" or "alkyl group" may mean a radical of a saturated aliphatic functional group having 1 to 60 carbon atoms linked by a single bond and including a straight chain alkyl group, branched chain alkyl group, cycloalkyl (alicyclic) group, alkyl-substituted cycloalkyl group, or cycloalkyl-substituted alkyl group, unless otherwise specified.

As used herein, the term "haloalkyl group" or "halogenalkyl group" may mean a halogen-substituted alkyl group unless otherwise specified.

As used herein, the term "alkenyl" or "alkynyl" may have a double bond or a triple bond, respectively, and may include a straight or branched chain group and may have 2 to 60 carbon atoms unless otherwise specified.

As used herein, the term "cycloalkyl" may refer to an alkyl forming a ring having 3 to 60 carbon atoms, unless otherwise specified.

As used herein, the term "alkoxy group" or "alkyloxy group" refers to an alkyl group to which an oxygen radical is bonded, and may have 1 to 60 carbon atoms unless otherwise specified.

As used herein, the term "alkenoxyl group", "alkenoxy group", "alkenyloxyl group", or "alkenyloxy group" refers to an alkenyl group to which an oxygen radical is attached, and may have 2 to 60 carbon atoms unless otherwise specified.

As used herein, the terms "aryl group" and "arylene group" each may have 6 to 60 carbon atoms unless otherwise specified, but are not limited thereto. In the disclosure, the aryl group or the arylene group may include a monocyclic type, a ring assembly, a fused polycyclic system, a spiro compound, and the like. For example, the aryl group includes, but is not limited to, phenyl, biphenyl, naphthyl, anthryl, indenyl, phenanthryl, triphenylenyl, pyrenyl, peryleneyl, chrysenyl, naphthacenyl, or fluoranthenyl. The naphthyl may include 1-naphthyl and 2-naphthyl, and the anthryl may include 1-anthryl, 2-anthryl and 9-anthryl.

In the disclosure, the term "fluorenyl group" or "fluorenylene group" may refer to a monovalent or divalent functional group, respectively, of fluorene, unless otherwise specified. The "fluorenyl group" or "fluorenylene group" may mean a substituted fluorenyl group or a substituted fluorenylene group. "Substituted fluorenyl group" or "substituted fluorenylene group" may refer to a monovalent or divalent functional group of substituted fluorene. "Substituted fluorene" may mean that at least one of the following substituents R, R', R" and R"' is a functional group other than hydrogen. It may include a case where R and R' are bonded to each other to form a spiro compound together with the carbon to which they are bonded.

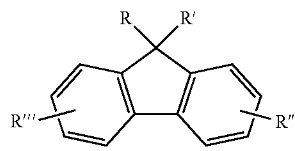

As used herein, the term "spiro compound" has a 'spiro union', and the spiro union means a union formed as two rings share only one atom. In this case, the atom shared by the two rings may be referred to as a 'spiro atom'.

As used herein, the term "heterocyclic group" may include not only an aromatic ring, such as a "heteroaryl group" or "heteroarylene group" but also a non-aromatic ring and, unless otherwise specified, means a ring with 2 to 50 carbon atoms and one or more heteroatoms, but is not limited thereto. As used herein, the term "heteroatom" refers to N, O, S, P or Si unless otherwise specified, and the heterocyclic group may mean a monocyclic group containing a heteroatom, a ring assembly, a fused polycyclic system, or a spyro compound.

The "heterocyclic group" may include a ring containing SO2 instead of carbon forming the ring. For example, the "heterocyclic group" may include the following compounds.

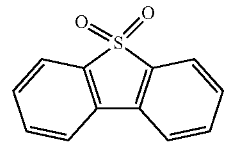 [SMILES: O=S1(=O)c2ccccc2-c2ccccc21]

As used herein, the term "ring" may include monocycles and polycycles, may include hydrocarbon rings as well as heterocycles containing at least one heteroatom, or may include aromatic and non-aromatic rings.

As used herein, the term "polycycle" may include ring assemblies, fused polycyclic systems, and spiro compounds, may include aromatic as well as non-aromatic compounds, or may include heterocycles containing at least one heteroatom as well as hydrocarbon rings.

As used herein, the term "aliphatic ring group" refers to a cyclic hydrocarbon other than the aromatic hydrocarbon, may include a monocyclic type, a ring assembly, a fused polycyclic system, and a spiro compound and, unless otherwise specified, may mean a ring having 3 to 60 carbon atoms. For example, a fusion of benzene, which is an aromatic ring, and cyclohexane, which is a non-aromatic ring, also corresponds to an aliphatic ring.

As used herein, the term "alkylsilyl group" may refer to a monovalent substituent in which three alkyl groups are bonded to a Si atom.

As used herein, the term "arylsilyl group" may refer to a monovalent substituent in which three aryl groups are bonded to a Si atom.

As used herein, the term "alkylarylsilyl group" may refer to a monovalent substituent in which one alkyl group and two aryl groups are bonded to a Si atom or two alkyl groups and one aryl group are bonded to the Si atom.

As used herein, the term "ring assembly" means that two or more ring systems (single or fused ring systems) are directly connected to each other through single or double bonds. For example, in the case of an aryl group, a biphenyl group or a terphenyl group may be a ring assembly but is not limited thereto.

As used herein, the term "fused polycyclic system" refers to a type of fused rings sharing at least two atoms. For example, in the case of an aryl group, a naphthalenyl group, a phenanthrenyl group, or a fluorenyl group may be a fused polycyclic system, but is not limited thereto.

When prefixes are named successively, it may mean that the substituents are listed in the order specified first. For example, an arylalkoxy group may mean an alkoxy group substituted with an aryl group, an alkoxycarbonyl group may mean a carbonyl group substituted with an alkoxy group, and an arylcarbonylalkenyl group may mean an alkenyl group substituted with an arylcarbonyl group. The arylcarbonyl group may be a carbonyl group substituted with an aryl group.

Unless otherwise explicitly stated, in the term "substituted" or "unsubstituted" as used herein, "substituted" may mean being substituted with one or more substitutents selected from the group consisting of halogen, an amino group, a nitrile group, a nitro group, a $C_1$-$C_{20}$ alkyl group, a $C_1$-$C_{20}$ alkoxy group, a $C_1$-$C_{20}$ alkylamine group, a $C_1$-$C_{20}$ alkylthiophene group, a $C_6$-$C_{20}$ arylthiophene group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_8$-$C_{20}$ arylalkenyl group, a silane group, a boron group, a germanium group, and a $C_2$-$C_{20}$ heterocyclic group including at least one heteroatom selected from the group consisting of O, N, S, Si and P, but is not limited to the substitutents.

In the disclosure, the 'functional group names' corresponding to the aryl group, arylene group, and heterocyclic group provided as examples of the symbols and their substituents may be described with 'the names of the functional groups reflecting the valence', but may also be described with 'the names of the parent compounds.' For example, in the case of 'phenanthrene', which is a type of aryl group, its name may be specified with its group identified, such as 'phenanthryl (group)' for the monovalent group, and 'phenanthrylene (group)' as the divalent groui, but may also be specified as 'phenanthrene', which is the name of the parent compound, regardless of the valence. Similarly, pyrimidine may be specified as 'pyrimidine' regardless of the valence or may also be specified as pyrimidinyl (group) for the monovalence and as pyrimidylene (group) for the divalence. Therefore, in the disclosure, when the type of the substituent is specified with the name of the parent compound, it may mean an n-valent 'group' formed by detachment of the hydrogen atom bonded to a carbon atom and/or a heteroatom of the parent compound.

Further, unless explicitly stated, the formulas used in the disclosure may be applied in the same manner as the definition of the substituent by the following formulas.

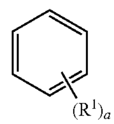

When a is 0, it means that the substituent $R_1$ does not exist, meaning that hydrogen is bonded to each of the carbon atoms forming the benzene ring. In this case, the chemical formula or chemical compound may be specified without expressing the hydrogen bonded to the carbon. Further, when a is 1, one substituent $R_1$ is bonded to any one of the carbon atoms forming the benzene ring, and when a is 2 or 3, it may be bonded as follows. When a is an integer of 4 to 6, it is bonded to the carbon of the benzene ring in a similar manner, and when a is an integer of 2 or more, $R_1$ may be identical or different.

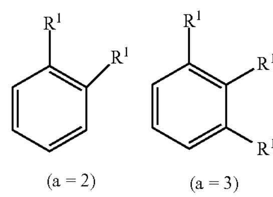

(a = 2) (a = 3)

In the disclosure, when substituents are bonded to each other to form a ring, it may mean that adjacent groups are bonded to each other to form a monosycle or fused polycycle, and the monocycle or fused polycycle may include heterocycles containing at least one heteroatom as well as hydrocarbon rings and may include aromatic and non-aromatic rings.

In the disclosure, organic light emitting element may mean a component(s) between the anode and the cathode or an organic light emitting diode including an anode, a cathode, and component(s) positioned therebetween.

In some cases, in the disclosure, organic light emitting element may mean an organic light emitting diode and a panel including the same, or an electronic device including the panel and circuitry. The electronic device may include, e.g., a display device, a lighting device, a solar cell, a portable or mobile terminal (e.g., a smart phone, a tablet, a PDA, an electronic dictionary, or PMP), a navigation terminal, a game device, various TVs, and various computer monitors but, without limited thereto, may include any type of device including the component(s).

FIG. 1 is a view schematically illustrating an organic light emitting element according to embodiments of the disclosure.

The organic light emitting element 100 according to embodiments of the disclosure includes a first electrode 110, a second electrode 120, and an organic material layer 130 positioned between the first electrode 110 and the second electrode 120.

For example, the first electrode 110 may be the anode electrode, and the second electrode 120 may be the cathode electrode.

For example, the first electrode 110 may be a transparent electrode, and the second electrode 130 may be a reflective electrode. In another example, the first electrode 110 may be a reflective electrode, and the second electrode 130 may be a transparent electrode.

The organic material layer 130 is a layer positioned between the first electrode 110 and the second electrode 120 and including an organic material and may be composed of a plurality of layers.

The organic material layer 130 includes a compound represented by chemical formula 1. The compound represented by chemical formula 1 is described below in detail.

The organic material layer 130 may include a light emitting layer. The organic layer 130 may further include at least one of a hole injection layer, a hole transport layer, an electron transport layer, and an electron injection layer.

For example, the organic material layer 130 may include a hole injection layer positioned on the first electrode 110, a hole transport layer positioned on the hole injection layer, a light emitting layer positioned on the hole transport layer, an electron transport layer positioned on the light emitting layer, and an electron injection layer positioned on the electron transport layer. In such an example, the first electrode 110 may be the anode electrode, and the second electrode 120 may be the cathode electrode.

The light emitting layer is a layer in which as holes and electrons transferred from the first electrode 110 and the second electrode 130 meet to emit light and may include, e.g., a host material and a dopant.

The light emitting layer may include the compound represented by chemical formula 1 described above. The compound represented by chemical formula 1 may be the host compound of the light emitting layer. For example, the compound represented by chemical formula 1 may be a phosphorescent host compound of the light emitting layer.

The light emitting layer may further include a host compound different from the compound represented by chemical formula 1 described above. The type of the host compound that may be additionally included is not particularly limited, and a known host compound may be used.

Figure 2:
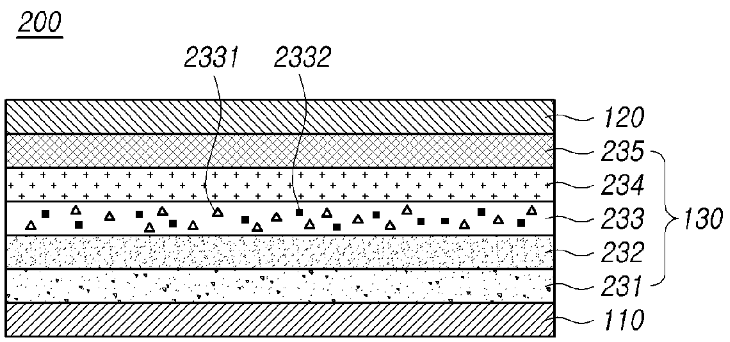

FIG. 2 is a view schematically illustrating an organic light emitting element according to embodiments of the disclosure.

The organic light emitting element 200 according to embodiments of the disclosure includes a first electrode 110, a second electrode 120, and an organic material layer 130 positioned between the first electrode 110 and the second electrode 120.

For example, the first electrode 110 may be the anode electrode, and the second electrode 120 may be the cathode electrode.

For example, the first electrode 110 may be a transparent electrode, and the second electrode 120 may be a reflective electrode. In another example, the first electrode 110 may be a reflective electrode, and the second electrode 120 may be a transparent electrode.

The organic material layer 130 is a layer positioned between the first electrode 110 and the second electrode 120 and including an organic material and may be composed of a plurality of layers.

The organic material layer 130 includes a compound represented by chemical formula 1. The compound represented by chemical formula 1 is described below in detail.

The organic material layer 130 may include a hole injection layer 231 positioned on the first electrode 110, a hole transport layer 232 positioned on the hole injection layer 231, a light emitting layer 233 positioned on the hole transport layer 232, an electron transport layer 234 positioned on the light emitting layer 233, and an electron injection layer 235 positioned on the electron transport layer 234. In such an example, the first electrode 110 may be the anode electrode, and the second electrode 120 may be the cathode electrode. The organic material layer 130 may not include some of the layers shown in FIG. 2 or may include an additional functional layer, such as a light emitting assist layer.

The light emitting layer 233 may include the compound represented by chemical formula 1 described above.

The light emitting layer 233 may include a host compound 2331 and a dopant 2332. The host compound 2331 may be a compound represented by chemical formula 1 described above. The host compound 2331 may further include another compound different from the compound represented by chemical formula 1 described above. For example, the host compound 2331 may include a compound represented by chemical formula 1 and a biscarbazole-based compound.

The type of the dopant 2332 is not particularly limited. For example, the dopant 2332 may be a green phosphorescent dopant. For example, the dopant 2332 may be a metal complex, such as of iridium.

Figure 3:
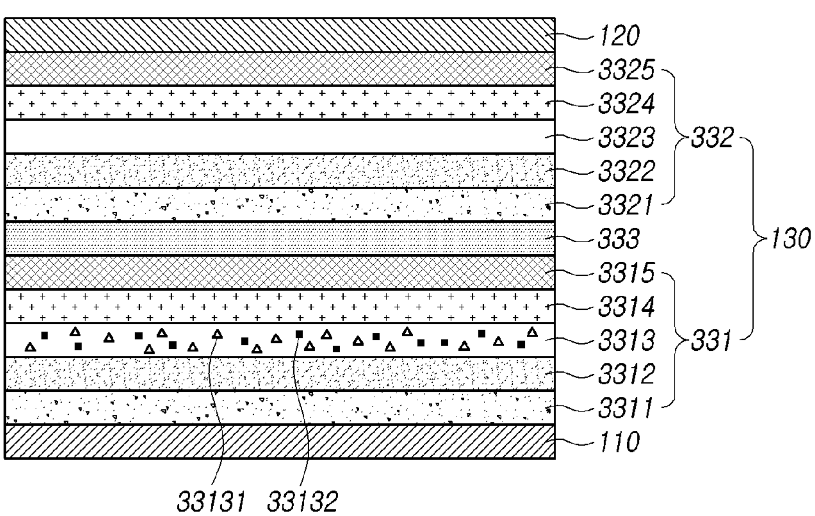
FIG. 3 is a view schematically illustrating an organic light emitting element according to embodiments of the disclosure.

FIG. 3 is a view schematically illustrating an organic light emitting element according to embodiments of the disclosure.

Referring to FIG. 3, the organic material layer 130 includes a first stack 331, a second stack 332, and a charge generation layer 333 positioned between the first stack 331 and the second stack 332.

The organic light emitting element 300 may be a tandem-type organic light emitting element including a plurality of stacks each including a light emitting layer. The plurality of light emitting layers may be formed of the same material or different materials. The first stack 331 may include a first light emitting layer 3313. The second stack 332 may include a second light emitting layer 3323. The first light emitting layer 3313 and the second light emitting layer 3323 may be formed of the same material or different materials.

The first stack 331 may include a first light emitting layer 3313. The first light emitting layer 3313 may include, e.g., a first host compound 33131 and a first dopant 33132.

The first stack 231 may further include at least one of a hole injection layer, a hole transport layer, an electron transport layer, and an electron injection layer.

For example, the first stack 331 may include a first hole injection layer 3311 positioned on the first electrode 110, a first hole transport layer 3312 positioned on the first hole injection layer 3311, a first light emitting layer 3313 positioned on the first hole transport layer 3312, a first electron transport layer 3314 positioned on the first light emitting layer 3313, and a first electron injection layer 3315 positioned on the first electron transport layer 3314. In such an example, the first electrode 110 may be the anode electrode, and the second electrode 120 may be the cathode electrode.

The first stack 331 may not include some of the layers shown in FIG. 3 or may include an additional functional layer, such as a light emitting assist layer.

The first light emitting layer 3313 may include the compound represented by chemical formula 1 described above.

The first light emitting layer 3313 may include a first host compound 33131 and a first dopant 33132. The first host compound 33131 may be a compound represented by chemical formula 1 described above. The first host compound 33131 may further include another compound different from the compound represented by chemical formula 1 described above. For example, the first host compound 33131 may include a compound represented by chemical formula 1 and a biscarbazole-based compound.

The type of the first dopant 33132 is not particularly limited. For example, the first dopant 33132 may be a green phosphorescent dopant. For example, the first dopant 33132 may be a metal complex, such as of iridium.

The second stack 332 may include a second light emitting layer 3323. The second light emitting layer 3323 may include, e.g., a second host compound and a second dopant.

The second stack 332 may further include at least one of a hole injection layer, a hole transport layer, an electron transport layer, and an electron injection layer.

For example, the second stack 332 may include a second hole injection layer 3321 positioned on the second electrode 110, a second hole transport layer 3322 positioned on the second hole injection layer 3321, a second light emitting layer 3323 positioned on the second hole transport layer 3322, a second electron transport layer 3324 positioned on the second light emitting layer 3323, and a second electron injection layer 3325 positioned on the second electron transport layer 3324. In such an example, the first electrode 110 may be the anode electrode, and the second electrode 120 may be the cathode electrode. The second stack 332 may not include some of the layers shown in FIG. 3 or may include an additional functional layer, such as a light emitting assist layer.

The second light emitting layer 3323 may emit light of the same color as, or a different color from, the light emitted by the first light emitting layer 3313. In the disclosure, that the light emitting layers emit light of the same color means that the light emitting layers emit not only light of colors with the same color coordinates but also light of colors similar to each other to be classified as pixels representing the same color in the technical field of the disclosure.

The second light emitting layer 3323 may include a second host compound and a second dopant.

The type of the second host compound is not particularly limited. The second host compound may be the same as, or different from, the first host compound 33131.

The type of the second dopant is not particularly limited. The second dopant may be the same as, or different from, the first dopant 33132.

In embodiments of the disclosure, the second light emitting layer 3323 may emit light of the same color as the light emitted by the first light emitting layer 3313. In the above-described embodiments, the first light emitting layer 3323 may include the compound represented by chemical formula 2 described above.

In embodiments in which the first light emitting layer 3313 and the second light emitting layer 3323 emit light of the same color, the second host compound may be a compound represented by chemical formula 1 described above. The second host compound may further include another compound different from the compound represented by chemical formula 1 described above. For example, the second host compound may include a compound represented by chemical formula 1 and a biscarbazole-based compound.

In embodiments in which the first light emitting layer 3313 and the second light emitting layer 3323 emit light of the same color, the type of the second dopant is not particularly limited and may be the same as the first dopant 33132. For example, the second dopant may be a green phosphorescent dopant. For example, the second dopant may be a metal complex, such as of iridium.

The charge generation layer 333 may be formed between the plurality of light emitting layers to smoothly distribute charges, thereby increasing the current efficiency of the light emitting layer. Accordingly, the charge generation layer 333 is positioned between the first stack 331 including the first light emitting layer 3313 and the second stack 332 including the second light emitting layer 3323.

The charge generation layer 333 may include a p-type charge generation layer and an n-type charge generation layer to smoothly distribute charges. When the first electrode 110 is the anode electrode, and the second electrode 120 is the cathode electrode, the p-type charge generation layer may be positioned on the side of the cathode electrode, and the n-type charge generation layer may be positioned on the side of the anode electrode.

Although FIG. 3 illustrates a tandem-type organic light emitting element including two stacks, embodiments of the disclosure are not limited thereto but may include tandem-type organic light emitting elements including two or more stacks. When the organic light emitting element 300 includes an additional stack, an additional charge generation layer may be positioned between the additional stack and the first stack 331 or second stack 332 adjacent thereto.

Figure 4:
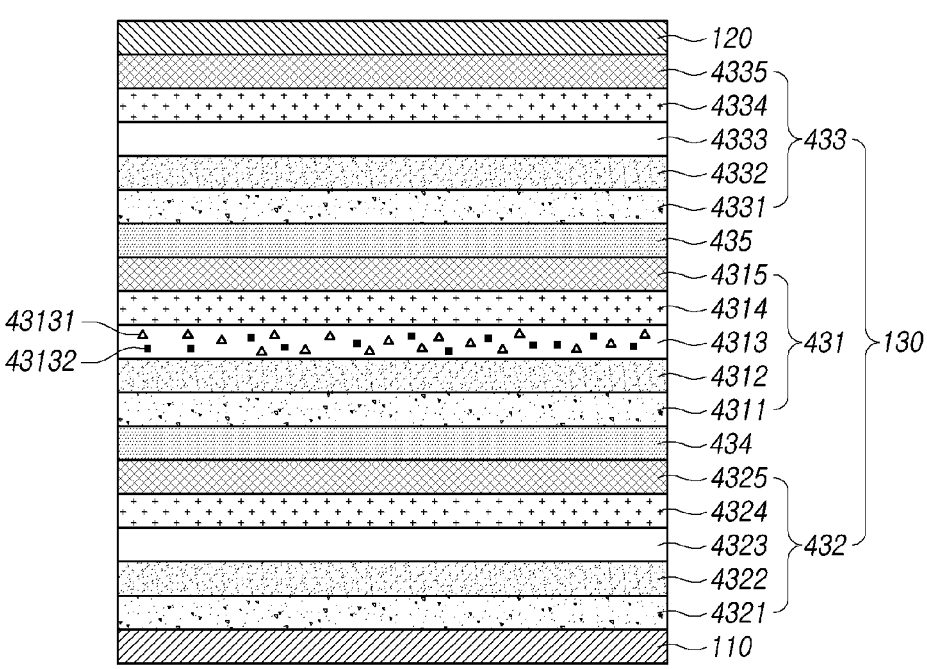
FIG. 4 is a view schematically illustrating an organic light emitting element according to embodiments of the disclosure.

FIG. 4 is a view schematically illustrating an organic light emitting element according to embodiments of the disclosure.

Referring to FIG. 4, the organic material layer 130 includes a first stack 431, a second stack 432, a third stack 433, a first charge generation layer 434 positioned between the first stack 431 and the second stack 432, and a second charge generation layer 435 positioned between the first stack 431 and the third stack 433. In the embodiments illustrated in FIG. 4, the first stack 431 is positioned between the second stack 432 and the third stack 433, but embodiments of the disclosure including three stacks are limited to this structure, and the positions of the first stack 431, the second stack 432, and the third stack 433 may be exchanged with each other.

The organic light emitting element 400 may be a tandem-type organic light emitting element including a plurality of stacks each including a light emitting layer. The plurality of light emitting layers may be formed of the same material or different materials.

The first stack 431 may include a first light emitting layer 4313. The first light emitting layer 4313 may include, e.g., a first host compound 43131 and a first dopant 43132.

The first stack 431 may further include at least one of a hole injection layer, a hole transport layer, an electron transport layer, and an electron injection layer.

For example, the first stack 431 may include a first hole injection layer 4311 positioned on the first electrode 110, a first hole transport layer 4312 positioned on the first hole injection layer 4311, a first light emitting layer 4313 positioned on the first hole transport layer 4312, a first electron transport layer 4314 positioned on the first light emitting layer 4313, and a first electron injection layer 4315 positioned on the first electron transport layer 4314. In such an example, the first electrode 110 may be the anode electrode, and the second electrode 120 may be the cathode electrode. The first stack 431 may not include some of the layers shown in FIG. 4 or may include an additional functional layer, such as a light emitting assist layer.

The first light emitting layer 4313 may include the compound represented by chemical formula 1 described above.

The first light emitting layer 4313 may include a first host compound 43131 and a first dopant 43132. The first host compound 43131 may be a compound represented by chemical formula 1 described above. The first host compound 43131 may further include another compound different from the compound represented by chemical formula 1 described above. For example, the first host compound 43131 may include a compound represented by chemical formula 1 and a biscarbazole-based compound.

The type of the first dopant 43132 is not particularly limited. For example, the first dopant 43132 may be a green phosphorescent dopant. For example, the first dopant 43132 may be a metal complex, such as of iridium.

The second stack 432 may include a second light emitting layer 4323. The second light emitting layer 4323 may include, e.g., a second host compound 43231 and a second dopant 43232.

The second stack 432 may further include at least one of a hole injection layer, a hole transport layer, an electron transport layer, and an electron injection layer.

For example, the second stack 432 may include a second hole injection layer 4321 positioned on the second electrode 110, a second hole transport layer 4322 positioned on the second hole injection layer 4321, a second light emitting layer 4323 positioned on the second hole transport layer 4322, a second electron transport layer 4324 positioned on the second light emitting layer 4323, and a second electron injection layer 4325 positioned on the second electron transport layer 4324. In such an example, the first electrode 110 may be the anode electrode, and the second electrode 120 may be the cathode electrode. The second stack 432 may not include some of the layers shown in FIG. 4 or may include an additional functional layer, such as a light emitting assist layer.

The second light emitting layer 4323 may emit light of the same color as or a different color from, the light emitted by the first light emitting layer 4313.

The second light emitting layer 4323 may include a second host compound and a second dopant.

The type of the second host compound is not particularly limited. The second host compound may be the same as, or different from, the first host compound 43131.

The type of the second dopant is not particularly limited. The second dopant may be the same as, or different from, the first dopant 43132.

In embodiments of the disclosure, the second light emitting layer 4323 may emit light of the same color as the light emitted by the first light emitting layer 4313. In the above-described embodiments, the first light emitting layer 4323 may include the compound represented by chemical formula 2 described above.

In embodiments in which the first light emitting layer 4313 and the second light emitting layer 4323 emit light of the same color, the second host compound may be a compound represented by chemical formula 1 described above. The second host compound may further include another compound different from the compound represented by chemical formula 1 described above. For example, the second host compound may include a compound represented by chemical formula 1 and a biscarbazole-based compound.

In embodiments in which the first light emitting layer 4313 and the second light emitting layer 4323 emit light of the same color, the type of the second dopant is not particularly limited and may be the same as the first dopant 43132. For example, the second dopant may be a green phosphorescent dopant. For example, the second dopant may be a metal complex, such as of iridium.

The third stack 433 may include a third light emitting layer 4333. The third light emitting layer 4333 may include, e.g., a third host compound and a third dopant.

The third stack 432 may further include at least one of a hole injection layer, a hole transport layer, an electron transport layer, and an electron injection layer.

For example, the third stack 432 may include a third hole injection layer 4331 positioned on the third electrode 110, a third hole transport layer 4332 positioned on the third hole injection layer 4331, a third light emitting layer 4333 positioned on the third hole transport layer 4332, a third electron transport layer 4334 positioned on the third light emitting layer 4333, and a third electron injection layer 4335 positioned on the third electron transport layer 4334. In such an example, the first electrode 110 may be the anode electrode, and the second electrode 120 may be the cathode electrode. The third stack 433 may not include some of the layers shown in FIG. 4 or may include an additional functional layer, such as a light emitting assist layer.

The third light emitting layer 4333 may emit light of the same color as or a different color from, the light emitted by the first light emitting layer 4313.

The third light emitting layer 4333 may include a third host compound and a third dopant.

The type of the third host compound is not particularly limited. The third host compound may be the same as, or different from, the first host compound 43131.

The type of the third dopant is not particularly limited. The third dopant may be the same as, or different from, the first dopant 43132.

In embodiments of the disclosure, the third light emitting layer 4333 may emit light of the same color as the light emitted by the first light emitting layer 4313. In the above-described embodiments, the first light emitting layer 4333 may include the compound represented by chemical formula 3 described above.

In embodiments in which the first light emitting layer 4313 and the third light emitting layer 4333 emit light of the same color, the third host compound may be a compound represented by chemical formula 1 described above. The third host compound may further include another compound different from the compound represented by chemical formula 1 described above. For example, the third host compound may include a compound represented by chemical formula 1 and a biscarbazole-based compound.

In embodiments in which the first light emitting layer 4313 and the third light emitting layer 4333 emit light of the same color, the type of the second dopant is not particularly limited and may be the same as the first dopant 43132. For example, the second dopant may be a green phosphorescent dopant. For example, the second dopant may be a metal complex, such as of iridium.

The first host compound 43131, the second host compound, and the third host compound may be the same as or different from each other. One or more of the first host compound 43131, the second host compound, and the third host compound may be a compound represented by chemical formula 1 described above. Accordingly, one of the first host compound 43131, the second host compound, and the third host compound may include a compound represented by chemical formula 1 described above. Two of the first host compound 43131, the second host compound, and the third host compound may include a compound represented by chemical formula 1 described above. All of the first host compound 43131, the second host compound, and the third host compound may include a compound represented by chemical formula 1 described above. When there are two or more light emitting layers containing a host compound including the compound represented by chemical formula 1, the two or more light emitting layers may emit light of the same color.

The first dopant 33132, the second dopant, and the third dopant may be the same as or different from each other.

As the first stack 431, the second stack 432, and the third stack 433 are configured as described above, the holes and electrons transferred from the first electrode 110 and the second electrode 120 meet at the first light emitting layer 4313, the second light emitting layer 4323, and the third light emitting layer 4333, emitting light.

The first charge generation layer 434 and second charge generation layer 435 may be formed between the plurality of light emitting layers to smoothly distribute charges, thereby increasing the current efficiency of the light emitting layer. Accordingly, the first charge generation layer 434 may be positioned between the first stack 431 including the first light emitting layer 4313 and the second stack 432 including the second light emitting layer 4323, and the second charge generation layer 435 may be positioned between the second stack 432 including the second light emitting layer 433 and the third stack 433 including the third light emitting layer 4333.

The first charge generation layer 434 and second charge generation layer 435 may include a p-type charge generation layer and an n-type charge generation layer to smoothly distribute charges. When the first electrode 110 is the anode electrode, and the second electrode 120 is the cathode electrode, the p-type charge generation layer may be positioned on the side of the cathode electrode, and the n-type charge generation layer may be positioned on the side of the anode electrode.

The first charge generation layer 434 and the second charge generation layer 435 may be the same as or different from each other. The first charge generation layer 434 and the second charge generation layer 435 may be formed of the same material or different materials.

The compound represented by chemical formula 1 described above is described below.

The compound represented by chemical formula 1 described above may be represented by chemical formula 1 as follows.

[Chemical formula 1]

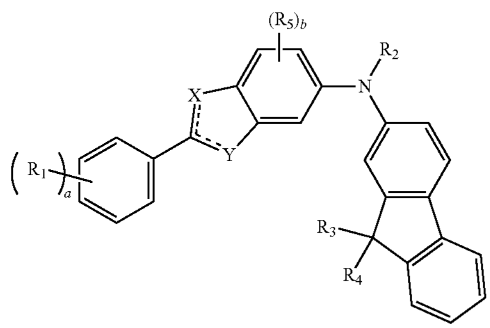

In chemical formula 1, either X or Y is N, and the other is S or 0.

a is an integer from 0 to 5.

$R_1$ is each independently selected from the group consisting of a $C_1$-$C_{20}$ alkyl group; a $C_3$-$C_{30}$ cycloalkyl group; an aryloxy group; an arylthioxy group; a fluorenyl group; and a $C_6$-$C_{60}$ aryl group.

When $R_1$ is an aryl group, the aryl group may be each independently a $C_6$-$C_{30}$ aryl group, a $C_6$-$C_{20}$ aryl group, or a $C_6$-$C_{12}$ aryl group.

$R_2$ is selected from the group consisting of a $C_3$-$C_{30}$ cycloalkyl group; an aryloxy group; an arylthioxy group; a fluorenyl group; and a $C_6$-$C_{60}$ aryl group.

When $R_2$ is an aryl group, the aryl group may be each independently a $C_6$-$C_{30}$ aryl group, a $C_6$-$C_{20}$ aryl group, or a $C_6$-$C_{12}$ aryl group.

$R_3$ and $R_4$ may be each independently selected from the group consisting of i) a $C_1$-$C_{20}$ alkyl group; and a $C_6$-$C_{60}$ aryl group; or may be bonded to each other to form a ring.

When one or more of $R_3$ and $R_4$ are aryl groups, the aryl groups each may independently be a $C_6$-$C_{30}$ aryl group, a $C_6$-$C_{20}$ aryl group, or a $C_6$-$C_{12}$ aryl group.

b is an integer from 0 to 3.

$R_5$ is each independently a $C_6$-$C_{60}$ aryl group.

When $R_5$ is an aryl group, the aryl group may be each independently a $C_6$-$C_{30}$ aryl group, a $C_6$-$C_{20}$ aryl group, or a $C_6$-$C_{12}$ aryl group.

The alkyl group, cycloalkyl group, aryloxy group, arylthioxy group, fluorenyl group and aryl group each are further substituted with one or more substituents selected from the group consisting of a halogen group; a $C_1$-$C_{20}$ alkyl group; a $C_2$-$C_{20}$ alkenyl group; a $C_2$-$C_{20}$ alkynyl group; a fluorenyl group; a $C_6$-$C_{20}$ aryl group; and a $C_2$-$C_{20}$ heterocyclic group.

One or more of the hydrogen atoms contained in the compound represented by chemical formula 1 may be substituted with deuterium or tritium.

By including the compound represented by chemical formula 1 described above, the organic light emitting elements 100 and 200 may have high efficiency or long lifespan.

The compound represented by chemical formula 1 may be represented by any one of chemical formulas 1a and 1b below.

[Chemical formula 1a]

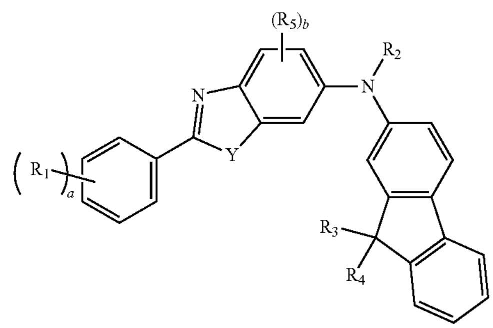

-continued

[Chemical formula 1b]

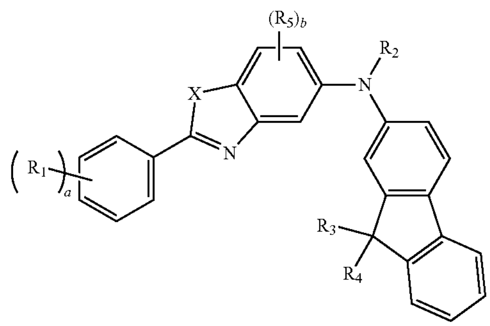

In chemical formula 1a and chemical formula 1b, X and Y are each S or 0.

$R_1$, $R_2$, $R_3$, $R_4$, $R_5$, a and b are the same as those defined above in chemical formula 1.

One or more of the hydrogen atoms contained in the compound represented by chemical formula 1a and chemical formula 1b may be substituted with deuterium or tritium.

The compound represented by chemical formula 1 described above may be one or more of the above-described compounds.

AZ1

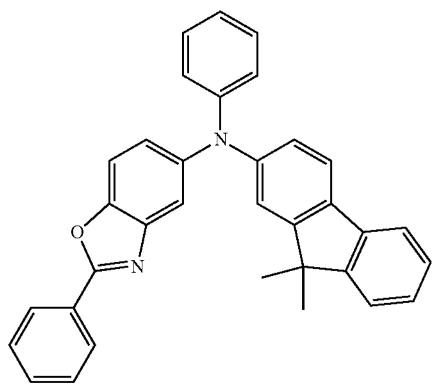

AZ2

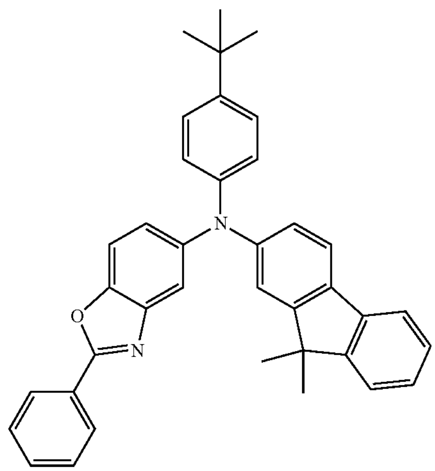

-continued

AZ3

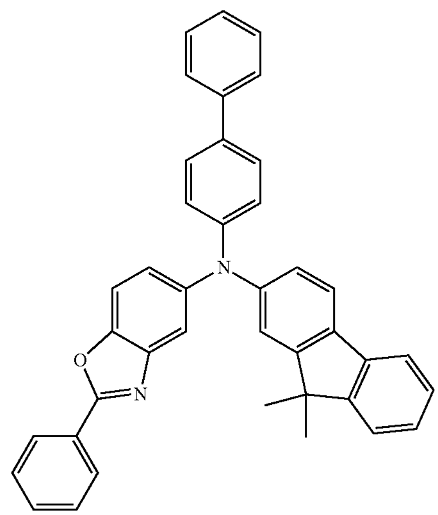

AZ4

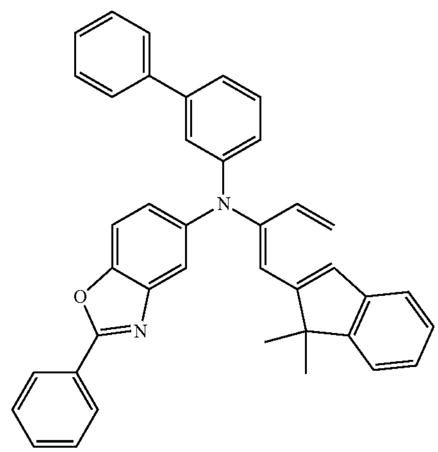

AZ5

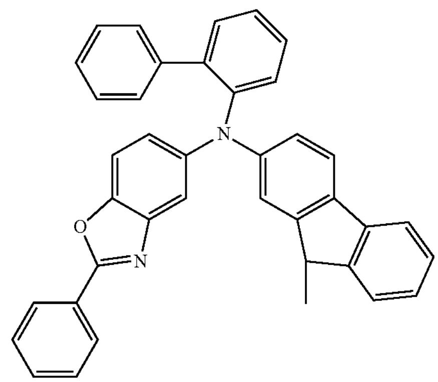

AZ6
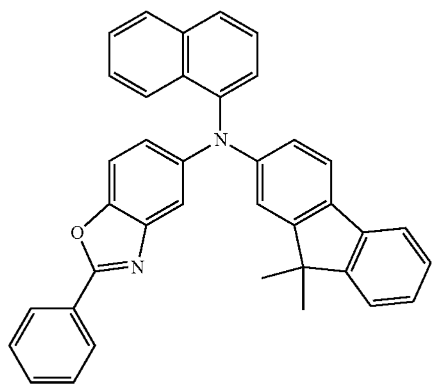
AZ7
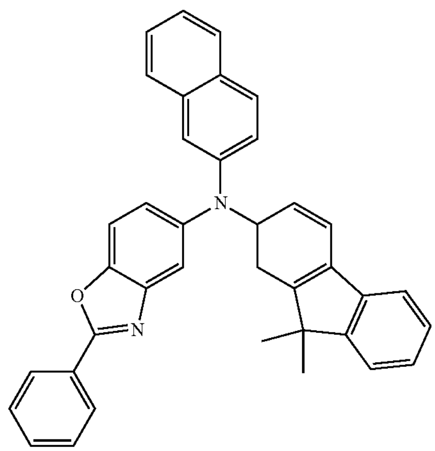
AZ8
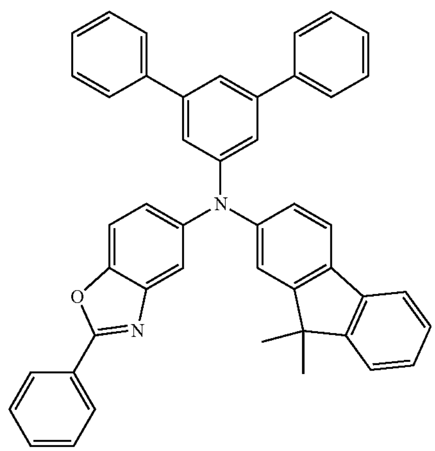
AZ9
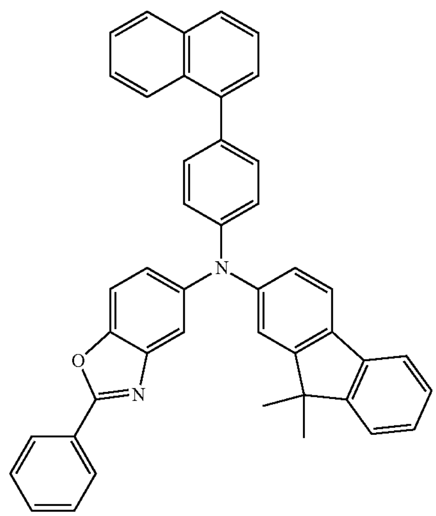
AZ10
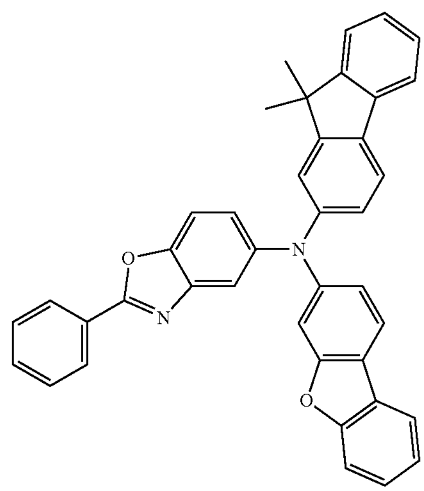
AZ11
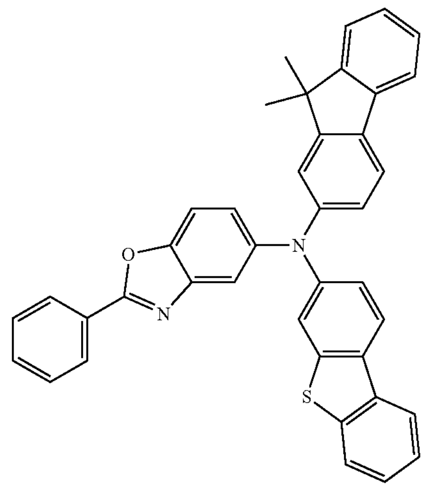

-continued
AZ12
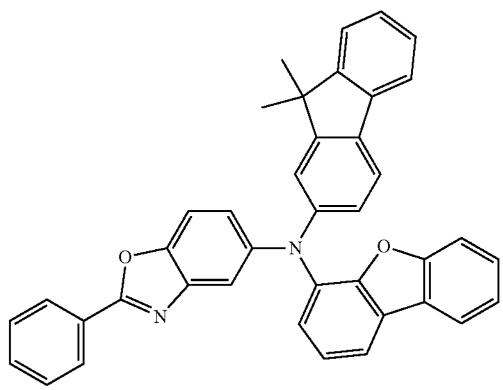
AZ13
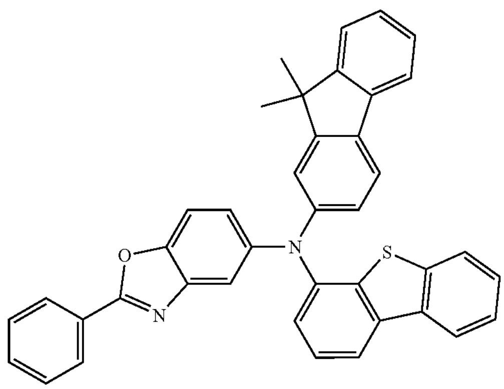
AZ14
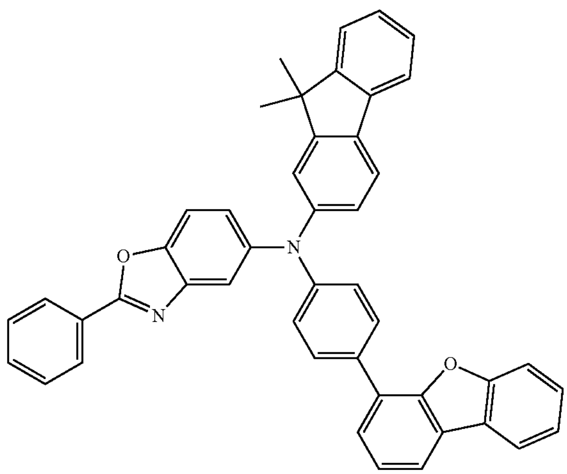
-continued
AZ15
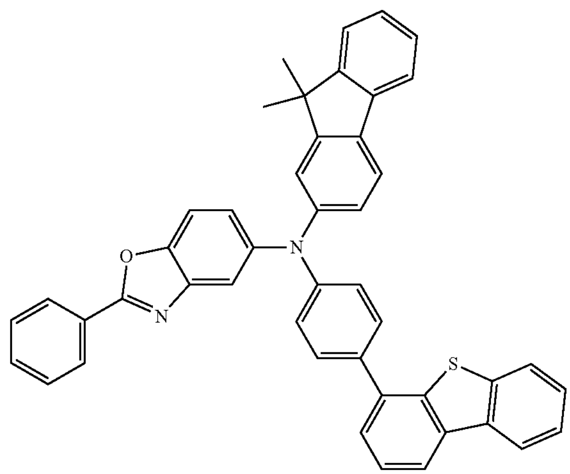
AZ16
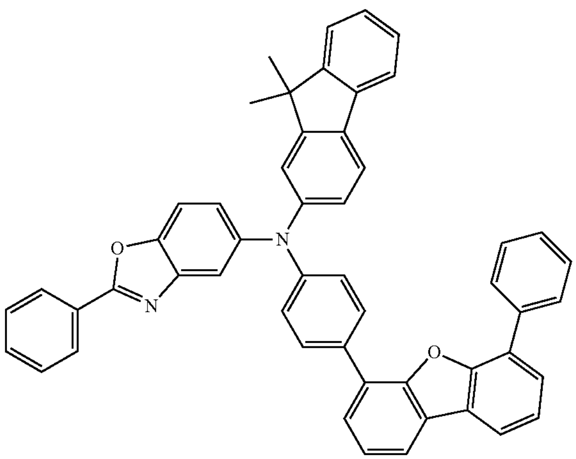
AZ17
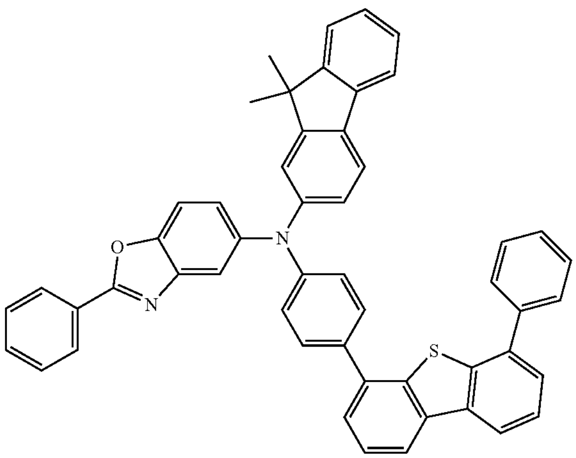

-continued
AZ18
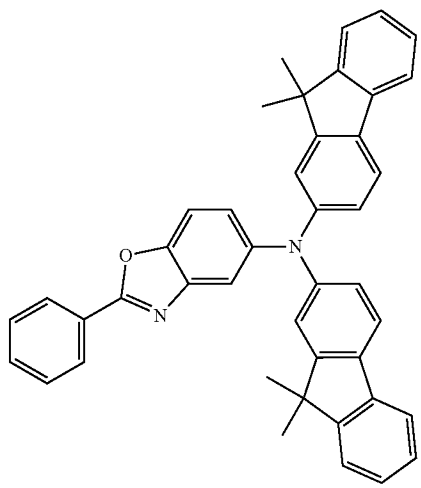
AZ19
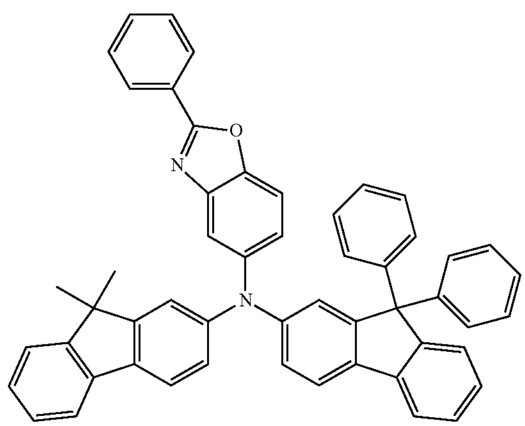
AZ20
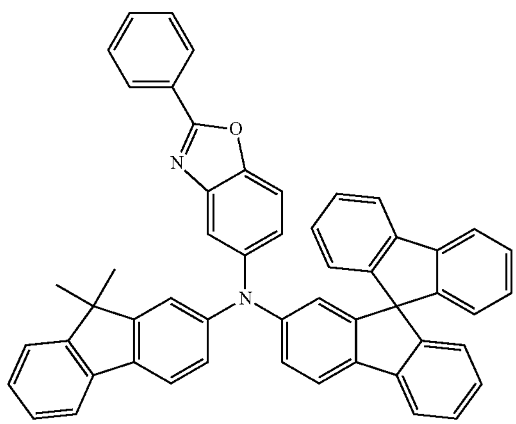
-continued
AZ21
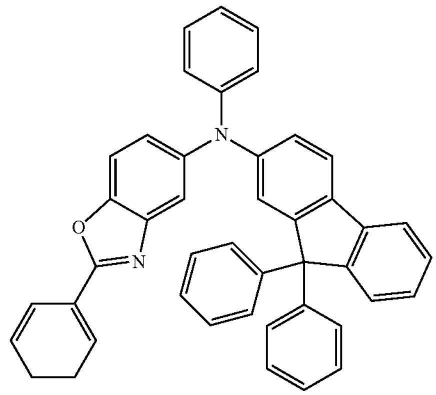
AZ22
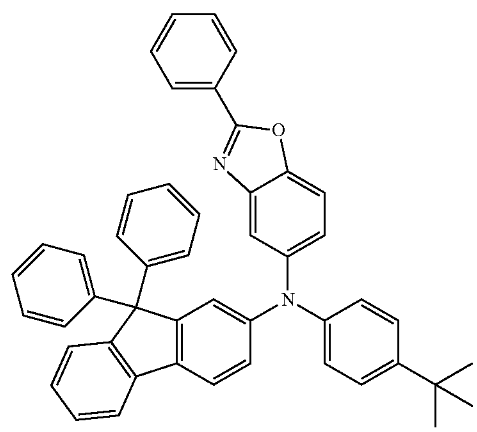
AZ23
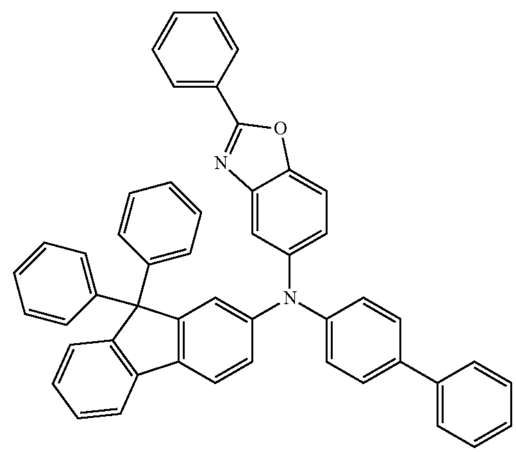

-continued
AZ24
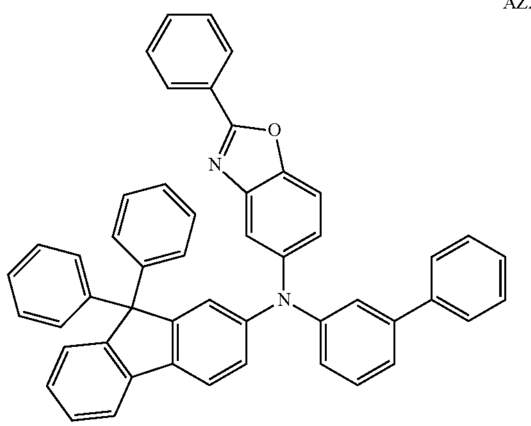
AZ25
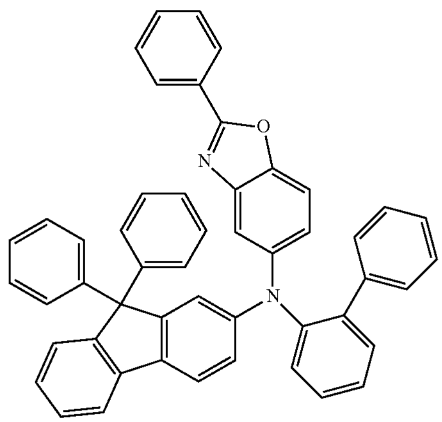
AZ26
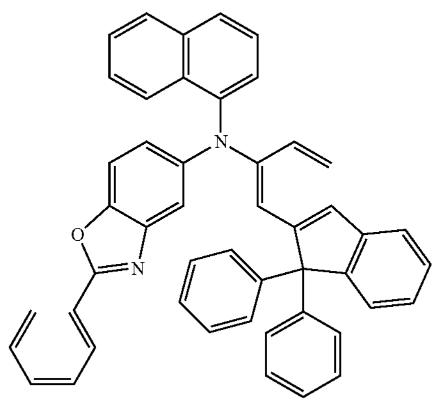
-continued
AZ27
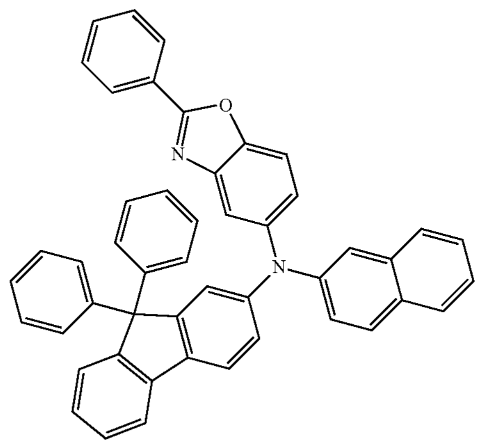
AZ28
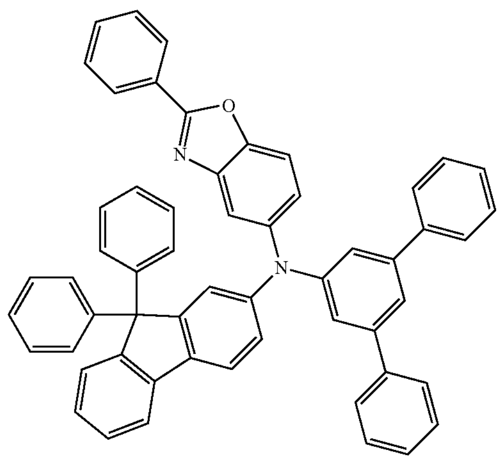
AZ29
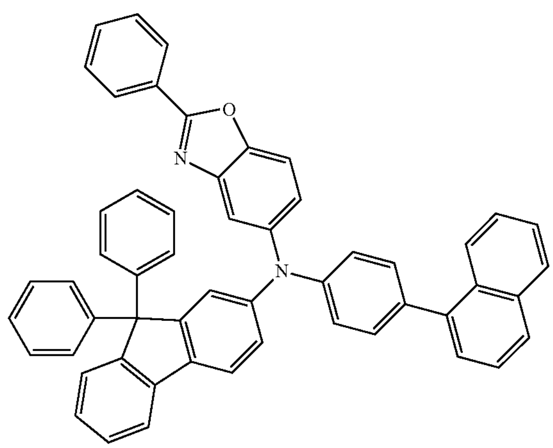

-continued
AZ30
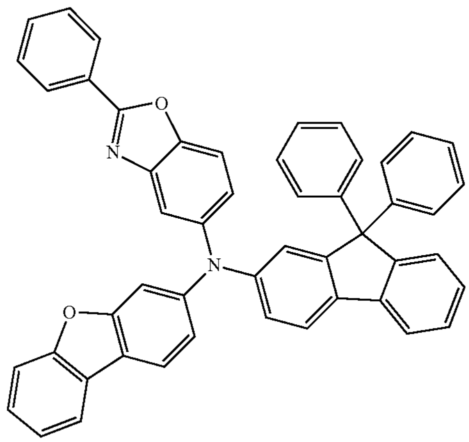
AZ31
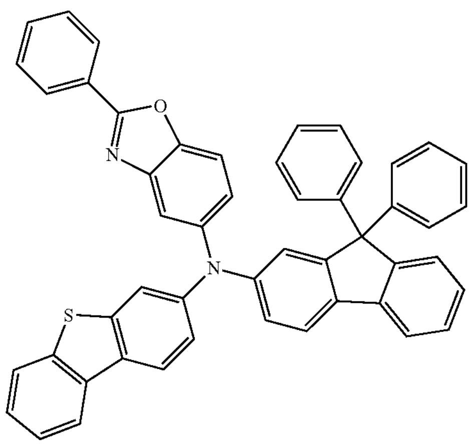
AZ32
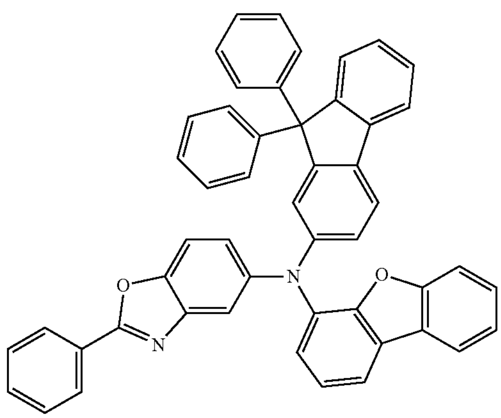
-continued
AZ33
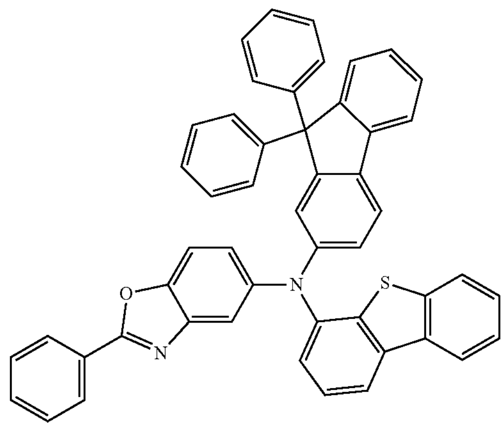
AZ34
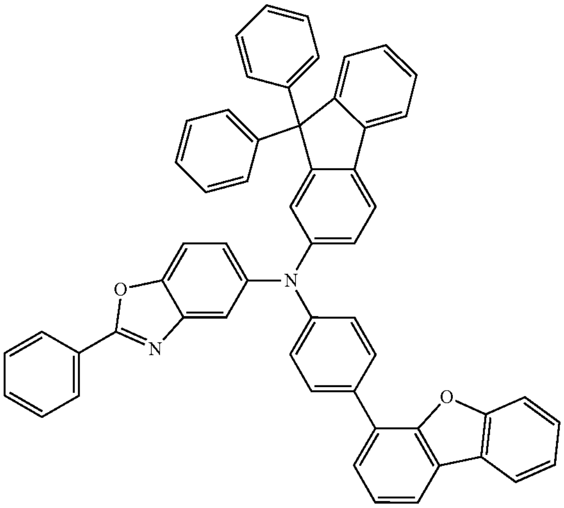
AZ35
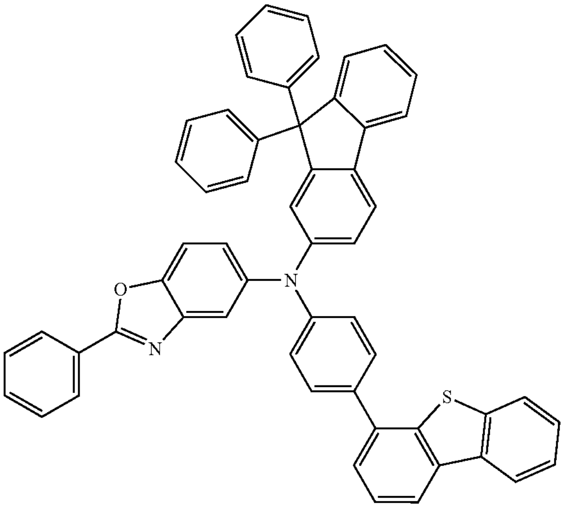

-continued
AZ36
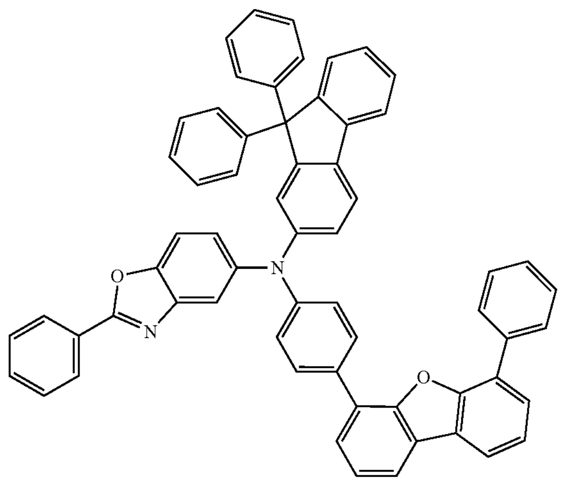
AZ37
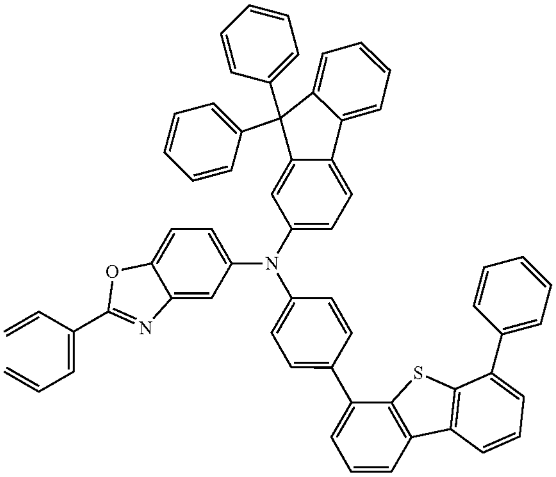
AZ38
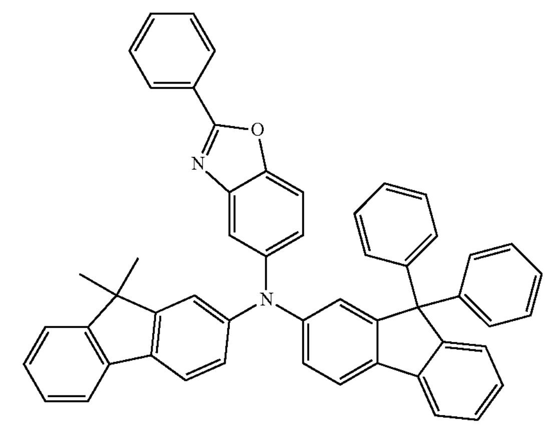
-continued
AZ39
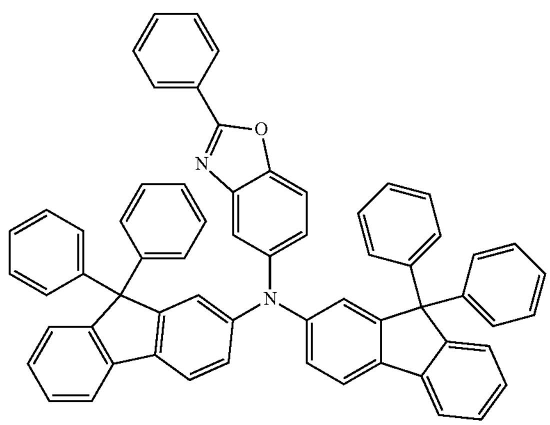
AZ40
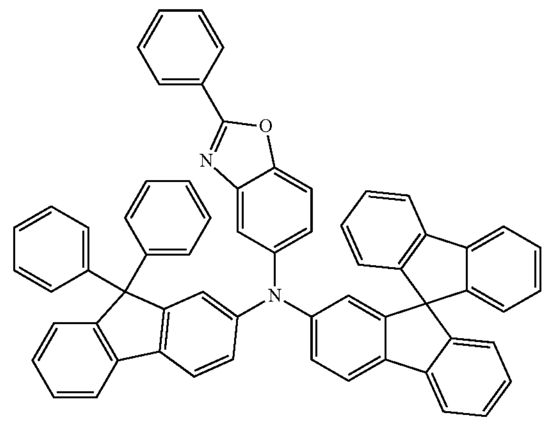
AZ41
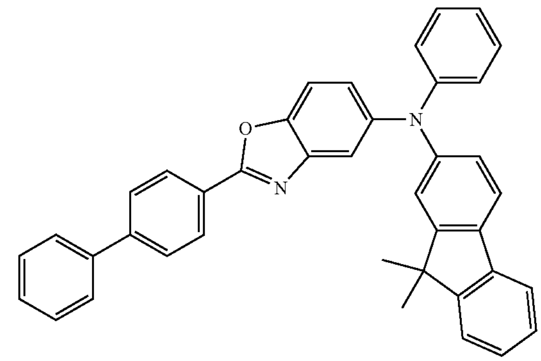

-continued
AZ42
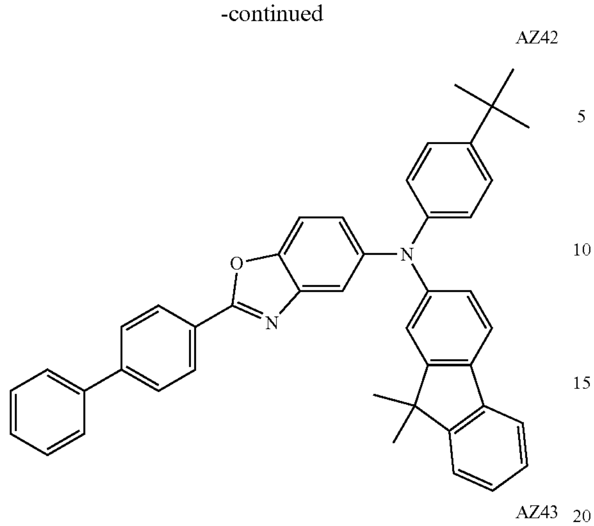
AZ43
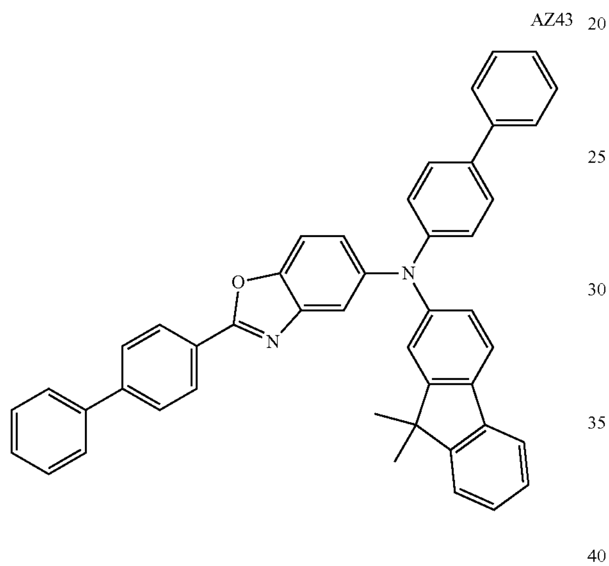
AZ44
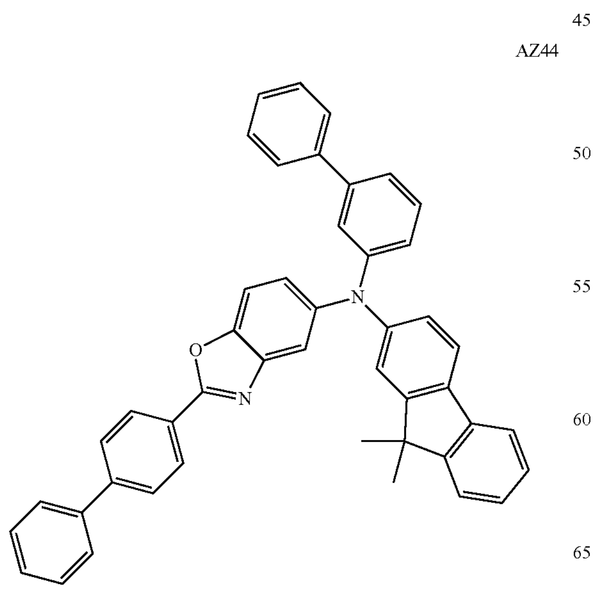
-continued
AZ45
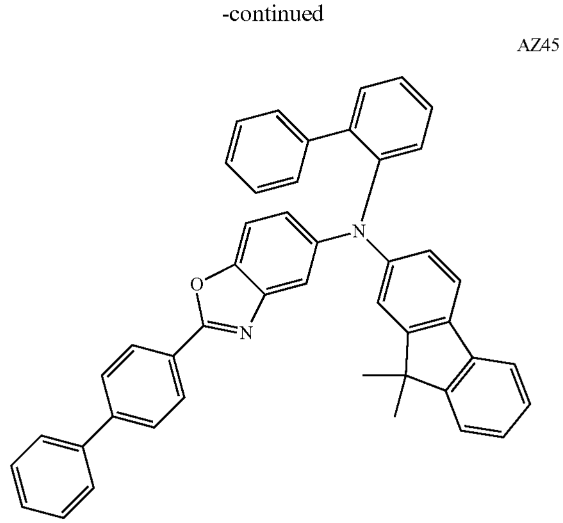
AZ46
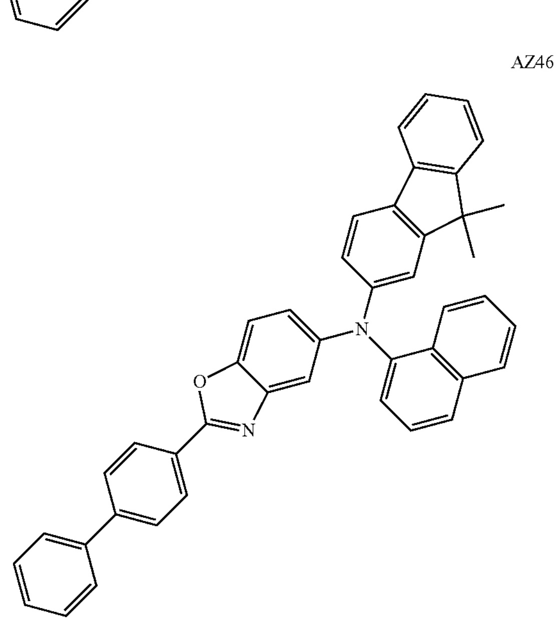
AZ47
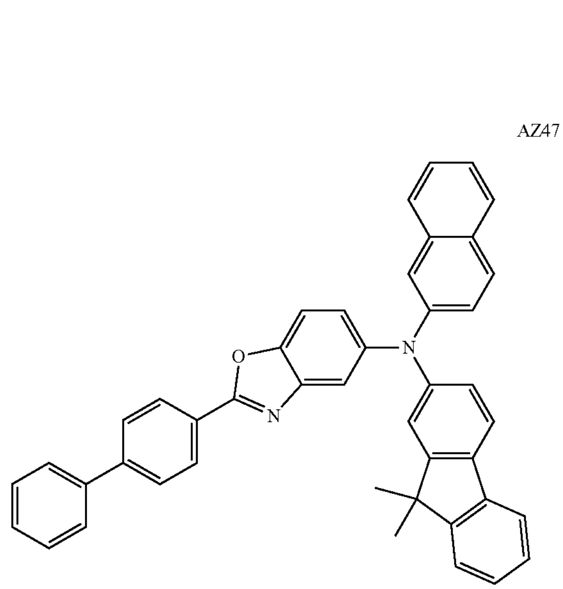

-continued
AZ48
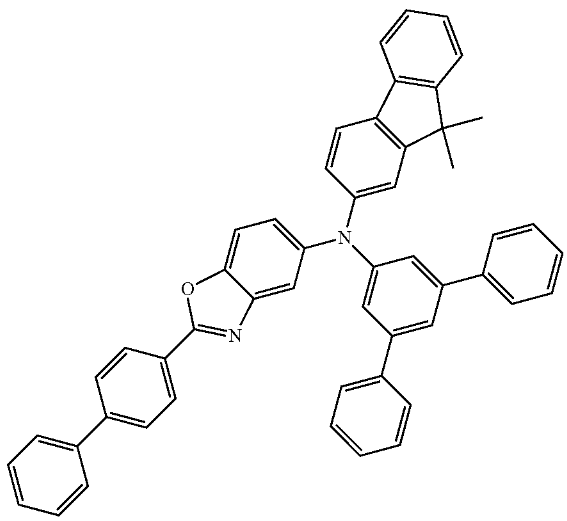
AZ49
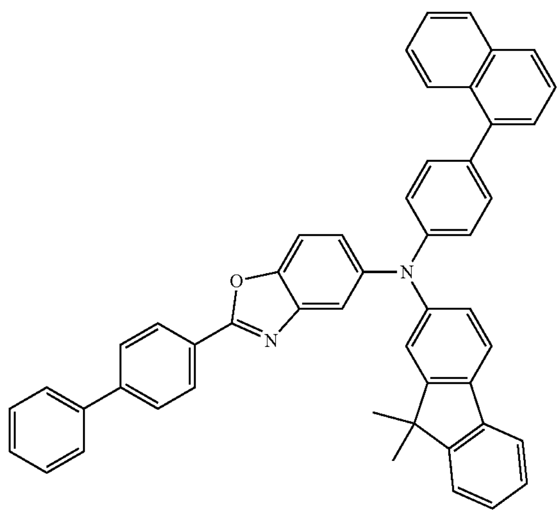
AZ50
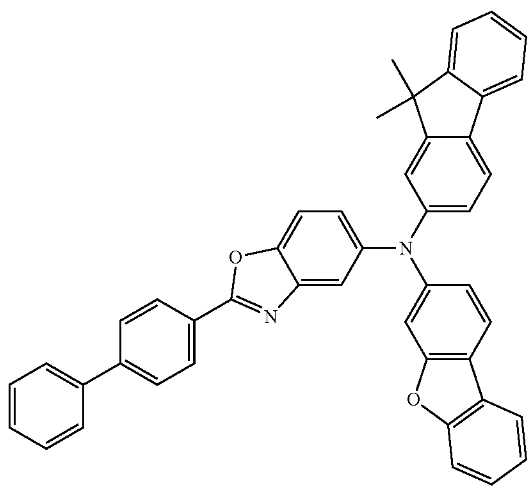
-continued
AZ51
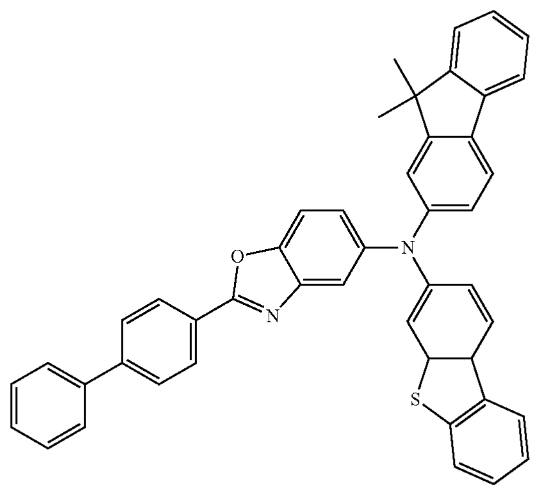
AZ52
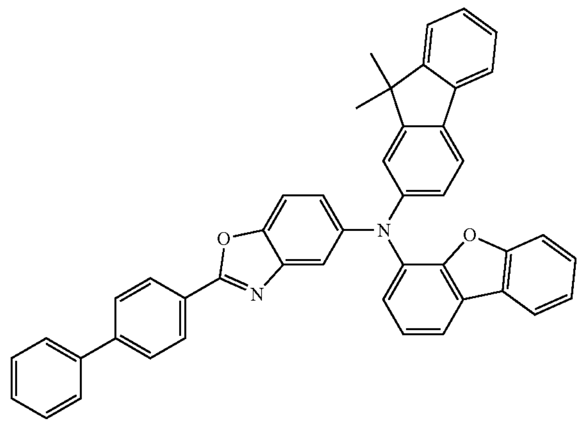
AZ53
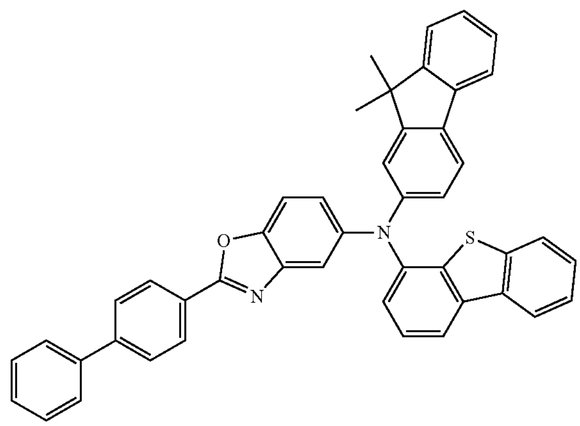

-continued
AZ54
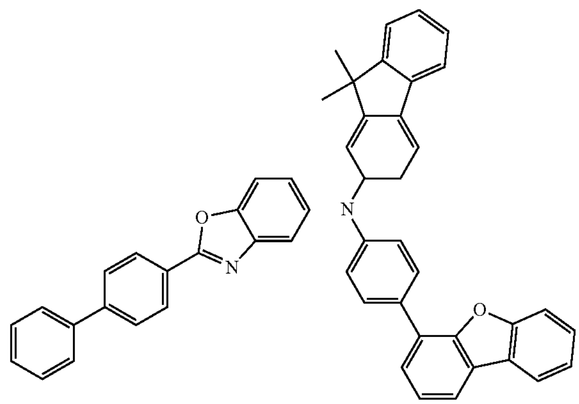
AZ55
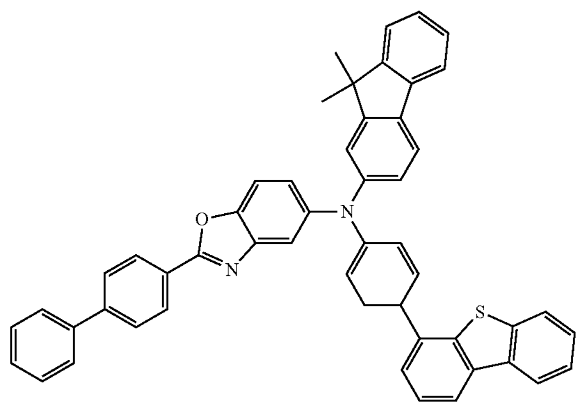
AZ56
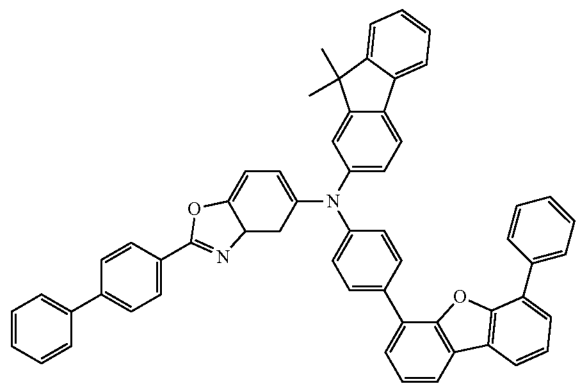
AZ57
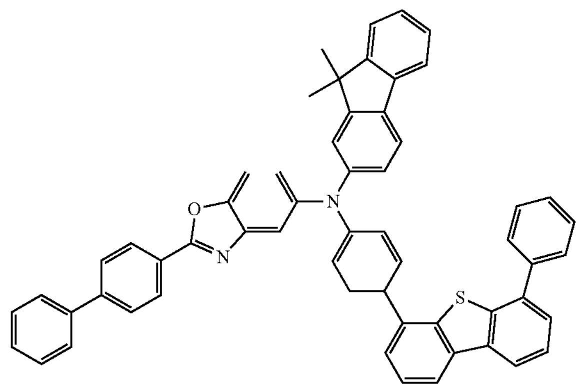
-continued
AZ58
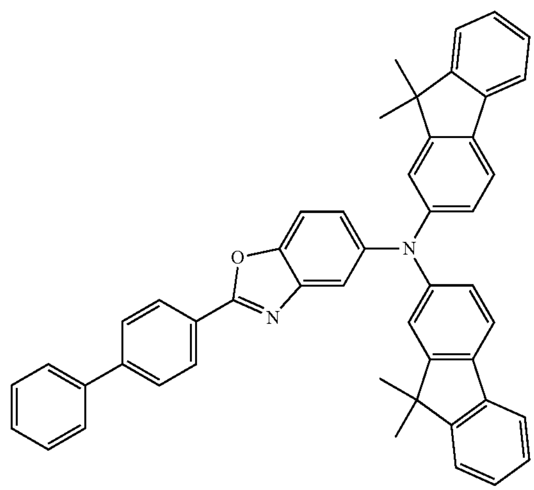
AZ59
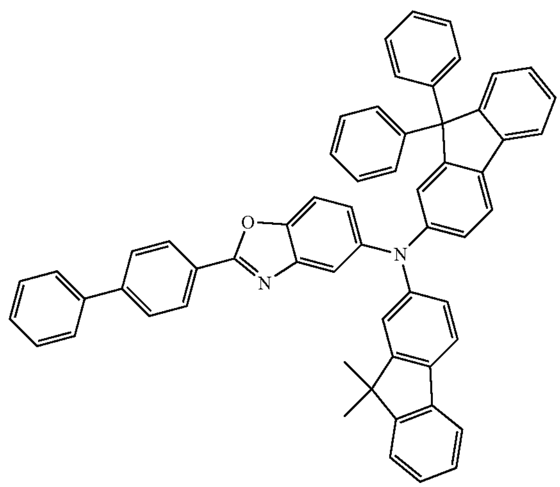
AZ60
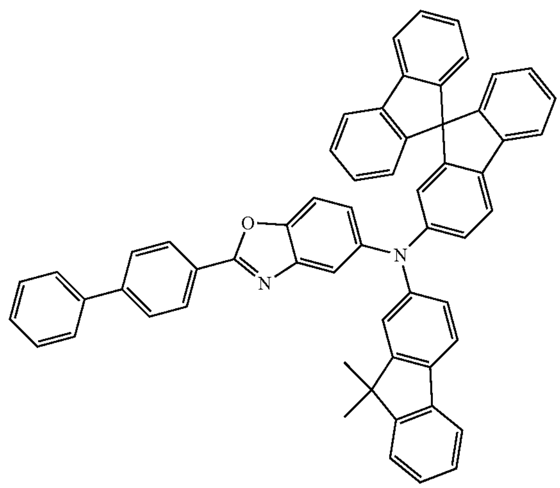

-continued
AZ61
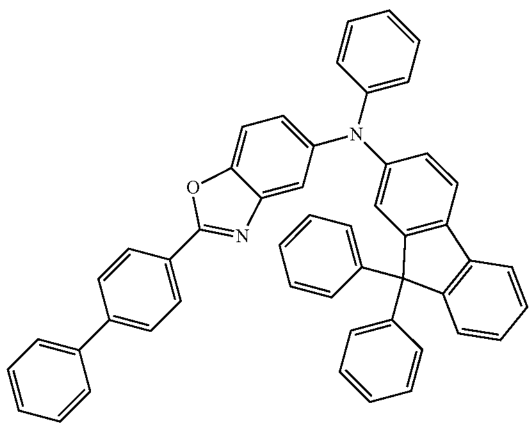
AZ62
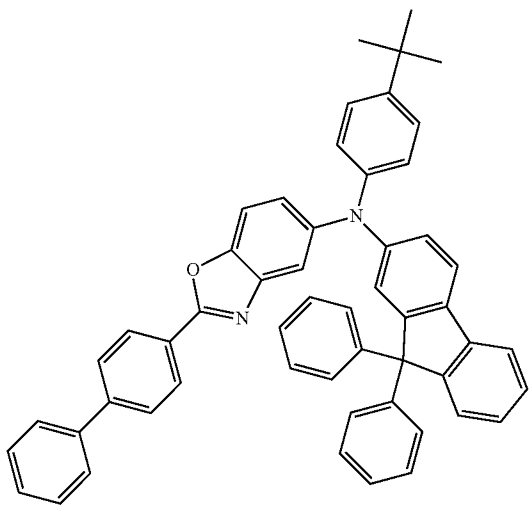
AZ63
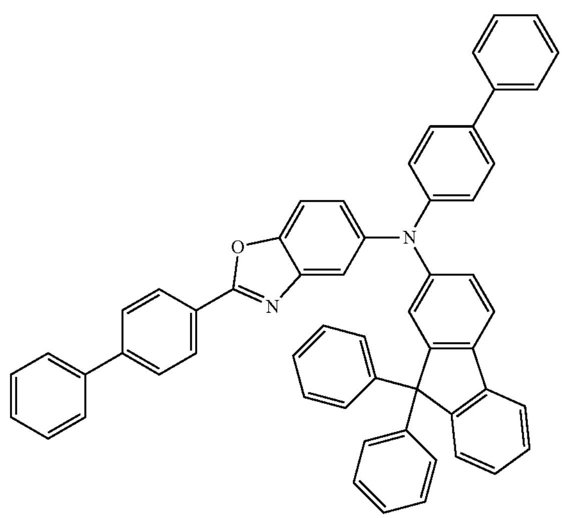
-continued
AZ64
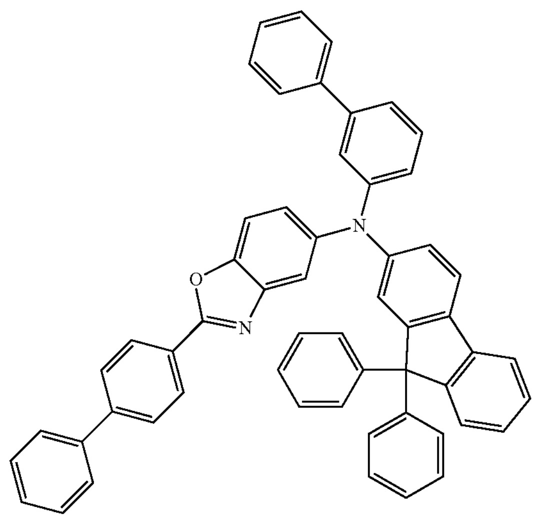
AZ65
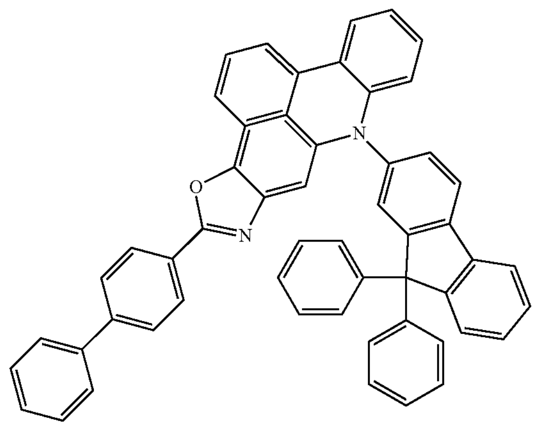
AZ66
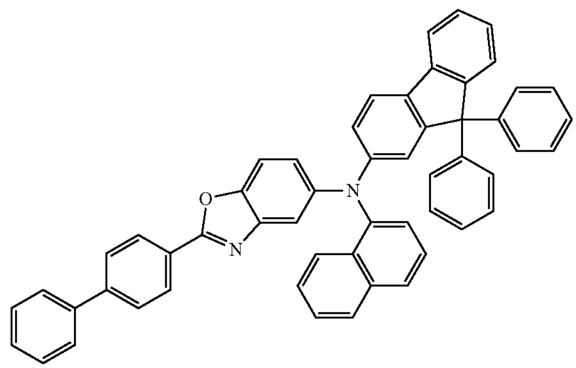

-continued
AZ67
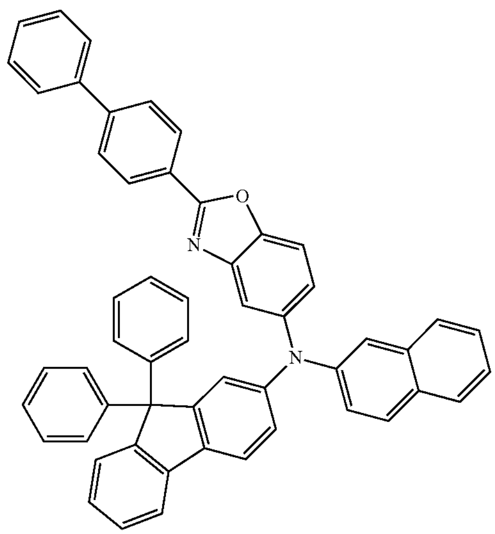
AZ68
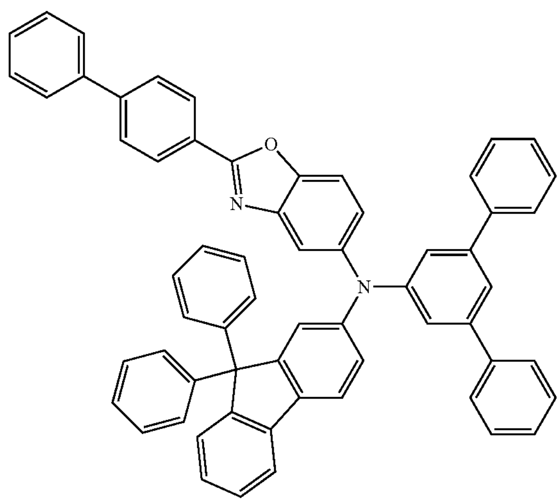
AZ69
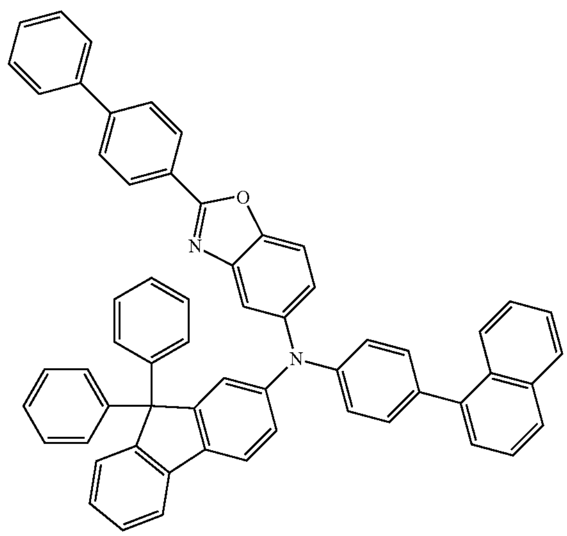
-continued
AZ70
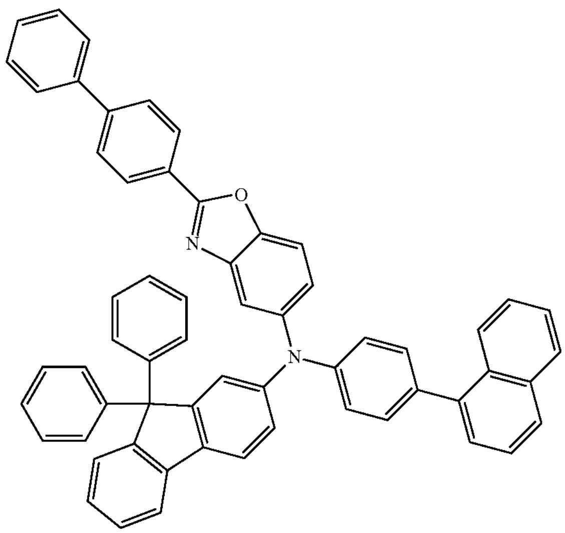
AZ71
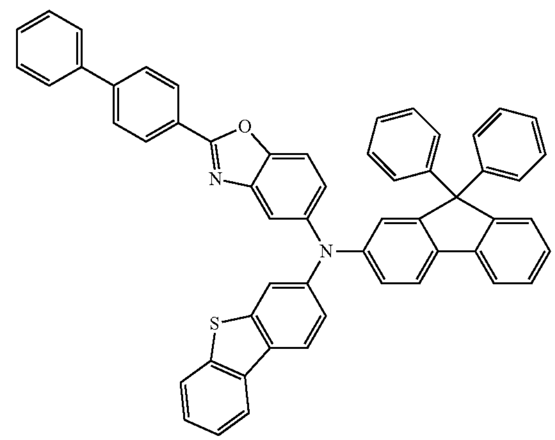
AZ72
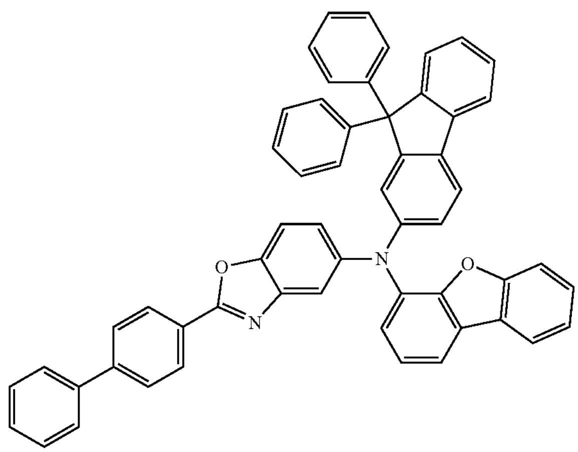

-continued
AZ73
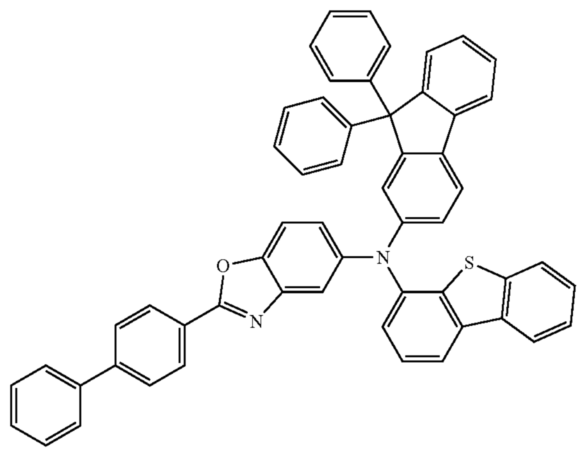
AZ74
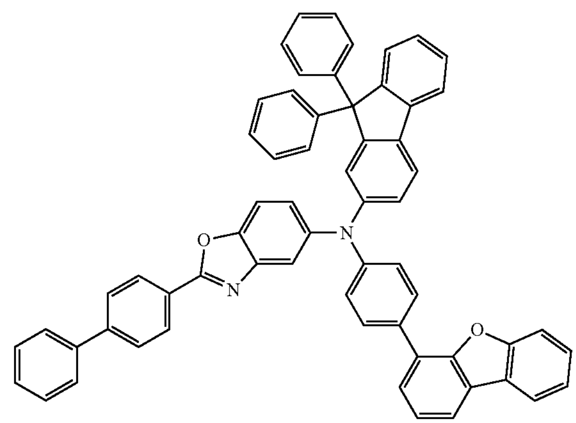
AZ75
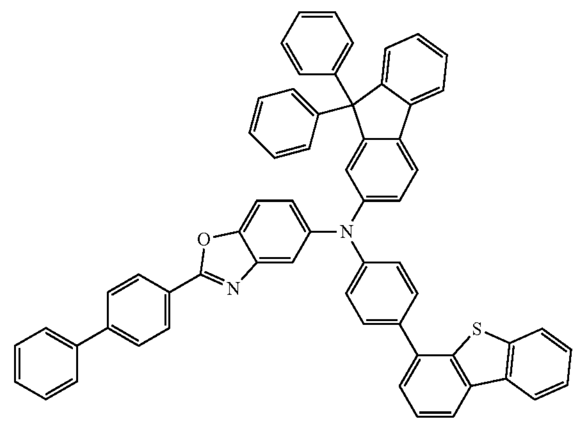
-continued
AZ76
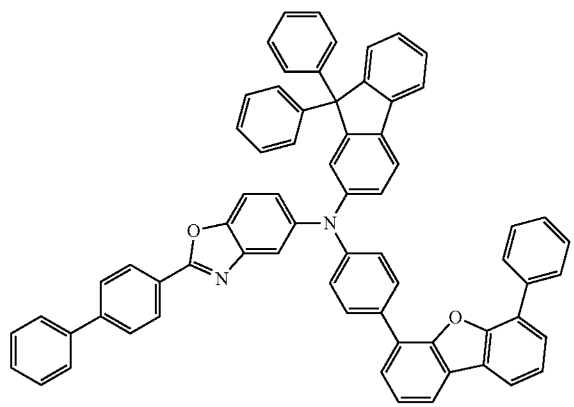
AZ77
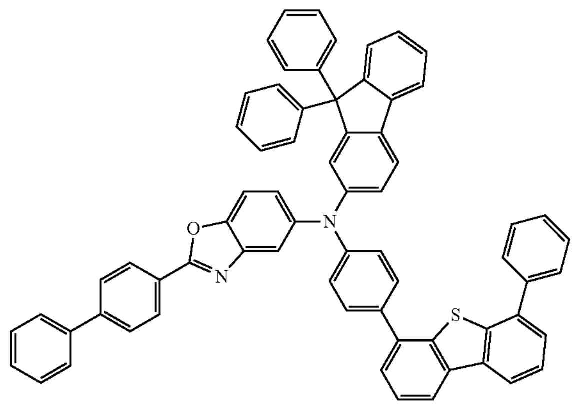
AZ78
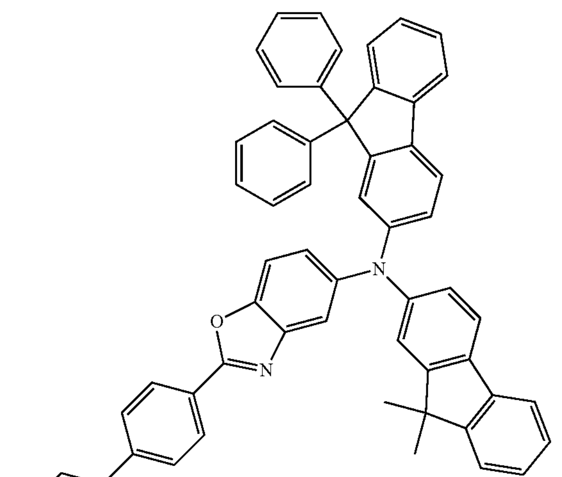

-continued
AZ79
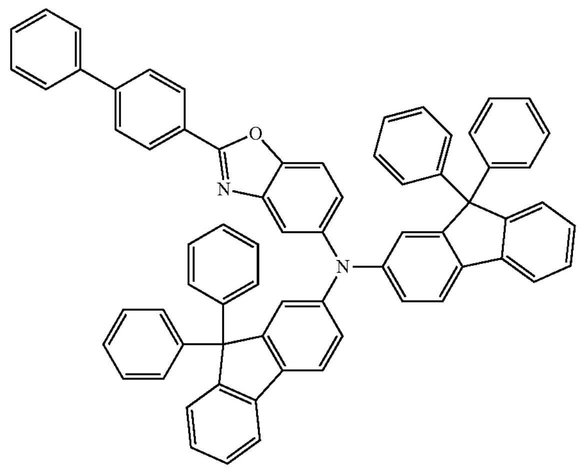
AZ80
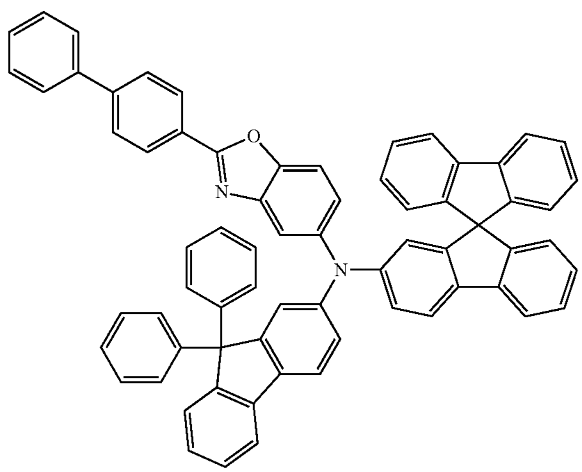
AZ81
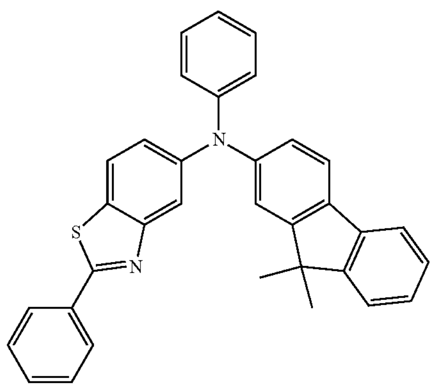
-continued
AZ82
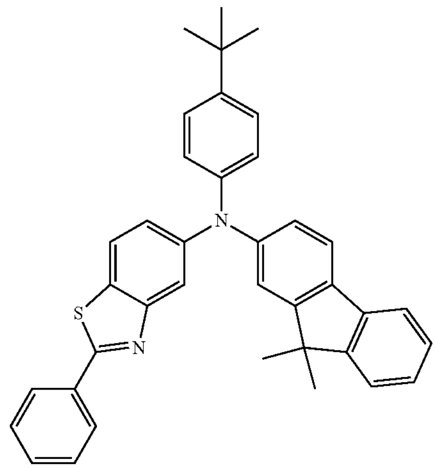
AZ83
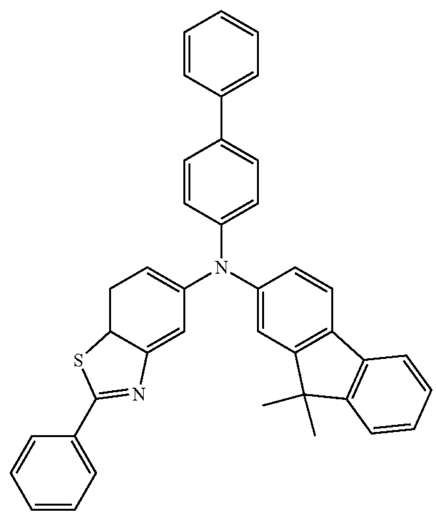
AZ84
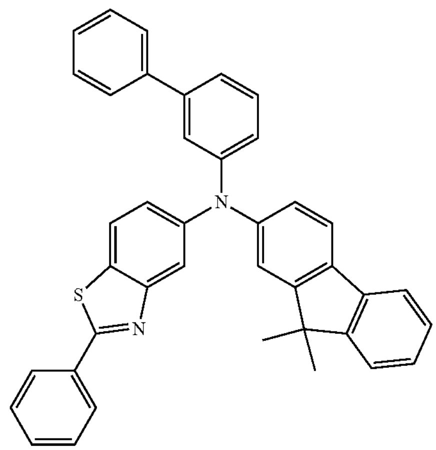

AZ85
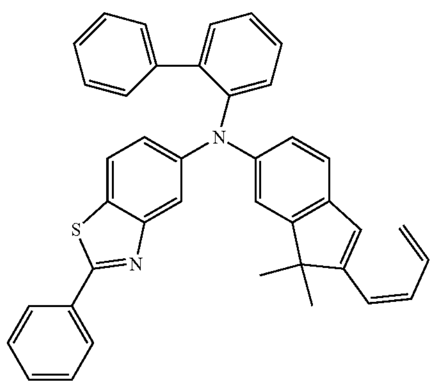
AZ86
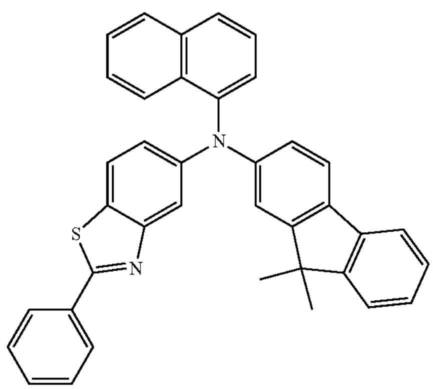
AZ87
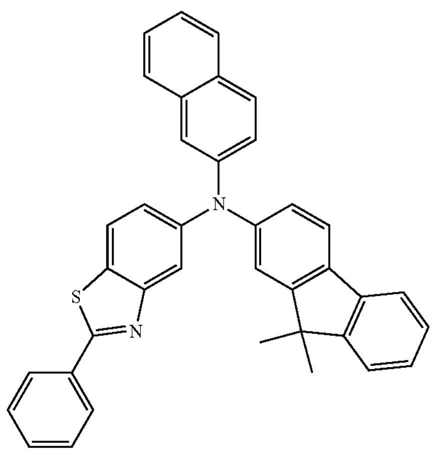
AZ88
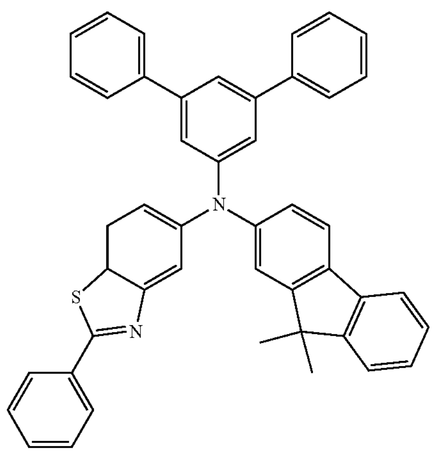
AZ89
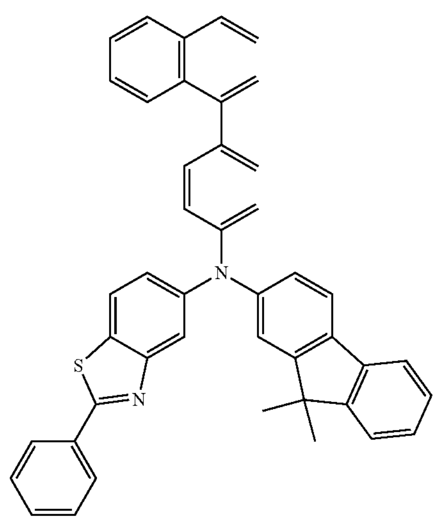
AZ90
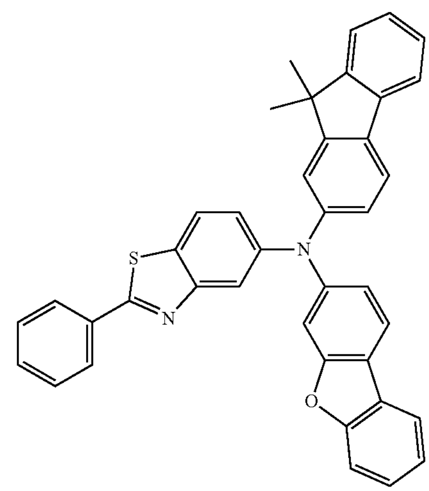
AZ91
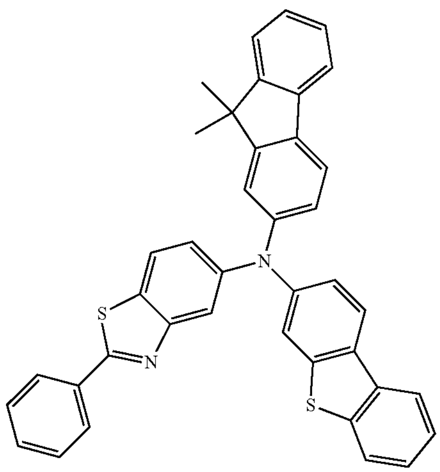

-continued
AZ92
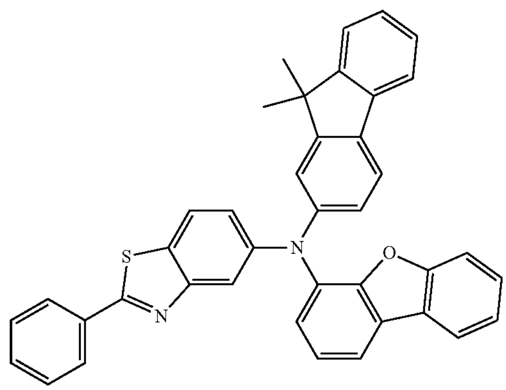
AZ93
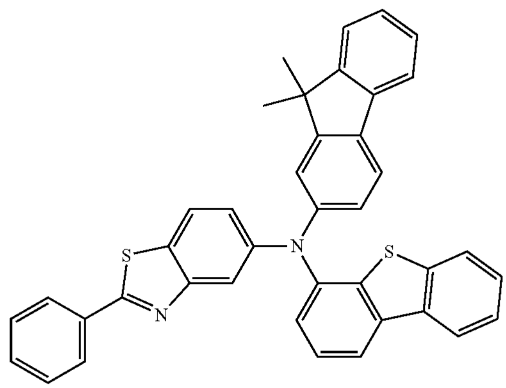
AZ94
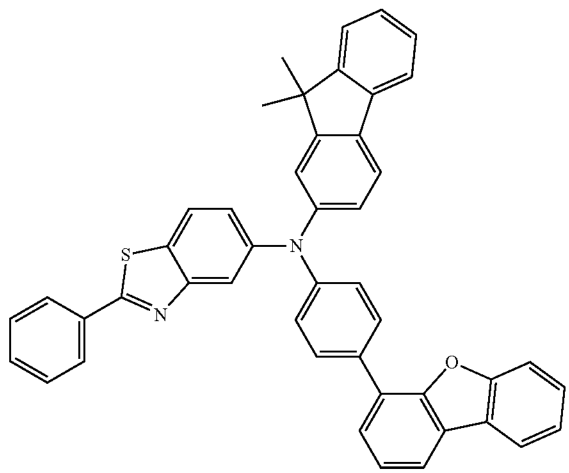
-continued
AZ95
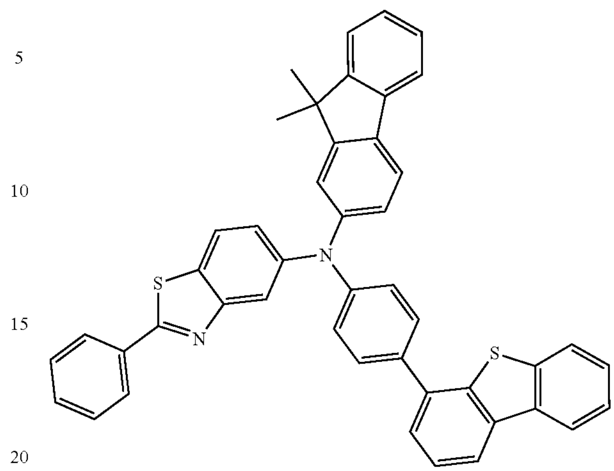
AZ96
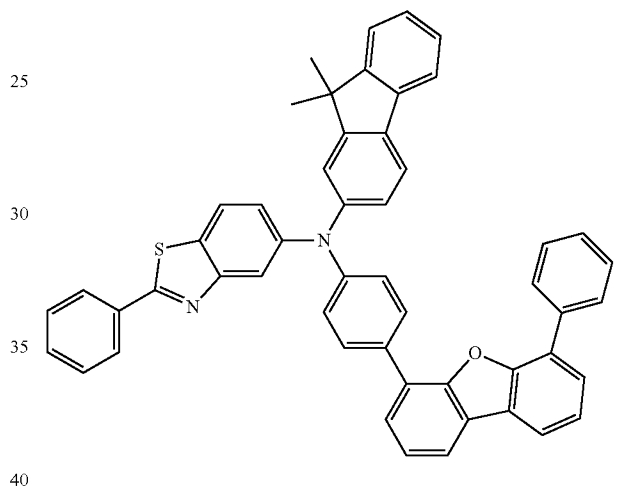
AZ97
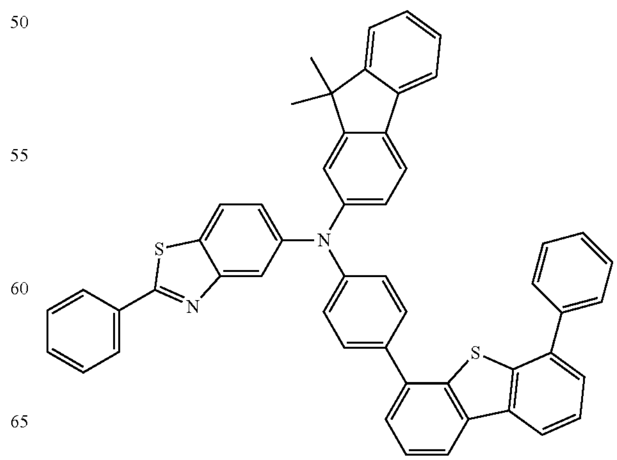

-continued
AZ98
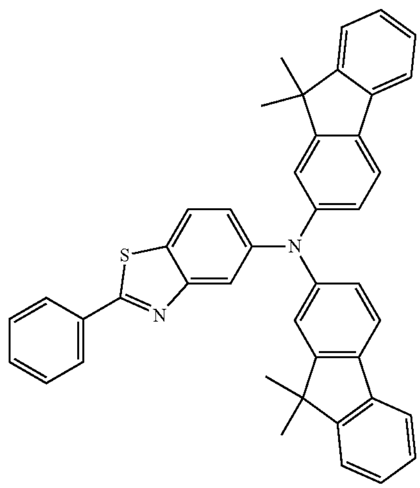
AZ99
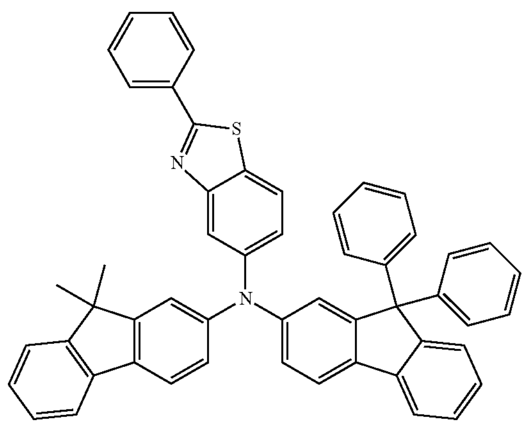
AZ100
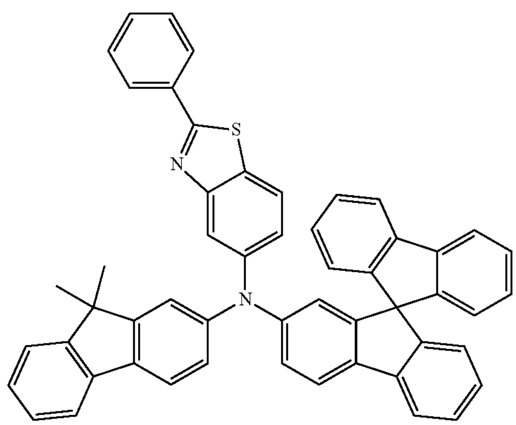
-continued
AZ101
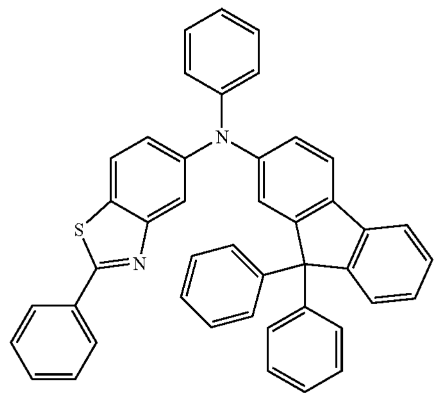
AZ102
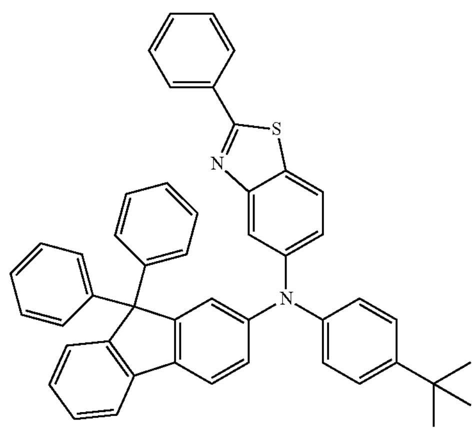
AZ103
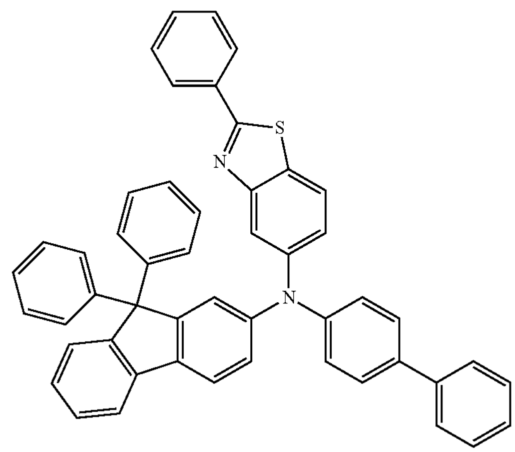

-continued
AZ104
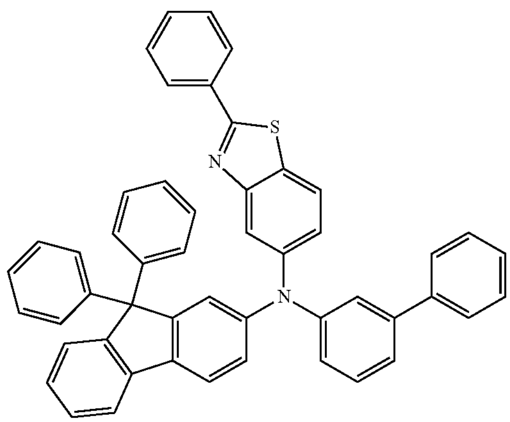
AZ105
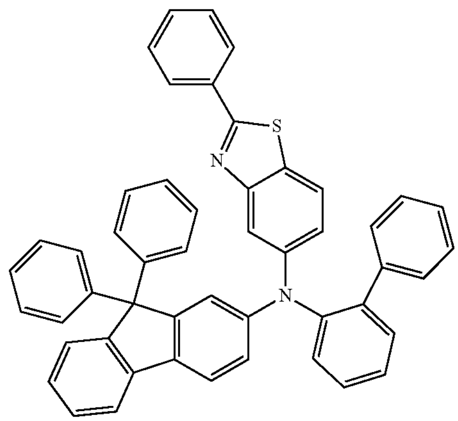
AZ106
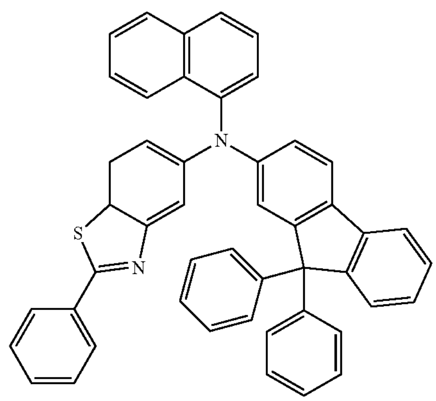
-continued
AZ107
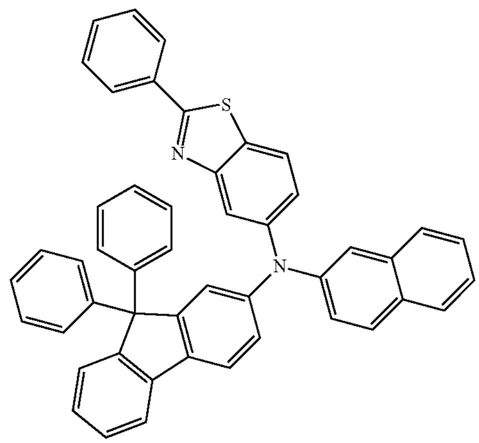
AZ108
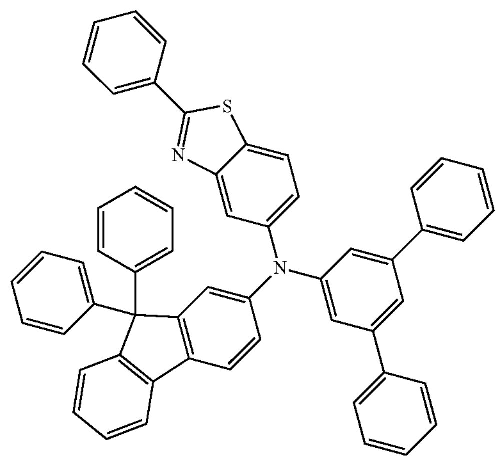
AZ109
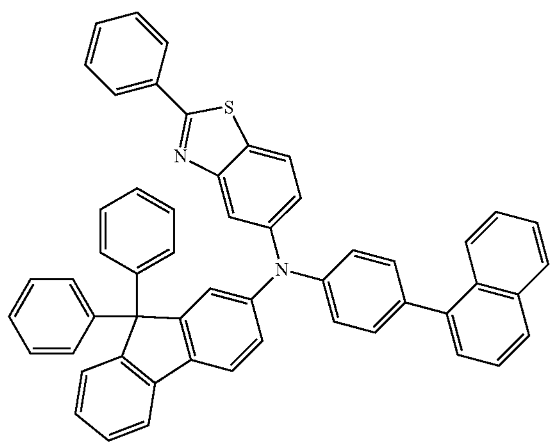

-continued
AZ110
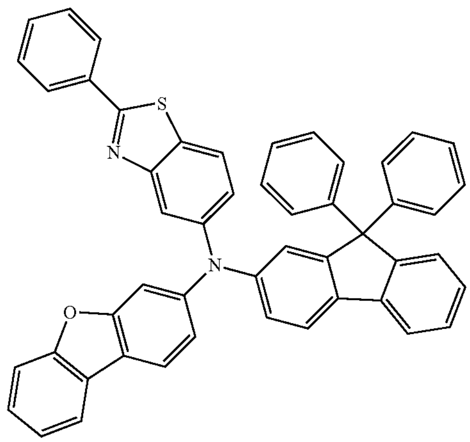
AZ111
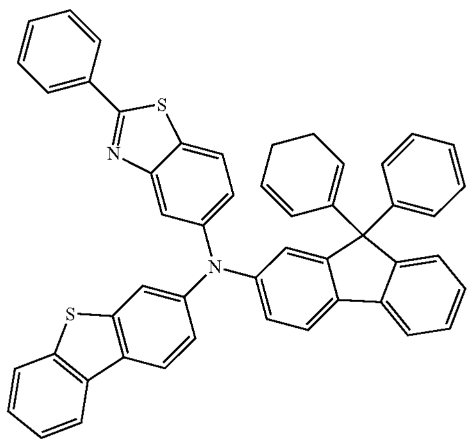
AZ112
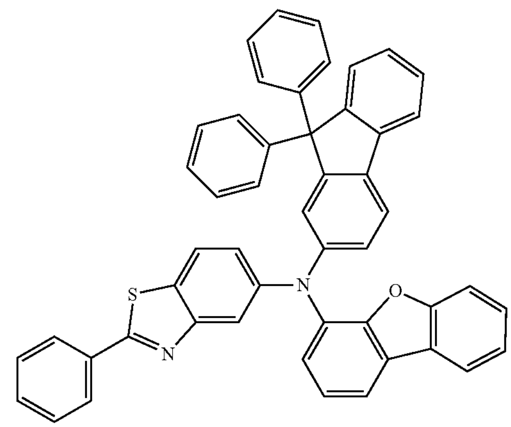
-continued
AZ113
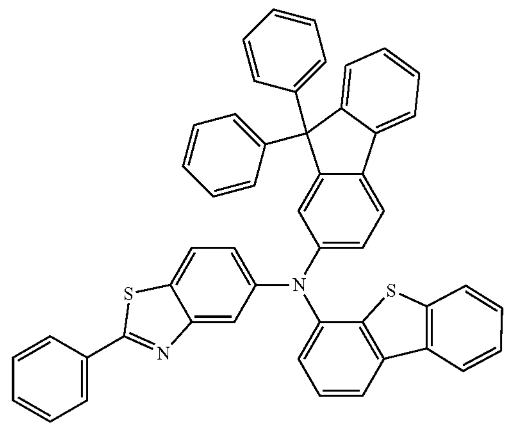
AZ114
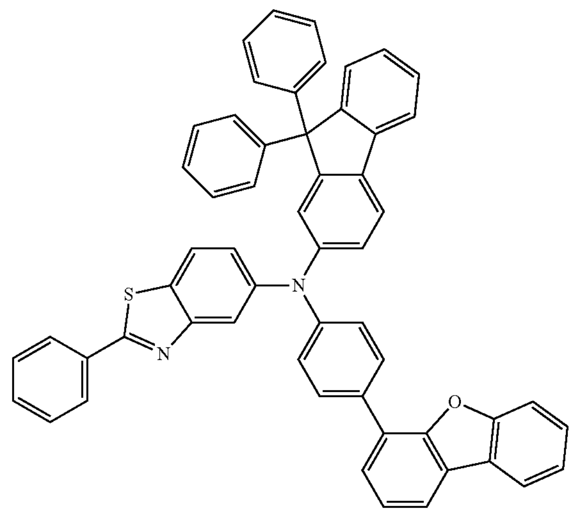
AZ115
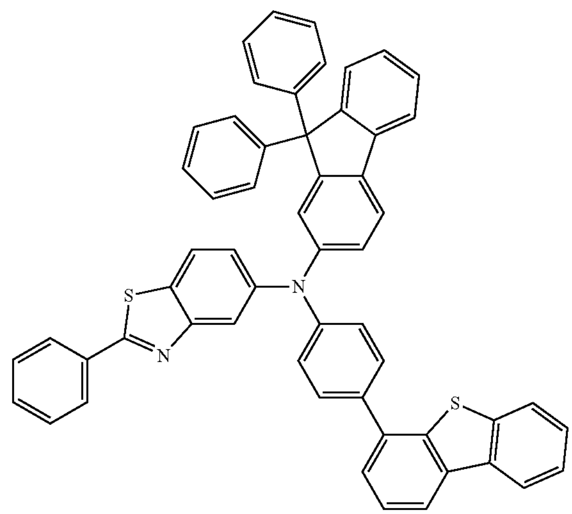

-continued
AZ116
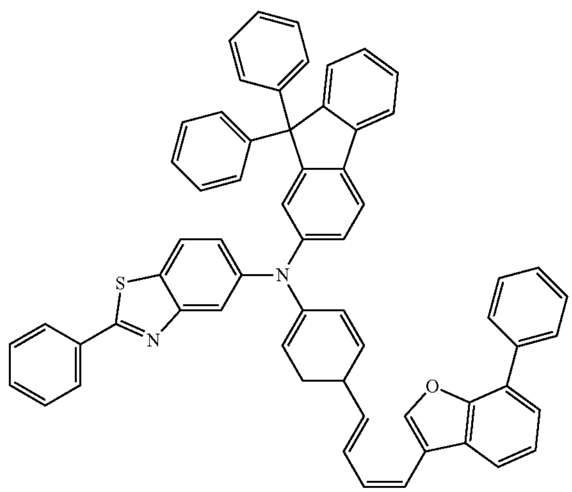
AZ117
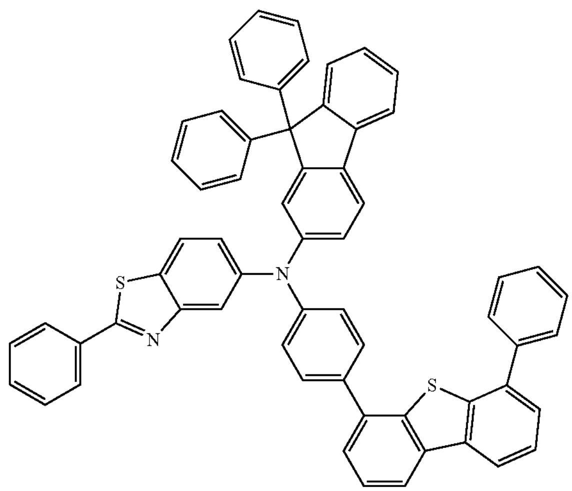
AZ118
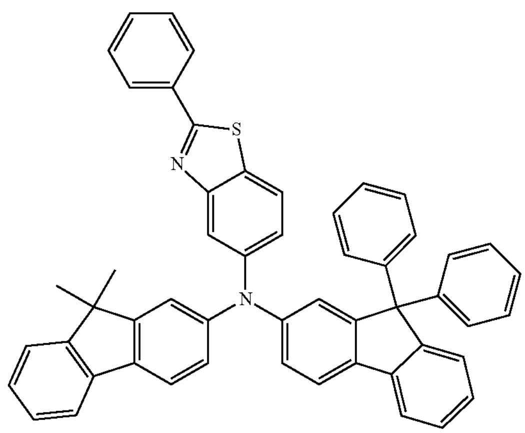
-continued
AZ119
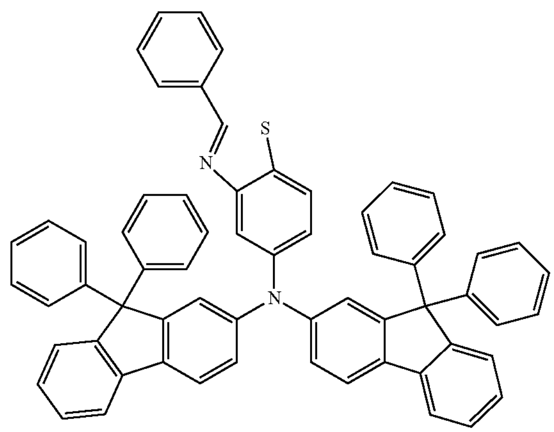
AZ120
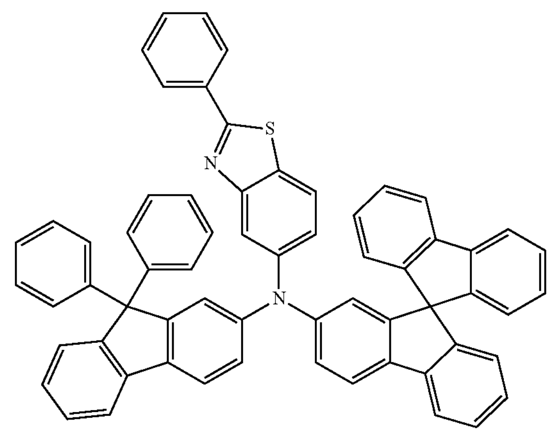
AZ121
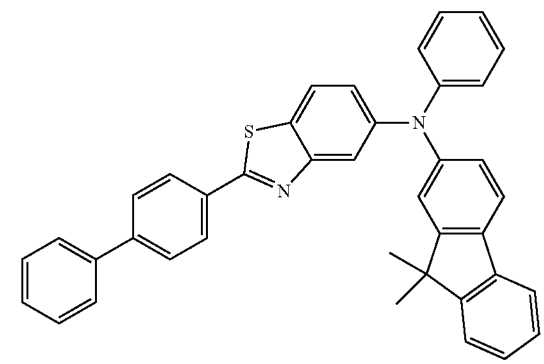

-continued
AZ122
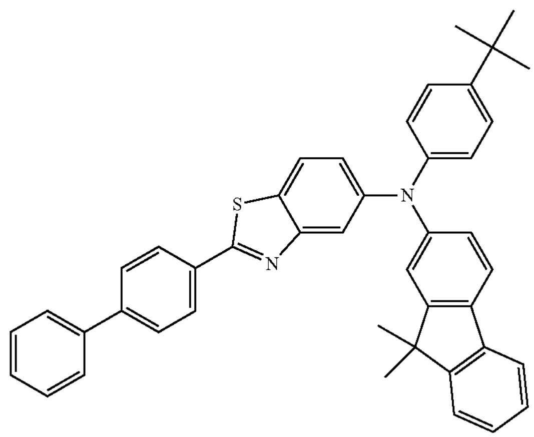
AZ123
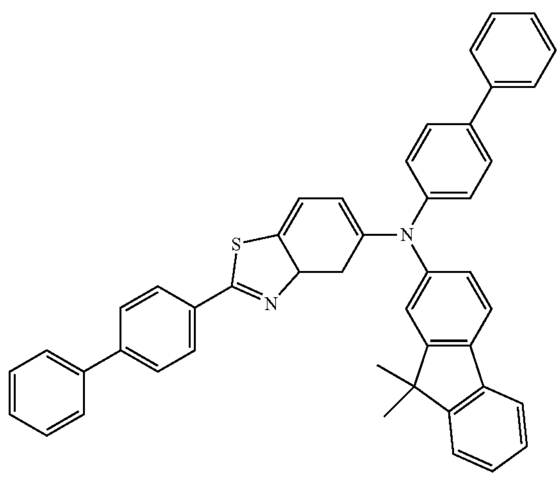
AZ124
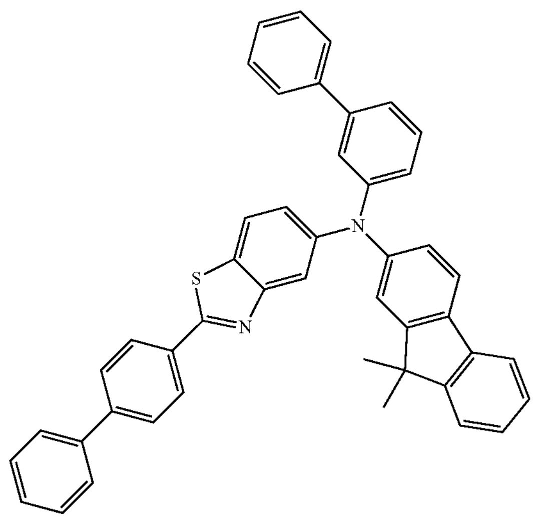
-continued
AZ125
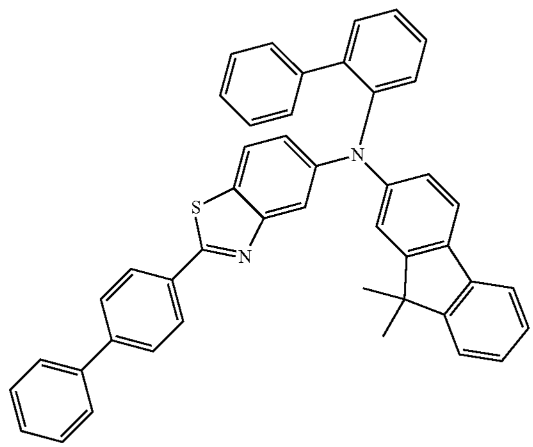
AZ126
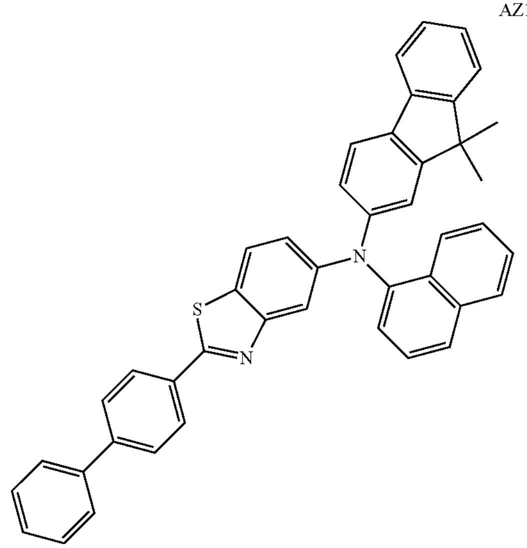
AZ127
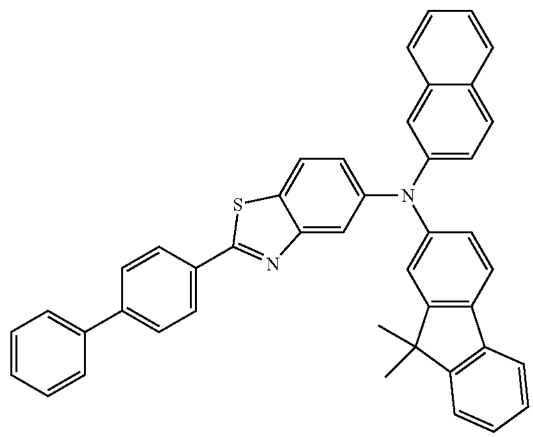

-continued
AZ128
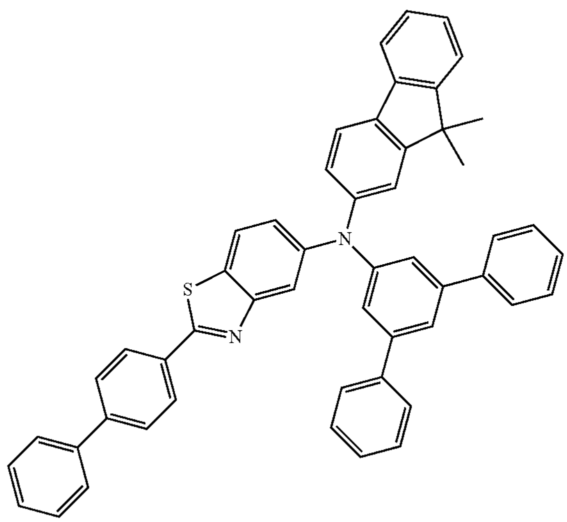
AZ129
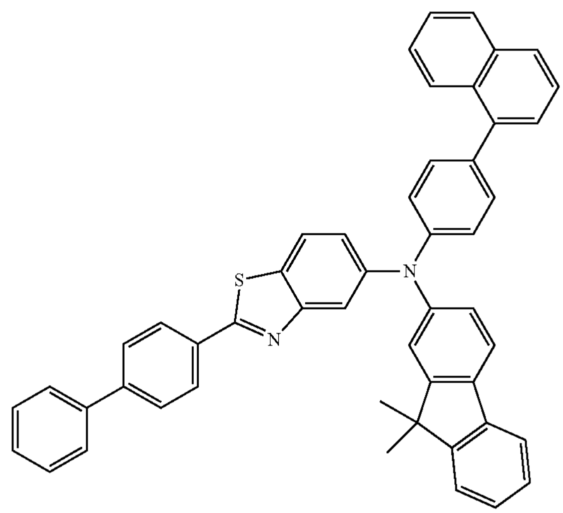
AZ130
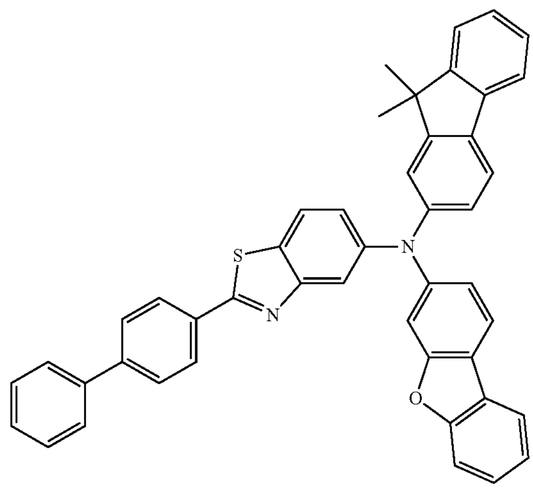
-continued
AZ131
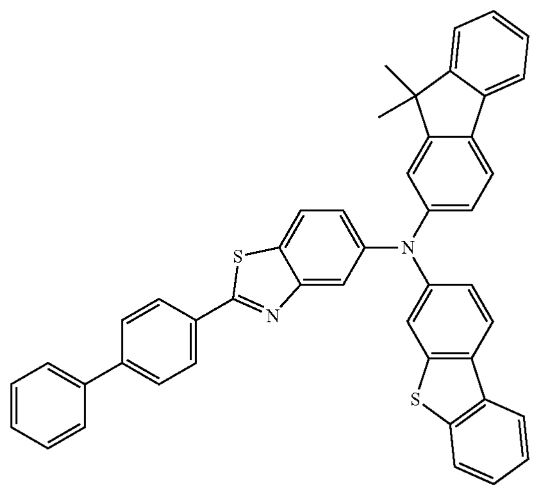
AZ132
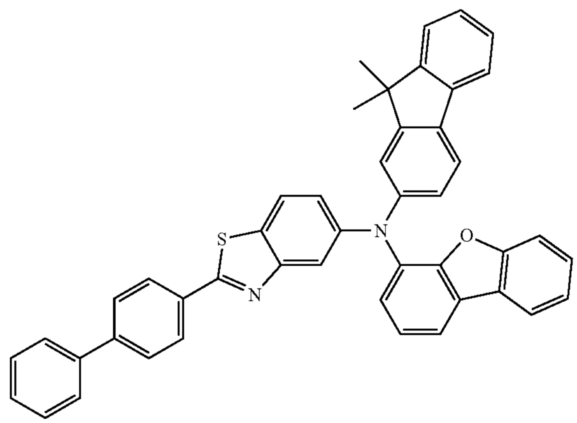
AZ133
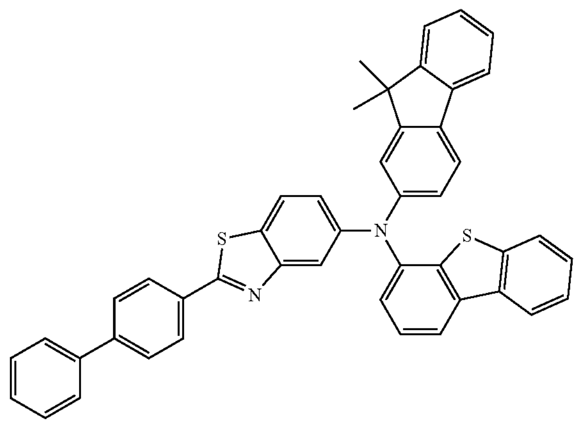

-continued
AZ134
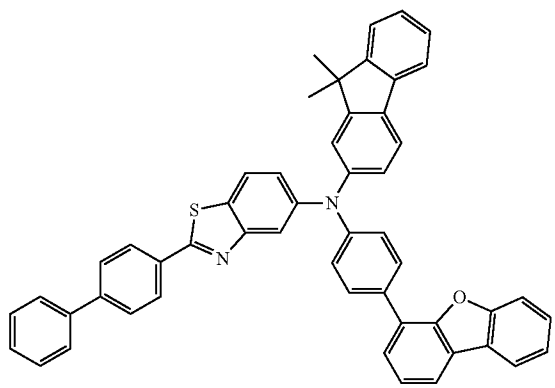
AZ135
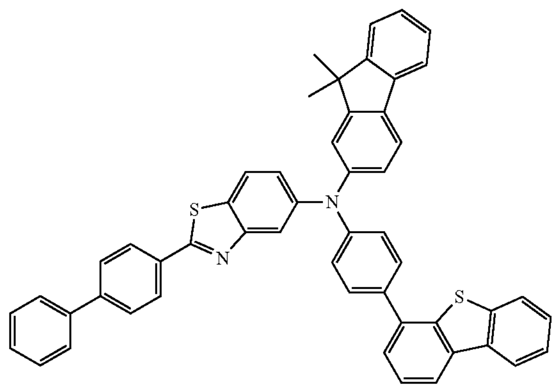
AZ136
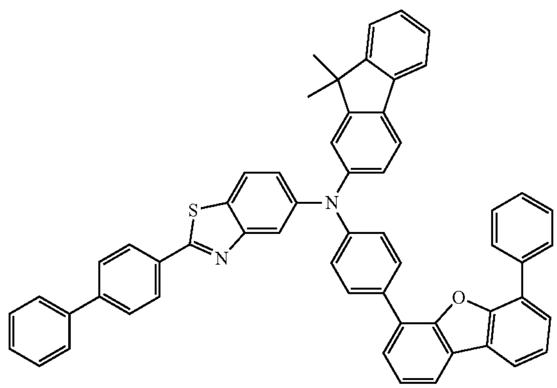
AZ137
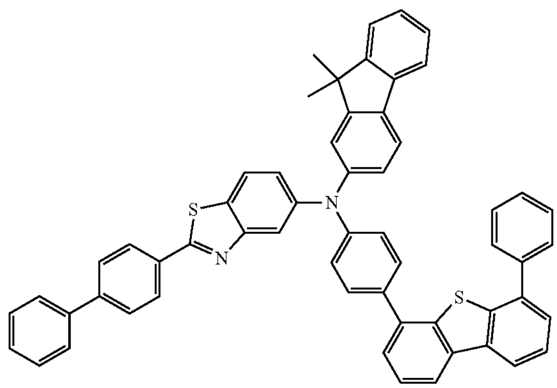
-continued
AZ138
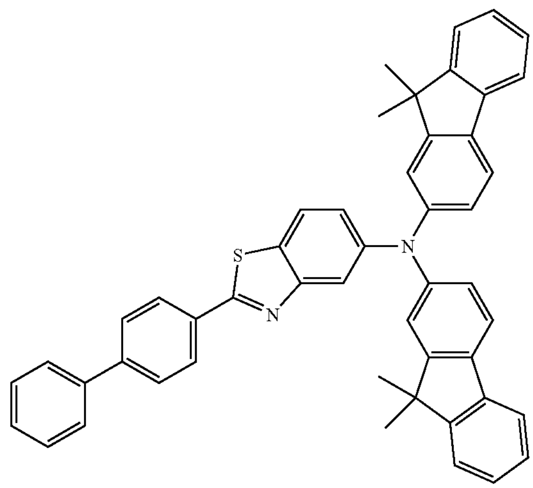
AZ139
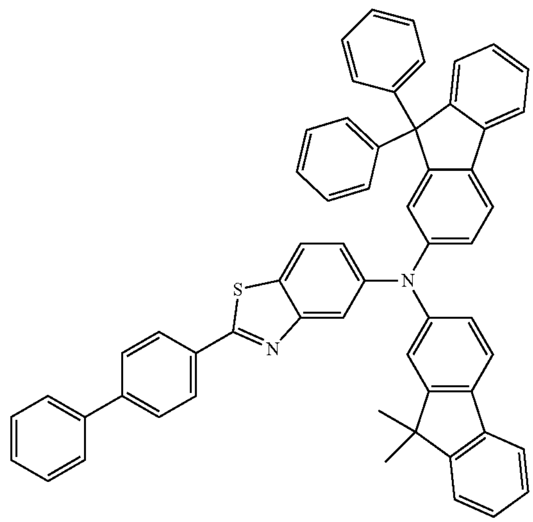
AZ140
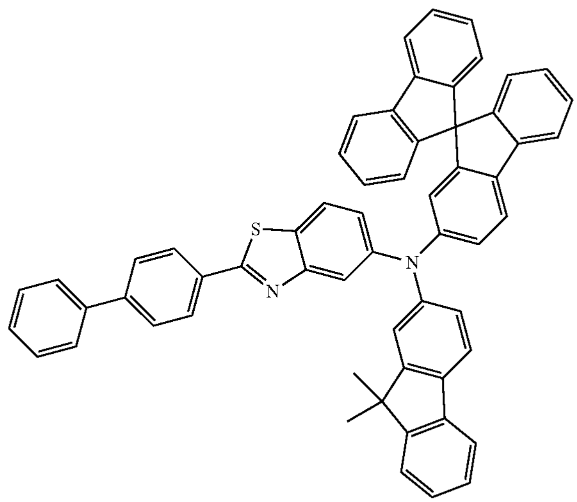

-continued
AZ141
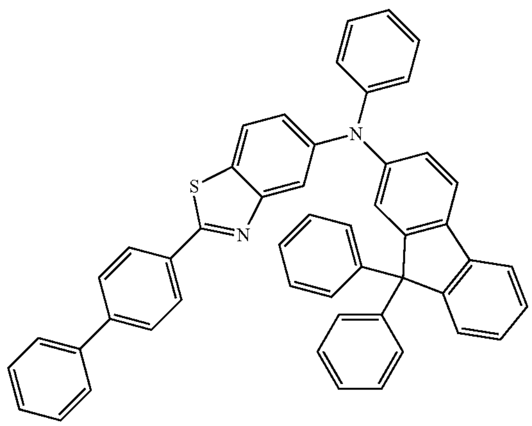
AZ142
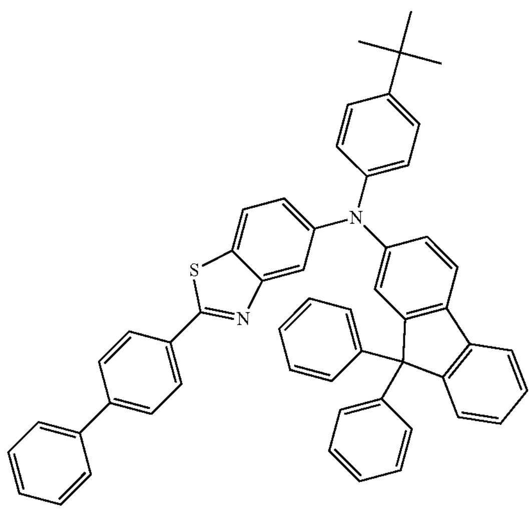
AZ143
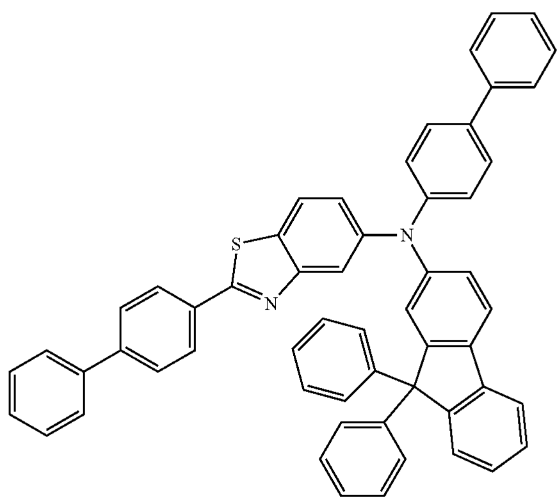
-continued
AZ144
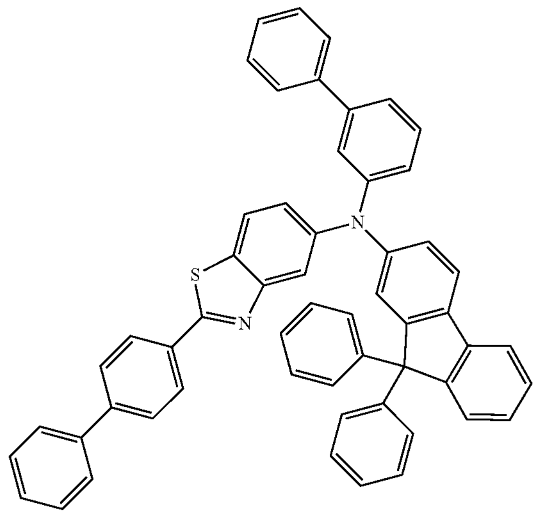
AZ145
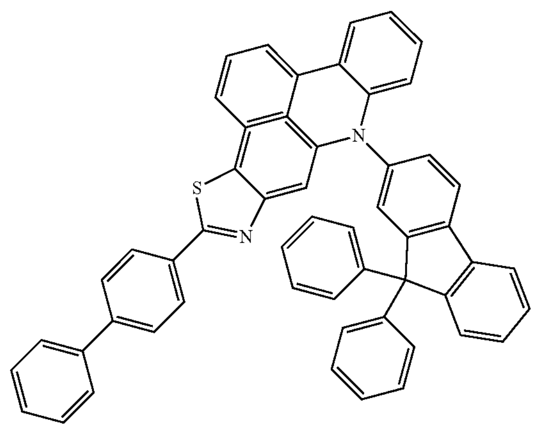
AZ146
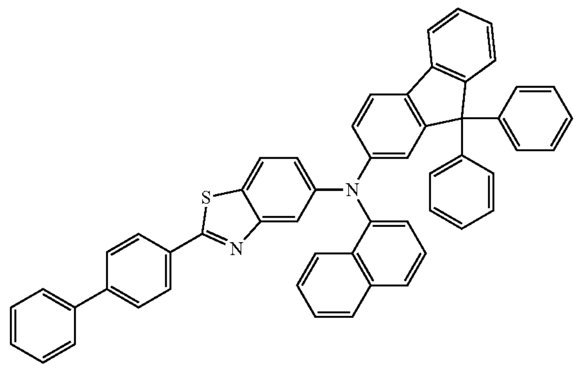

AZ147
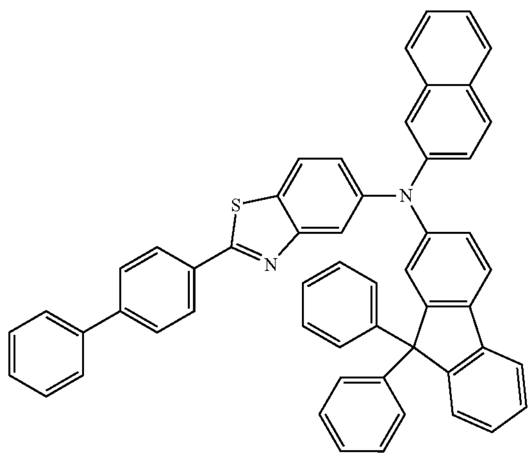
AZ148
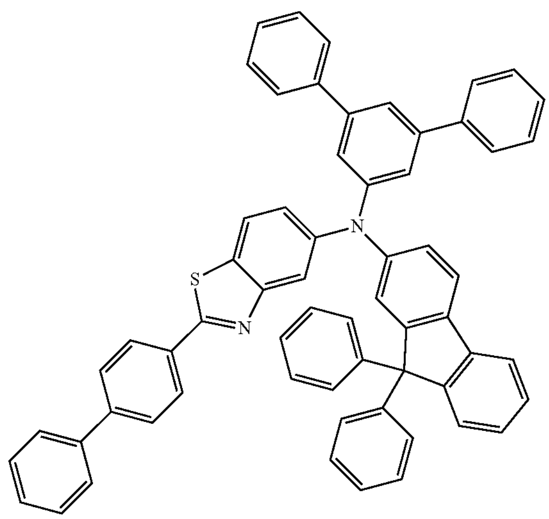
AZ149
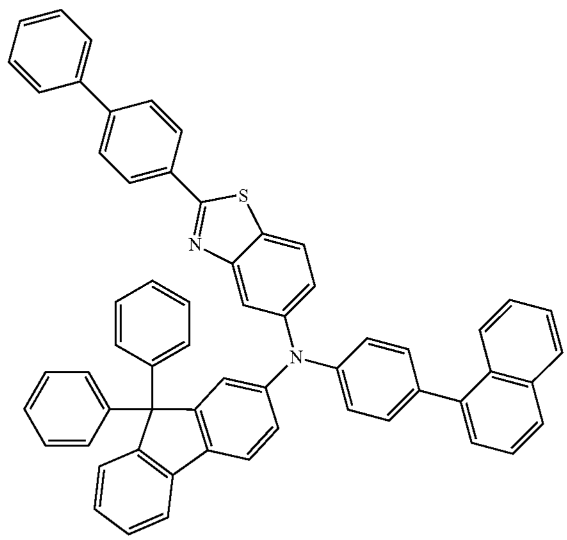
AZ150
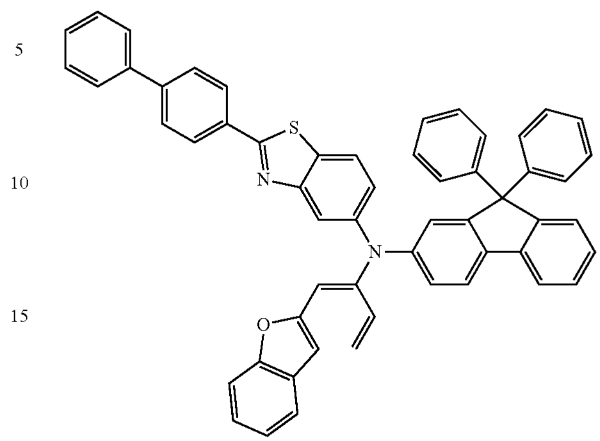
AZ151
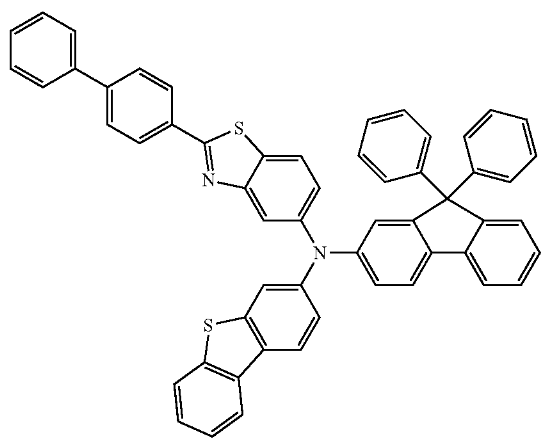
AZ152
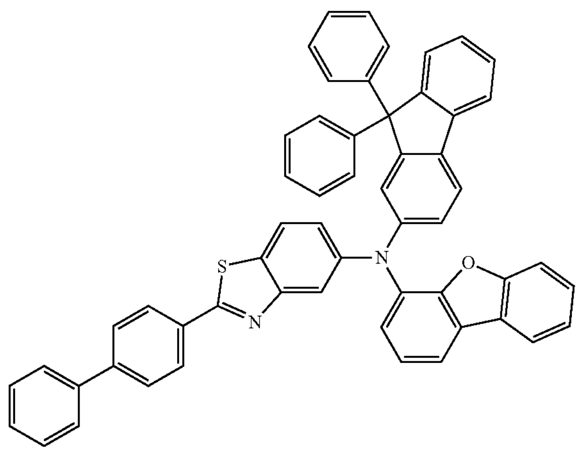

-continued
AZ153
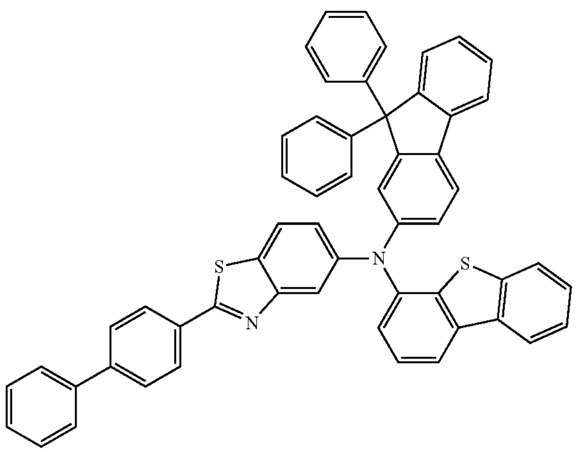
AZ154
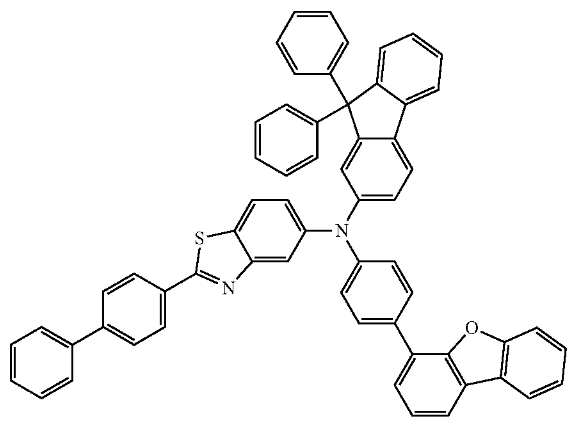
AZ155
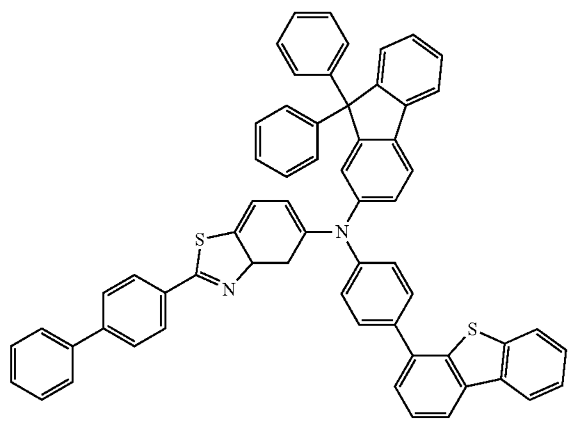
-continued
AZ156
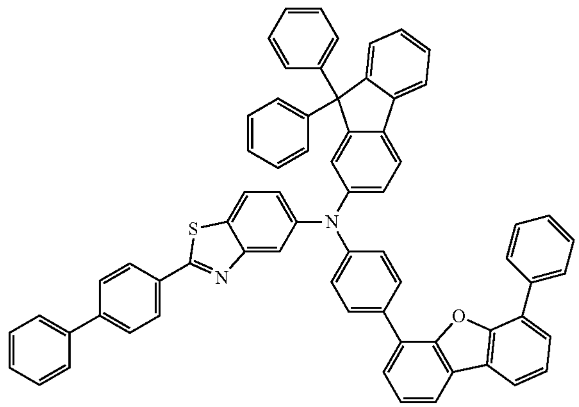
AZ157
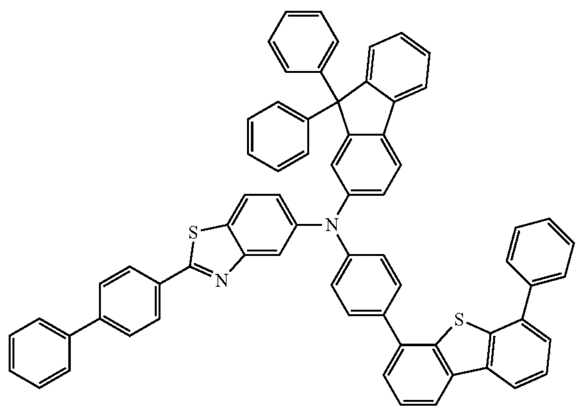
AZ158
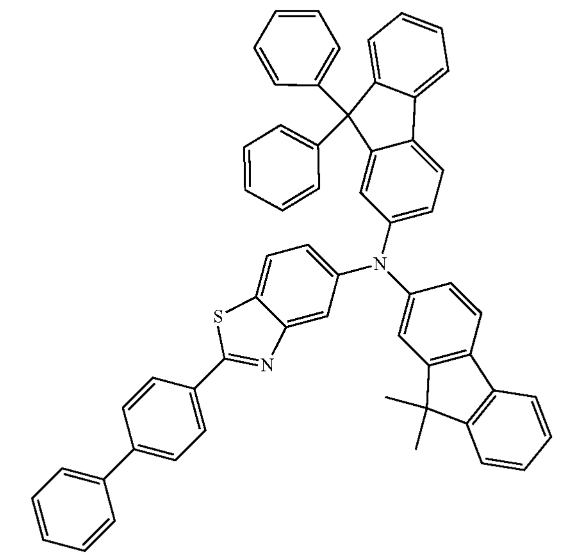

-continued
AZ159
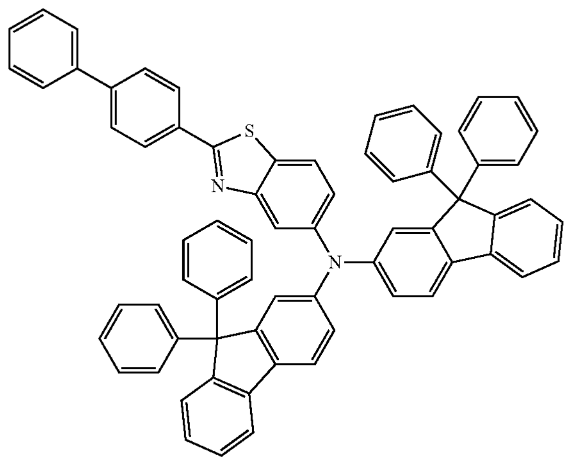
AZ160
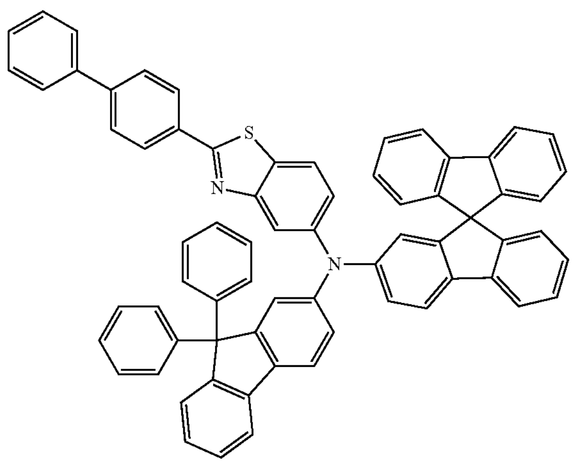
AK1
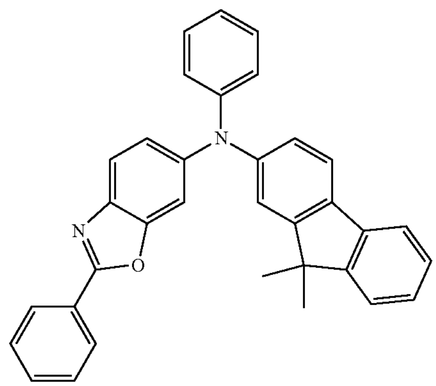
-continued
AK2
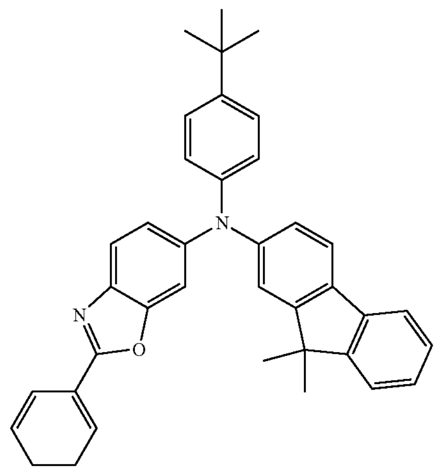
AK3
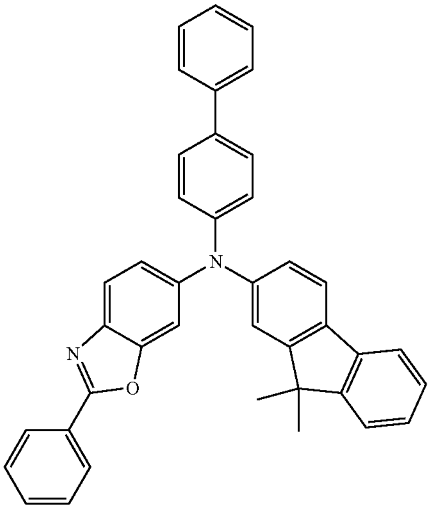
AK4
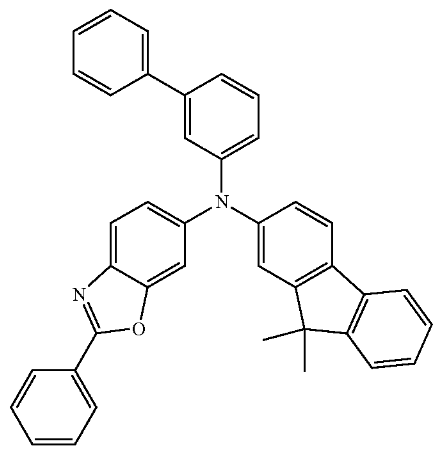

-continued
AK5
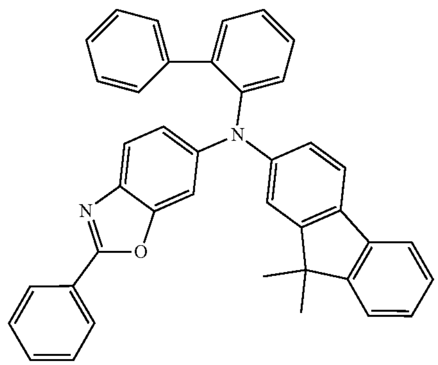
AK6
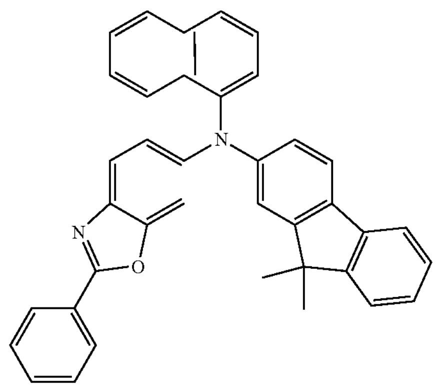
AK7
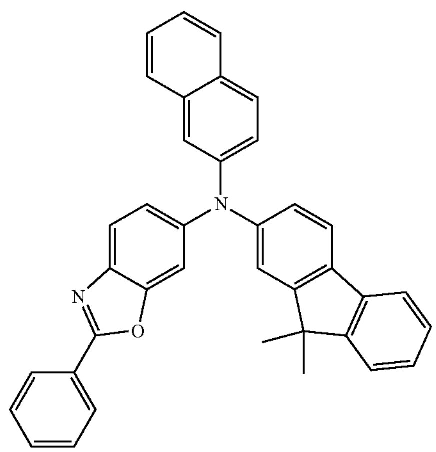
AK8
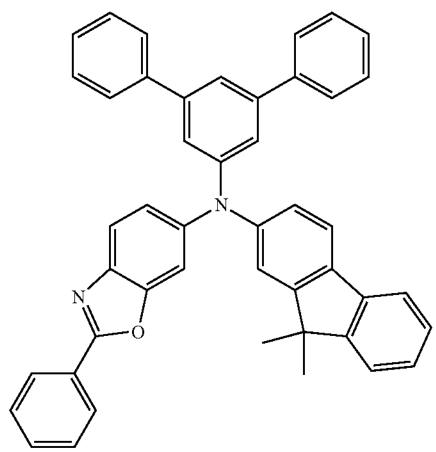
-continued
AK9
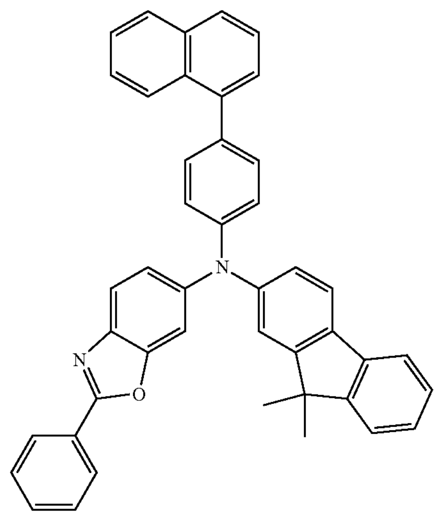
AK10
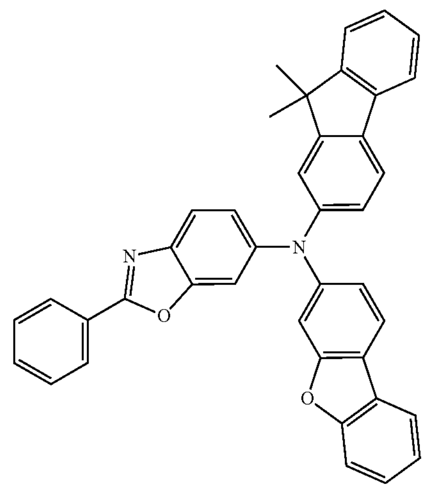
AK11
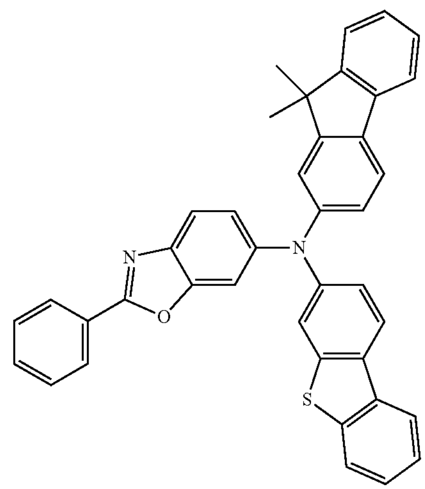

-continued
AK12
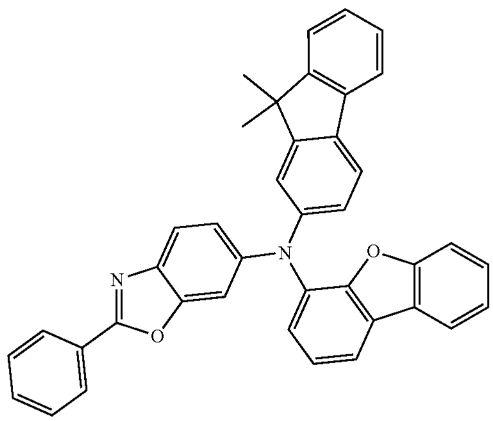
AK13
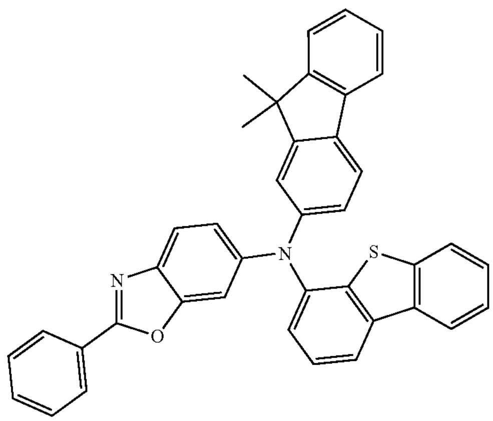
AK14
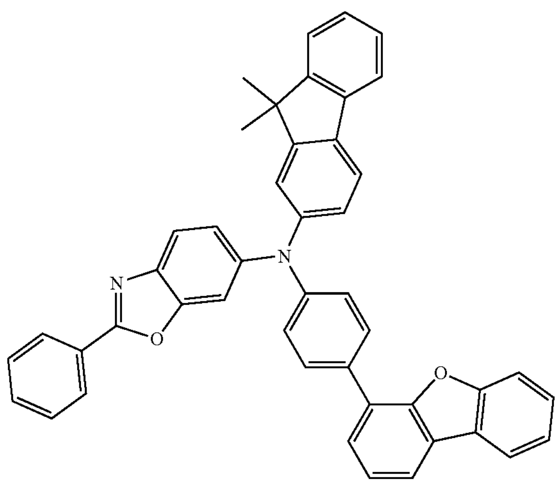
-continued
AK15
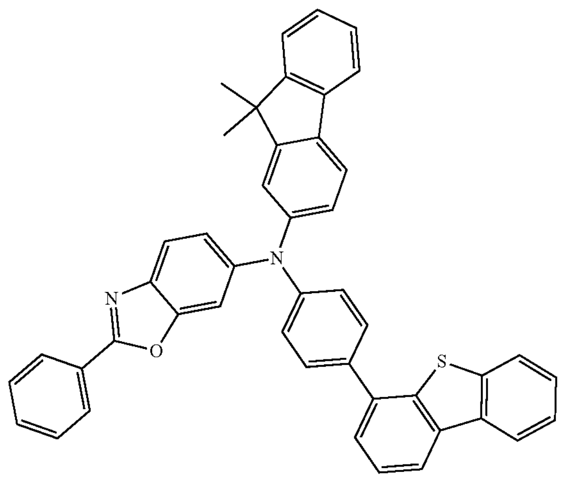
AK16
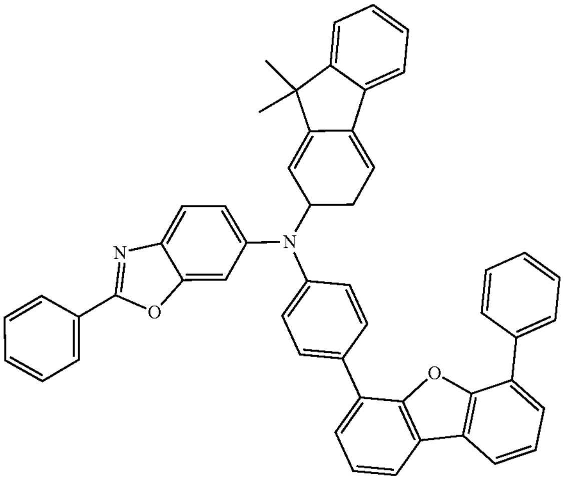
AK17
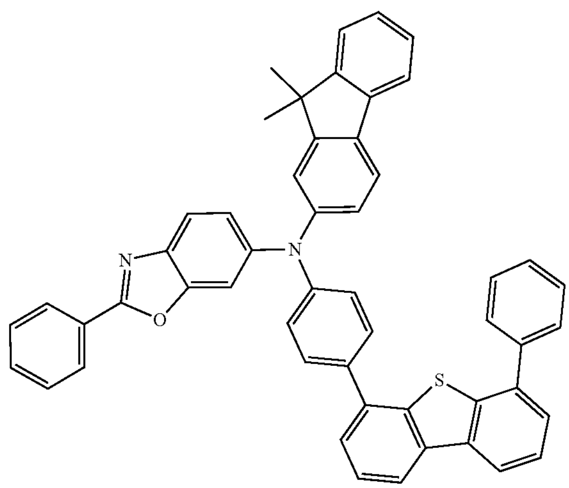

-continued
AK18
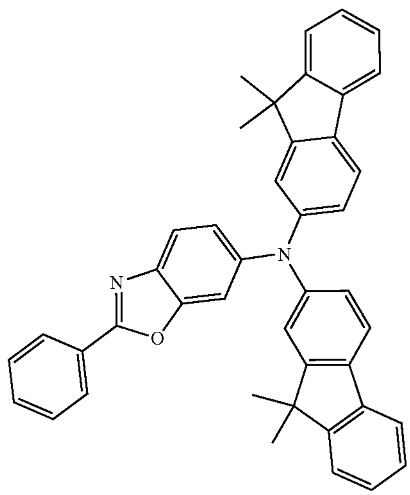
AK19
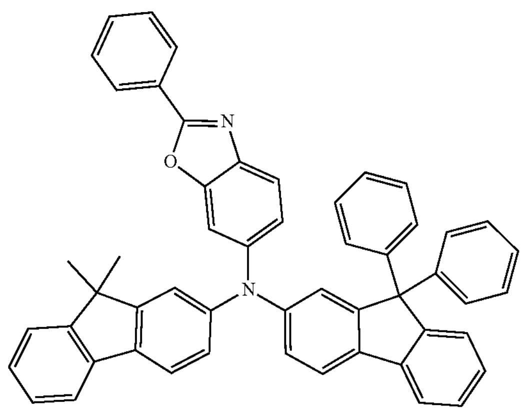
AK20
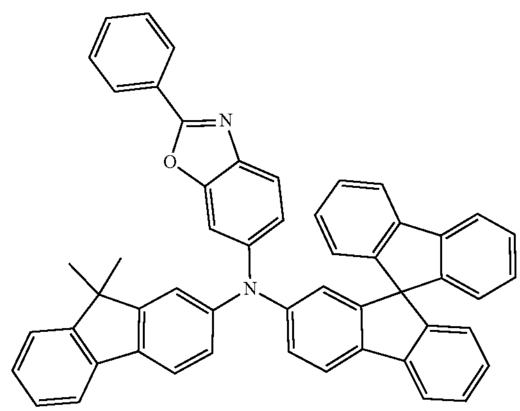
-continued
AK21
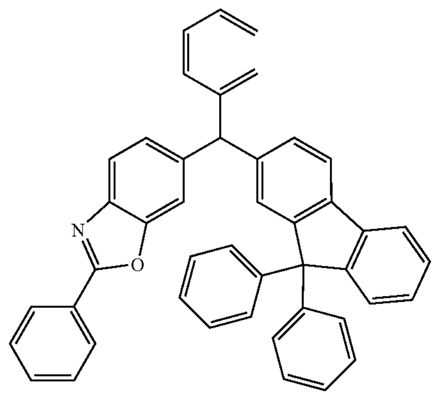
AK22
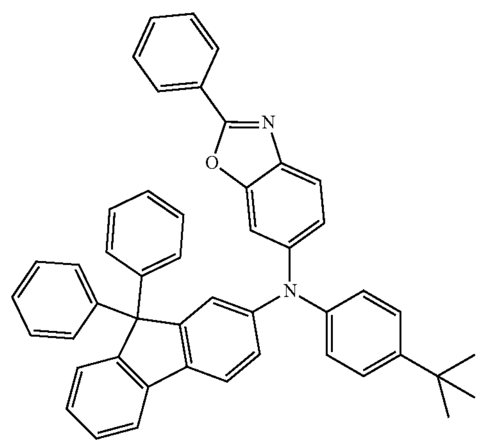
AK23
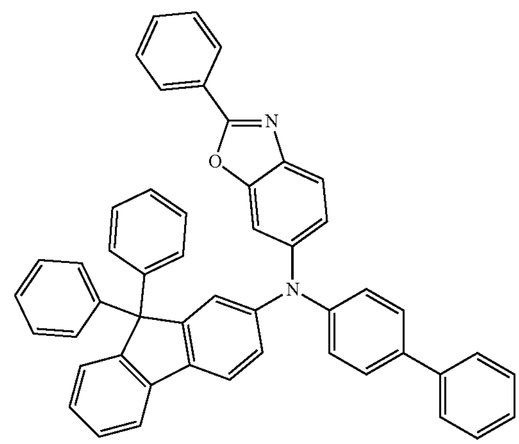

-continued
AK24
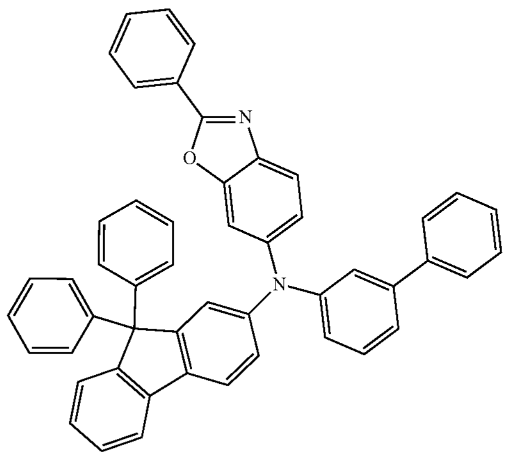
AK25
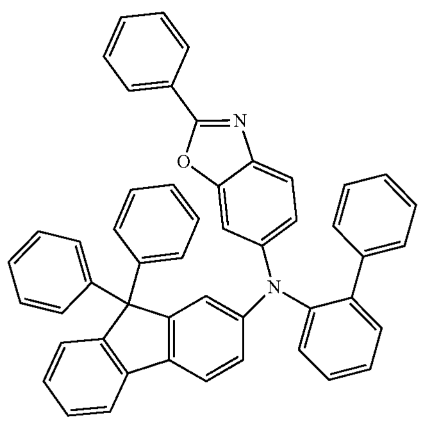
AK26
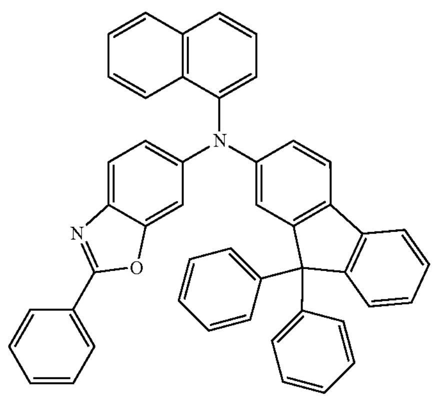
-continued
AK27
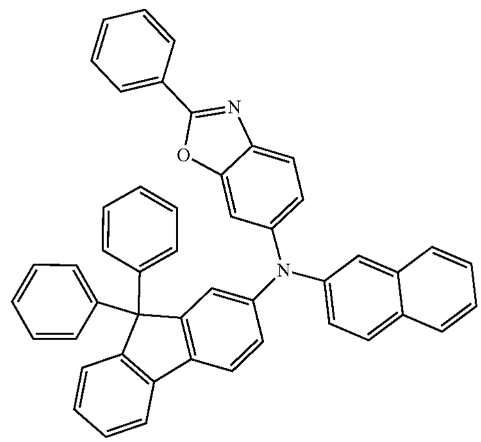
AK28
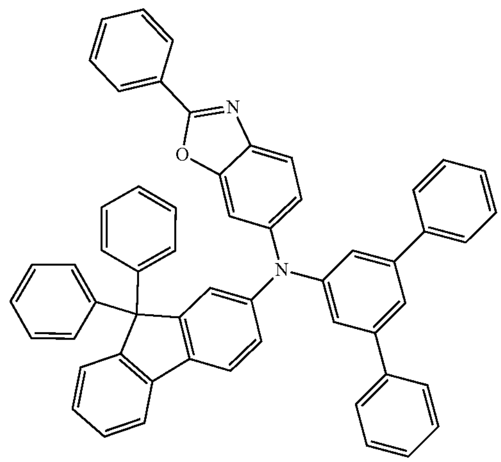
AK29
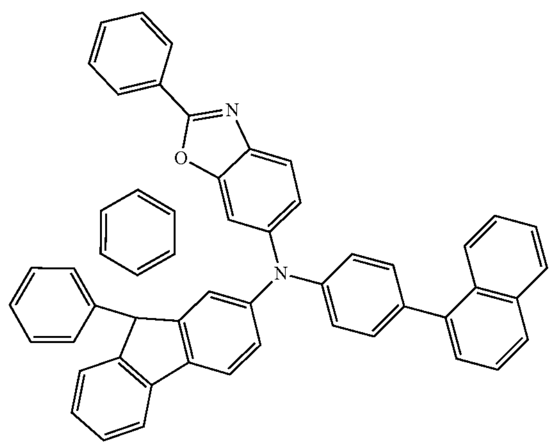

-continued
AK30
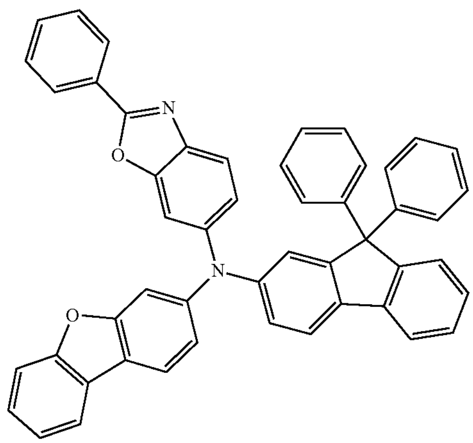
AK31
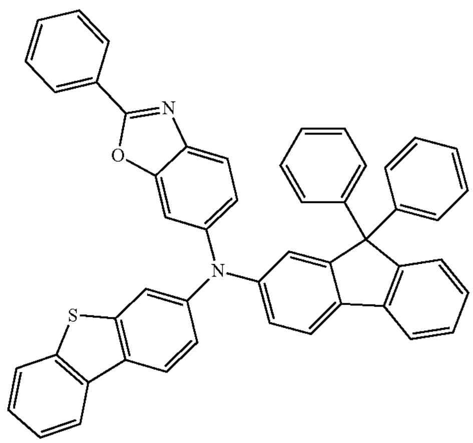
AK32
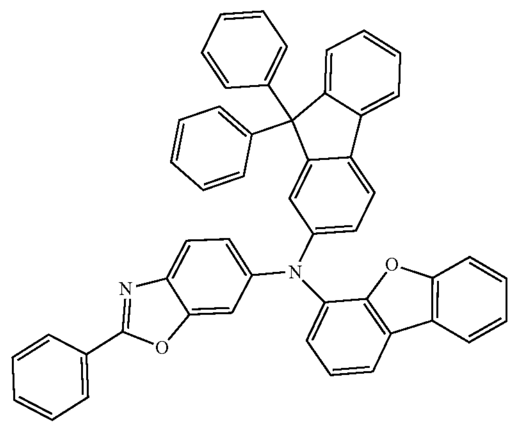
-continued
AK33
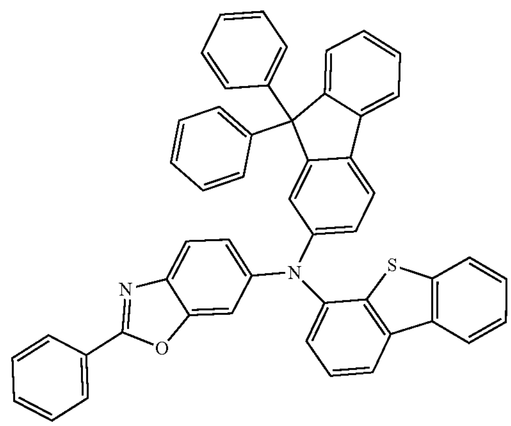
AK34
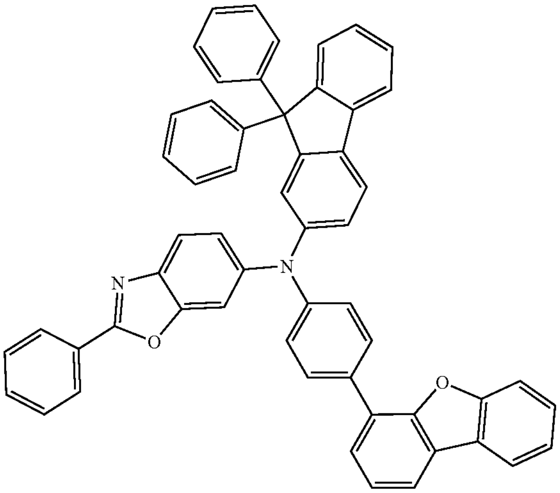
AK35
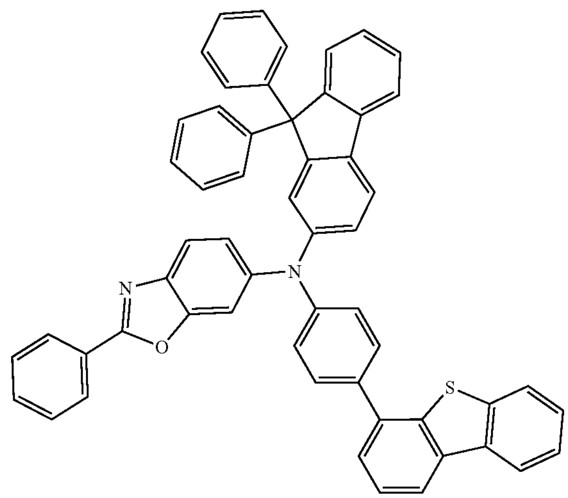

-continued
AK36
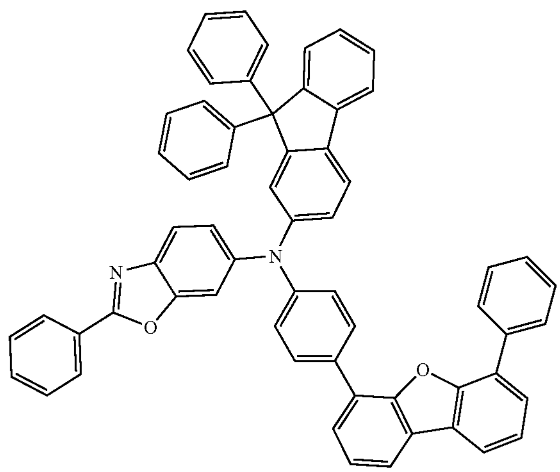
AK37
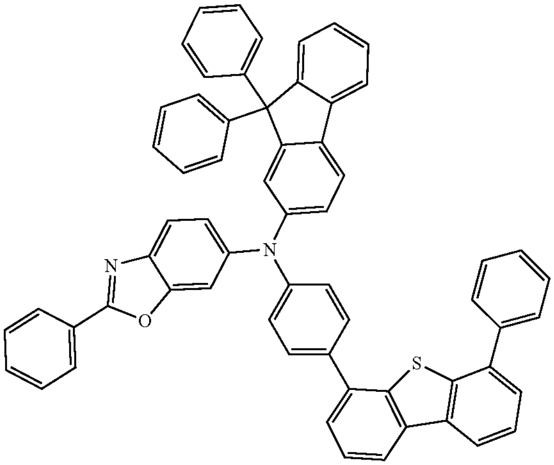
AK38
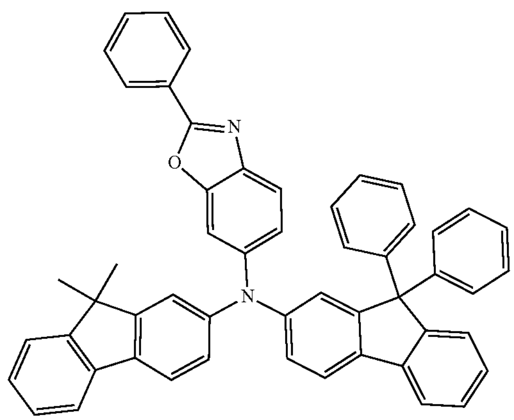
-continued
AK39
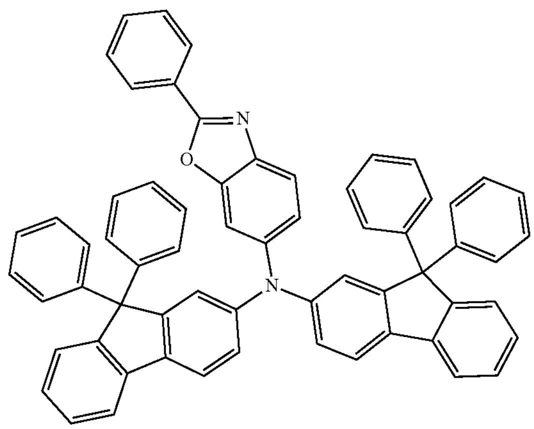
AK40
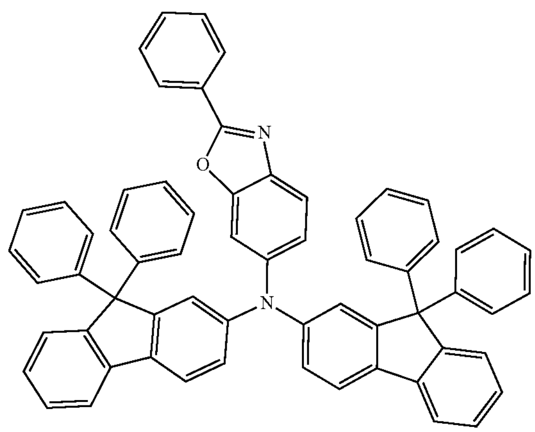
AK41
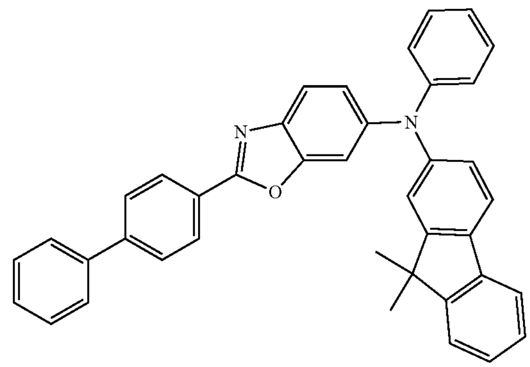

-continued
AK42
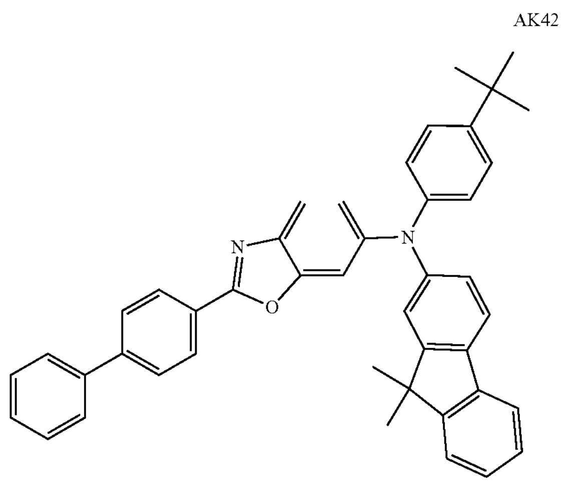
AK43
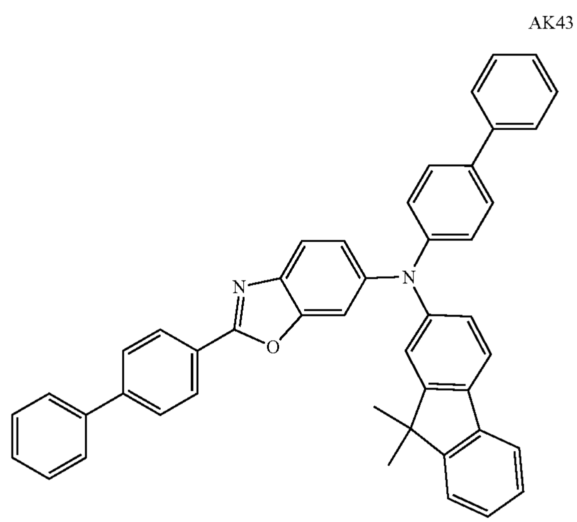
AK44
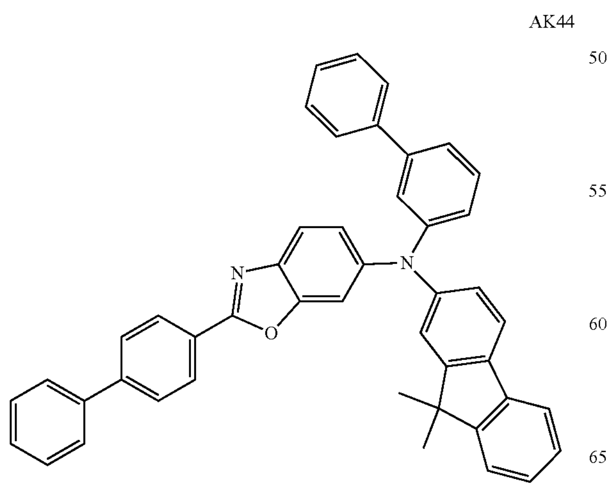
-continued
AK45
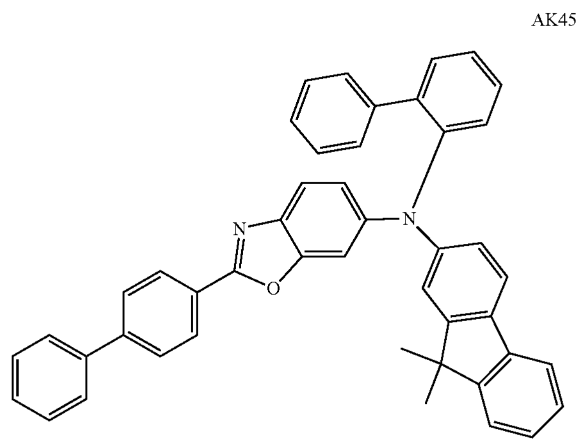
AK46
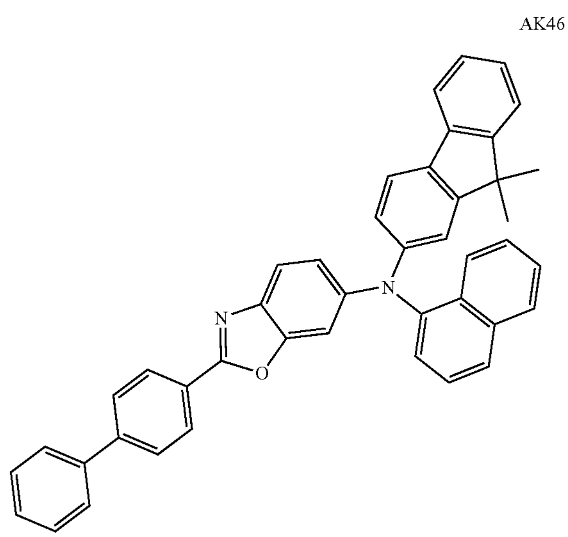
AK47
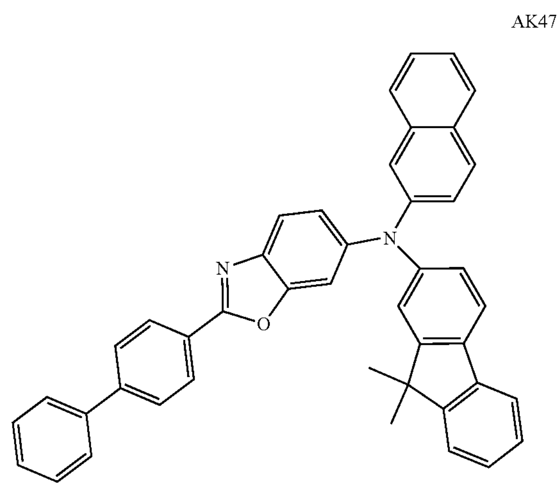

-continued
AK48
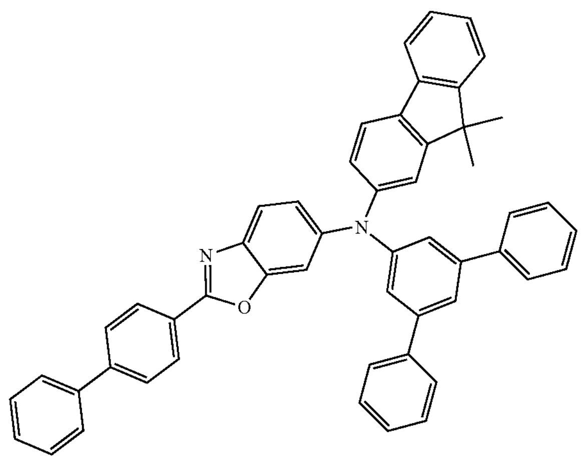
AK49
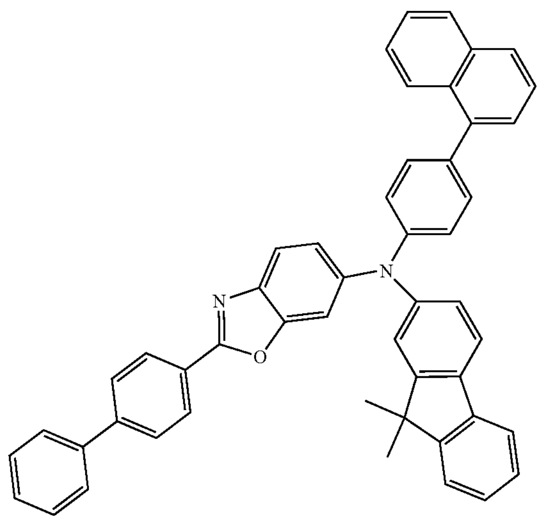
AK50
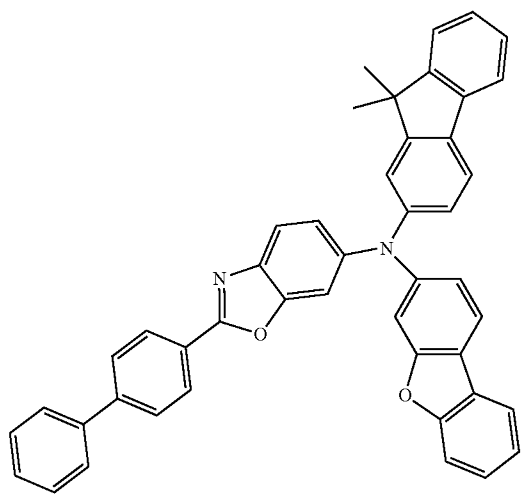
-continued
AK51
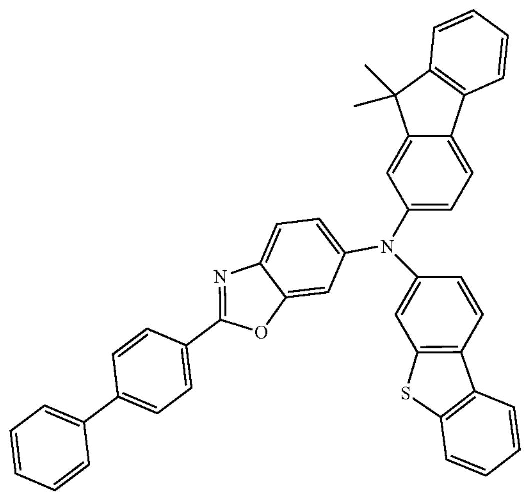
AK52
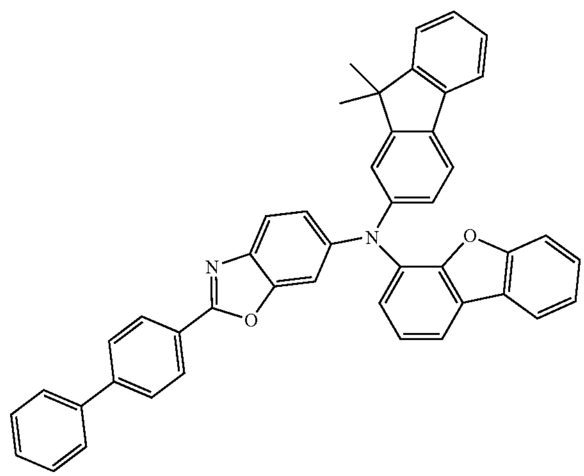
AK53
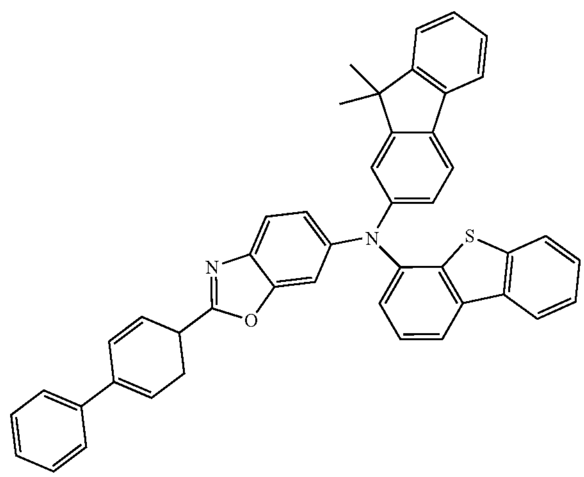

AK54
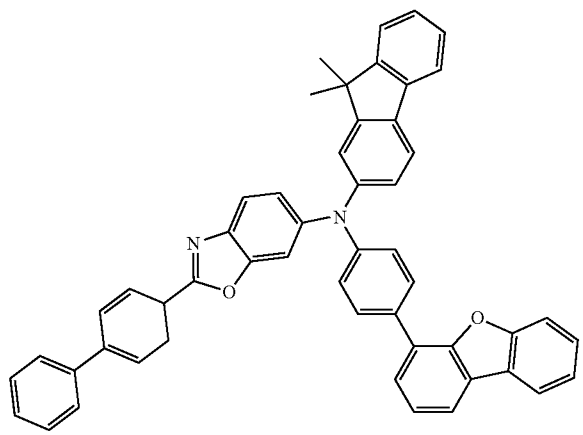
AK55
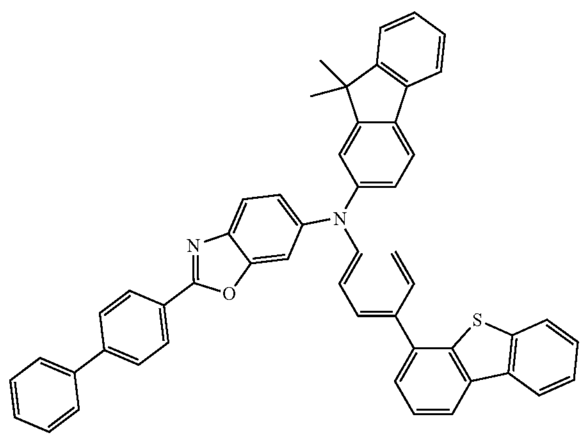
AK56
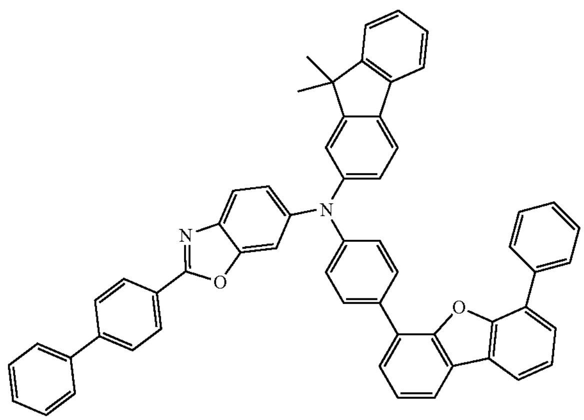
AK57
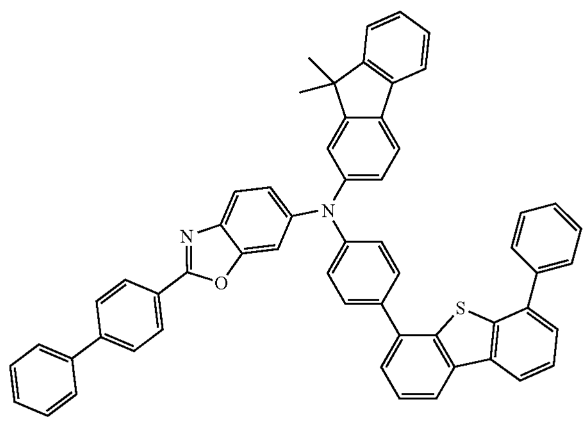
AK58
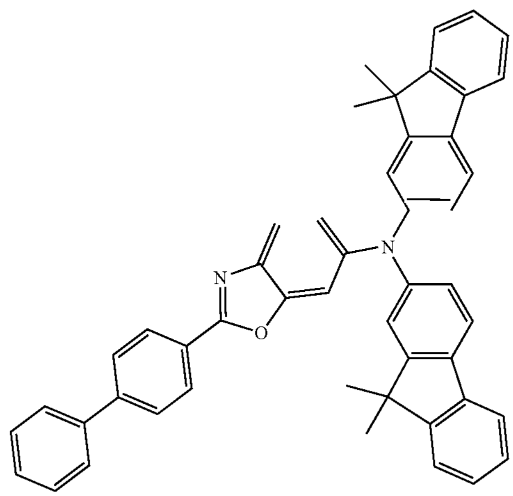
AK59
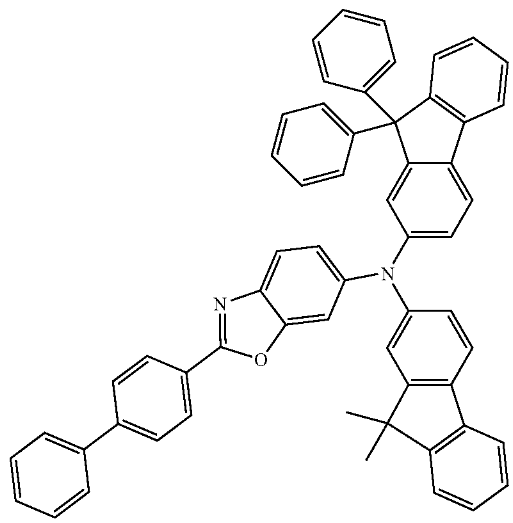

-continued
AK60
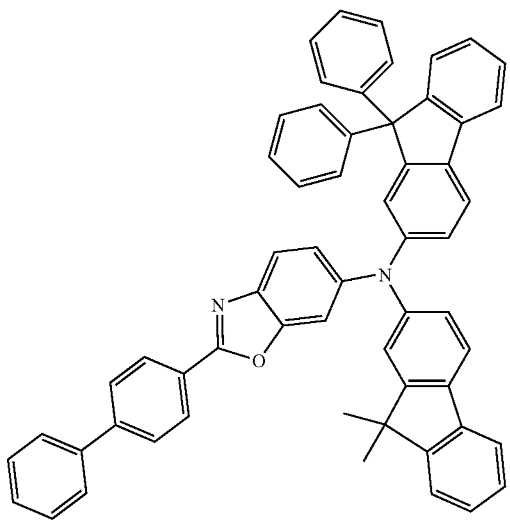
AK61
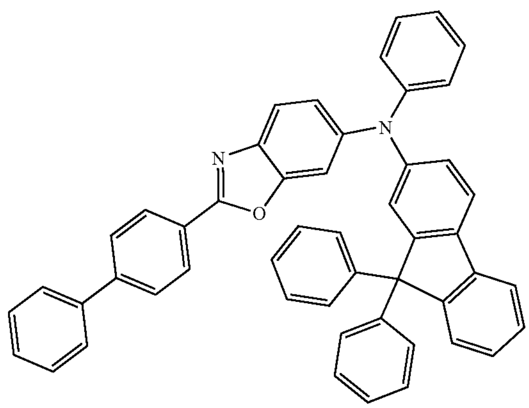
AK62
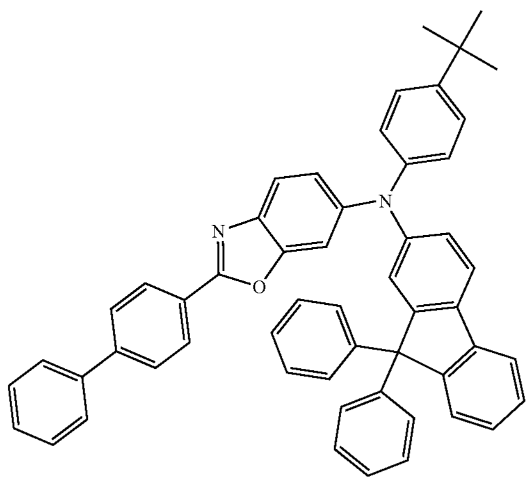
-continued
AK63
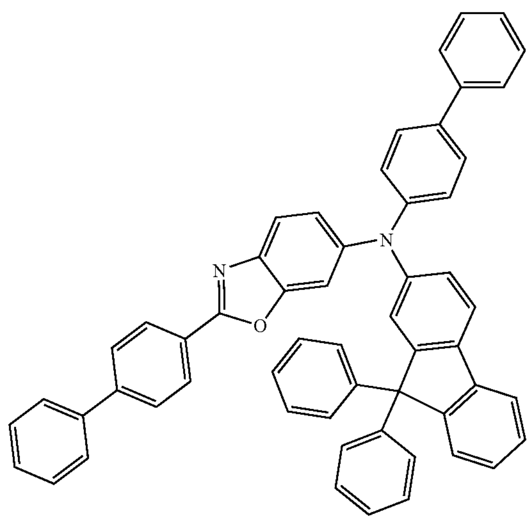
AK64
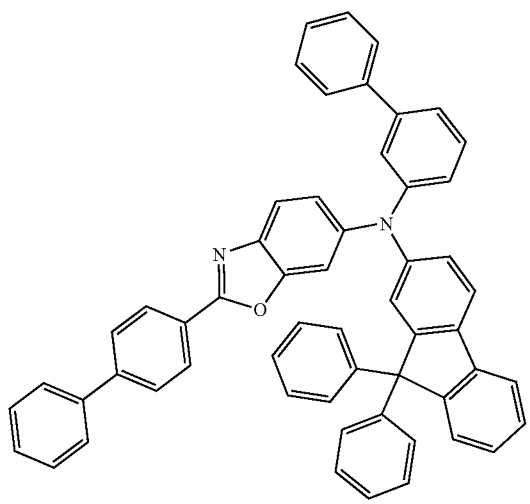
AK65
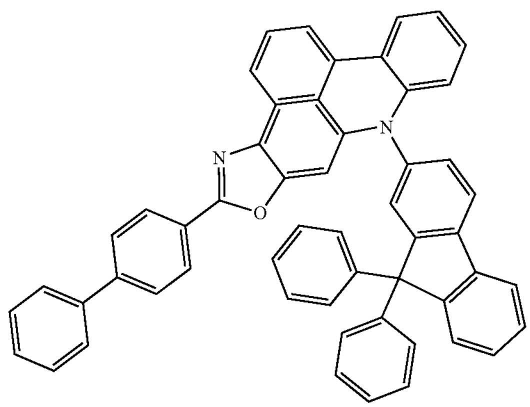

-continued
AK66
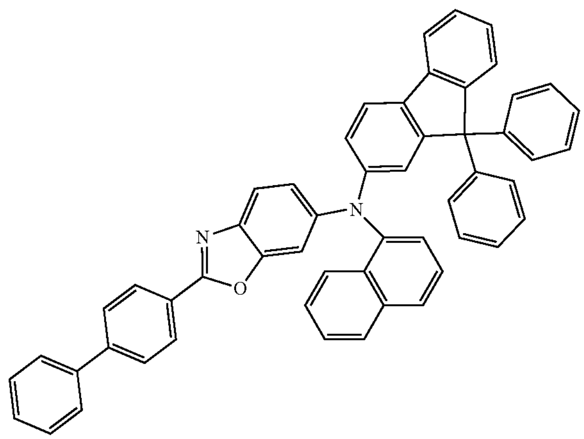
AK67
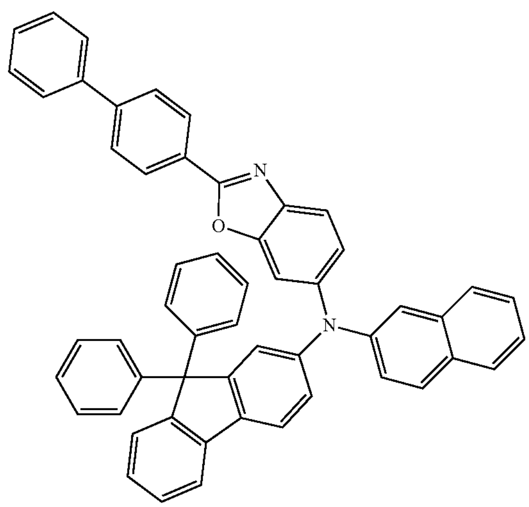
AK68
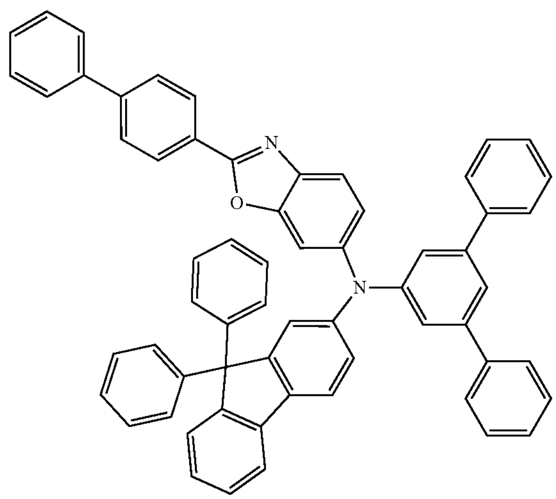
-continued
AK69
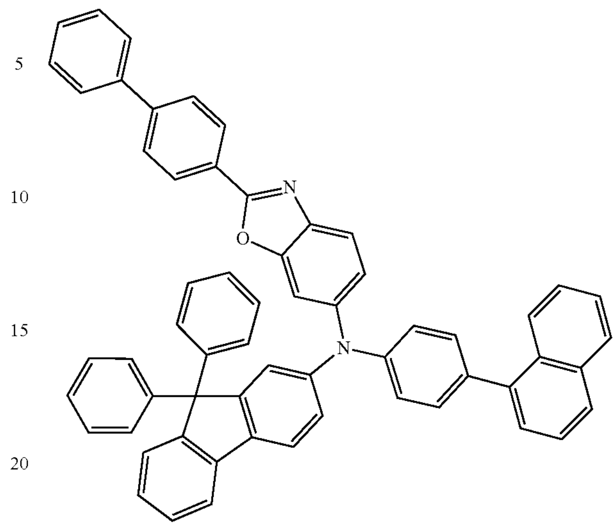
AK70
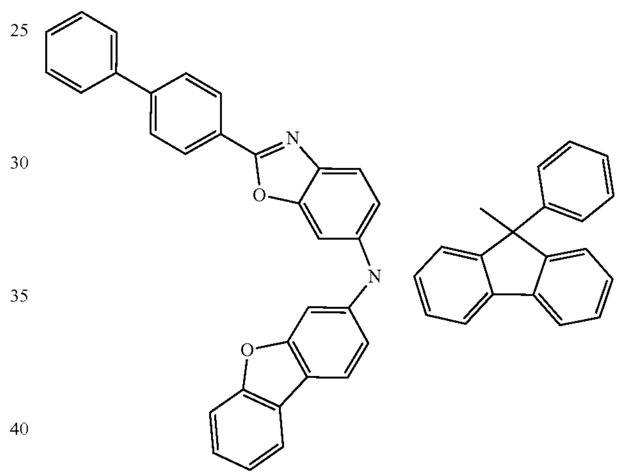
AK71
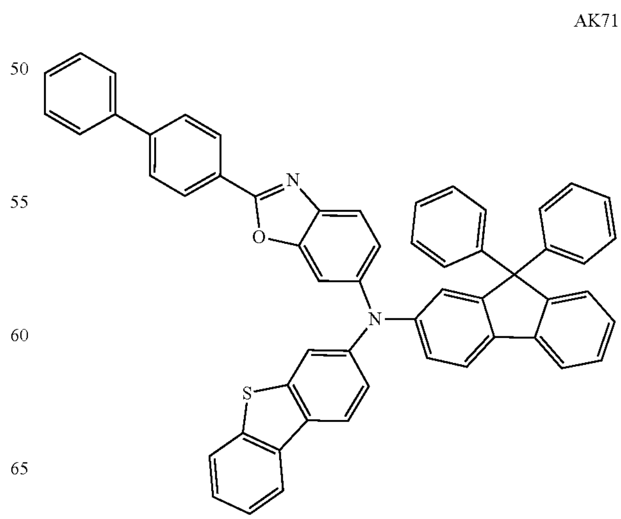

-continued
AK72
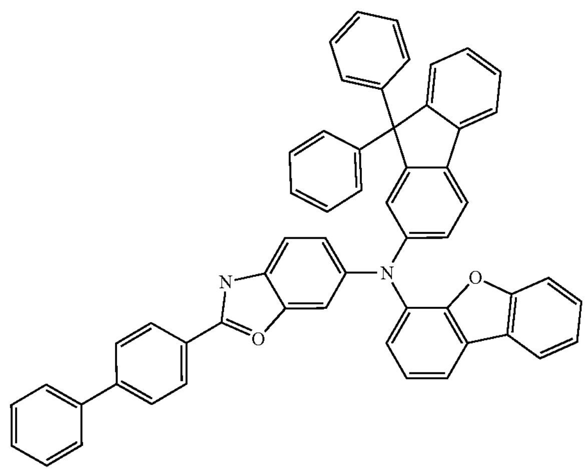
AK73
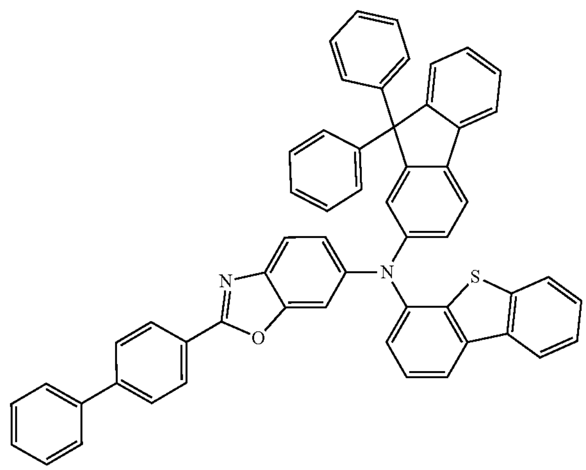
AK74
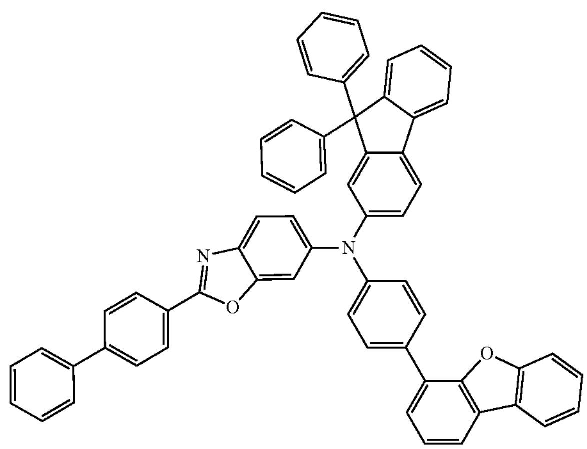
-continued
AK75
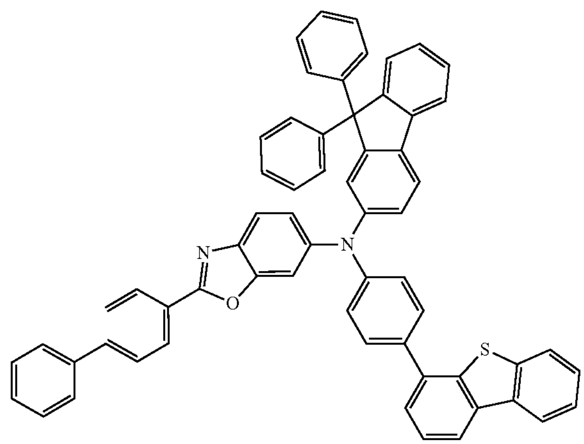
AK76
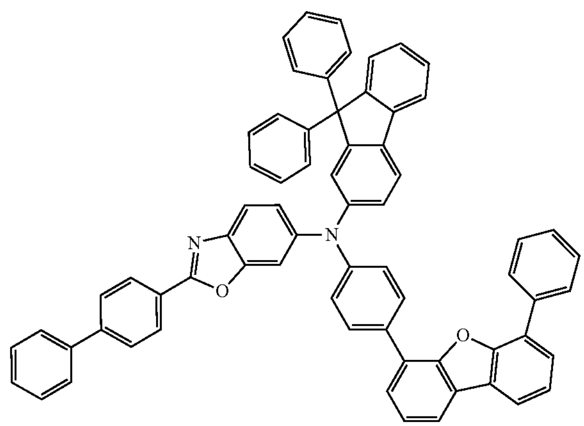
AK77
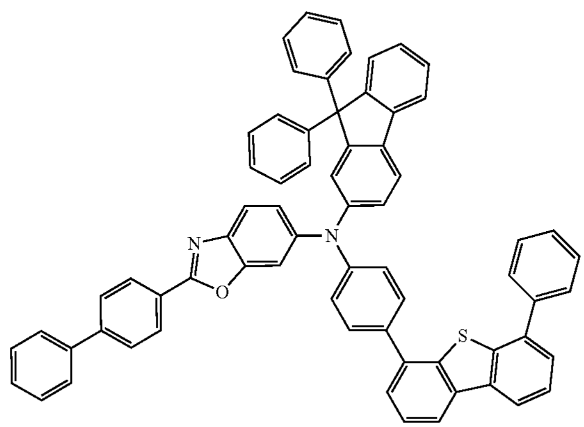

-continued
AK78
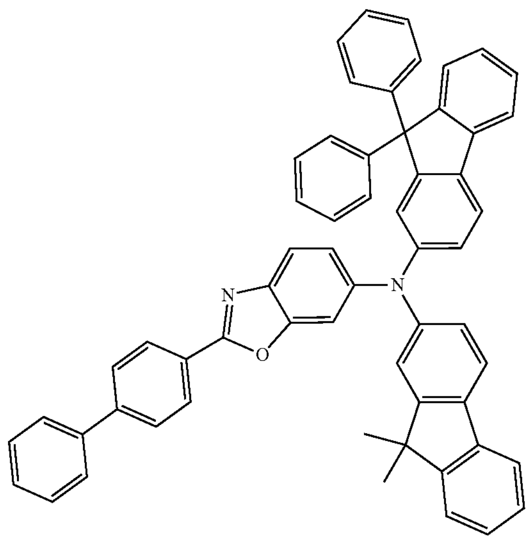
AK79
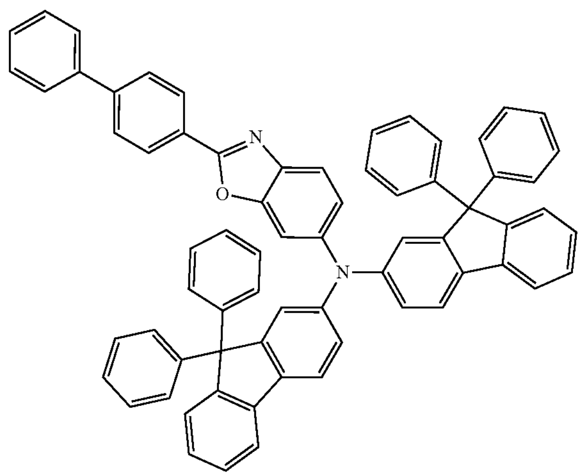
AK80
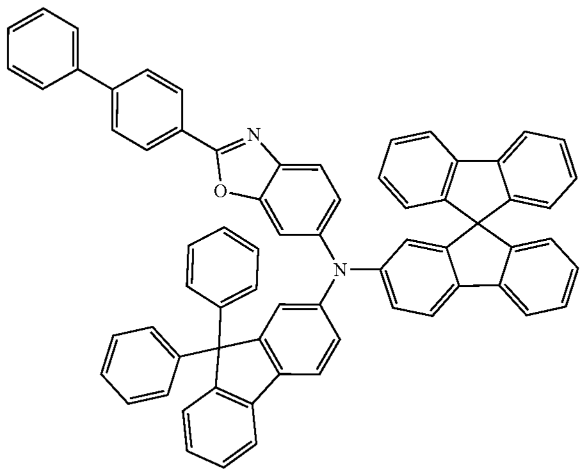
-continued
AK81
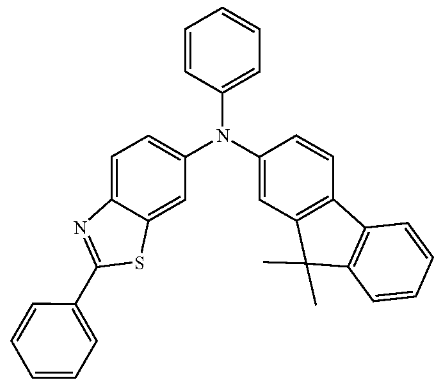
AK82
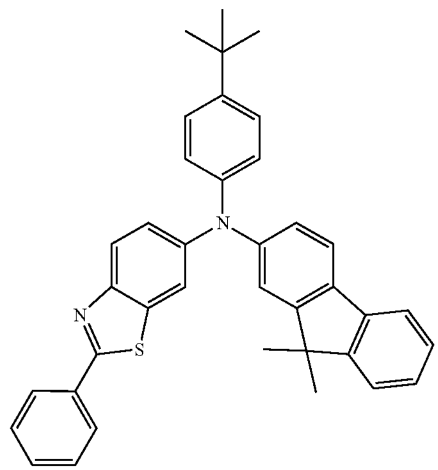
AK83
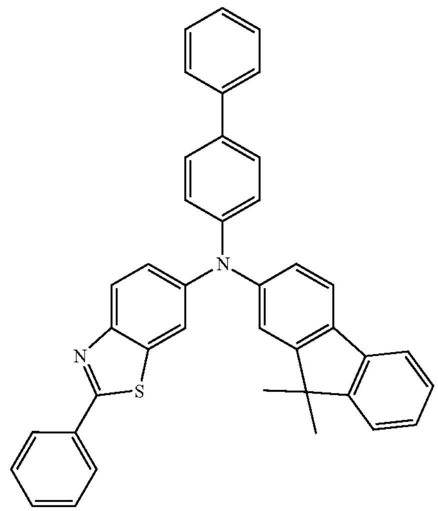

-continued
AK84
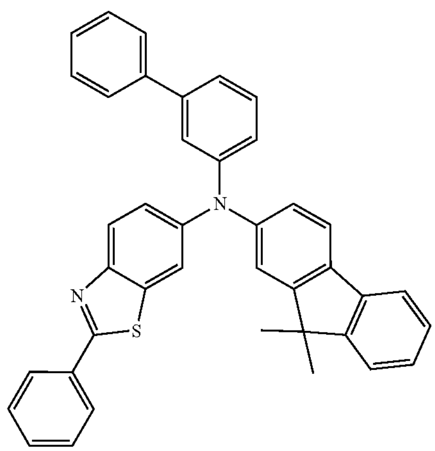
AK85
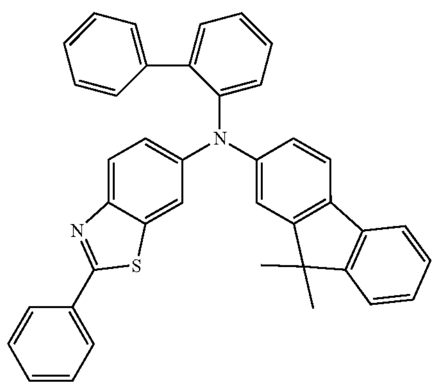
AK86
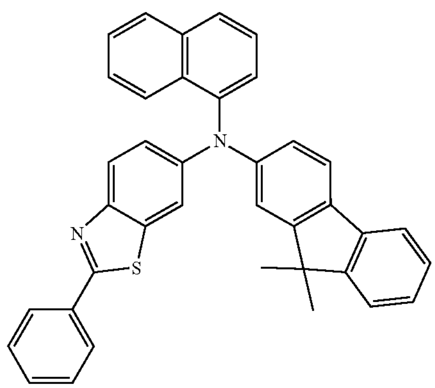
-continued
AK87
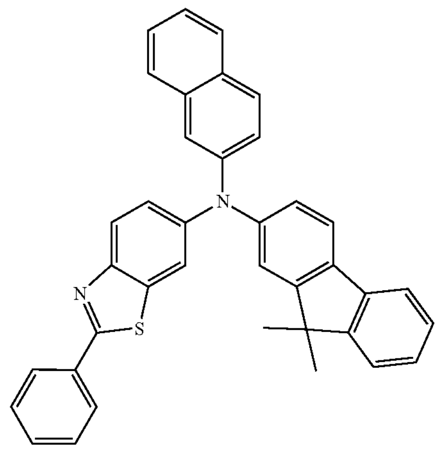
AK88
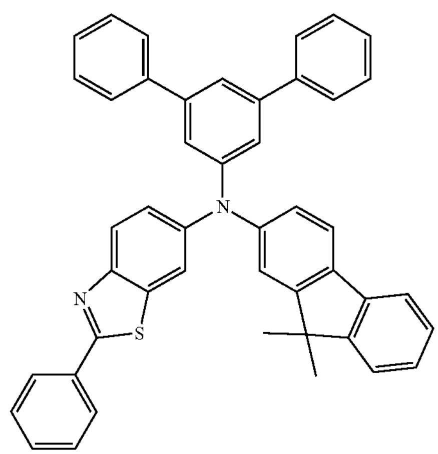
AK89
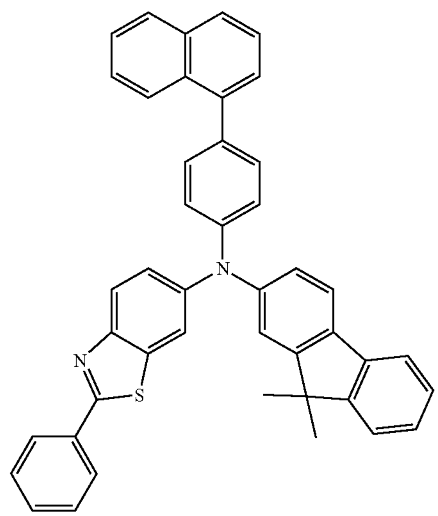

-continued
AK90
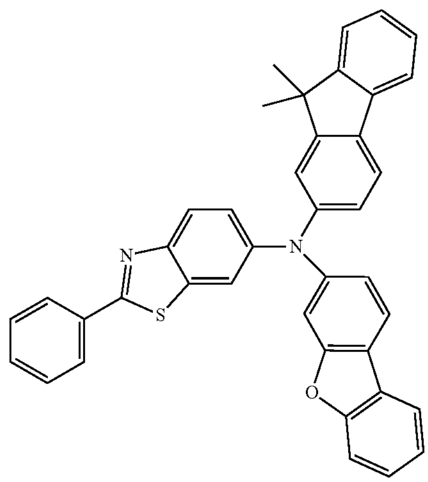
AK91
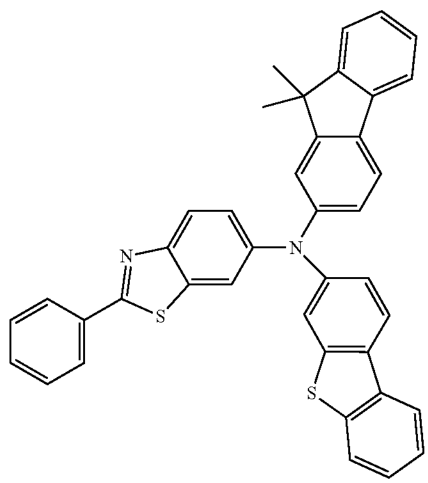
AK92
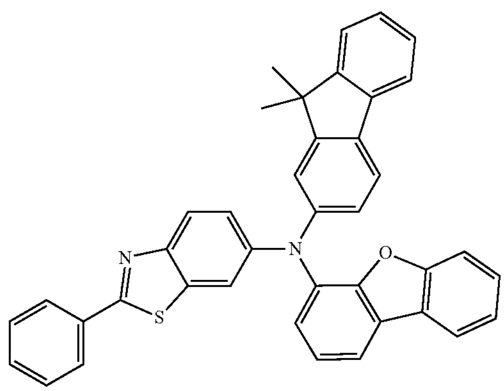
-continued
AK93
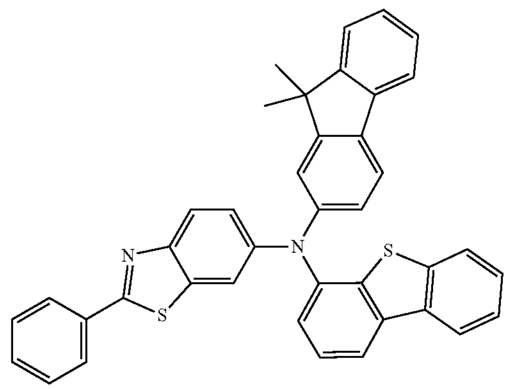
AK94
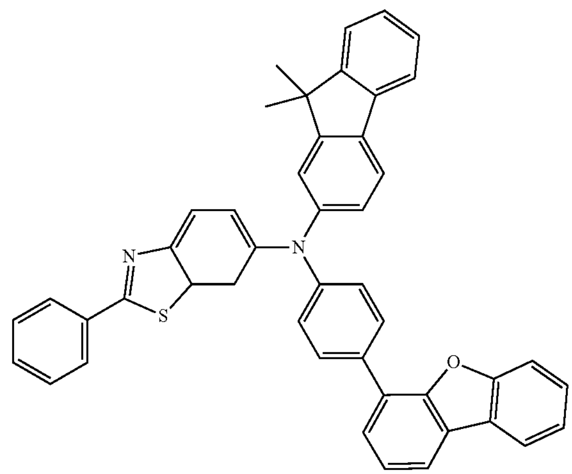
AK95
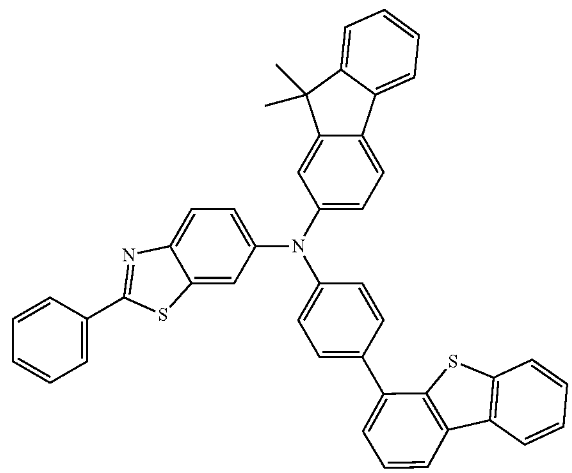

-continued
AK96
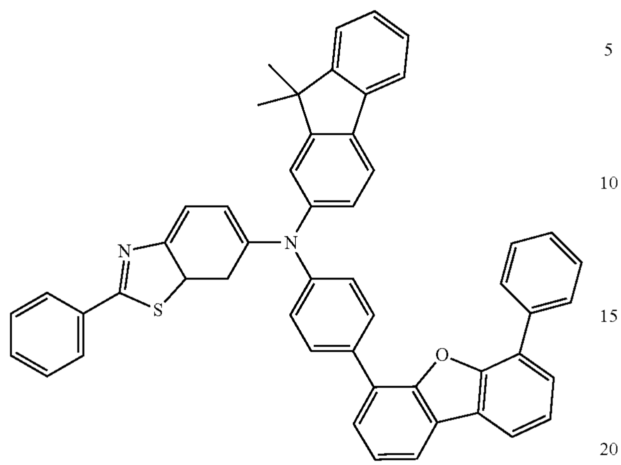
AK97
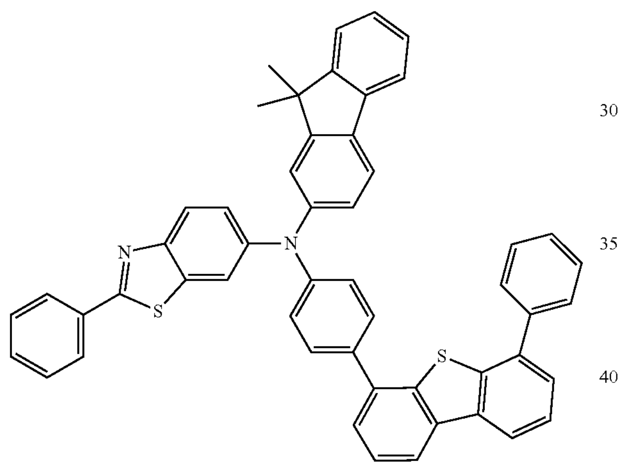
AK98
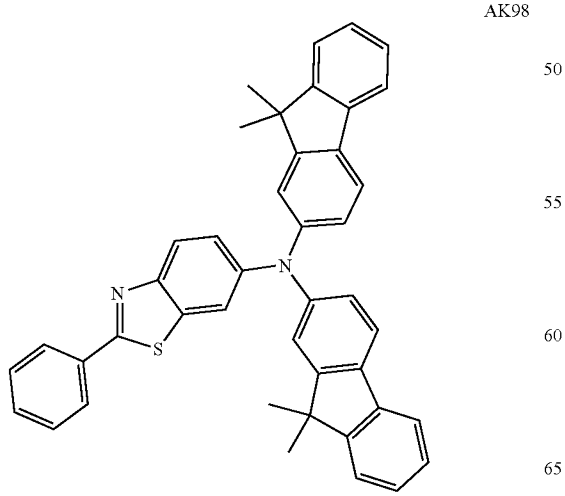
-continued
AK99
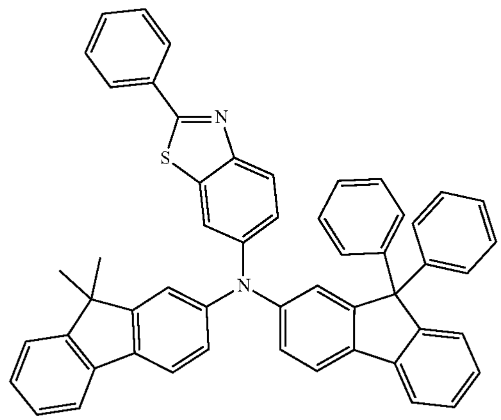
AK100
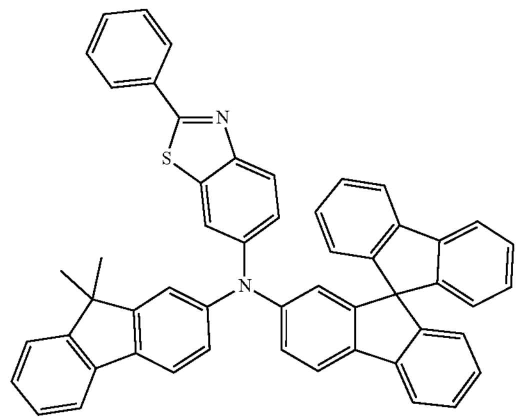
AK101
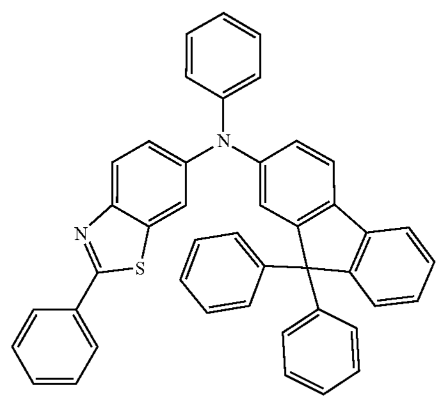

-continued
AK102
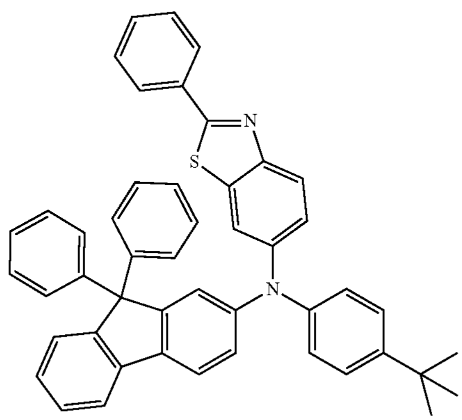
AK103
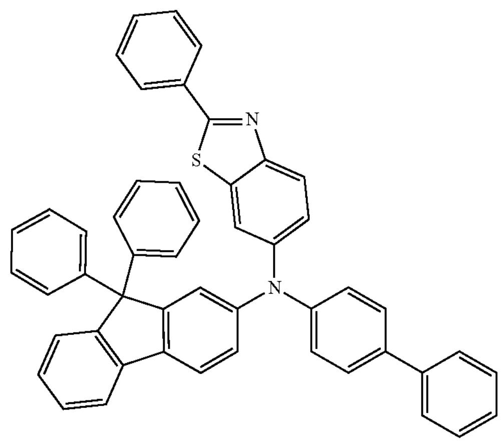
AK104
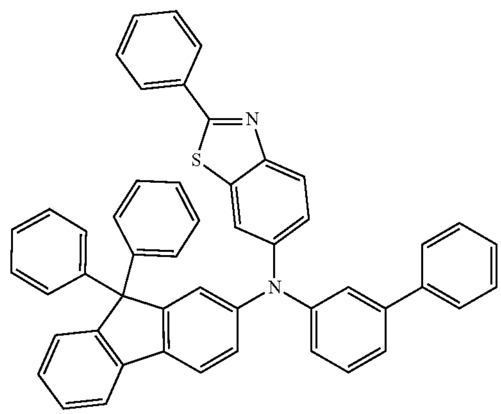
-continued
AK105
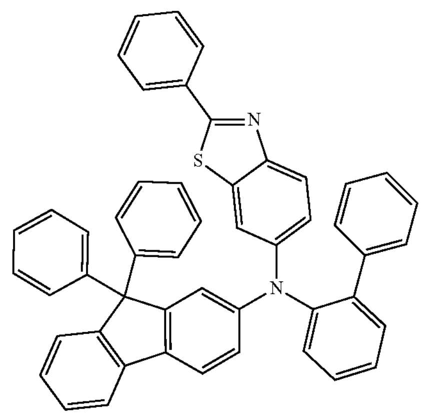
AK106
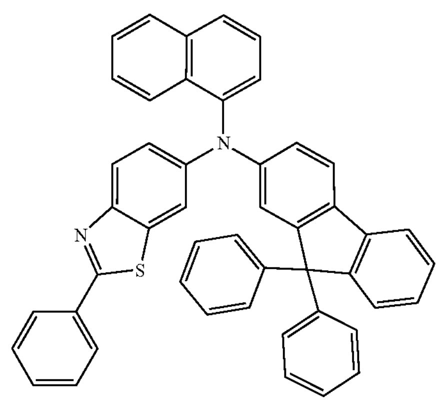
AK107
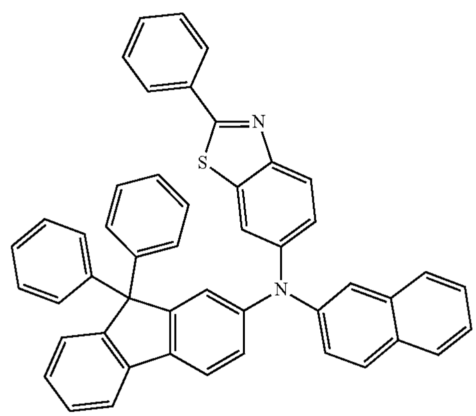
AK108
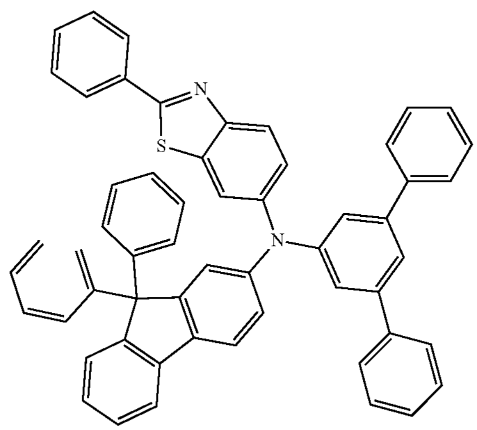

AK109
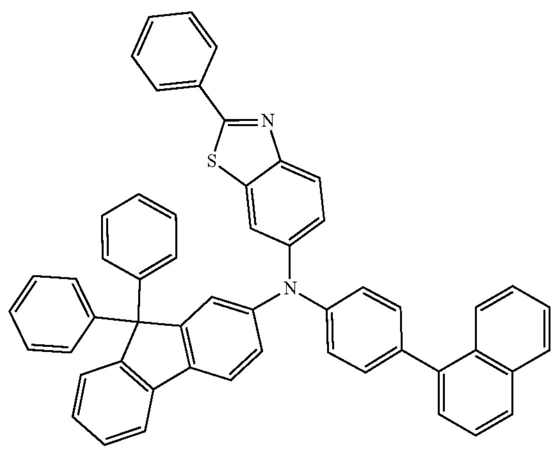
AK110
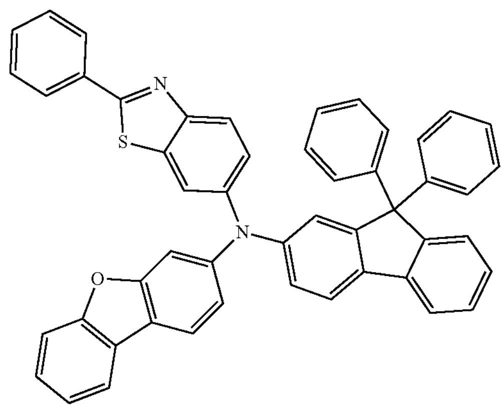
AK111
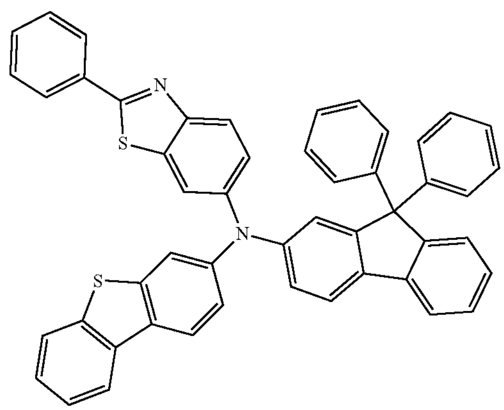
AK112
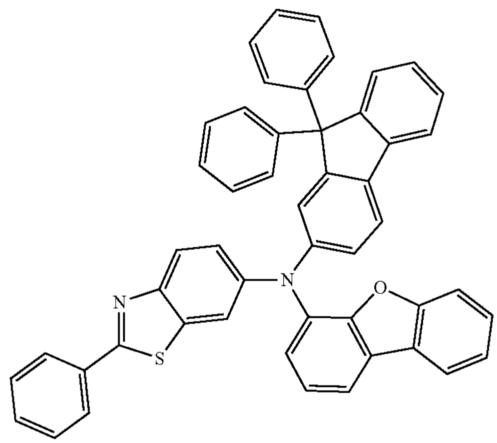
AK113
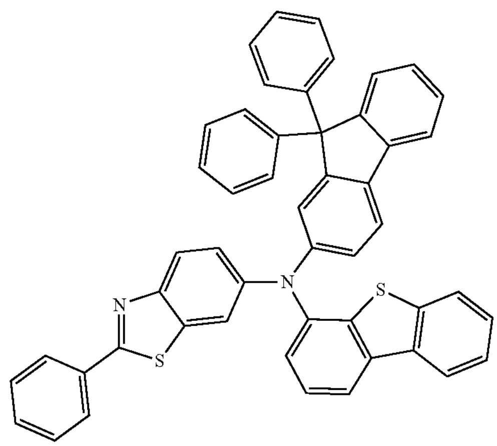
AK114
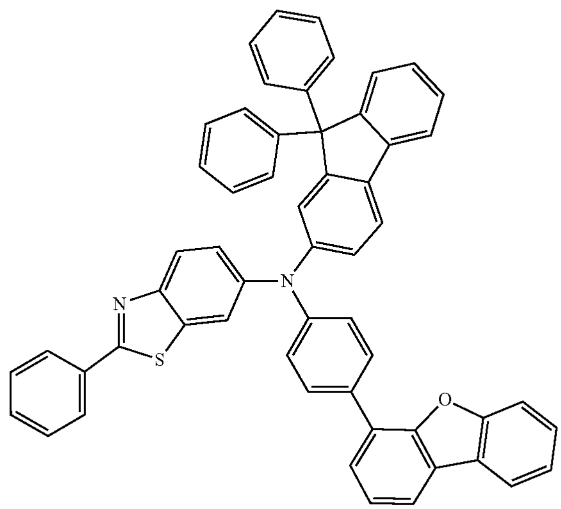

-continued
AK115
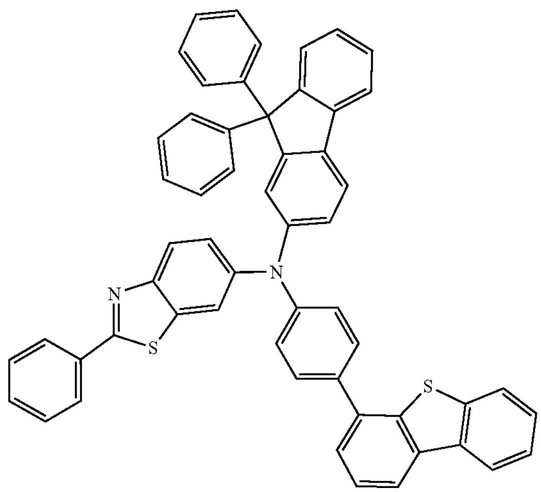
AK116
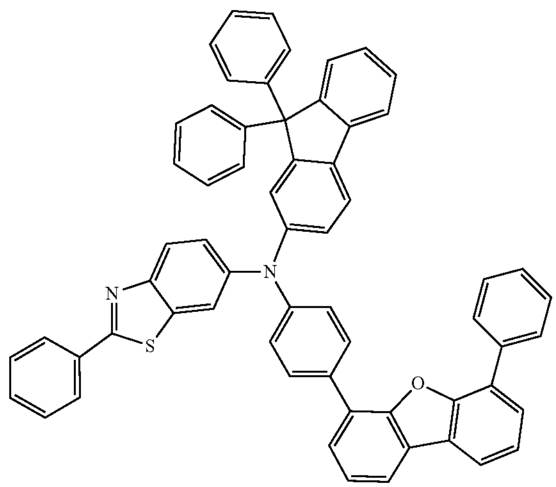
AK116
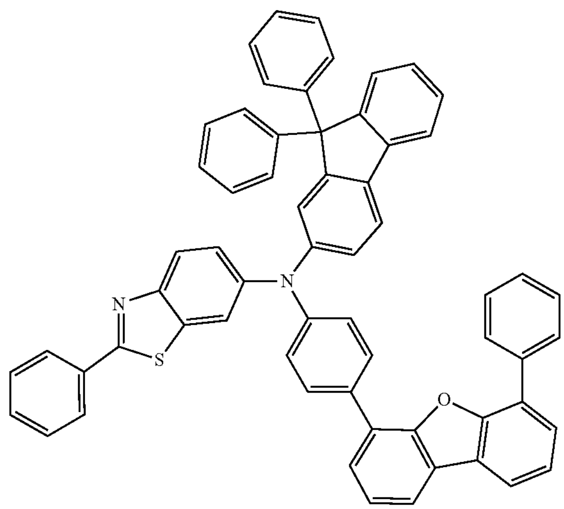
-continued
AK117
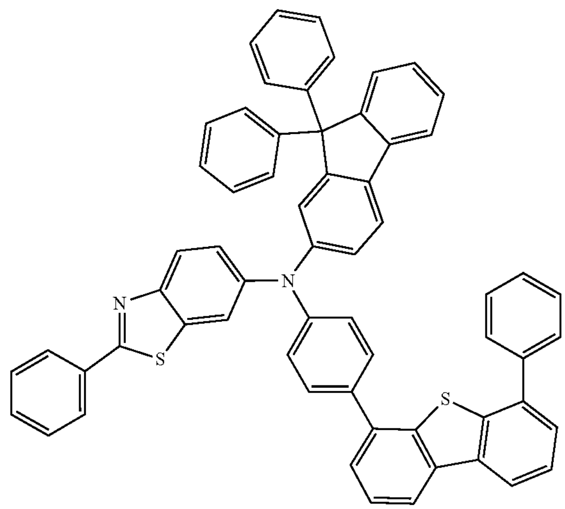
AK118
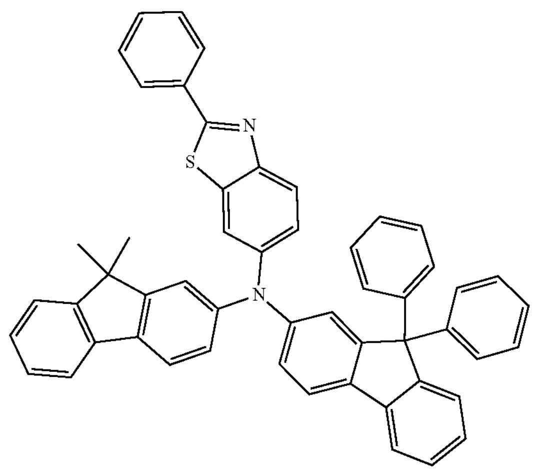
AK119
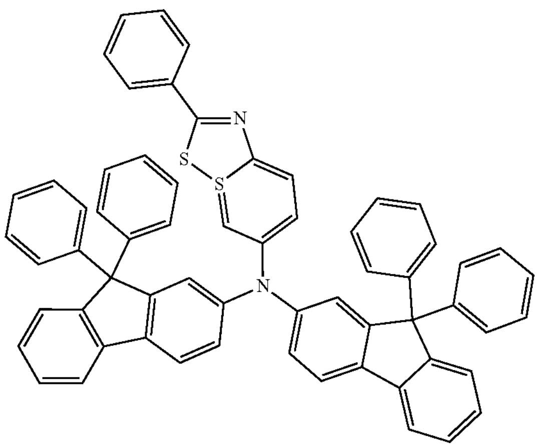

-continued
AK120
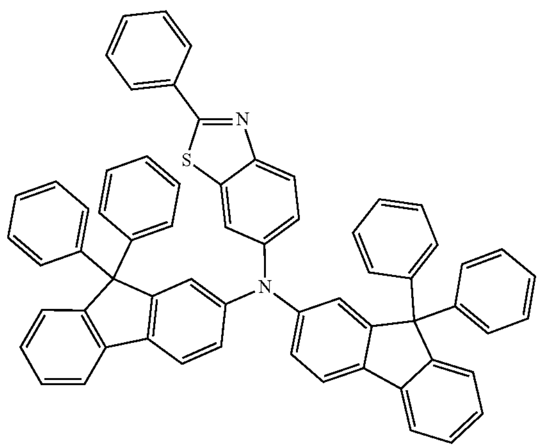
AK121
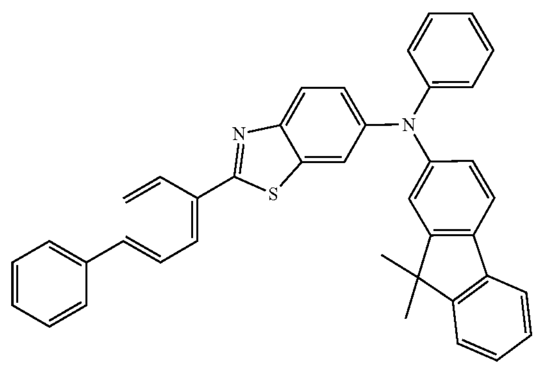
AK122
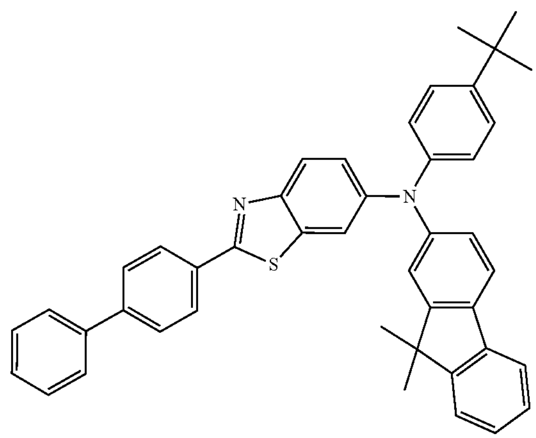
-continued
AK123
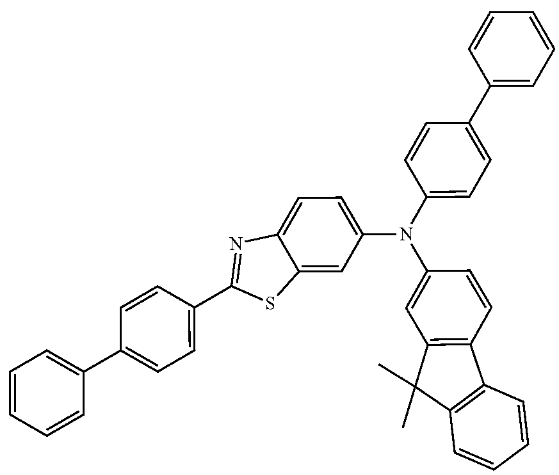
AK124
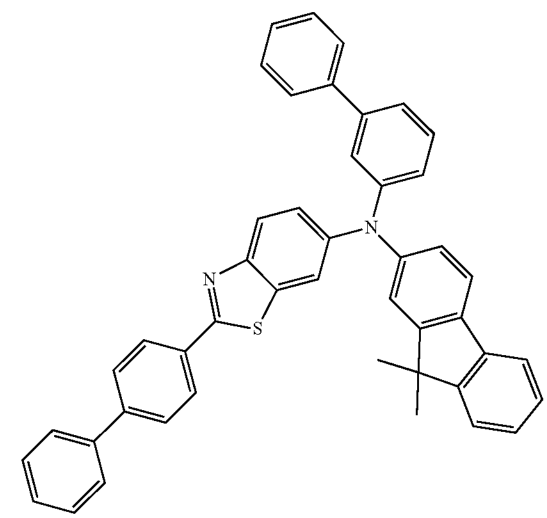
AK125
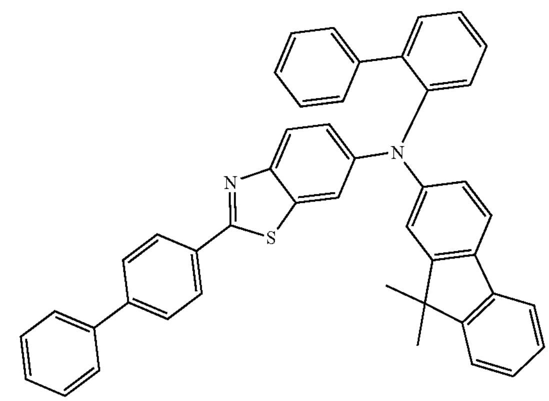

-continued
AK126
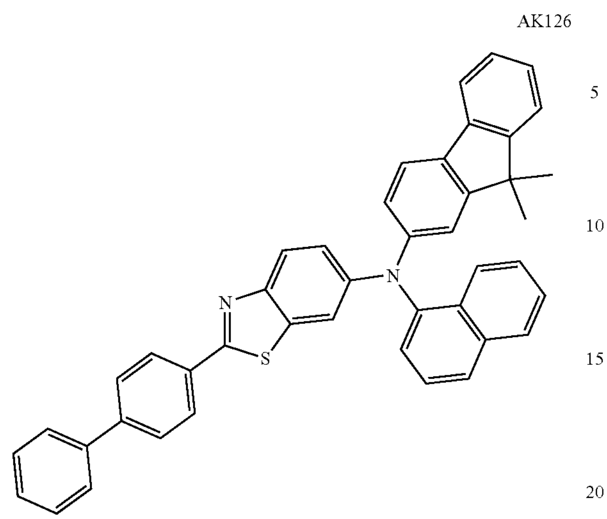
AK127
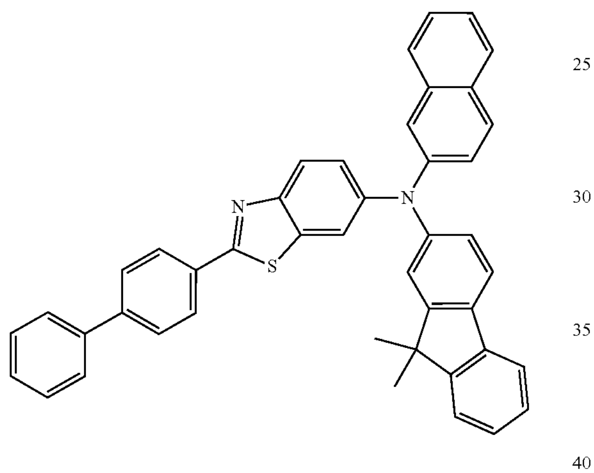
AK128
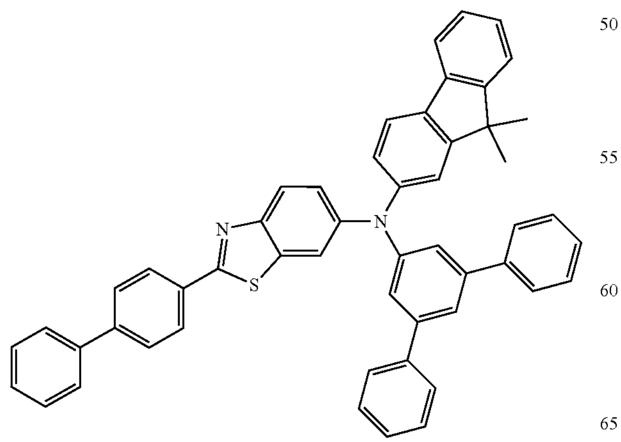
-continued
AK129
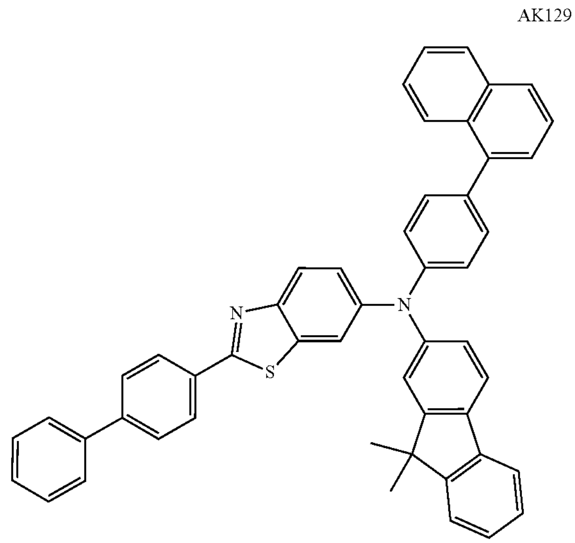
AK130
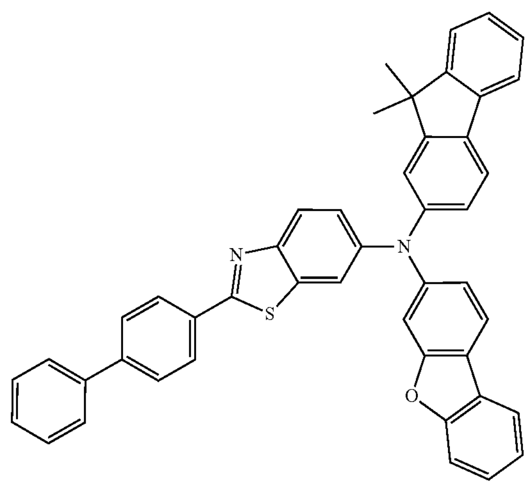
AK131
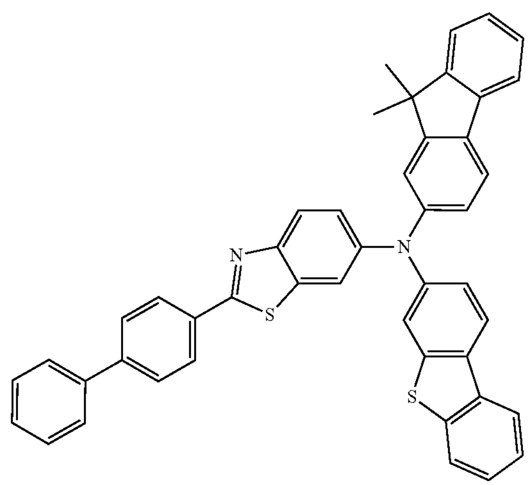

-continued
AK132
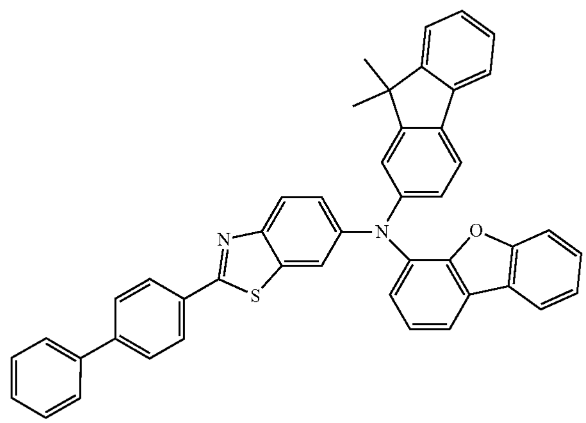
AK133
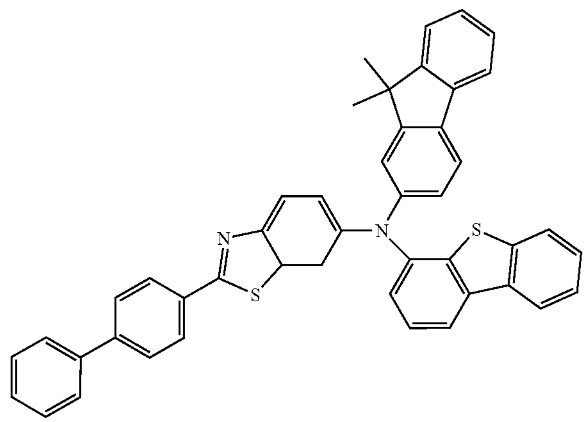
AK134
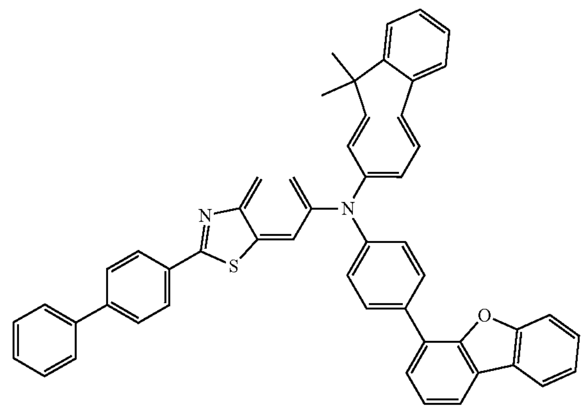
-continued
AK135
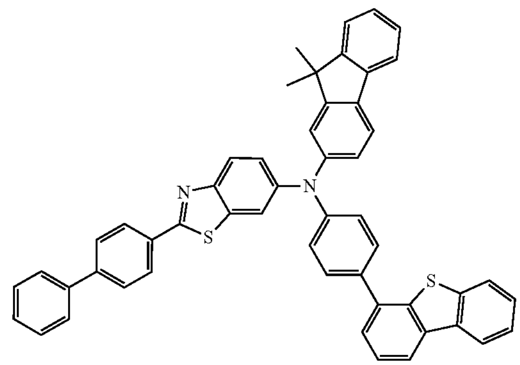
AK136
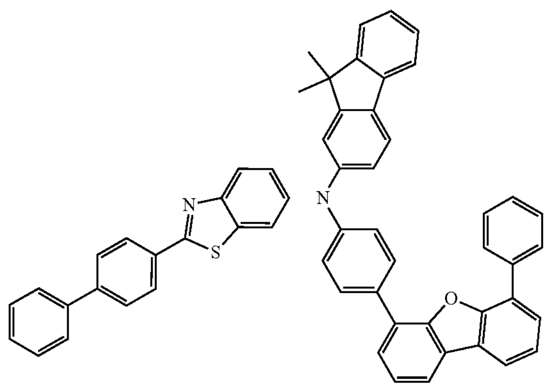
AK137
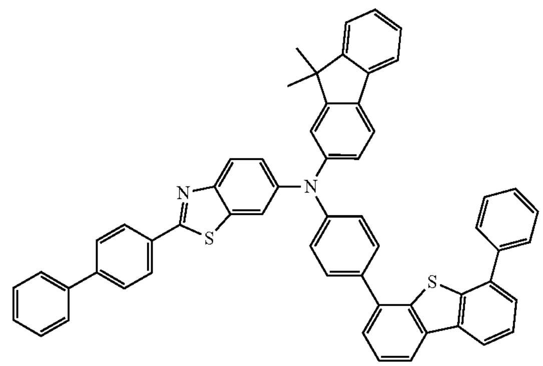

-continued
AK138
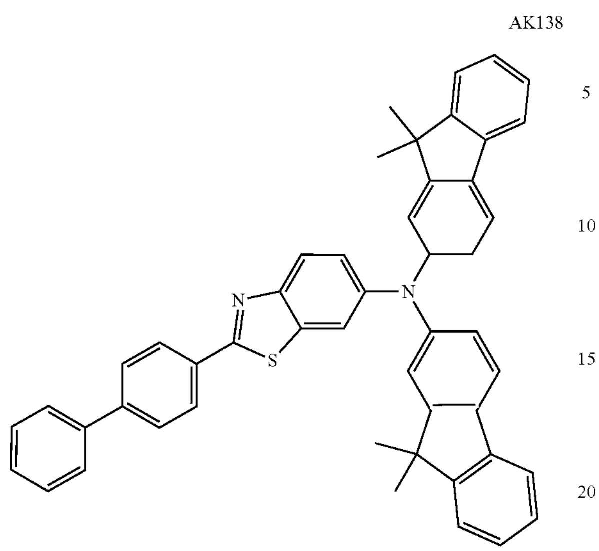
AK139
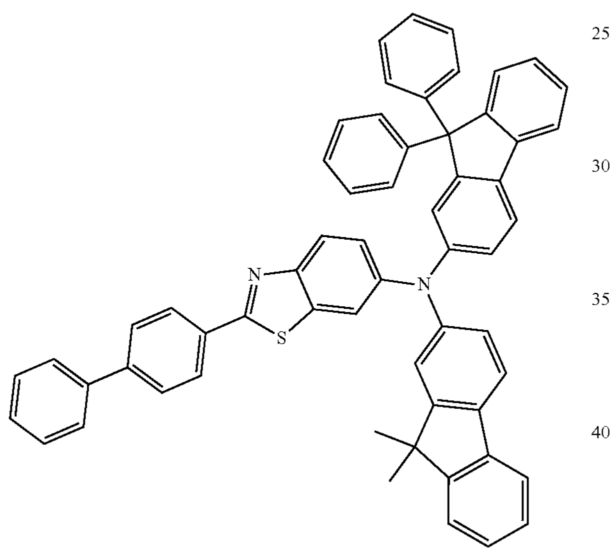
AK140
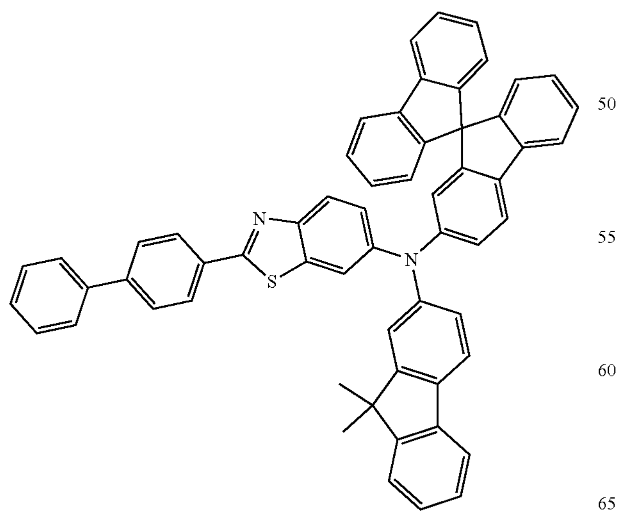
-continued
AK141
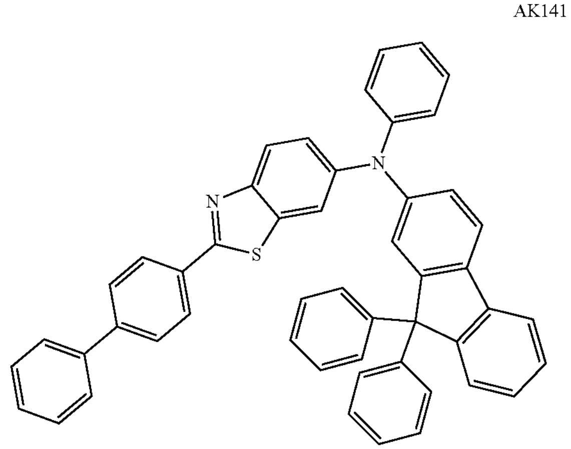
AK142
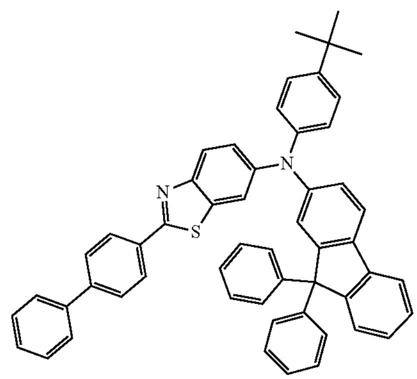
AK143
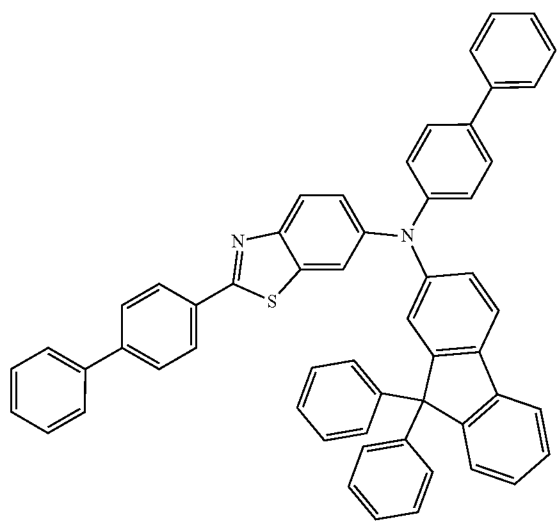

-continued
AK144
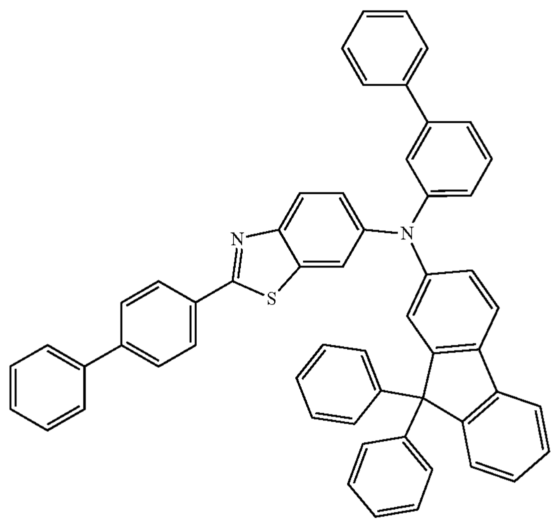
AK145
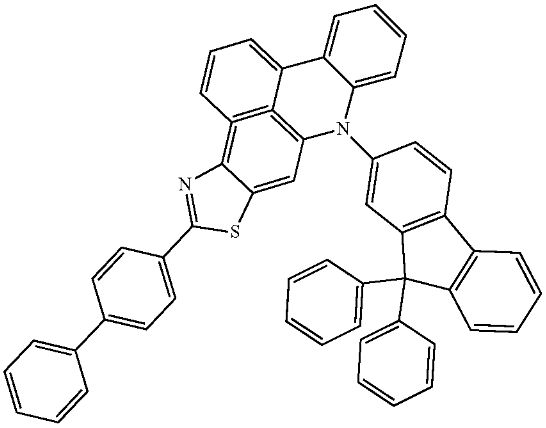
AK146
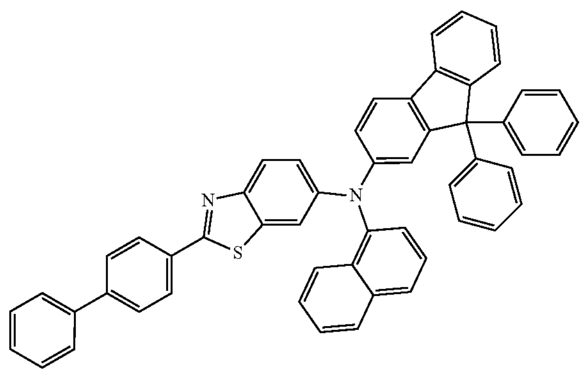
-continued
AK147
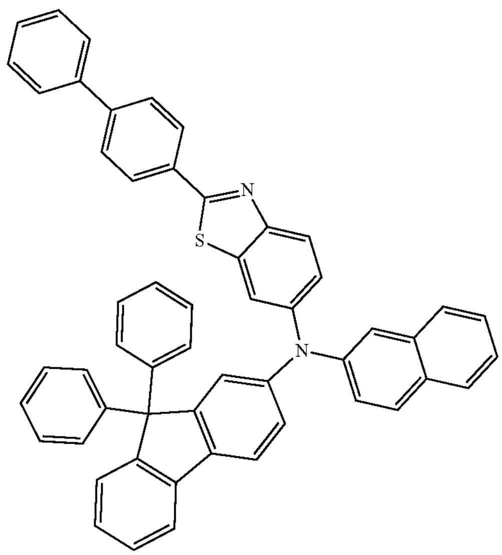
AK148
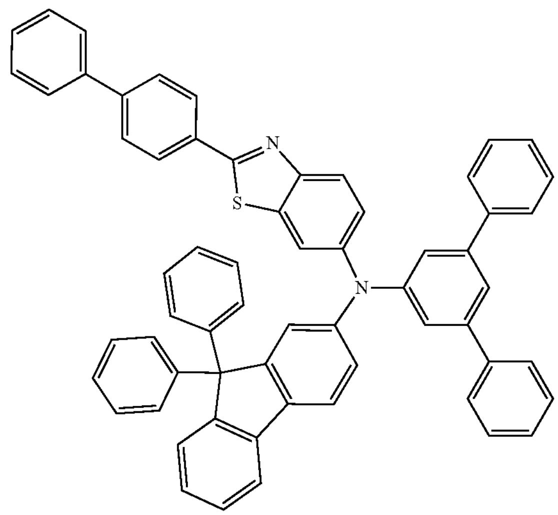
AK149
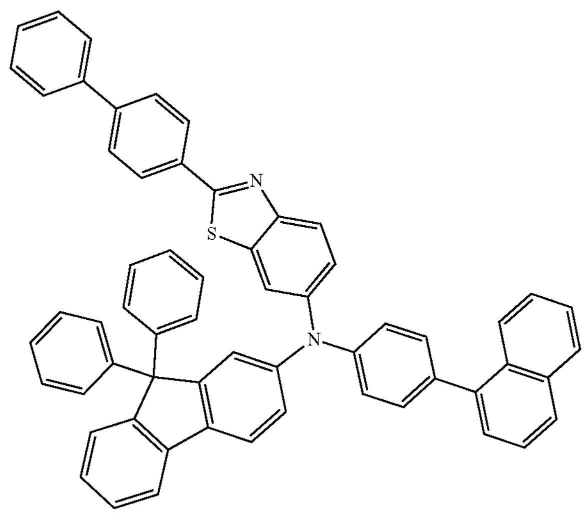

-continued
AK150
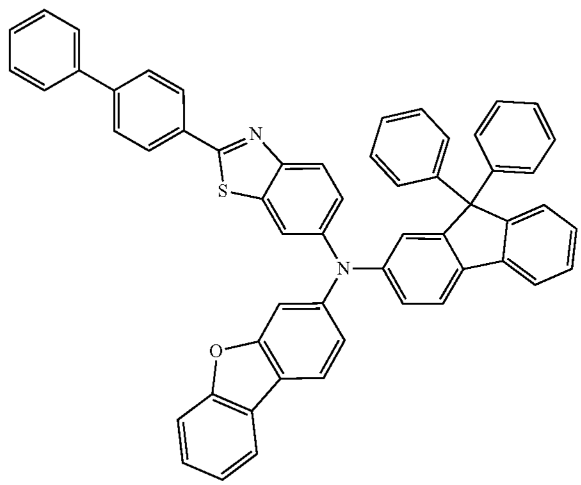
AK151
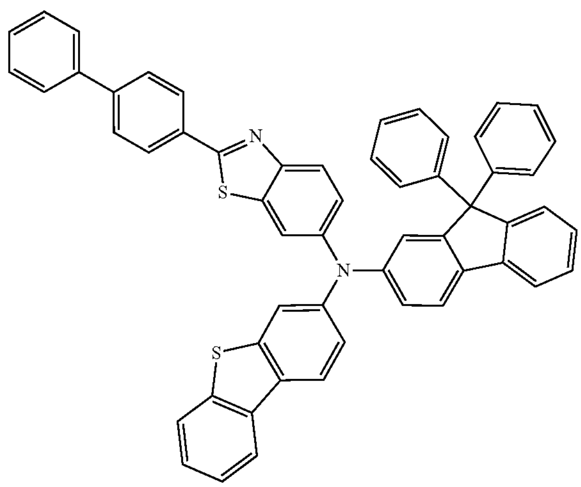
AK152
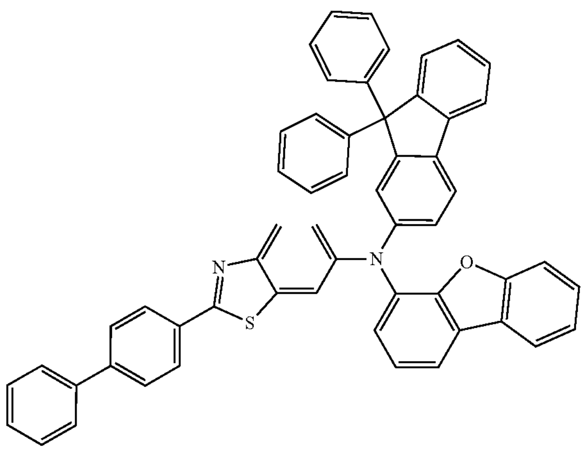
-continued
AK153
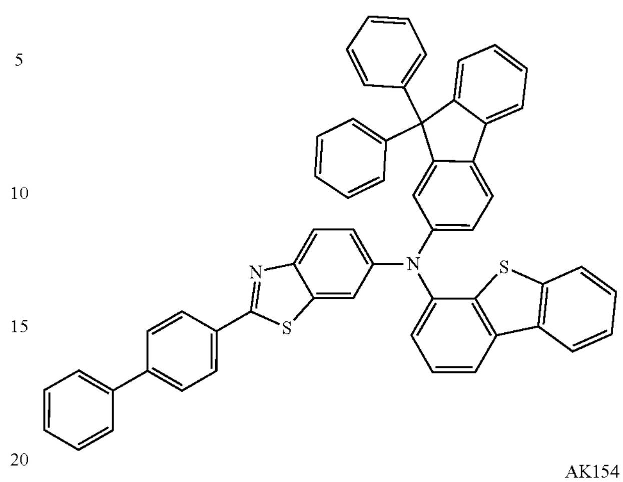
AK154
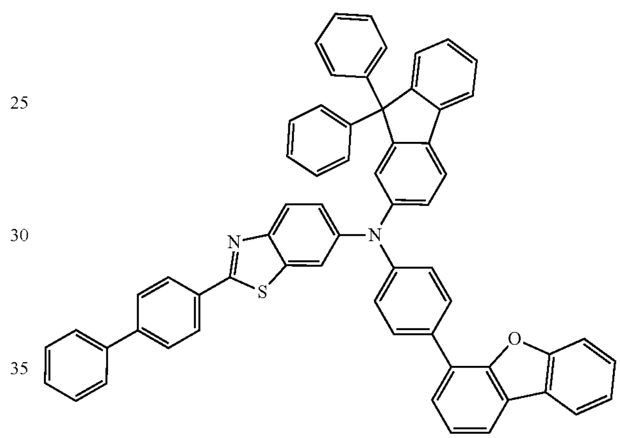
AK155
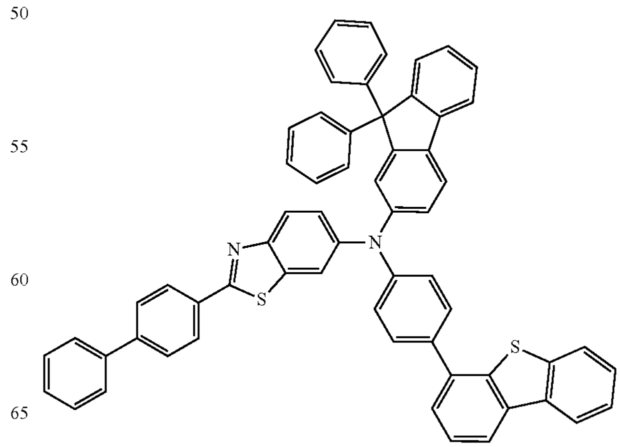

-continued

AK156

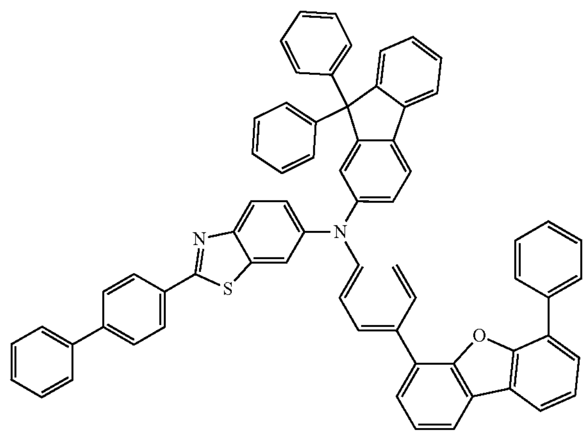

AK157

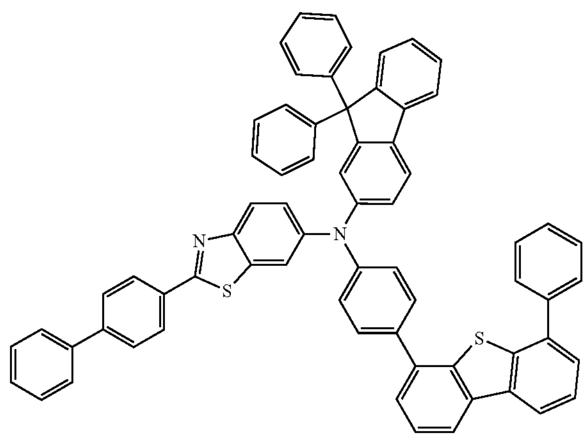

AK158

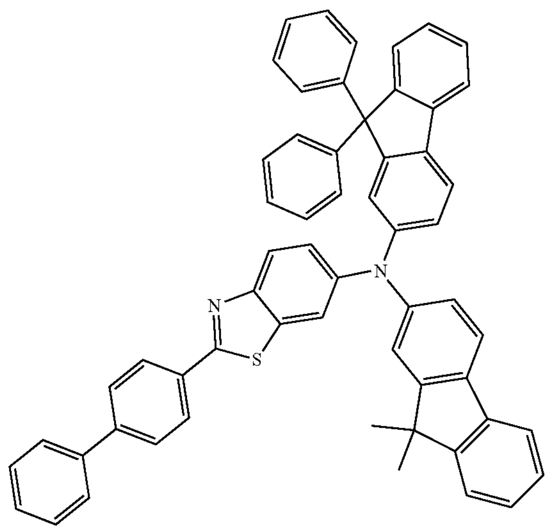

-continued

AK159

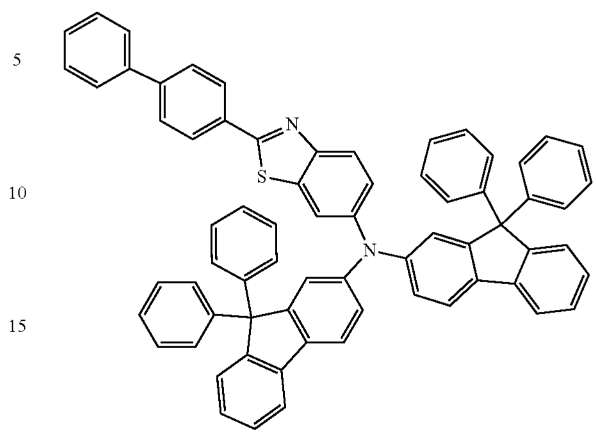

AK160

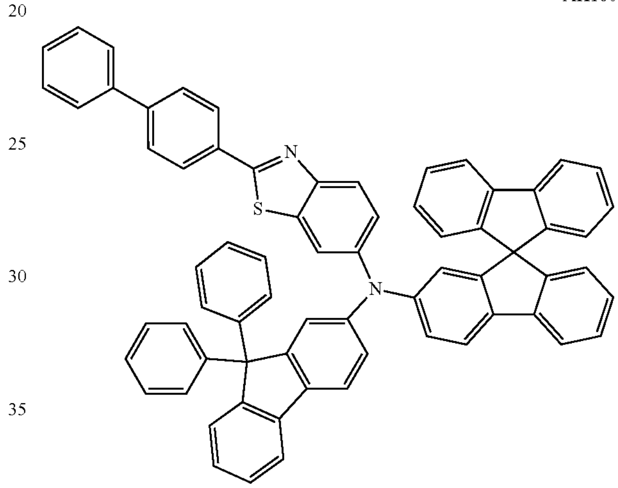

One or more of the hydrogen atoms contained in the AZ1 to AK160 may be substituted with deuterium or tritium.

The above description has been presented to enable any person skilled in the art to make and use the technical idea of the disclosure, and has been provided in the context of a particular application and its requirements. Various modifications, additions and substitutions to the described embodiments will be readily apparent to those skilled in the art, and the general principles defined herein may be applied to other embodiments and applications without departing from the spirit and scope of the disclosure. The above description and the accompanying drawings provide an example of the technical idea of the disclosure for illustrative purposes only. That is, the disclosed embodiments are intended to illustrate the scope of the technical idea of the disclosure. Thus, the scope of the disclosure is not limited to the embodiments shown, but is to be accorded the widest scope consistent with the claims. The scope of protection of the disclosure should be construed based on the following claims, and all technical ideas within the scope of equivalents thereof should be construed as being included within the scope of the disclosure.

An example of manufacturing an organic light emitting element according to embodiments of the disclosure are described below in detail with reference to embodiments thereof, but embodiments of the disclosure are not limited to the following embodiments.

Example of Preparing the Compound

Synthesis Method for AZ3

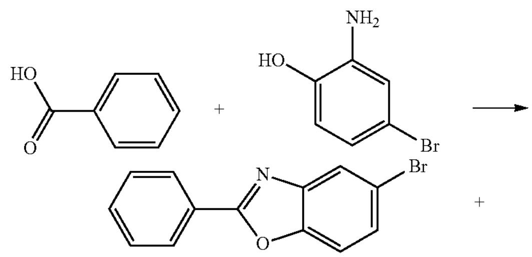

Intermediate A

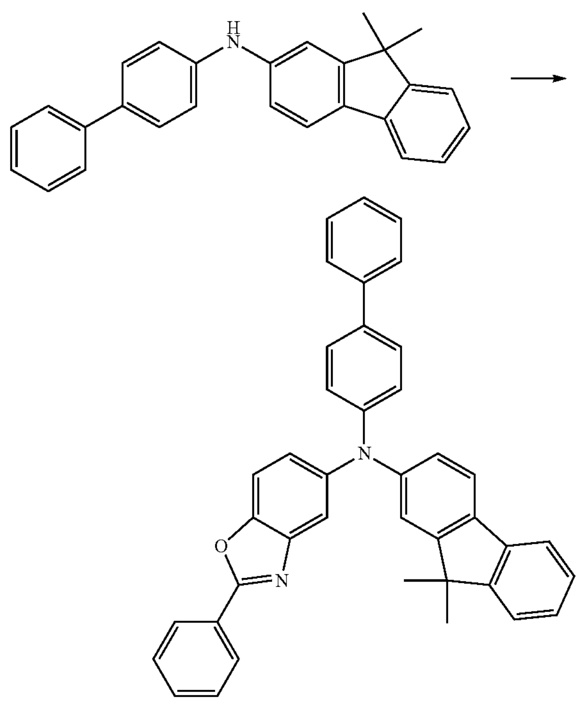

AZ3

Synthesis of Intermediate A

Benzoic acid (10 g, 0.082 mol), 2-amino-4-bromophenol (33.9 g, 0.180 mol), diisopropylethylamine(37.1 ml, 0.213 mol), 4M $K_2CO_3$ aqueous solution 80 ml, methylene chloride 300 ml are put in a round-bottom flask and stirred while reducing the temperature to 0° C. Deoxo-fluor reagent, 50% in THF (66.4 ml, 0.180 mol) diluted with 45 ml of MC is slowly added dropwise to the solution. After the dropwise addition is finished, the solution is stirred at 0° C. for 2 hours. After the reaction is finished by adding 150 ml of saturated aqueous sodium bicarbonate solution to the reaction solution, the solution is heated to room temperature. After the reaction solution is separated into layers to recover the organic layer, the organic layer was dried with $MgSO_4$ and concentrated under reduced pressure. The concentrated crude material was separated by column to obtain 19.1 g of intermediate A.

Synthesis of AZ3

An intermediate A (5 g, 0.018 mol), 2-(4-biphenylyl) amino-9,9-dimethylfluorene(7.9 g, 0.022 mol), palladium acetate (I) 0.08 g, 0,365 mmol), 2,2-Bis(diphenylphosphino)-1,1'-binaphthyl (0.23 g, 0.365 mmol), sodium-t-butoxide (2.63 g, 0.027 mol), and toluene 100 ml are put in a round-bottom flask and heated to 100° C. while b stirred for 8 hours. The reaction solution was hot-filtered through silicagel to remove impurities, and the filtrate was concentrated under reduced pressure to obtain a crude material. The obtained crude material was purified by MC/acetone to obtain 6.9 g of AZ3.

Synthesis Method for AZ5

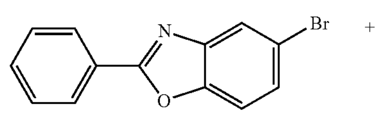

Intermediate A

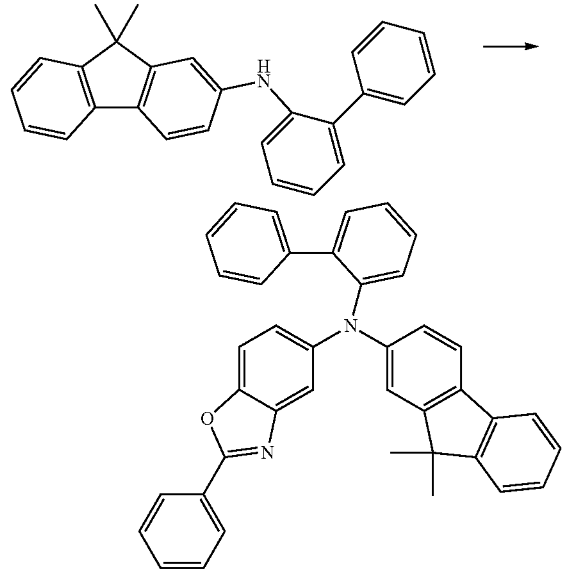

AZ5

The synthesis was carried out in the same way as in the synthesis method for AZ3 except that 2-(2-biphenylyl) amino-9,9-dimethylfluorene (7.9 g, 0.022 mol) was used instead of 2-(4-biphenylyl)amino-9,9-dimethylfluorene. As a result, 6.6 g of AZ5 was obtained.

Synthesis Method for AZ10

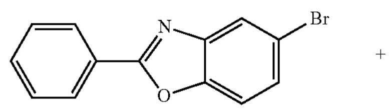

Intermediate A

-continued

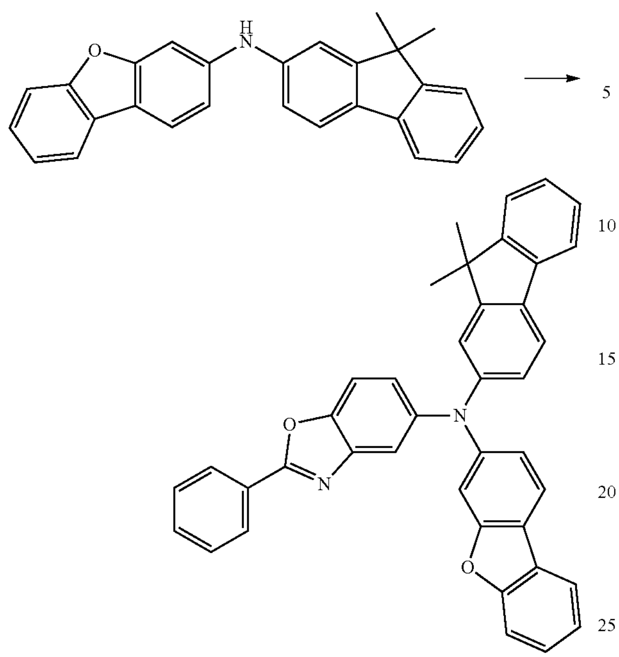

AZ10

The synthesis was carried out in the same way as in the synthesis method for AZ3 except that 2-(3-dibenzofuranyl) amino-9,9-dimethylfluorene (8.2 g, 0.022 mol) was used instead of 2-(4-biphenylyl)amino-9,9-dimethylfluorene. As a result, 7.1 g of AZ10 was obtained.

Synthesis Method for AZ11

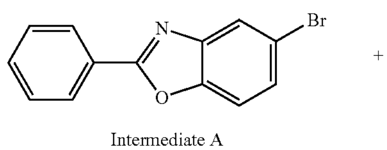

Intermediate A

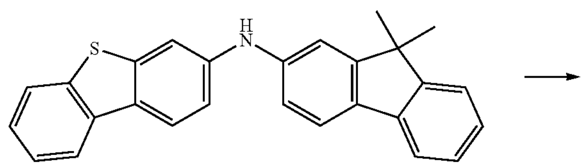

-continued

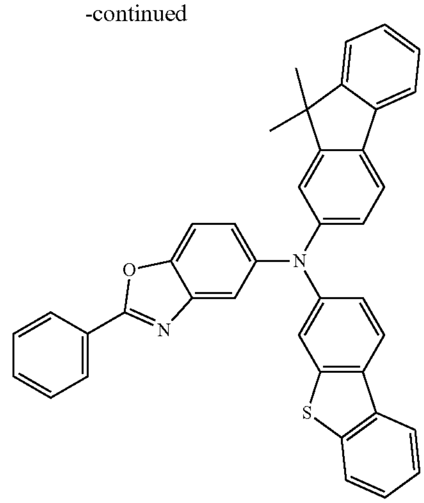

AZ11

The synthesis was carried out in the same way as in the synthesis method for AZ3 except that 2-(3-dibenzothiophenyl)amino-9,9-dimethylfluorene (8.6 g, 0.022 mol) was used instead of 2-(4-biphenylyl)amino-9,9-dimethylfluorene. As a result, 7.3 g of AZ11 was obtained.

Synthesis Method for AZ18

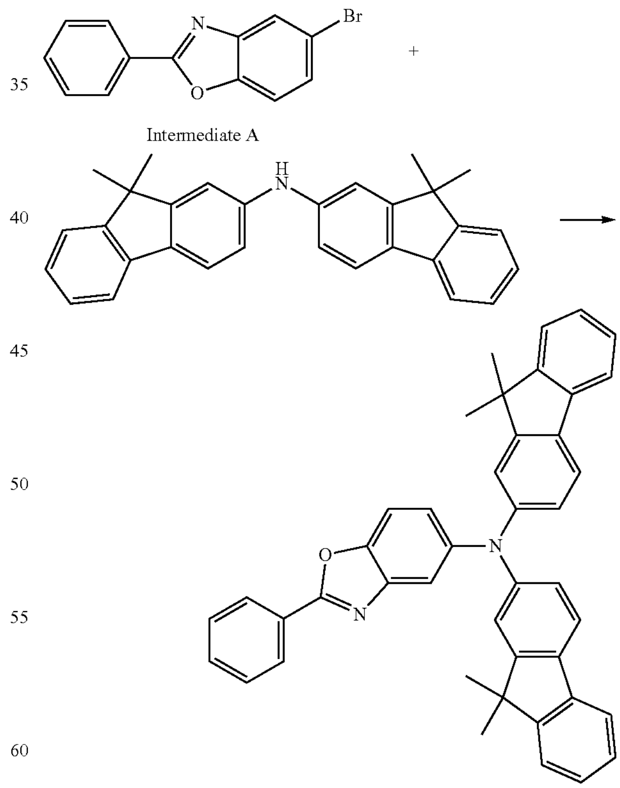

Intermediate A

AZ18

The synthesis was carried out using the same reagents and the same dosage and same method as in the synthesis method for AZ3 that bis(9,9-dimethyl-9H-fluoren-2-yl)

amine (8.8 g, 0.022 mol) was applied instead of 2-(4-biphenylyl)amino-9,9-dimethylfluorene and, as a result, 7.6 g of AZ18 was obtained.

Synthesis Method for AZ20

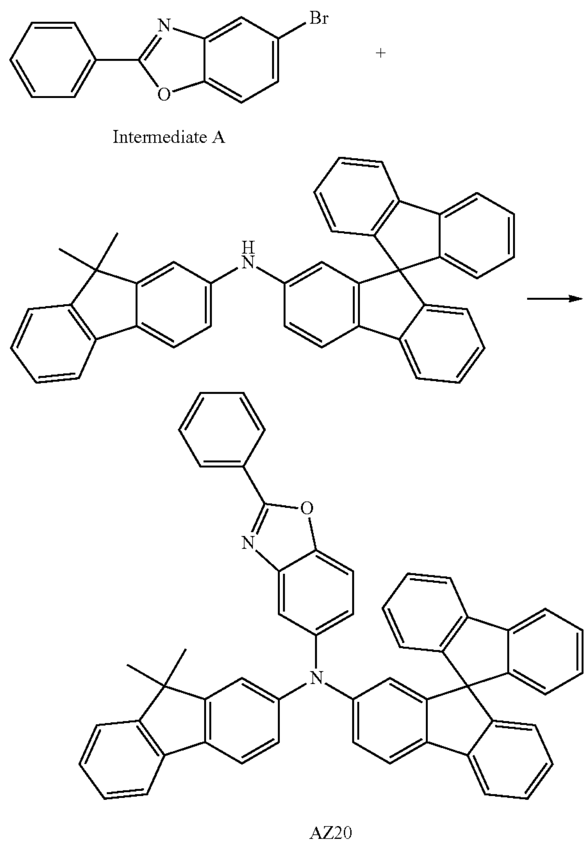

Intermediate A

AZ20

The synthesis was carried out in the same way as in the synthesis method for AZ3 except that (9,9-dimethylfluorene-2-yl)-9,9-spirobifluorene-2-amine(11.5 g, 0.022 mol) was used instead of 2-(4-biphenylyl)amino-9,9-dimethylfluorene. As a result, 9.0 g of AZ20 was obtained.

Synthesis Method for AZ23

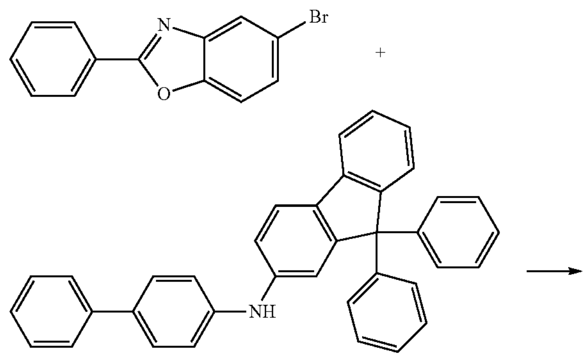

-continued

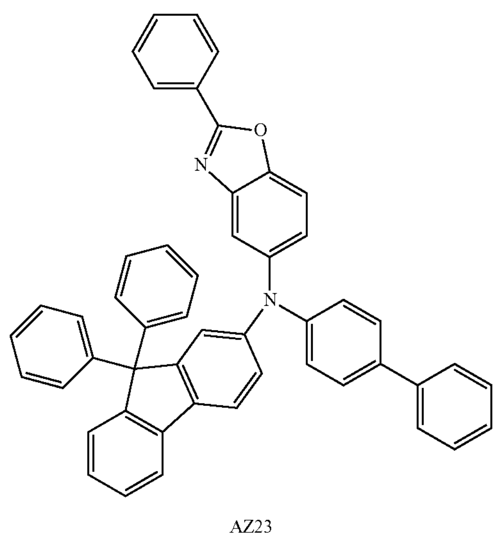

AZ23

The synthesis was carried out in the same way as in the synthesis method for AZ3 except that 2-(4-Biphenylyl) amino-9,9-diphenylfluorene (10.6 g, 0.022 mol) was used instead of 2-(4-biphenylyl)amino-9,9-dimethylfluorene. As a result, 8.8 g of AZ23 was obtained.

Synthesis Method for AZ43

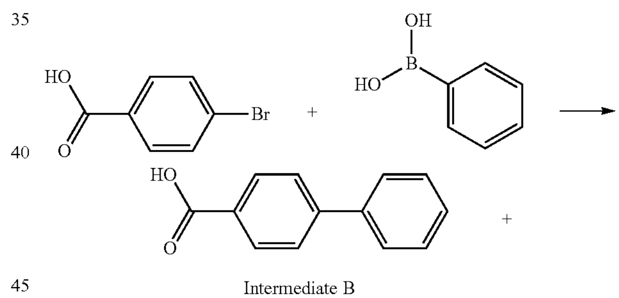

Intermediate B

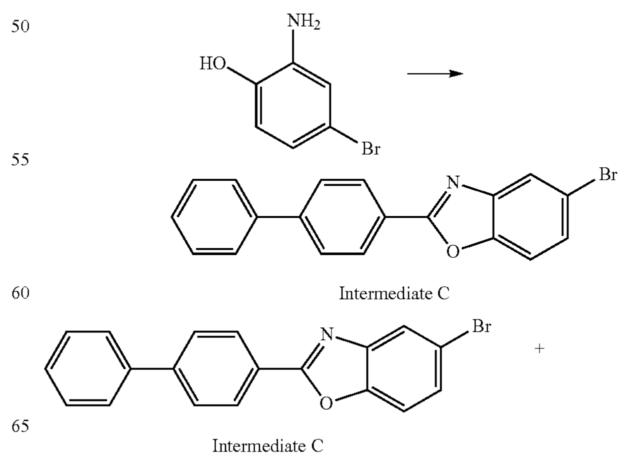

Intermediate C

Intermediate C

-continued

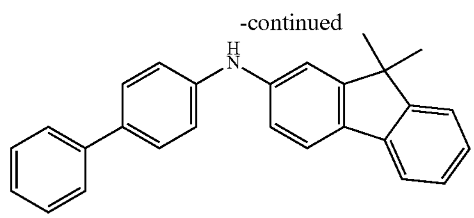

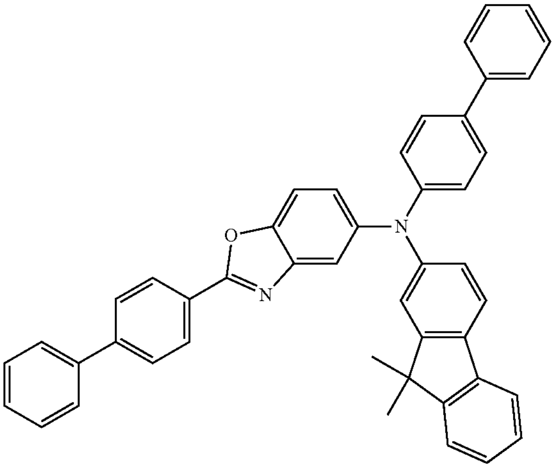

AZ43

Synthesis of Intermediate B 4-bromobenzoic acid(20 g, 0.099 mol), phenylboronic acid(14.6 g, 0.119 mol), tetrakis(triphenylphosphine)palladium(0) (2.3 g, 1.99 mmol), toluene 400 ml, and 4M $K_2CO_3$ (potassium carbonate) 100 ml were put in a round-bottom flask and stirred under reflux for 12 hours. After completion of the reaction, the reaction solution is separated into layers, the organic layer is recovered and concentrated under reduced pressure to obtain a crude product. The filtered crude was separated by column to obtain 17.7 g of intermediate B.

Synthesis of Intermediate C

An intermediate B (15 g, 0.076 mol), 2-amino-4-bromophenol (31.3 g, 0.166 mol), diisopropylethylamine(34.3 ml, 0.197 mol), 4M $K_2CO_3$ aqueous solution 75 ml, methylene chloride 350 ml are put in a round-bottom flask and stirred while reducing the temperature to 0° C. Deoxo-fluor reagent, 50% in THF (61.4 ml, 0.166 mol) diluted with 45 ml of MC is slowly added dropwise to the solution. After completion of the dropwise addition, the solution was stirred at 0° C. for 2 hours. The subsequent procedure was the same as that for the intermediate A and, as a result, 22.5 g of intermediate C was obtained.

Synthesis of AZ43

An intermediate C(5 g, 0.014 mol), 2-(4-Biphenylyl) amino-9,9-dimethylfluorene(6.2 g, 0.017 mol), instead of the intermediate A in the synthesis method for AZ3, palladium acetate(II) 0.06 g, 0.365 mmol), 2,2'-Bis(diphenylphosphino)-1,1'-binaphthyl (0.18 g, 0.365 mmol), sodium-t-butoxide (2.06 g, 0.021 mol), and toluene 100 ml are put and heated to 100° C. while being stirred for 8 hours. The reaction solution was hot filtered through silicagel to remove impurities, and the filtrate was concentrated under reduced pressure to obtain crude. After the obtained crude was purified by MC/acetone, 6.9 g of AZ43 was obtained.

Synthesis Method for AZ83

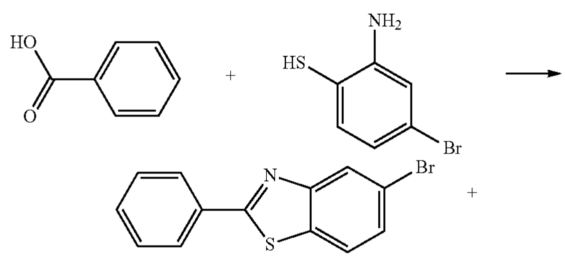

Intermediate D

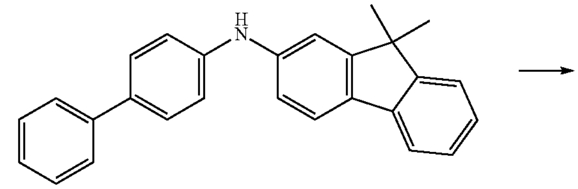

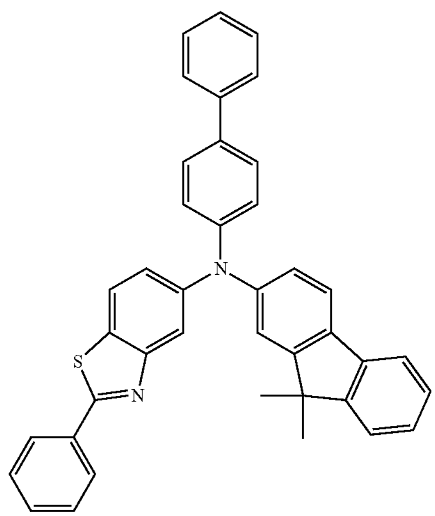

AZ83

Synthesis of Intermediate D

The same method as the synthesis method for the intermediate A except that 2-amino-4-bromobenzenethiol(36.8 g, 0.180 mol) was applied instead of 2-amino-4-bromophenol was performed and, as a result, 18.5 g of intermediate D was obtained.

Synthesis of AZ83

An intermediate D(5 g, 0.017 mol), 2-(4-Biphenylyl) amino-9,9-dimethylfluorene(7.5 g, 0.021 mol), instead of the intermediate A in the synthesis method for AZ3, palladium acetate(II) 0.08 g, 0.345 mmol), 2,2'-Bis(diphenylphosphino)-1,1'-binaphthyl (0.21 g, 0.345 mmol), sodium-t-butoxide (2.48 g, 0.026 mol), and toluene 100 ml are put and heated to 100° C. while being stirred for 8 hours.

The reaction solution was hot filtered through silicagel to remove impurities, and the filtrate was concentrated under reduced pressure to obtain crude. After the obtained crude was purified by MC/acetone, 6.7 g of AZ83 was obtained.

Synthesis of AZ92

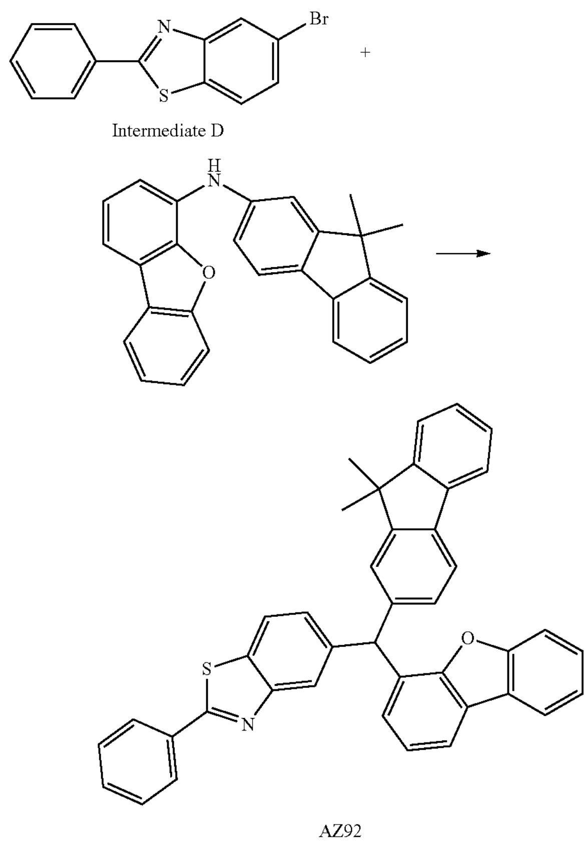

Intermediate D

AZ92

The synthesis was carried out in the same way as in the synthesis method for AZ3 except that 2-(4-dibenzofuranyl) amino-9,9-dimethylfluorene (7.8 g, 0.021 mol) was used instead of 2-(4-biphenylyl)amino-9,9-dimethylfluorene. As a result, 6.9 g of AZ92 was obtained.

Synthesis of AZ98

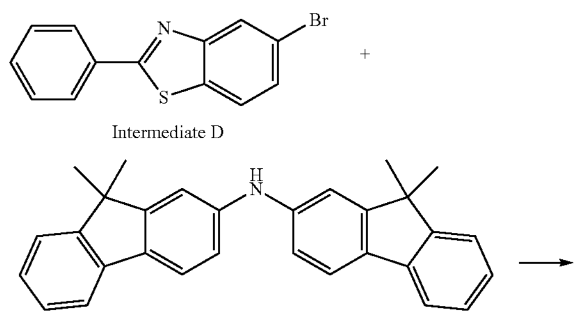

Intermediate D

-continued

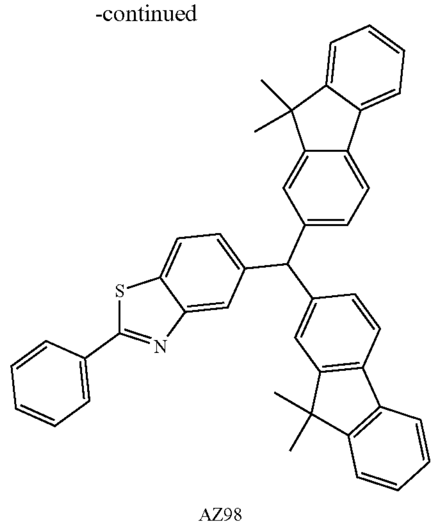

AZ98

The synthesis was carried out using the same reagents and the same dosage and same method as in the synthesis method for AZ83 that bis(9,9-dimethyl-9H-fluoren-2-yl) amine (8.8 g, 0.022 mol) was applied instead of 2-(4-biphenylyl)amino-9,9-dimethylfluorene and, as a result, 7.8 g of AZ98 was obtained.

Synthesis of AZ103

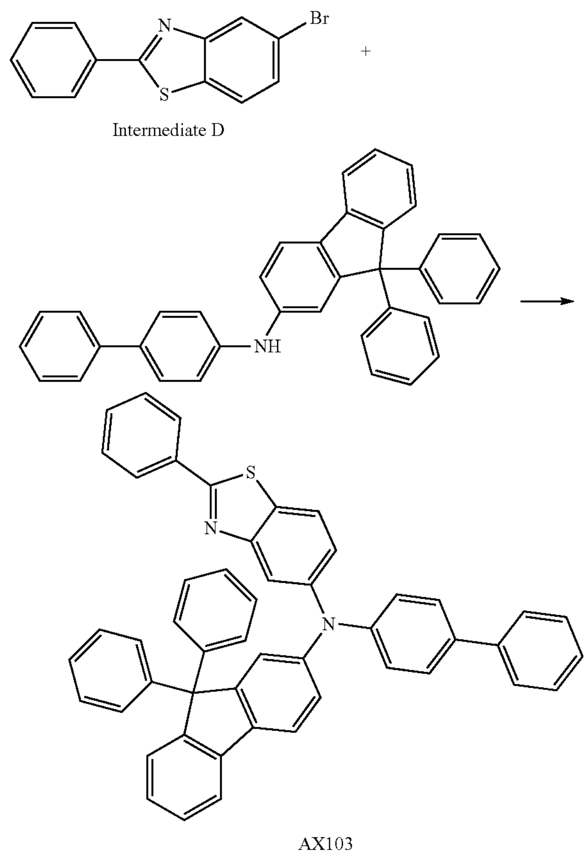

Intermediate D

AX103

The synthesis was carried out in the same way as in the synthesis method for AZ83 except that 2-(4-Biphenylyl)amino-9,9-diphenylfluorene (10.6 g, 0.022 mol) was used instead of 2-(4-biphenylyl)amino-9,9-dimethylfluorene. As a result, 9.0 g of AZ103 was obtained.

Synthesis Method for AK3

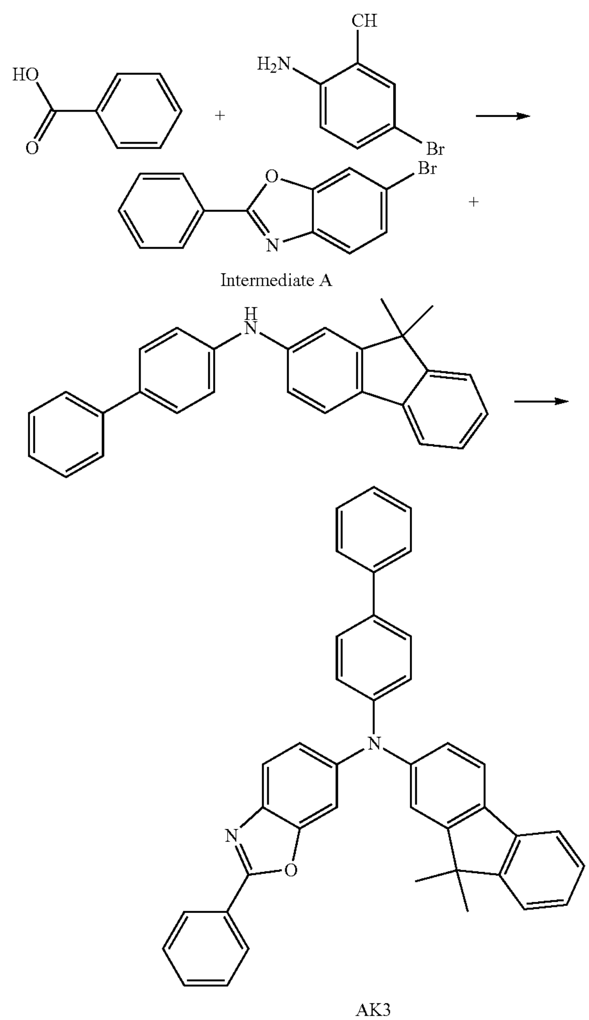

Intermediate A

AK3

Synthesis of Intermediate A

Benzoic acid (10 g, 0.082 mol), 2-amino-5-bromophenol (33.9 g, 0.180 mol), diisopropylethylamine(37.1 ml, 0.213 mol), 4M $K_2CO_3$ aqueous solution 80 ml, methylene chloride 300 ml are put in a round-bottom flask and stirred while reducing the temperature to 0° C. Deoxo-fluor reagent, 50% in THF (66.4 ml, 0.180 mol) diluted with 45 ml of MC is slowly added dropwise to the solution. After the dropwise addition is finished, the solution is stirred at 0° C. for 2 hours. After the reaction is finished by adding 150 ml of saturated aqueous sodium bicarbonate solution to the reaction solution, the solution is heated to room temperature. After the reaction solution is separated into layers to recover the organic layer, the organic layer was dried with MgSO4 and concentrated under reduced pressure. The concentrated crude was separated by column to obtain 18.4 g of intermediate A.

Synthesis of AK3

An intermediate A (5 g, 0.018 mol), 2-(4-biphenylyl)amino-9,9-dimethylfluorene(7.9 g, 0.022 mol), palladium acetate(II) 0.08 g, 0.365 mmol), 2,2'-Bis(diphenylphosphino)-1,1'-binaphthyl (0.23 g, 0.365 mmol), sodium-t-butoxide (2.63 g, 0.027 mol), and toluene 100 ml are put in a round-bottom flask and heated to 100° C. while being stirred for 8 hours. The reaction solution was hot filtered through silicagel to remove impurities, and the filtrate was concentrated under reduced pressure to obtain crude. After the obtained crude was purified by MC/acetone, 6.7 g of AK3 was obtained.

Synthesis of AK5

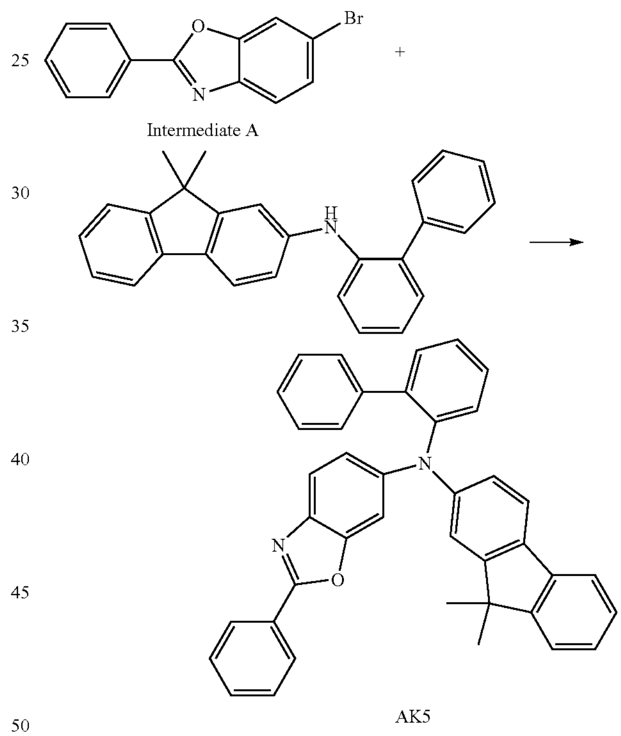

Intermediate A

AK5

The synthesis was carried out in the same way as in the synthesis method for AK3 except that 2-(2-biphenylyl)amino-9,9-dimethylfluorene (7.9 g, 0.022 mol) was used instead of 2-(4-biphenylyl)amino-9,9-dimethylfluorene. As a result, 6.6 g of AK5 was obtained.

Synthesis of AK10

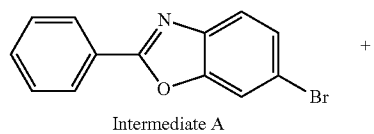

Intermediate A

-continued

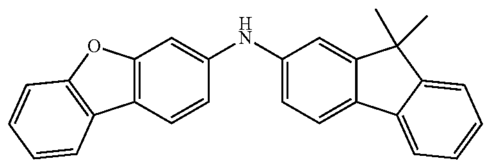

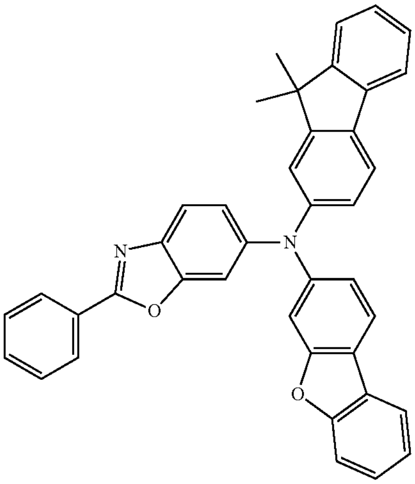

AK10

The synthesis was carried out in the same way as in the synthesis method for AK3 except that 2-(3-dibenzofuranyl) amino-9,9-dimethylfluorene (8.2 g, 0.022 mol) was used instead of 2-(4-biphenylyl)amino-9,9-dimethylfluorene. As a result, 6.9 g of AK10 was obtained.

Synthesis of AK11

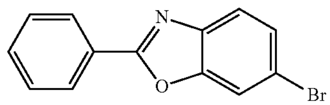

Intermediate A

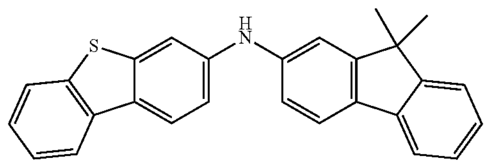

-continued

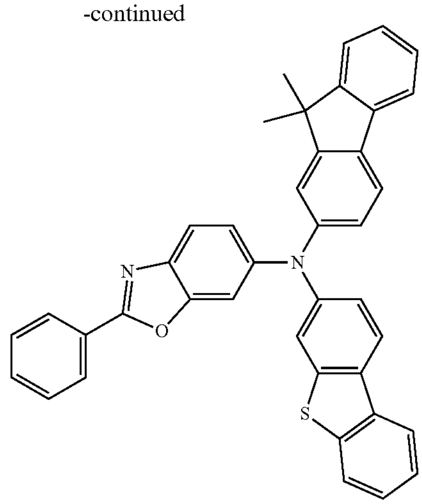

AK11

The synthesis was carried out in the same way as in the synthesis method for AK3 except that 2-(3-dibenzothiophenyl)amino-9,9-dimethylfluorene (8.6 g, 0.022 mol) was used instead of 2-(4-biphenylyl)amino-9,9-dimethylfluorene. As a result, 7.3 g of AK11 was obtained.

Synthesis of AK18

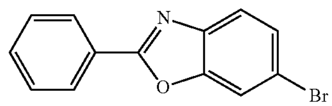

Intermediate A

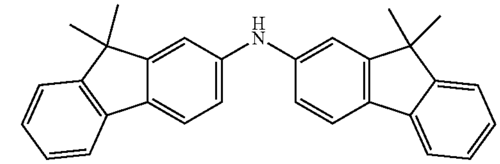

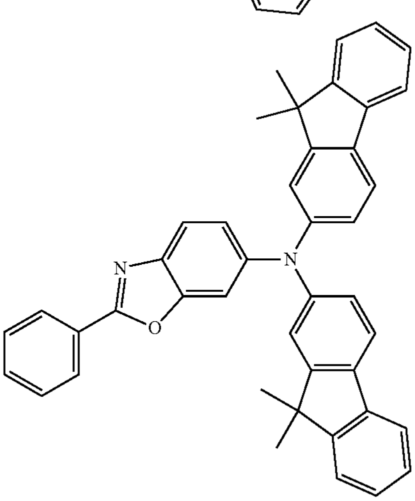

AK18

The synthesis was carried out using the same reagents and the same dosage and same method as in the synthesis method for AK3 that bis(9,9-dimethyl-9H-fluoren-2-yl)

amine (8.8 g, 0.022 mol) was applied instead of 2-(4-biphenylyl)amino-9,9-dimethylfluorene and, as a result, 7.5 g of AK18 was obtained.

Synthesis of AK20

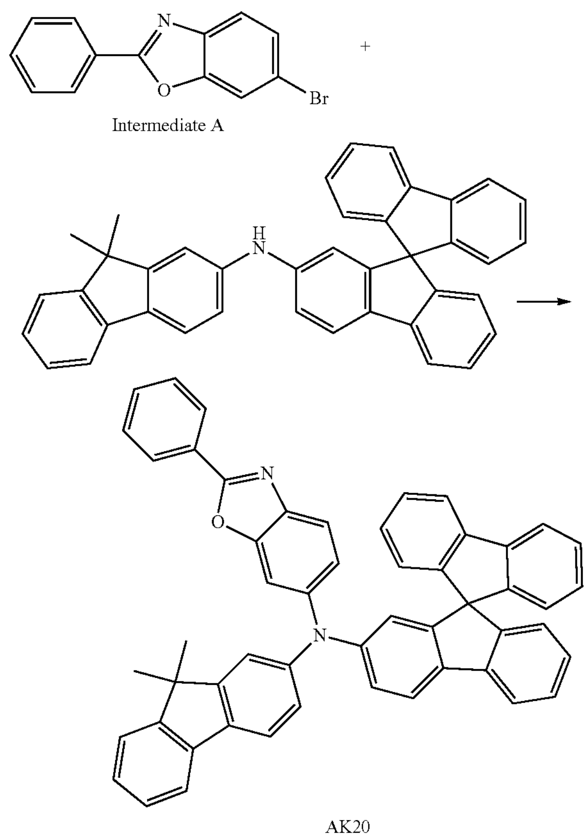

Intermediate A

AK20

The synthesis was carried out in the same way as in the synthesis method for AK3 except that (9,9-dimethylfluo-rene-2-yl)-9,9-spirobifluorene-2-amine(11.5 g, 0.022 mol) was used instead of 2-(4-biphenylyl)amino-9,9-dimethyl-fluorene. As a result, 9.1 g of AK20 was obtained.

Synthesis of AK23

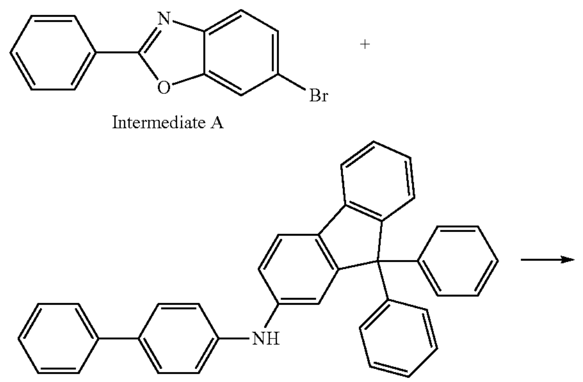

Intermediate A

-continued

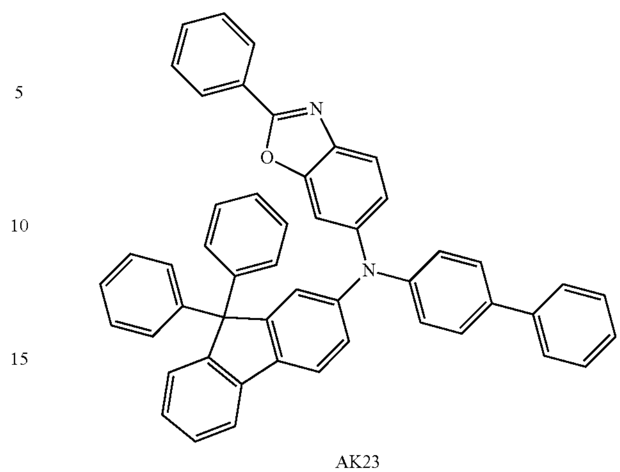

AK23

The synthesis was carried out in the same way as in the synthesis method for AK3 except that 2-(4-Biphenylyl) amino-9,9-diphenylfluorene (10.6 g, 0.022 mol) was used instead of 2-(4-biphenylyl)amino-9,9-dimethylfluorene. As a result, 8.7 g of AK23 was obtained.

Synthesis Method for AK43

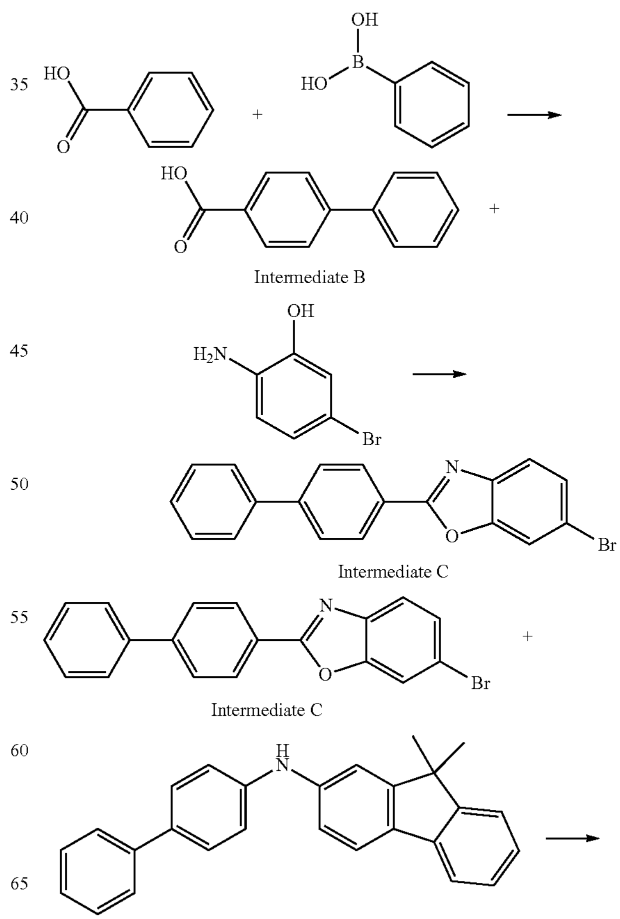

Intermediate B

Intermediate C

Intermediate C

-continued

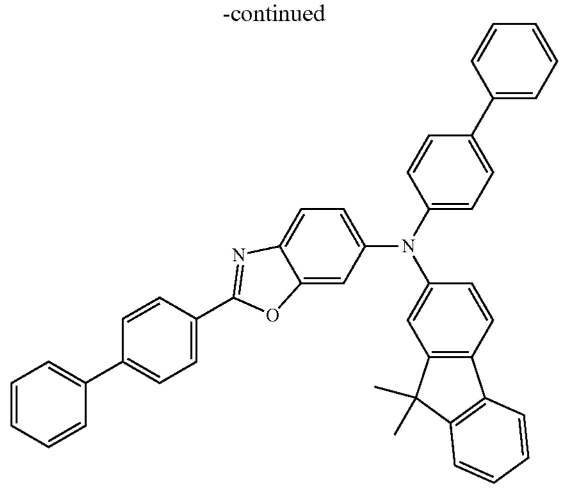

AK43

Synthesis of Intermediate B 4-bromobenzoic acid(20 g, 0.099 mol), phenylboronic acid(14.6 g, 0.119 mol), tetrakis(triphenylphosphine)palladium(0) (2.3 g, 1.99 mmol), toluene 400 ml, and 4M $K_2CO_3$ (potassium carbonate) 100 ml were put in a round-bottom flask and stirred under reflux for 12 hours. After completion of the reaction, the reaction solution is separated into layers, the organic layer is recovered and concentrated under reduced pressure to obtain a crude product. The filtered crude was separated by column to obtain 17.7 g of intermediate B.

Synthesis of Intermediate C

An intermediate B (15 g, 0.076 mol), 2-amino-5-bromophenol (31.3 g, 0.166 mol), diisopropylethylamine(34.3 ml, 0.197 mol), 4M K2CO3 aqueous solution 75 ml, methylene chloride 350 ml are put in a round-bottom flask and stirred while reducing the temperature to 0° C. Deoxo-fluor reagent, 50% in THF (61.4 ml, 0.166 mol) diluted with 45 ml of MC is slowly added dropwise to the solution. After completion of the dropwise addition, the solution was stirred at 0° C. for 2 hours. The subsequent procedure was the same as that for the intermediate A and, as a result, 22.2 g of intermediate C was obtained.

Synthesis of AK43

An intermediate C(5 g, 0.014 mol), 2-(4-Biphenylyl) amino-9,9-dimethylfluorene(6.2 g, 0.017 mol), instead of the intermediate A in the synthesis method for AK3, palladium acetate(II) 0.06 g, 0.365 mmol), 2,2'-Bis(diphenylphosphino)-1,1'-binaphthyl (0.18 g, 0.365 mmol), sodium-t-butoxide (2.06 g, 0.021 mol), and toluene 100 ml are put and heated to 100° C. while being stirred for 8 hours. The reaction solution was hot filtered through silicagel to remove impurities, and the filtrate was concentrated under reduced pressure to obtain crude. After the obtained crude was purified by MC/acetone, 6.7 g of AK43 was obtained.

Synthesis Method for AK83

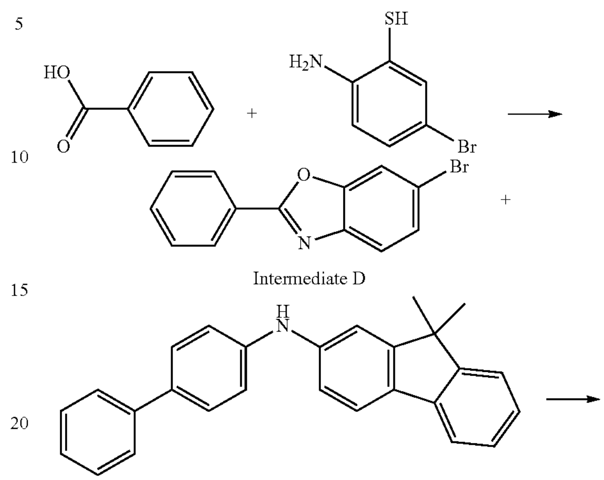

Intermediate D

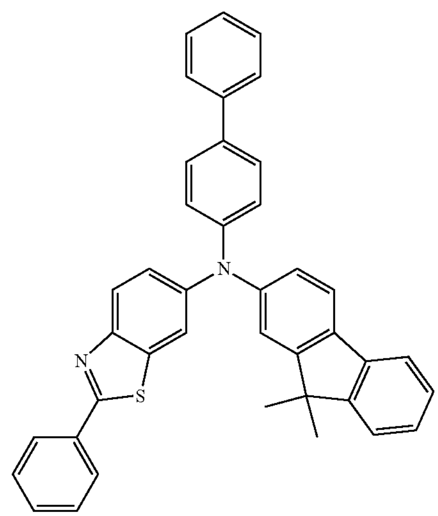

AK83

Synthesis of Intermediate D

The same method as the synthesis method for the intermediate A except that 2-amino-4-bromobenzenethiol(36.8 g, 0.180 mol) was applied instead of 2-amino-4-bromophenol was performed and, as a result, 18.5 g of intermediate D was obtained.

Synthesis of AK83

An intermediate D(5 g, 0.017 mol), 2-(4-Biphenylyl) amino-9,9-dimethylfluorene(7.5 g, 0.021 mol), instead of the intermediate A in the synthesis method for AK3, palladium acetate(II) 0.08 g, 0.345 mmol), 2,2'-Bis(diphenylphosphino)-1,1'-binaphthyl (0.21 g, 0.345 mmol), sodium-t-butoxide (2.48 g, 0.026 mol), and toluene 100 ml are put and heated to 100° C. while being stirred for 8 hours.

The reaction solution was hot filtered through silicagel to remove impurities, and the filtrate was concentrated under reduced pressure to obtain crude. After the obtained crude was purified by MC/acetone, 6.7 g of AK83 was obtained.

Synthesis of AK92

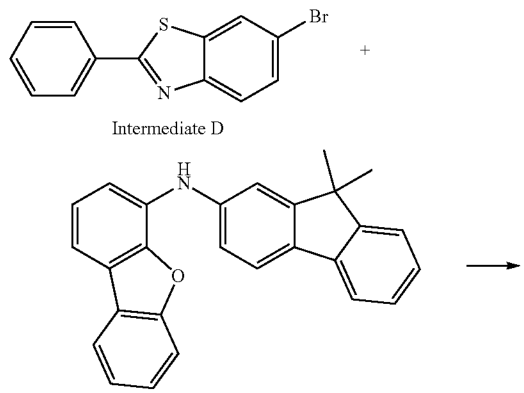

Intermediate D

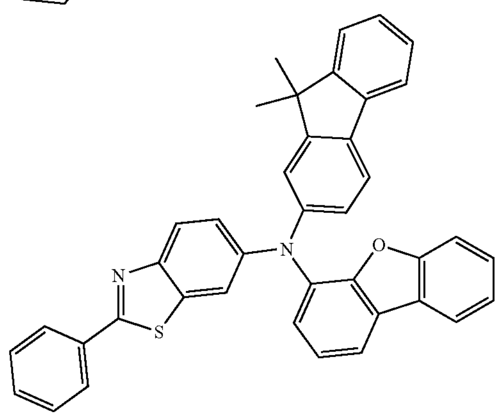

AK92

The synthesis was carried out in the same way as in the synthesis method for AK83 except that 2-(4-dibenzofuranyl) amino-9,9-dimethylfluorene (7.8 g, 0.021 mol) was used instead of 2-(4-biphenylyl)amino-9,9-dimethylfluorene. As a result, 7.0 g of AK92 was obtained.

Synthesis of AK98

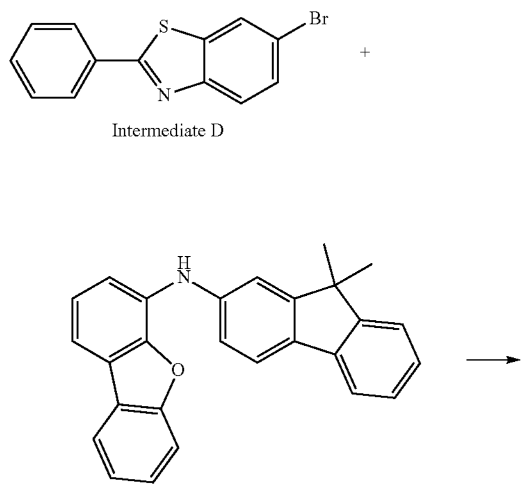

Intermediate D

-continued

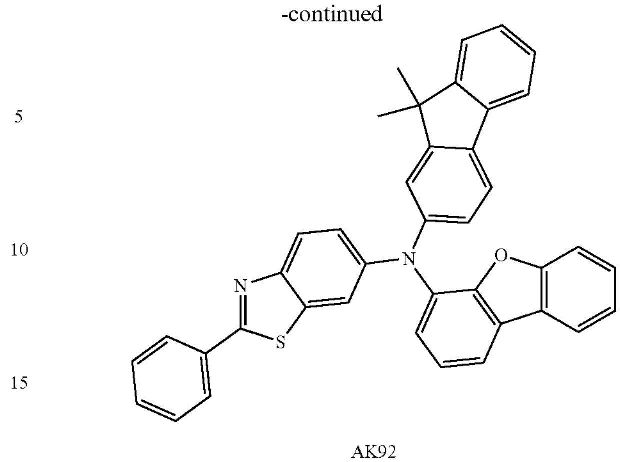

AK92

The synthesis was carried out using the same reagents and the same dosage and same method as in the synthesis method for AK83 that bis(9,9-dimethyl-9H-fluoren-2-yl) amine (8.8 g, 0.022 mol) was applied instead of 2-(4-biphenylyl)amino-9,9-dimethylfluorene and, as a result, 7.8 g of AK98 was obtained.

Synthesis of AK103

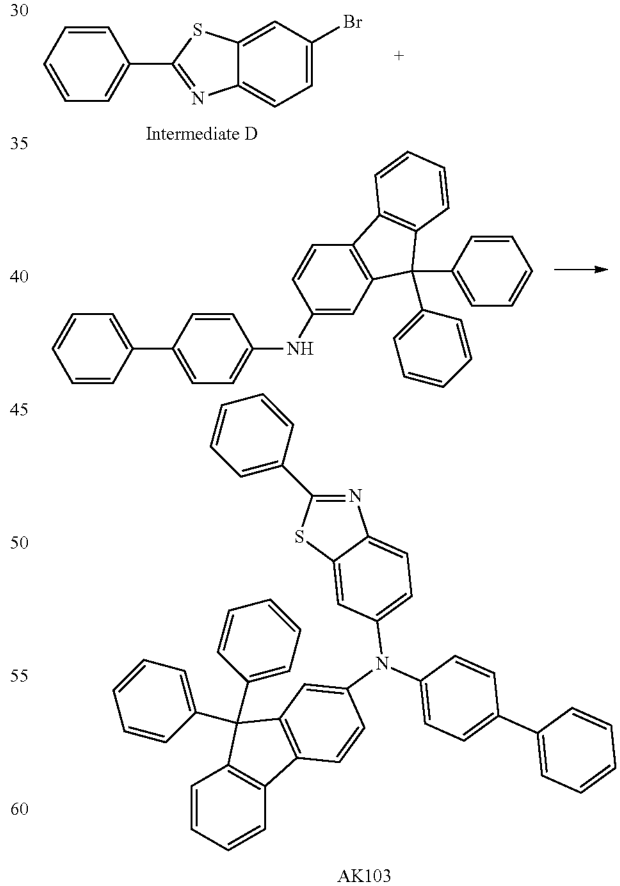

Intermediate D

AK103

The synthesis was carried out in the same way as in the synthesis method for AK83 except that 2-(4-Biphenylyl) amino-9,9-diphenylfluorene (10.6 g, 0.022 mol) was used instead of 2-(4-biphenylyl)amino-9,9-dimethylfluorene. As a result, 9.0 g of AK103 was obtained.

Manufacturing Evaluation of Organic Light Emitting Element

Comparison Example 1

An anode, a hole injection layer, a hole transport layer, a light emitting layer, an electron transport layer, an electron injection layer, and a cathode were formed on a substrate to manufacture an organic light emitting element having a mono structure as shown in Table 1 below. All the properties of the organic light emitting element manufactured in the disclosure were evaluated at room temperature using a constant current source and a photometer.

TABLE 1

| Components | Materials |
|---|---|
| anode | ITO (Indium tin oxide) |
| hole injection layer | HI1 |
| hole transport layer | HT1 |
| light emitting layer | EM1, EM2, EM3 |
| electron transport layer | ET1 |
| electron injection layer | LiF |
| cathode | Al |

The compounds used in the comparative examples are as follows.

HI1

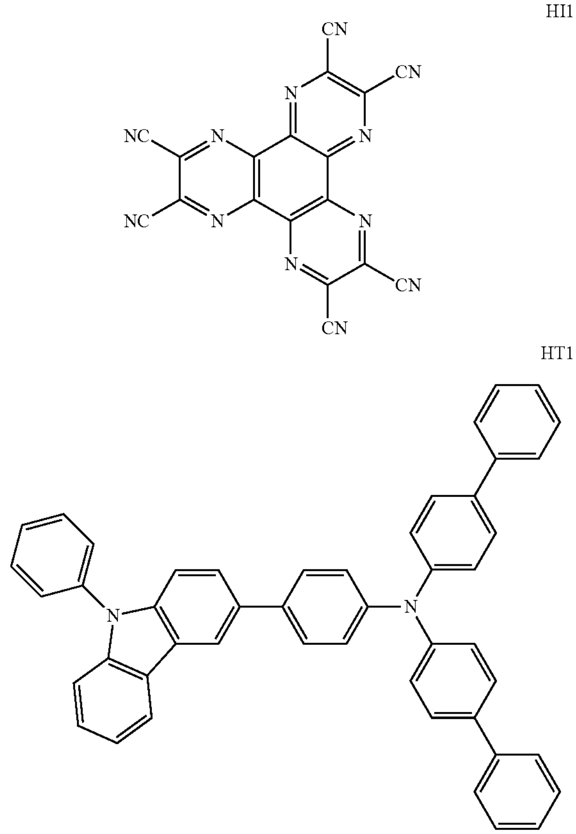

HT1

-continued

EM1

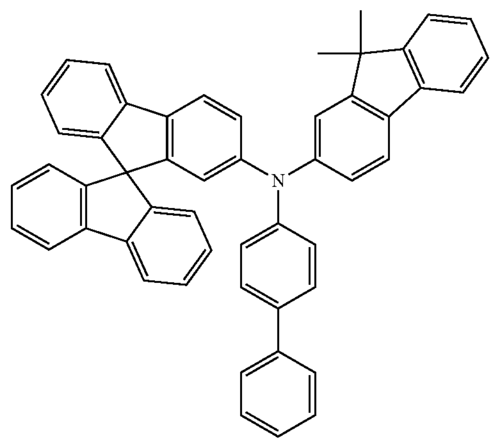

EM2

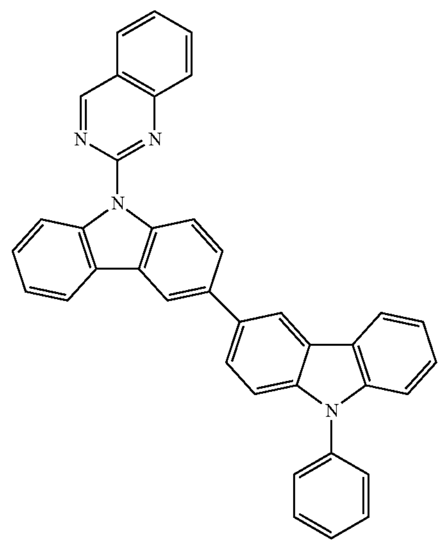

EM3

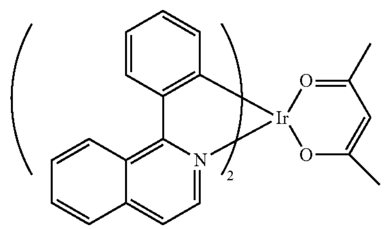

-continued

ET1

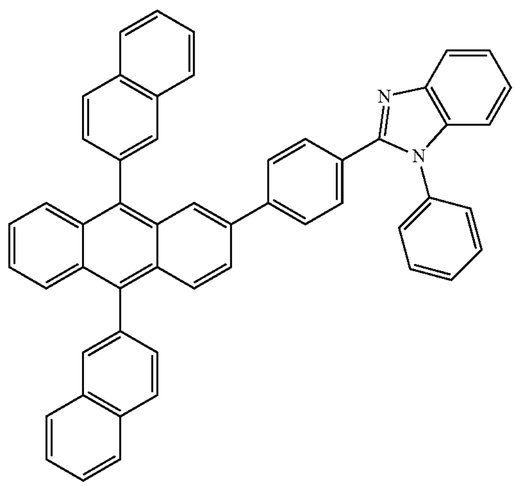

Comparative Example 2 and Embodiments 1 to 16

The organic light emitting element was manufactured in the same manner as in comparative example 1 except that the materials shown in Table 2 below were used instead of EM2 of the light emitting layer. The compound used in comparative example 2 is as follows.

CF1

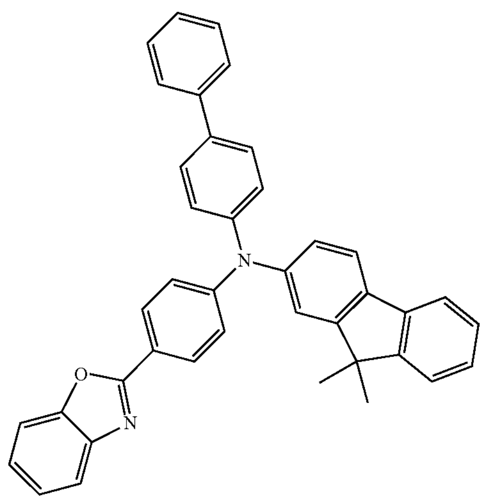

TABLE 2

| | light emitting layer material | voltage difference | efficiency (embodiment/ comparative example 1, %) | lifespan (embodiment/ comparative example 1, %) |
|---|---|---|---|---|
| Comparison example 1 | EM2 | — | — | — |
| comparison example 2 | CF1 | 0.18 | 98% | 98% |
| embodiment 1 | AZ3 | −0.14 | 112% | 105% |
| embodiment 2 | AZ5 | −0.12 | 112% | 108% |
| embodiment 3 | AZ10 | −0.23 | 116% | 110% |
| embodiment 4 | AZ11 | −0.20 | 118% | 108% |
| embodiment 5 | AZ18 | −0.32 | 104% | 102% |
| embodiment 6 | AZ2 0 | −0.20 | 104% | 105% |
| embodiment 7 | AZ23 | −0.18 | 113% | 110% |
| embodiment 8 | AZ4 3 | −0.12 | 111% | 108% |
| embodiment 9 | AZ83 | −0.10 | 112% | 105% |
| embodiment 10 | AZ92 | −0.14 | 115% | 106% |
| embodiment 11 | AZ98 | −0.28 | 104% | 101% |
| embodiment 12 | AZ103 | −0.16 | 113% | 107% |

Referring to Table 2, it may be seen that the organic light emitting element according to embodiments of the disclosure has better efficiency or lifespan than the organic light emitting elements of the comparative examples.

In comparative example 1, EM2 was used as the light emitting layer host compound. It may be seen that the embodiments using compounds including a core represented by chemical formula 1 have better efficiency and lifespan than comparative example 1.

In comparative example 2, CF1 was used as the light emitting layer host compound. CF1 differs from the compound represented by chemical formula 1 in that benzoxazole is linked to the nitrogen of the amine through a phenylene group. It may be seen that the embodiments using compounds represented by chemical formula 1, in which benzoxazole is directly bonded to the nitrogen of the amine, have better efficiency and lifespan than comparative example 2.

It will be apparent to those skilled in the art that various modifications and variations can be made in the organic light emitting element of the present disclosure without departing from the technical idea or scope of the disclosure. Thus, it is intended that the present disclosure cover the modifications and variations of this disclosure provided they come within the scope of the appended claims and their equivalents.

What is claimed is:

1. An organic light emitting element, comprising:

a first electrode;

a second electrode; and an organic material layer positioned between the first electrode and the second electrode, wherein the organic material layer includes a compound represented by chemical formula 1 below:

[Chemical formula 1]

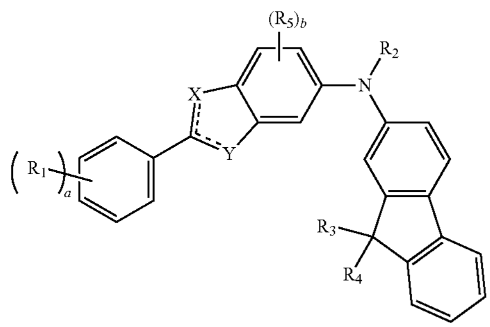

in chemical formula 1, either X or Y is N, and the other is S or O, wherein a is an integer from 0 to 5, $R_1$ is each independently selected from the group consisting of a $C_1$-$C_{20}$ alkyl group; a $C_3$-$C_{30}$ cycloalkyl group; an aryloxy group; an arylthioxy group; a fluorenyl group; and a $C_6$-$C_{60}$ aryl group, $R_2$ is selected from the group consisting of a $C_3$-$C_{30}$ cycloalkyl group; an aryloxy group; an arylthioxy group; a fluorenyl group; and a $C_6$-$C_{60}$ aryl group, $R_3$ and $R_4$ are each independently selected from the group consisting of i) a $C_1$-$C_{20}$ alkyl group; and a $C_6$-$C_{60}$ aryl group; or are bonded to each other to form a ring, b is an integer from 0 to 3, $R_5$ is each independently a $C_6$-$C_{60}$ aryl group, and the alkyl group, cycloalkyl group, aryloxy group, arylthioxy group, fluorenyl group and aryl group each are further substituted with one or more substituents selected from the group consisting of a halogen group; a $C_1$-$C_{20}$ alkyl group; a $C_2$-$C_{20}$ alkenyl group; a $C_2$-$C_{20}$ alkynyl group; a fluorenyl group; a $C_6$-$C_{20}$ aryl group; and a $C_2$-$C_{20}$ heterocyclic group, wherein the organic material layer includes a light emitting layer, wherein the light emitting layer includes the compound, wherein the compound is a host compound of the light emitting layer, and wherein the light emitting layer further includes a host compound different from the compound.

2. The organic light emitting element of claim 1, wherein the compound represented by chemical formula 1 is represented by either chemical formula 1a or chemical formula 1b below:

[Chemical formula 1a]

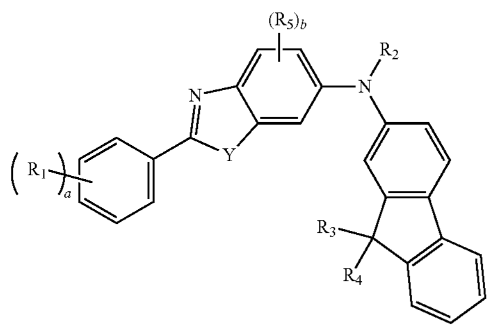

-continued

[Chemical formula 1b]

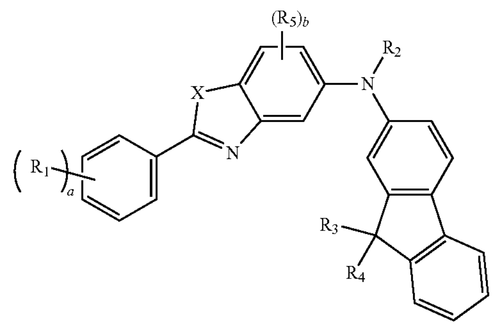

in chemical formula 1a and chemical formula 1b, X and Y each are S or O, and $R_1$, $R_2$, $R_3$, $R_4$, $R_5$, a and b are the same as those defined above in chemical formula 1.

3. The organic light emitting element of claim 1, wherein the compound represented by chemical formula 1 is one or more of compounds below:

AZ1

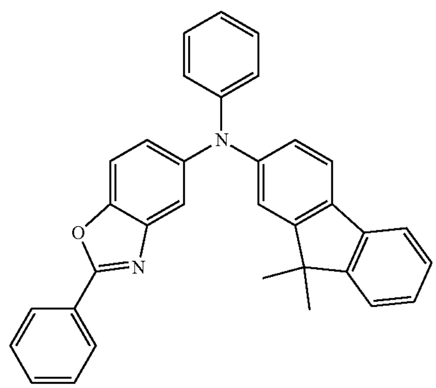

AZ2

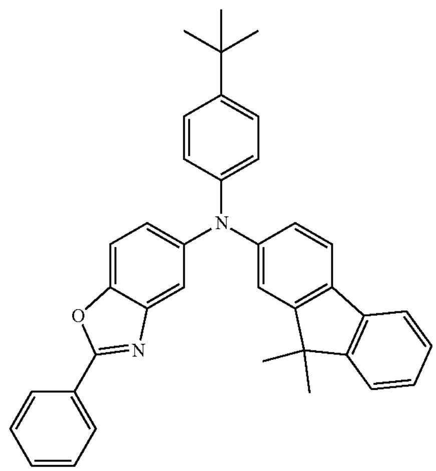

-continued
AZ3
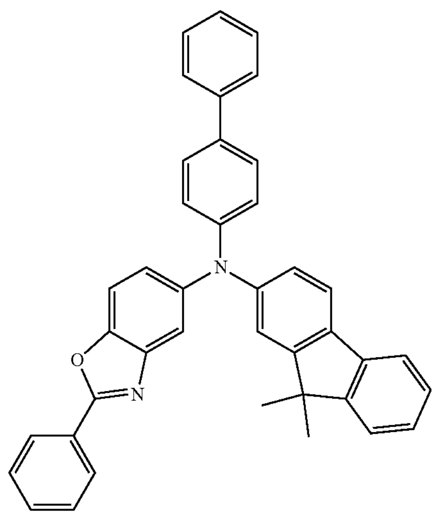
AZ4
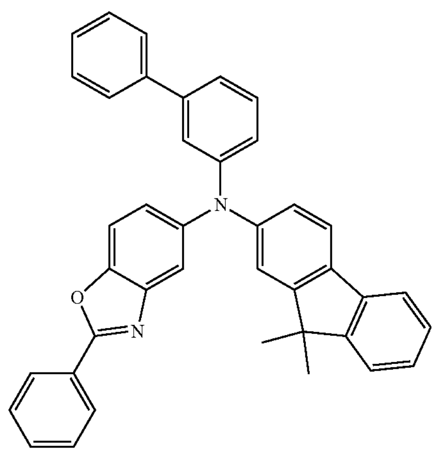
AZ5
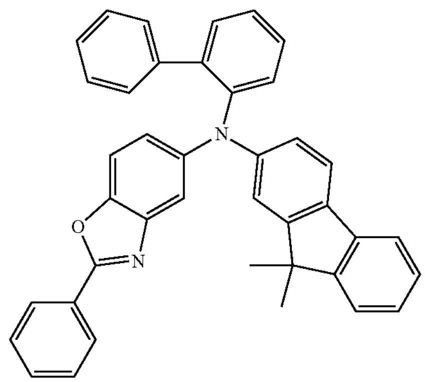
-continued
AZ6
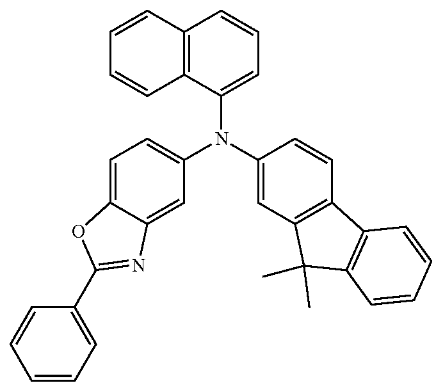
AZ7
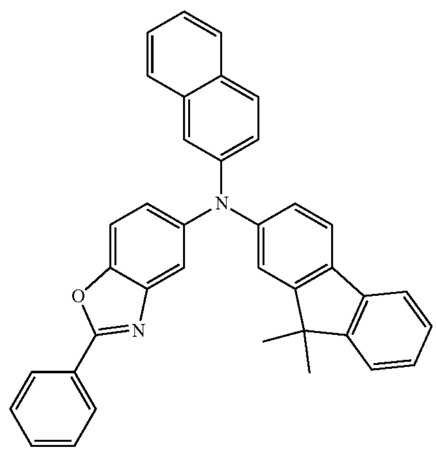
AZ8
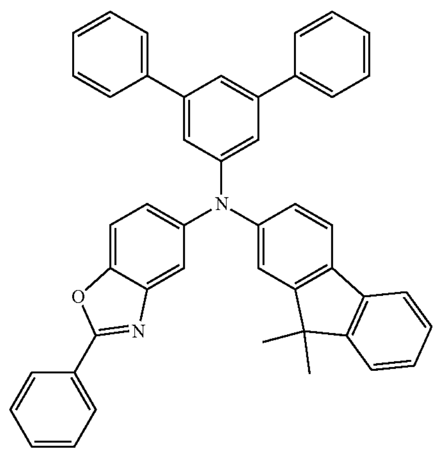

-continued
AZ9
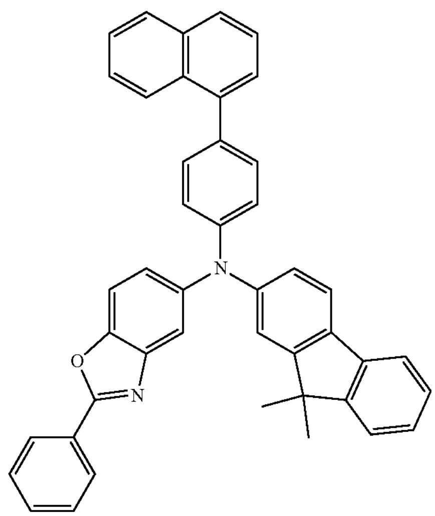
AZ10
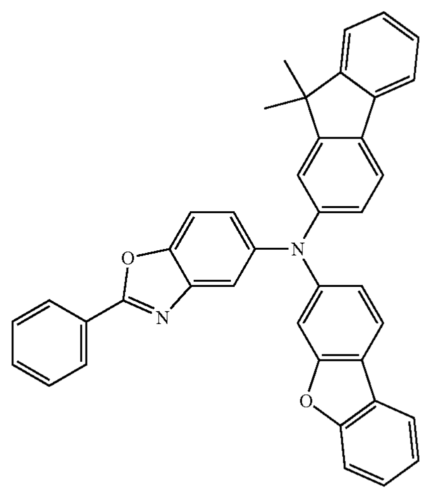
AZ11
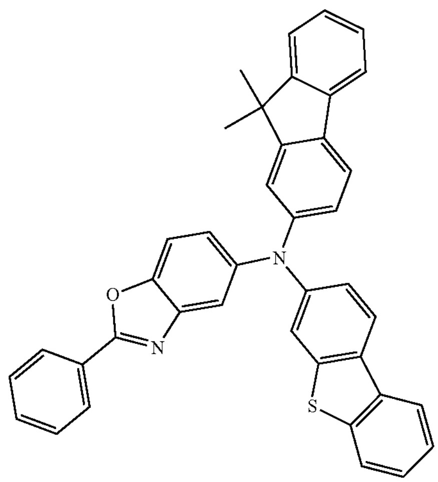
-continued
AZ12
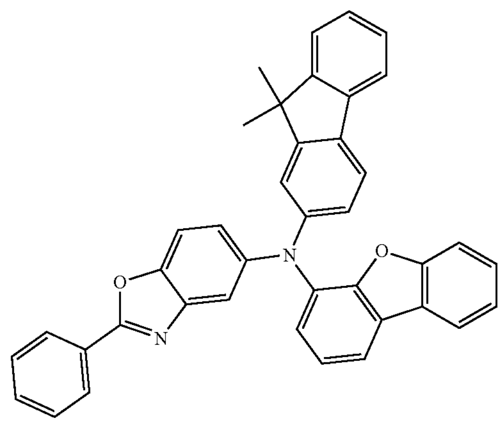
AZ13
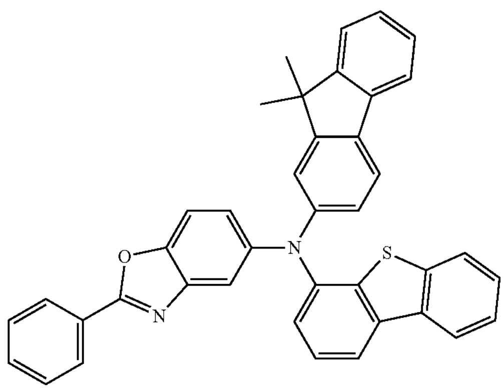
AZ14
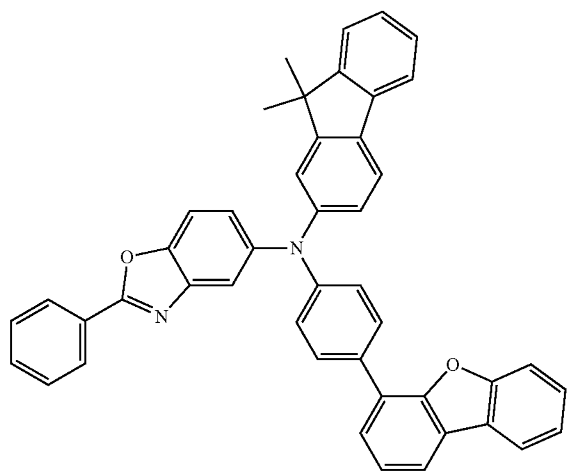

-continued
AZ15
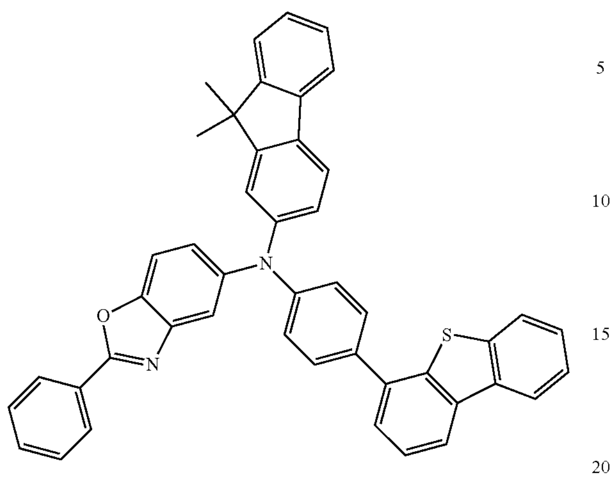
AZ16
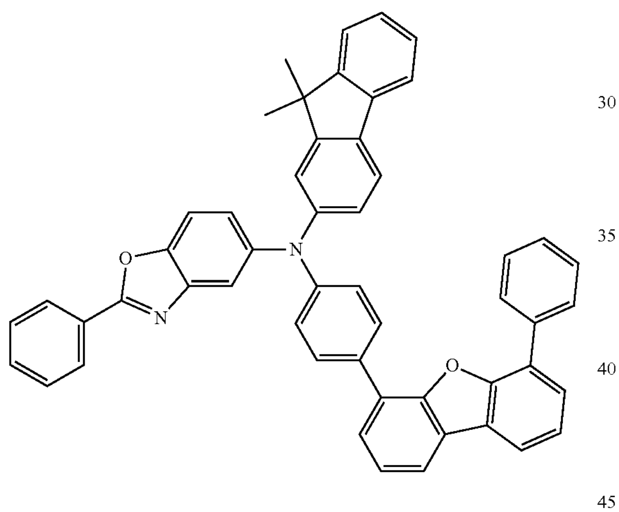
AZ17
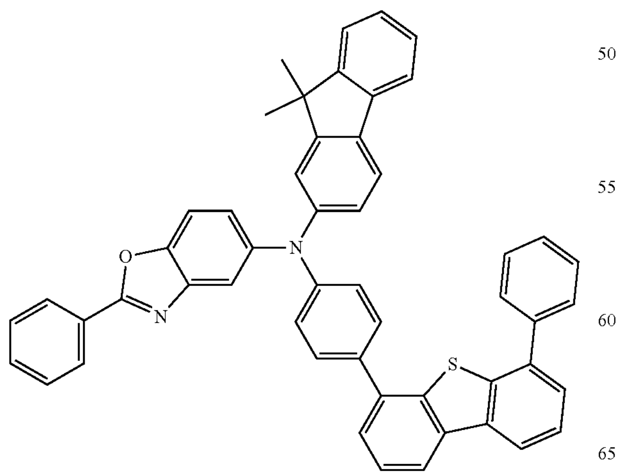
-continued
AZ18
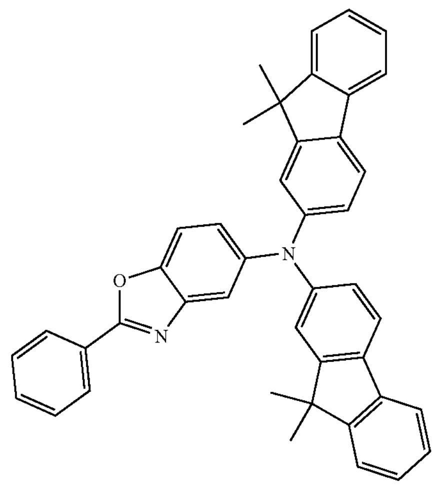
AZ19
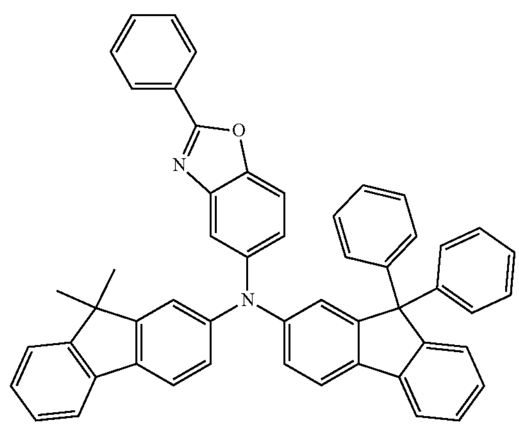
AZ20
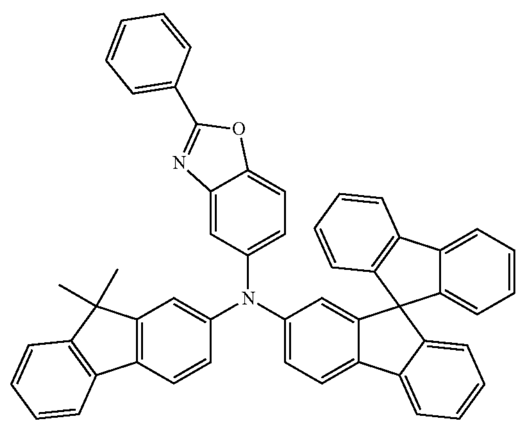

-continued
AZ21
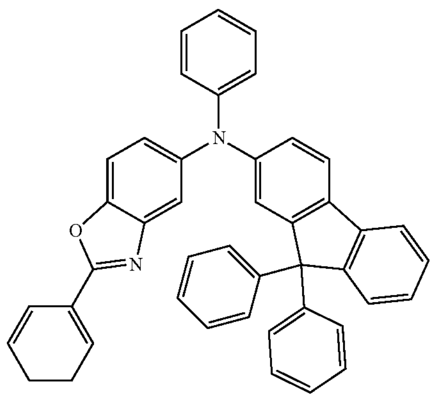
AZ22
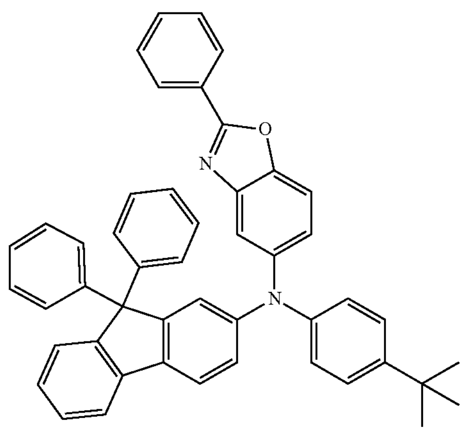
AZ23
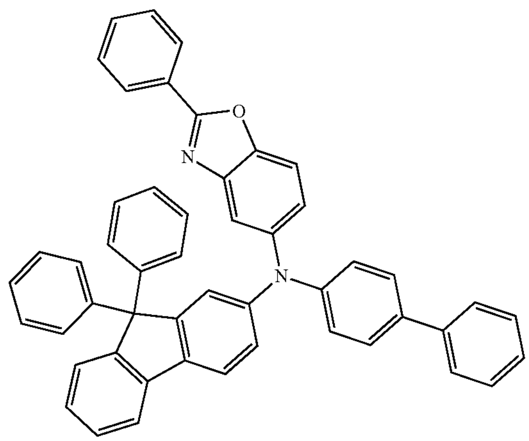
-continued
AZ24
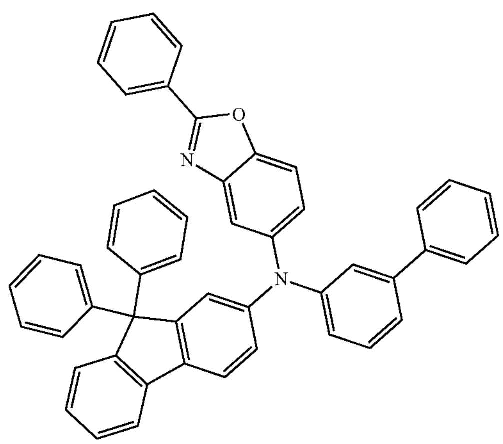
AZ25
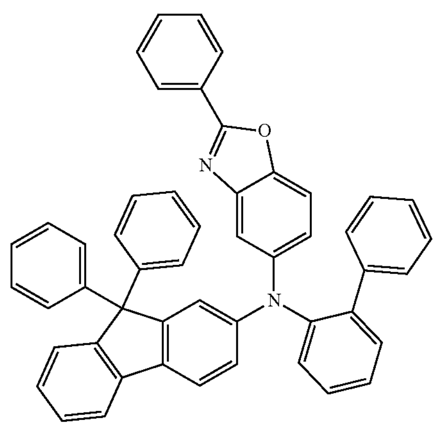
AZ26
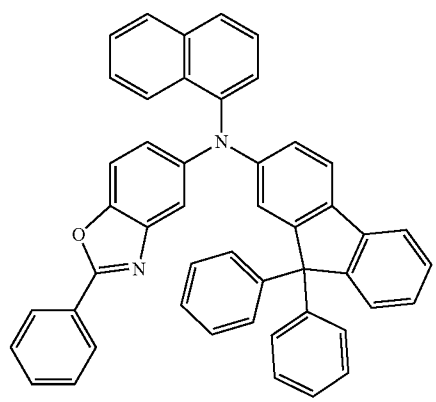

-continued
AZ27
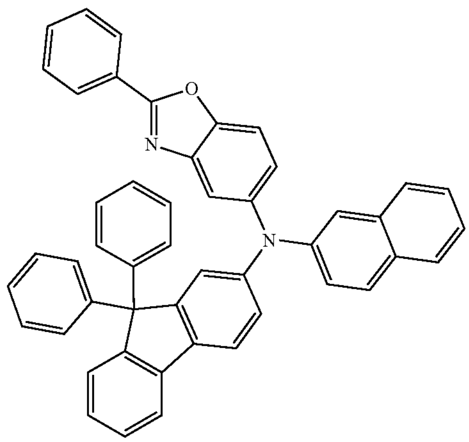
AZ28
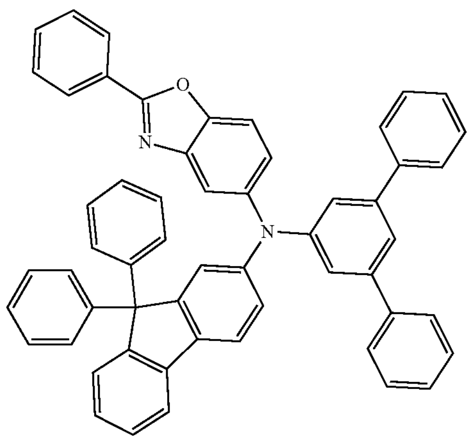
AZ29
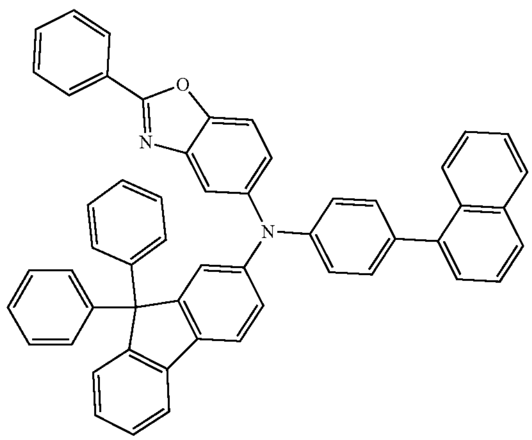
-continued
AZ30
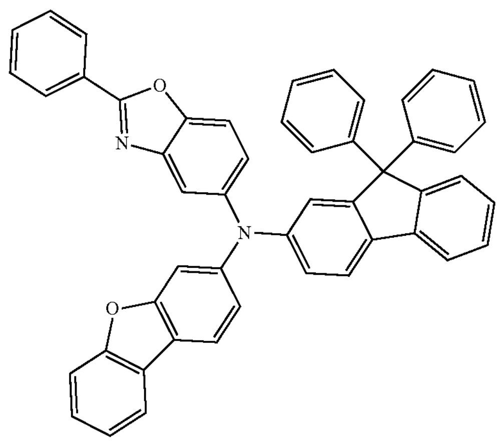
AZ31
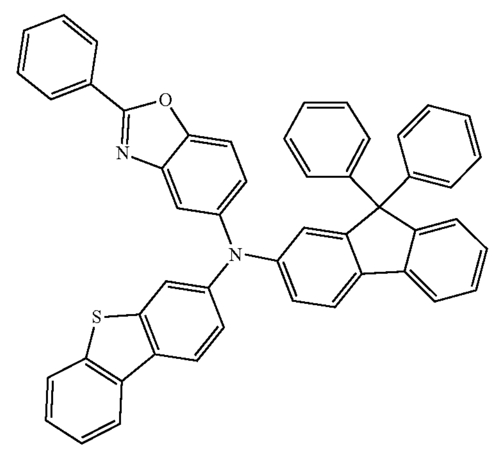
AZ32
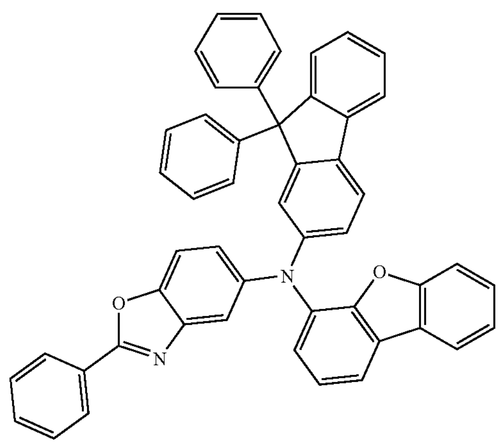

-continued
AZ33
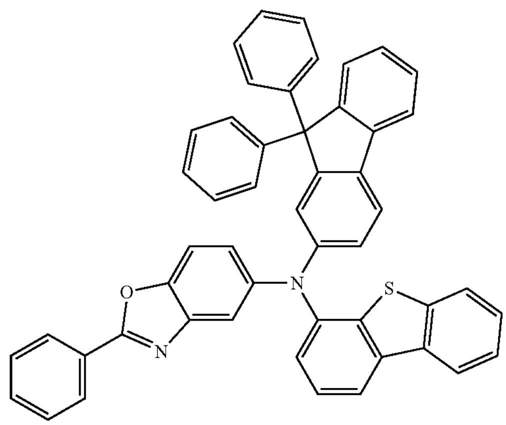
AZ34
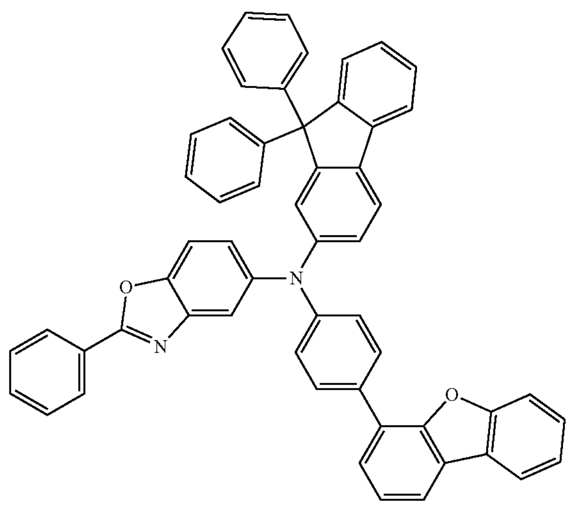
AZ35
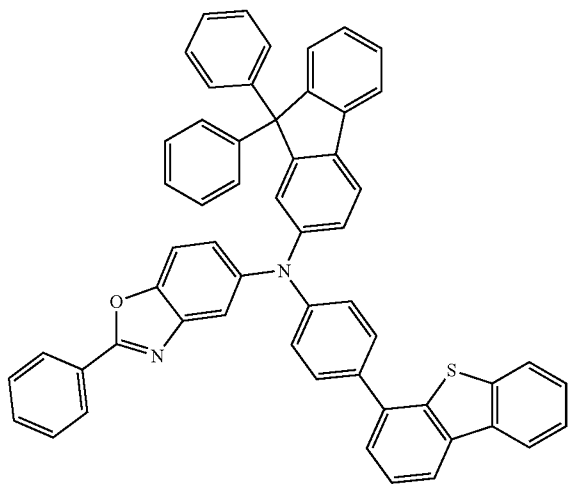
-continued
AZ36
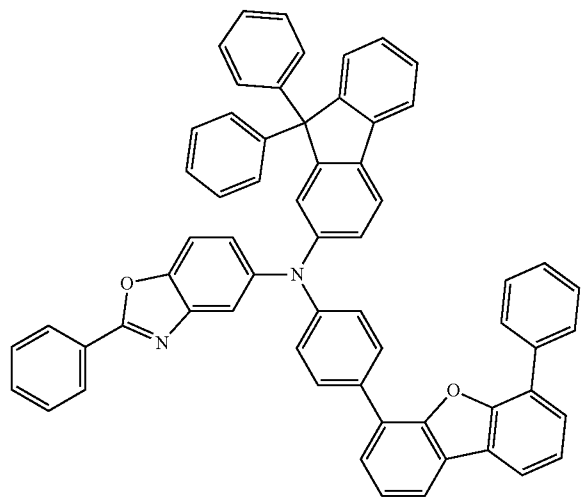
AZ37
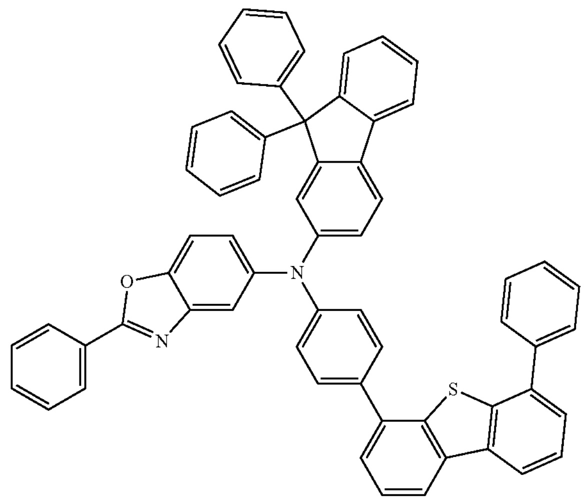
AZ38
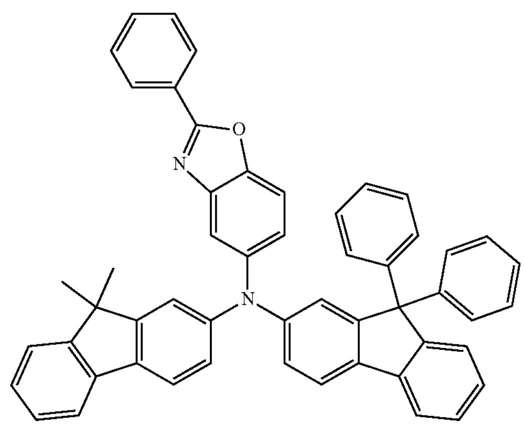

-continued
AZ39
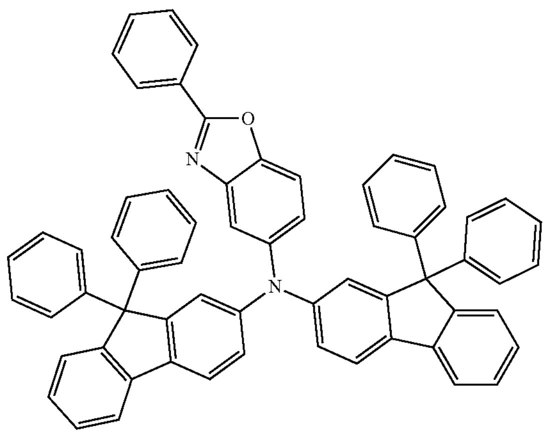
AZ40
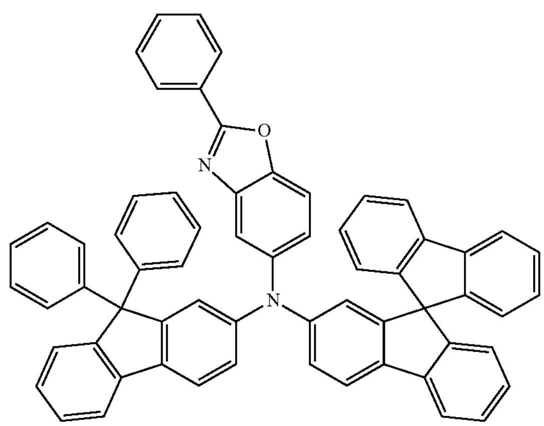
AZ41
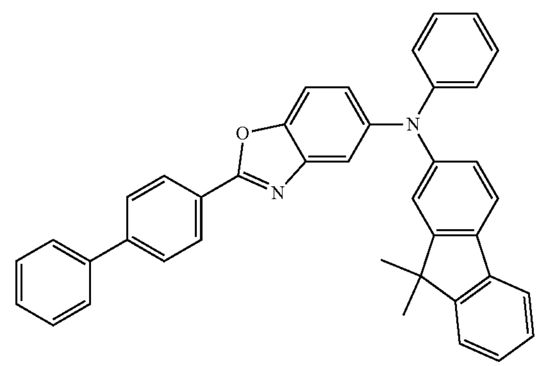
-continued
AZ42
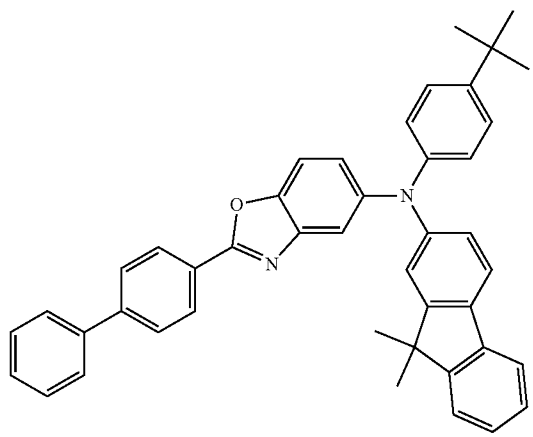
AZ43
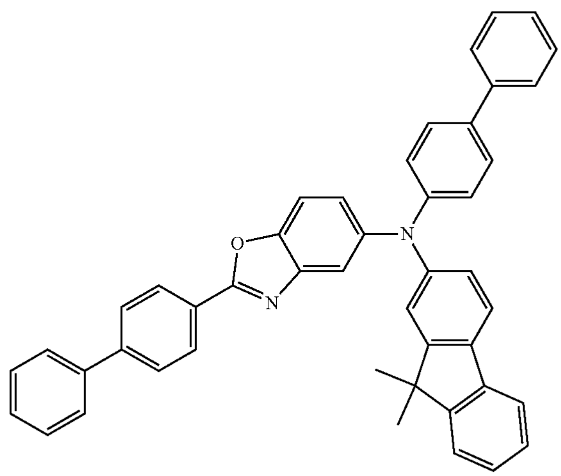
AZ44
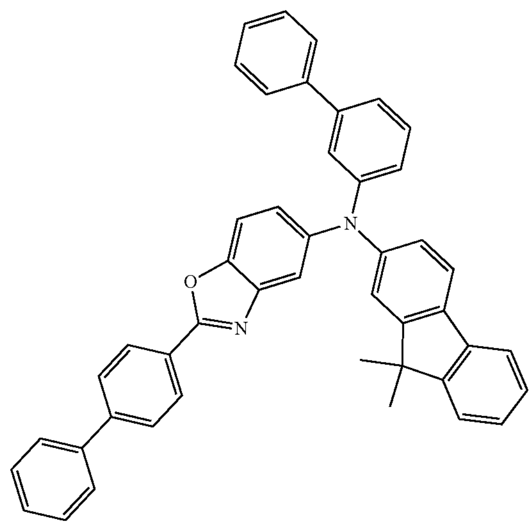

-continued
AZ45
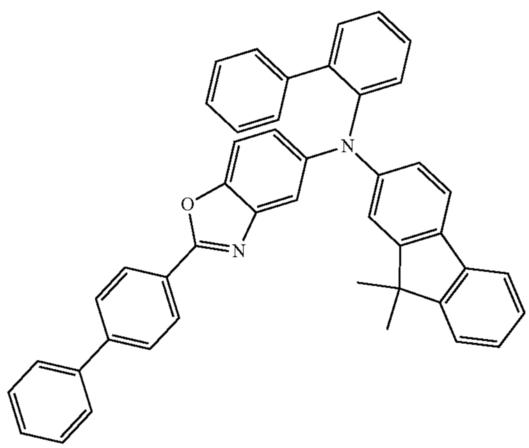
AZ46
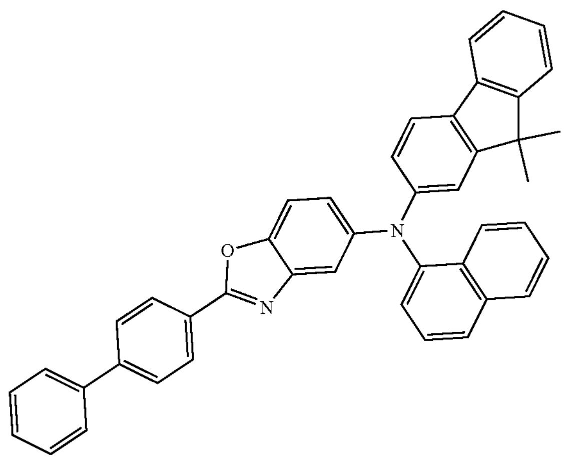
AZ47
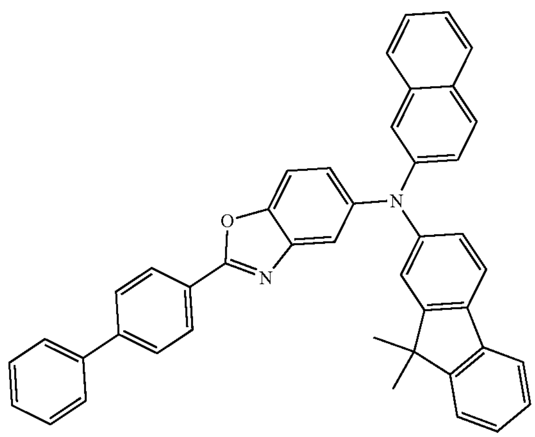
-continued
AZ48
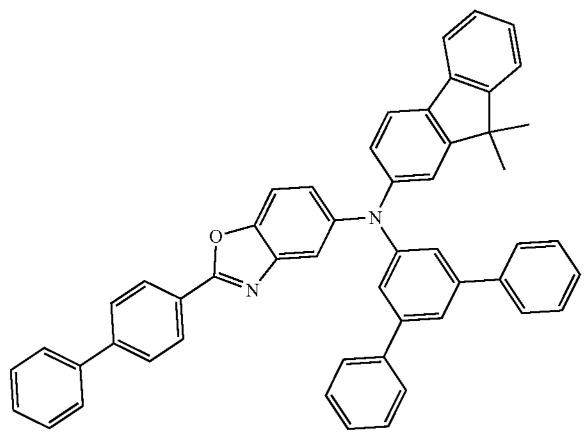
AZ49
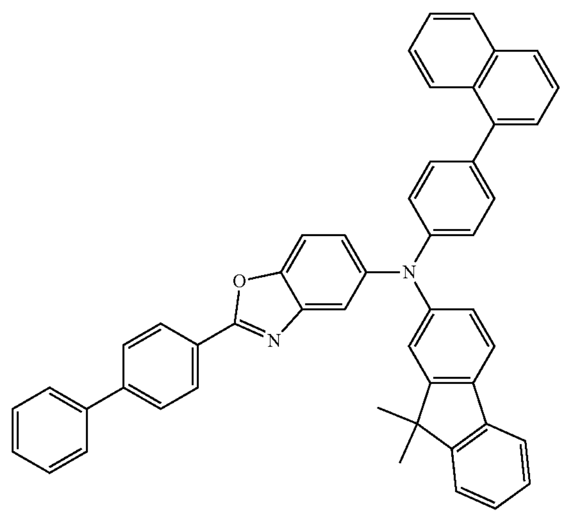
AZ50
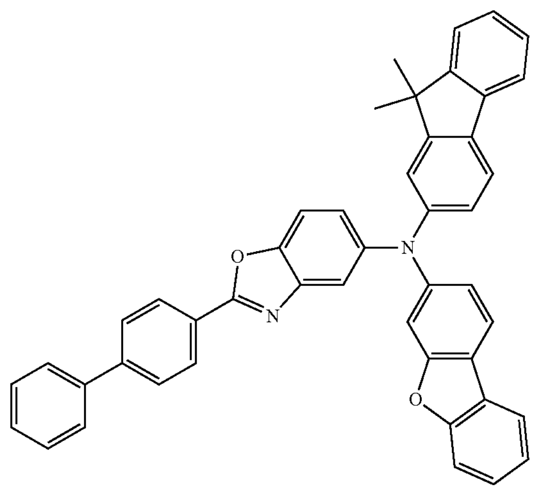

-continued
AZ51
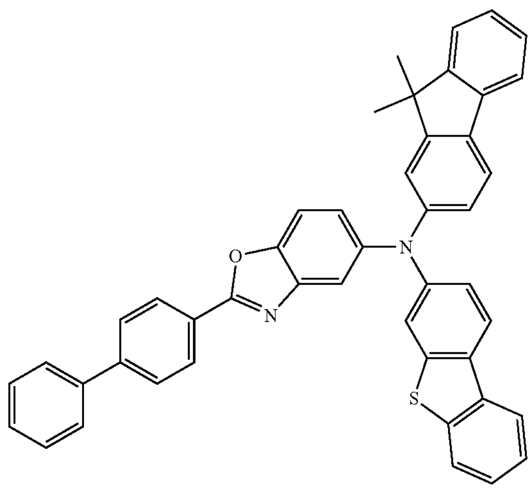
AZ52
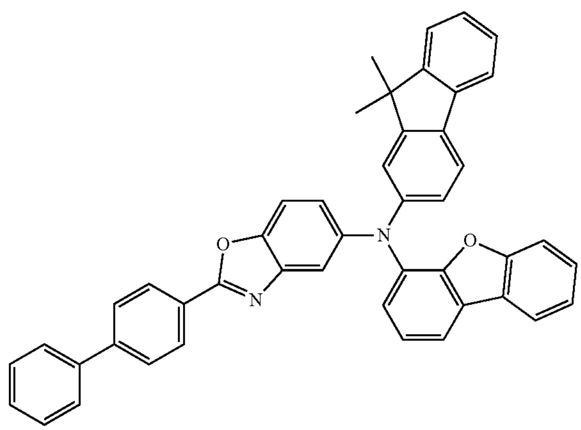
AZ53
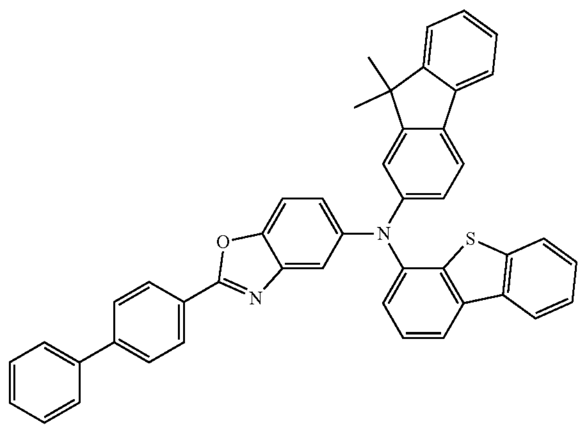
-continued
AZ54
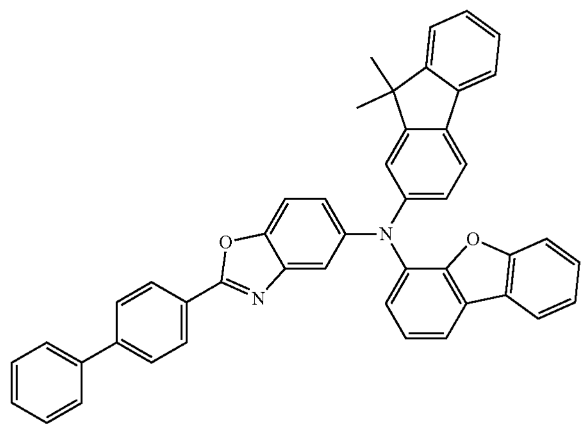
AZ55
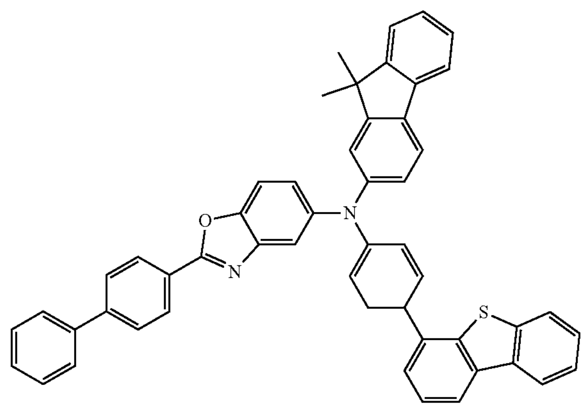
AZ56
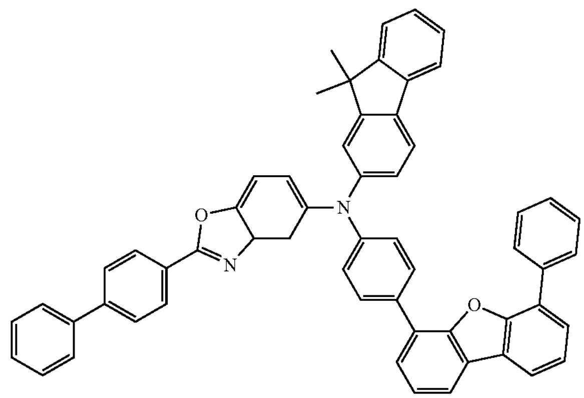

-continued
AZ57
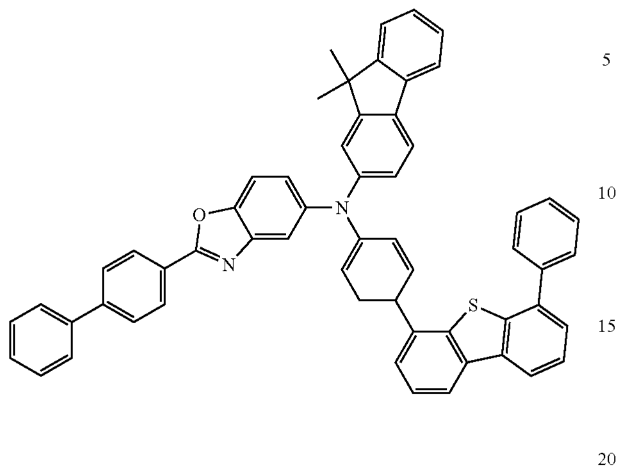
AZ58
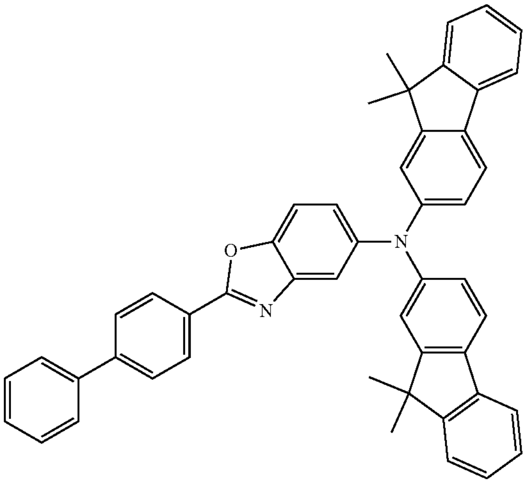
AZ59
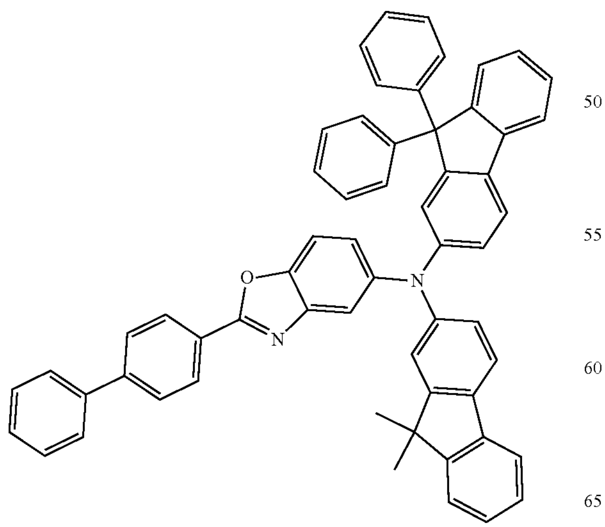
-continued
AZ60
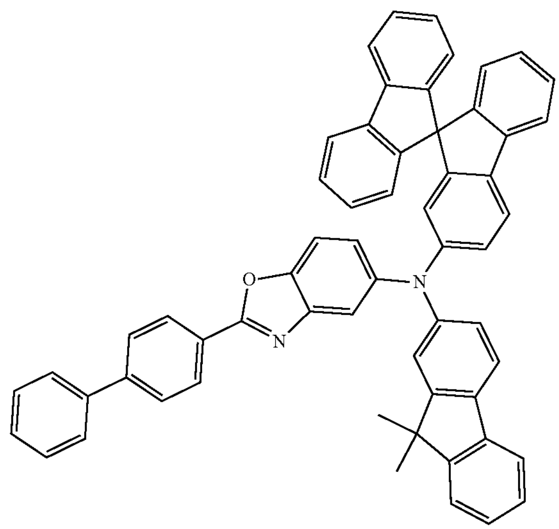
AZ61
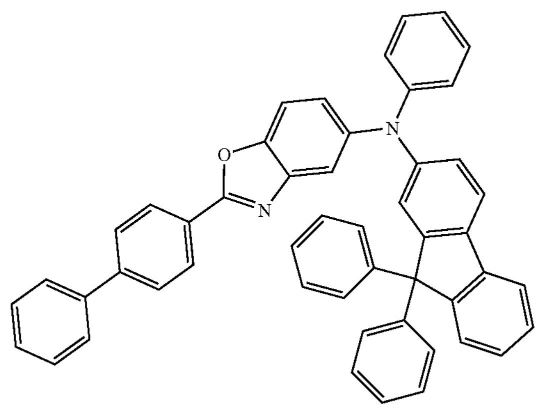
AZ62
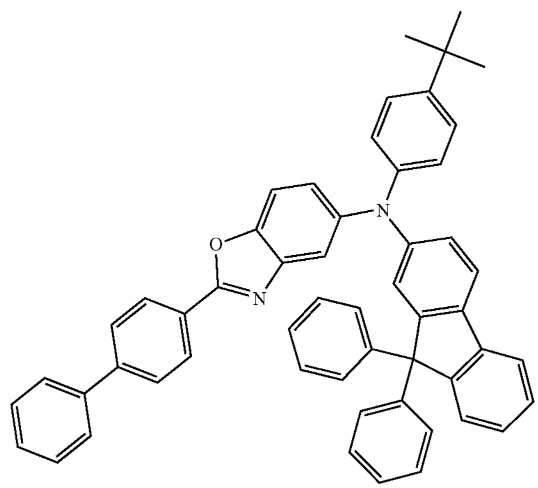

-continued
AZ63
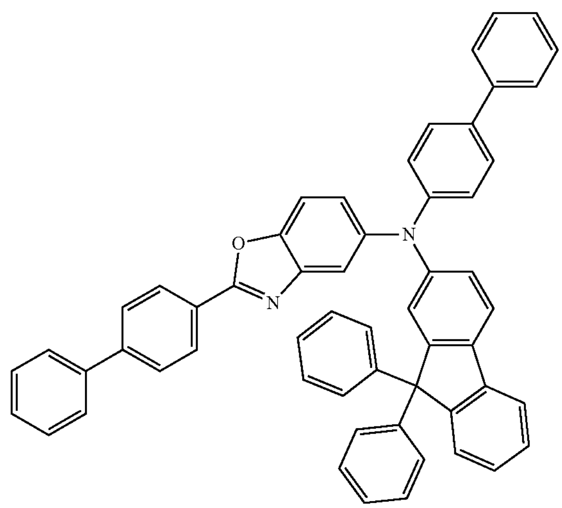
AZ64
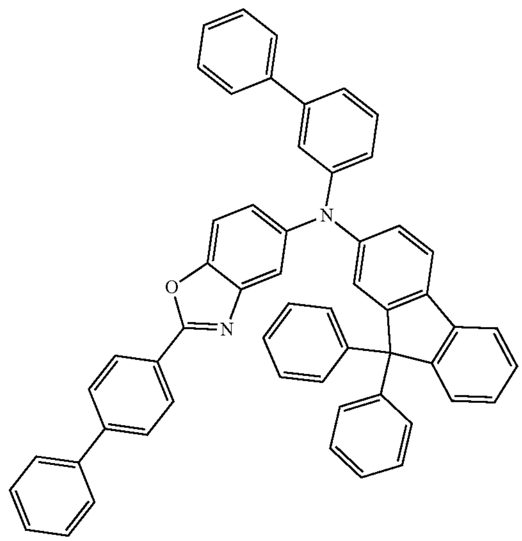
AZ65
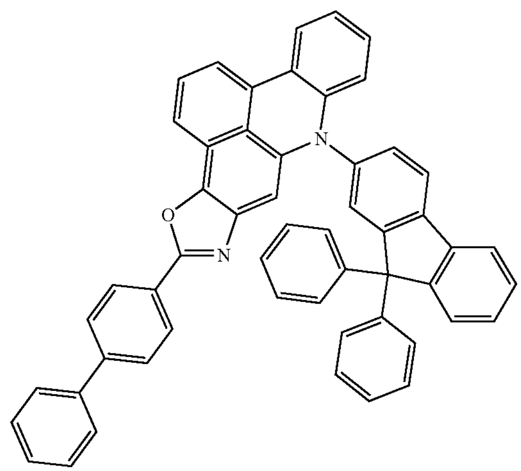
-continued
AZ66
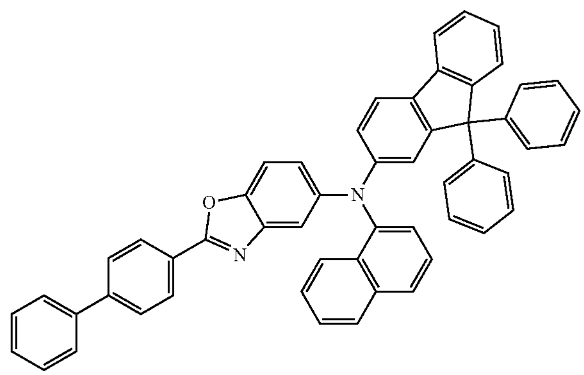
AZ67
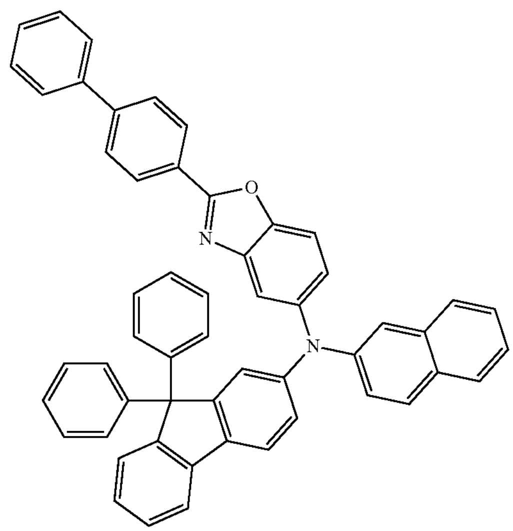
AZ68
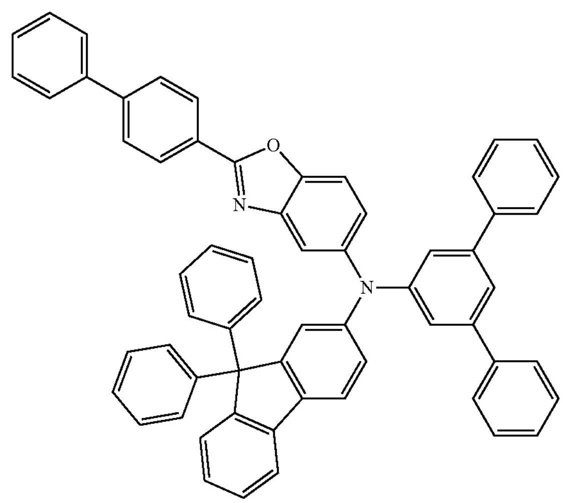

-continued
AZ69
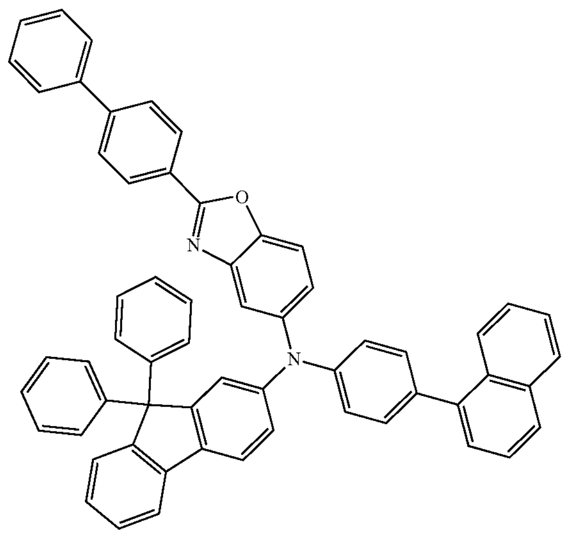
AZ70
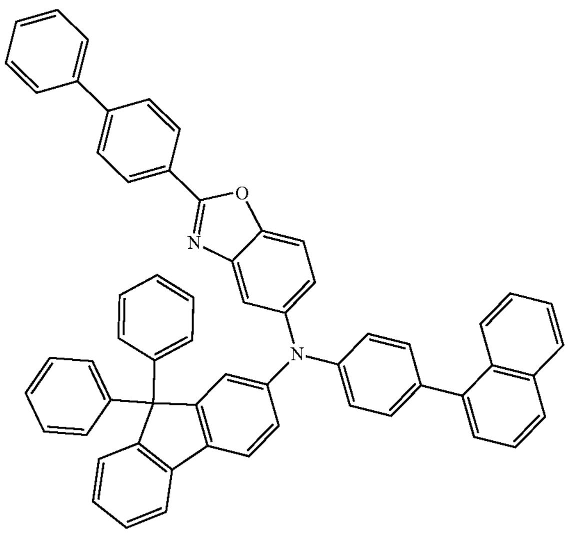
AZ71
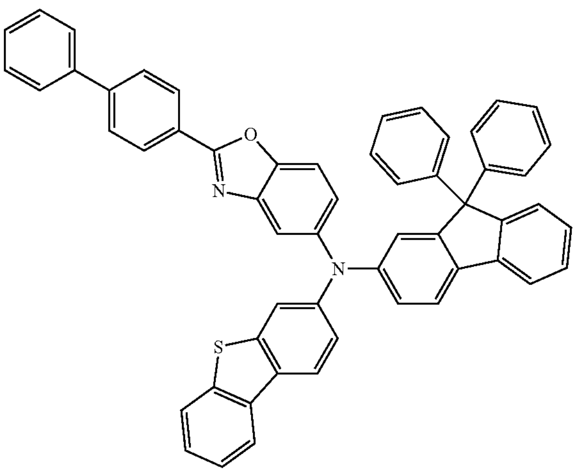
-continued
AZ72
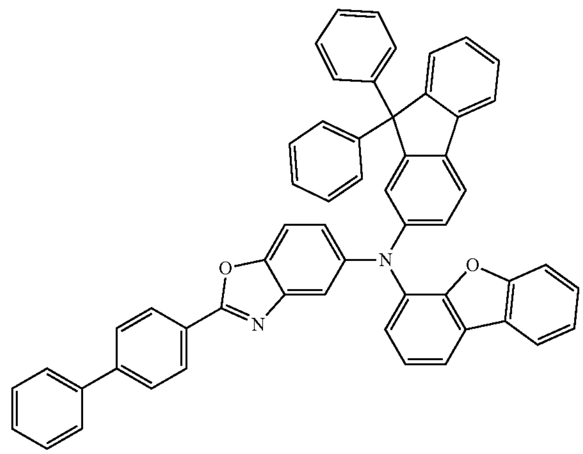
AZ73
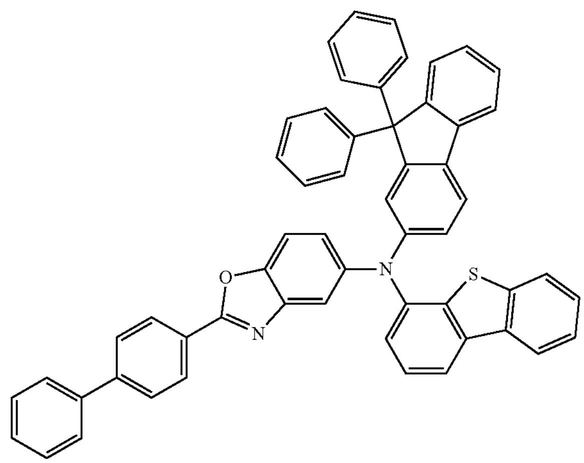
AZ74
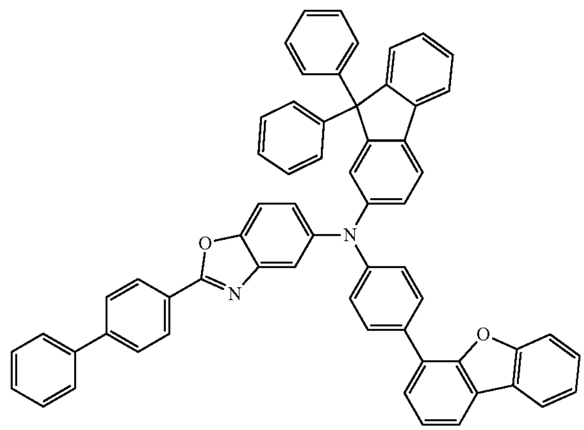

-continued
AZ75
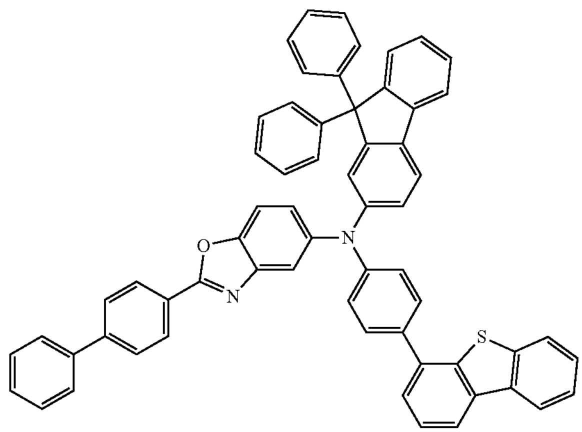
AZ76
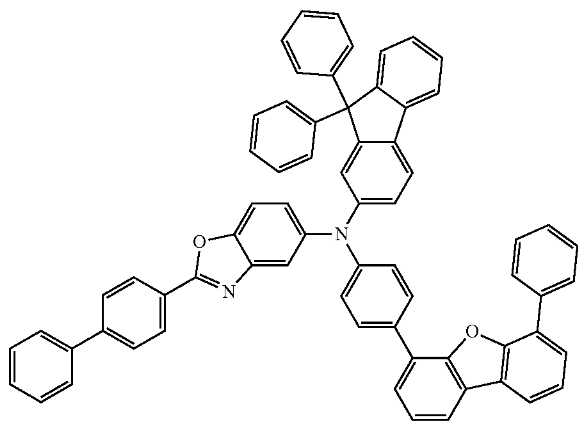
AZ77
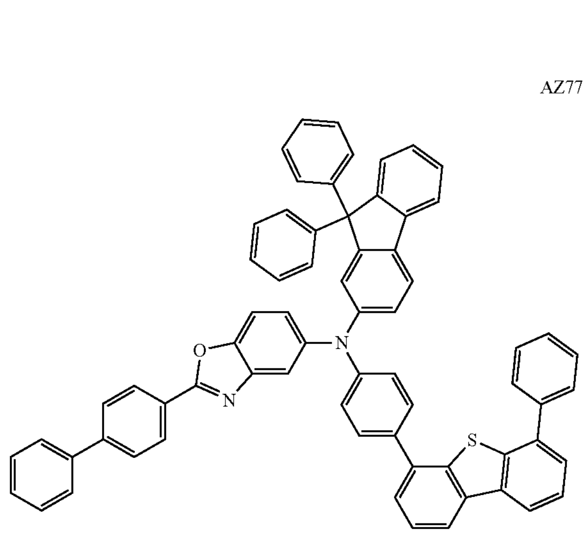
-continued
AZ78
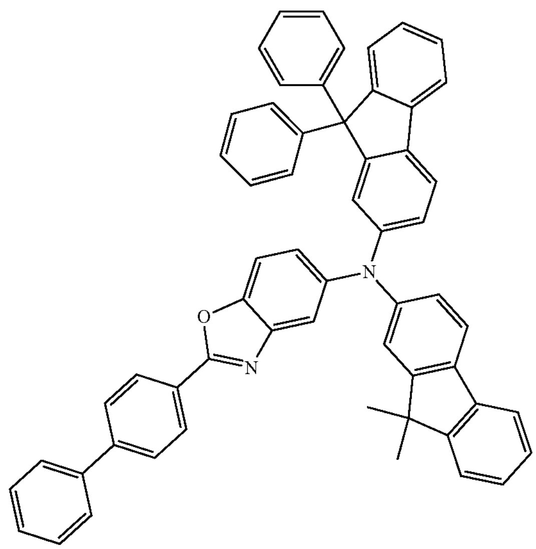
AZ79
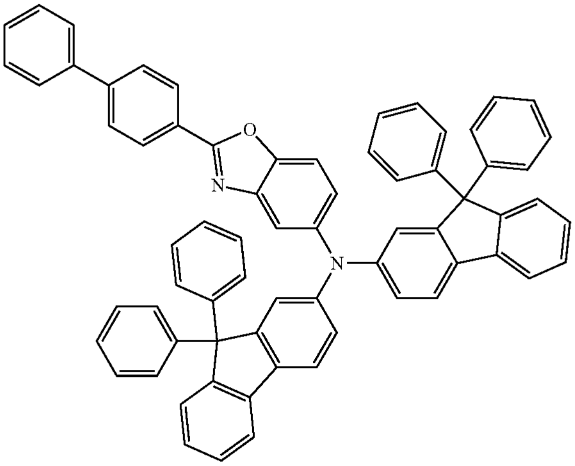
AZ80
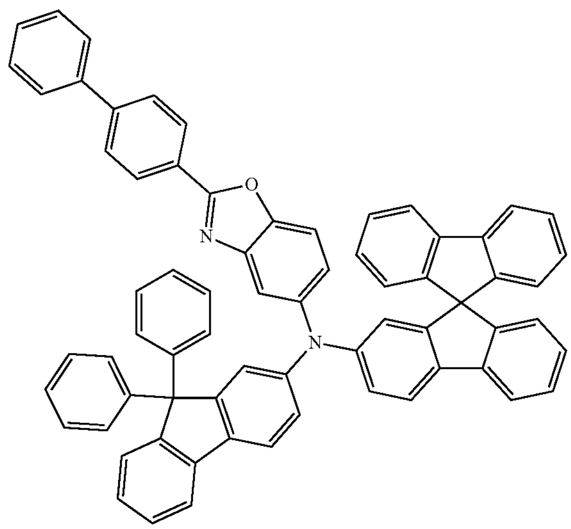

-continued
AZ81
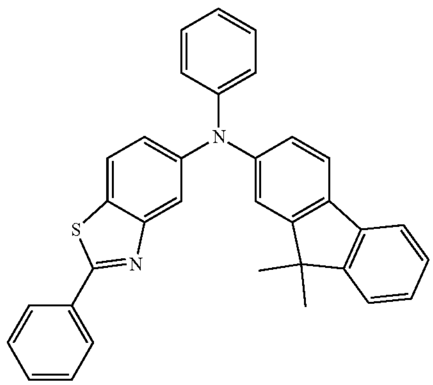
AZ82
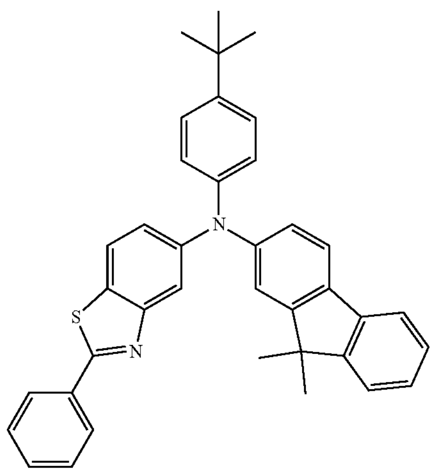
AZ83
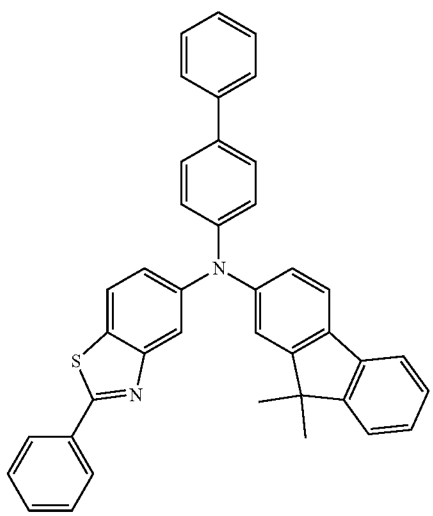
-continued
AZ84
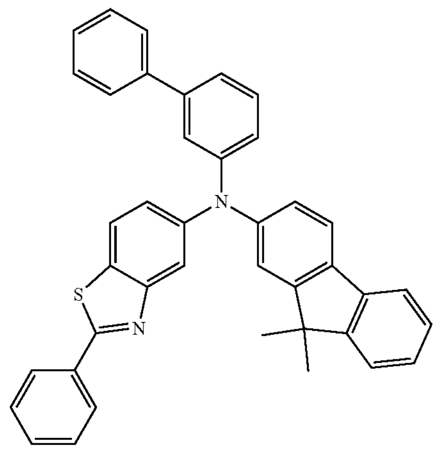
AZ85
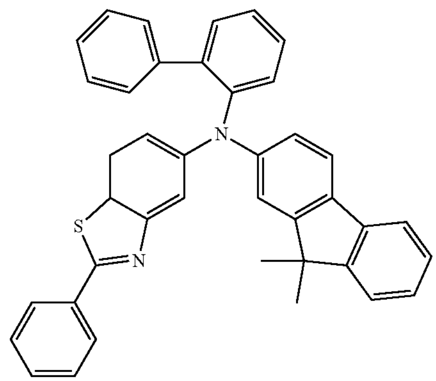
AZ86
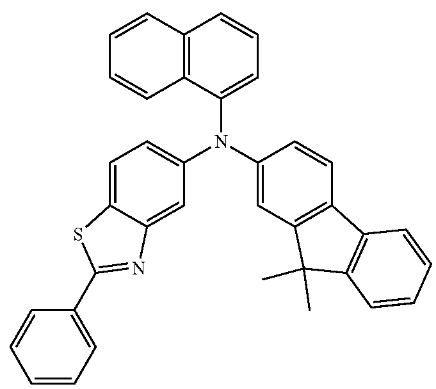
AZ87
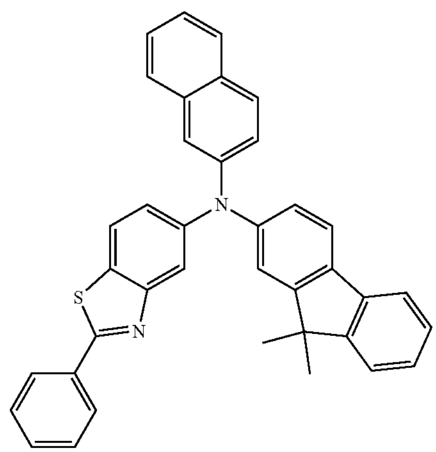

-continued
AZ88
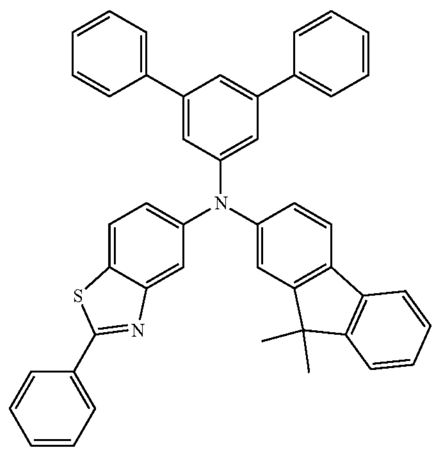
AZ89
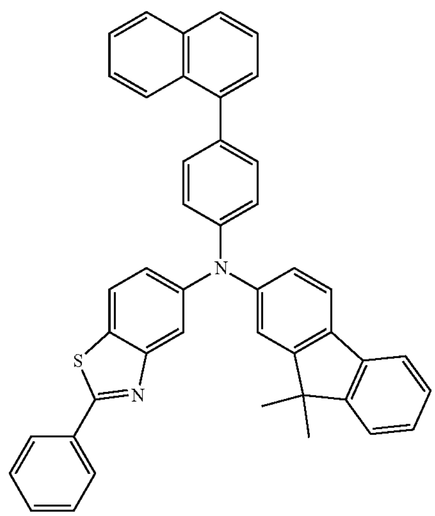
AZ90
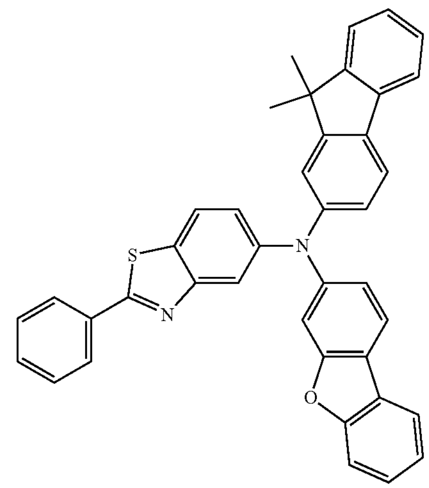
-continued
AZ91
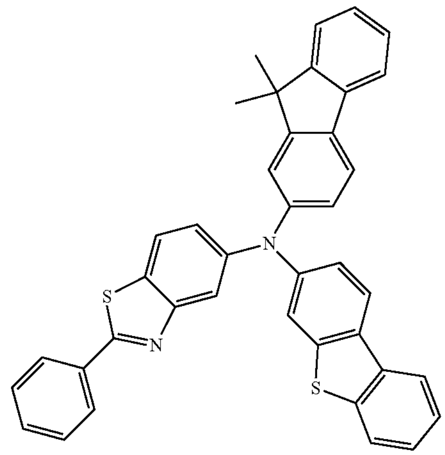
AZ92
AZ93
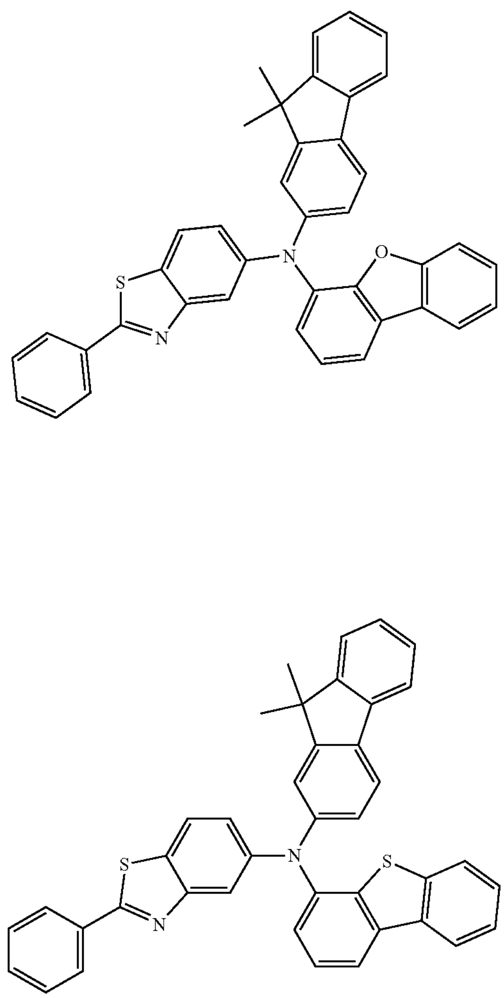

-continued
AZ94
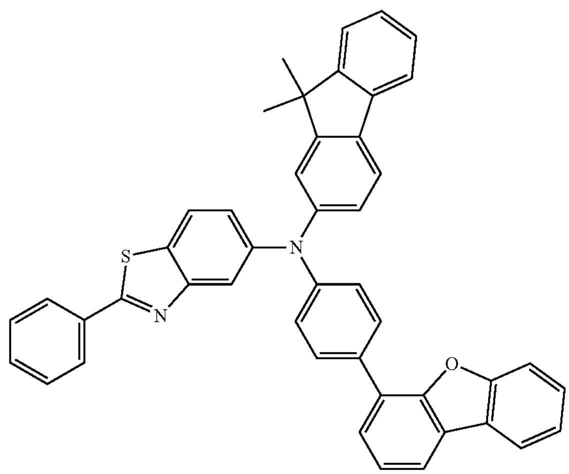
AZ95
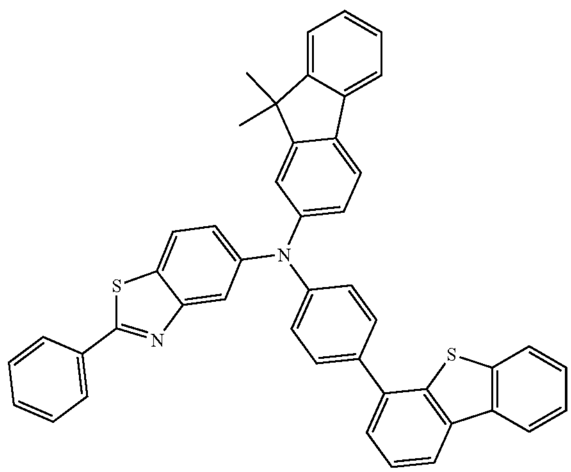
AZ96
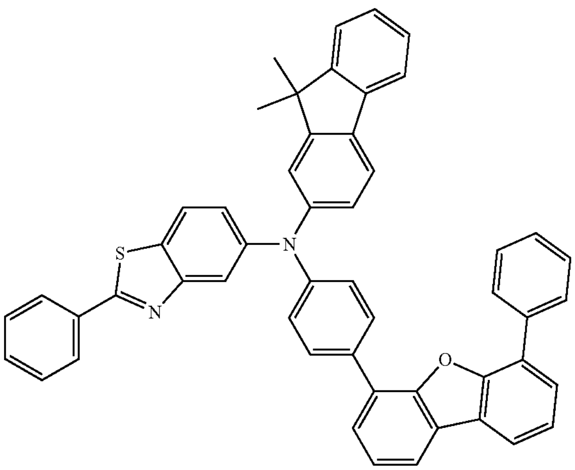
-continued
AZ97
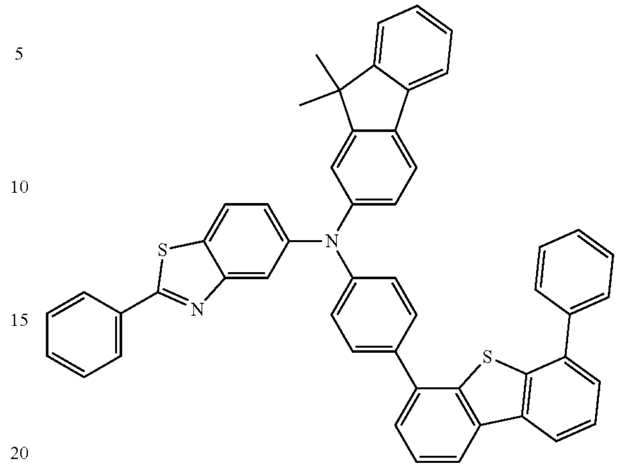
AZ98
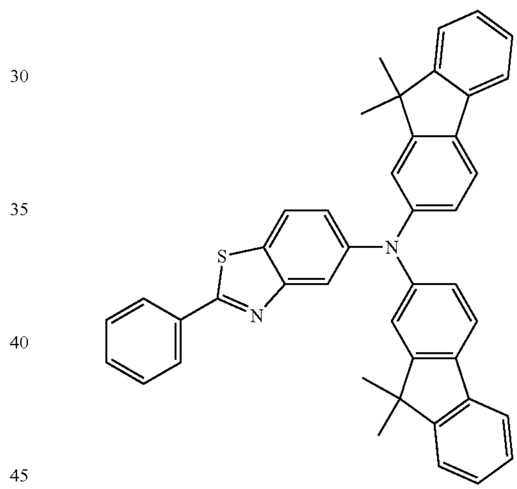
AZ99
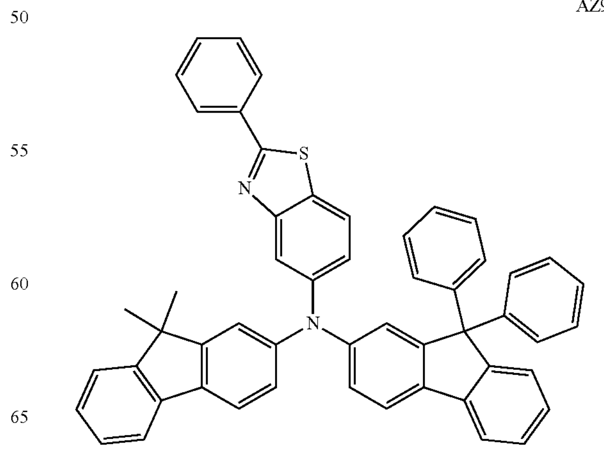

-continued
AZ100
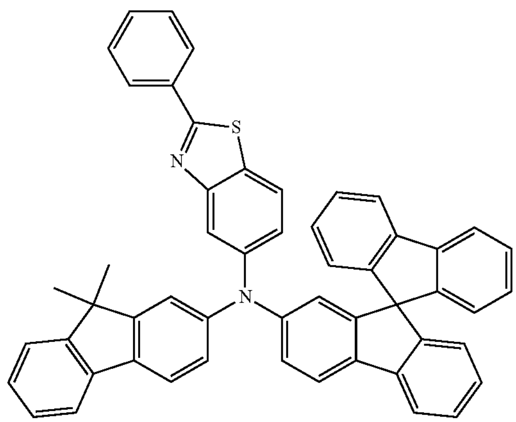
AZ101
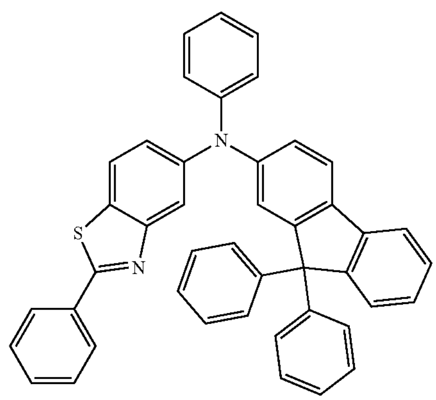
AZ102
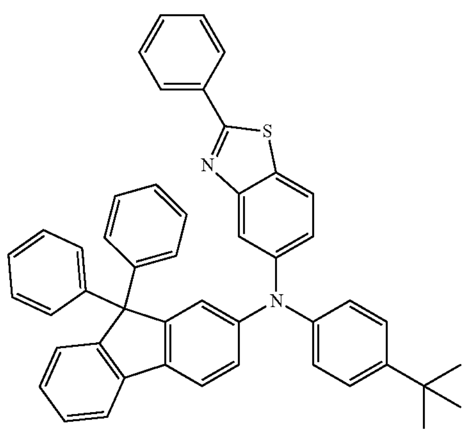
-continued
AZ103
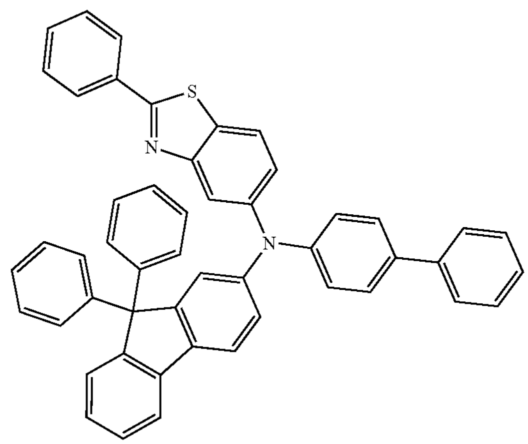
AZ104
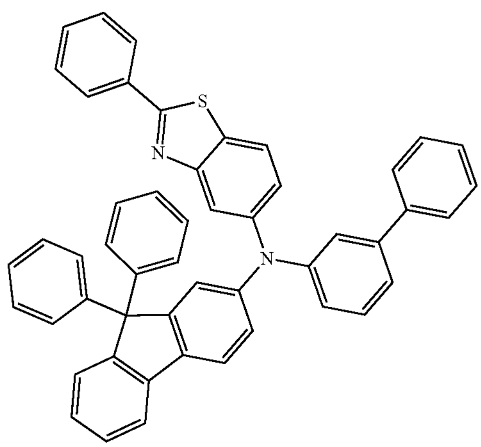
AZ105
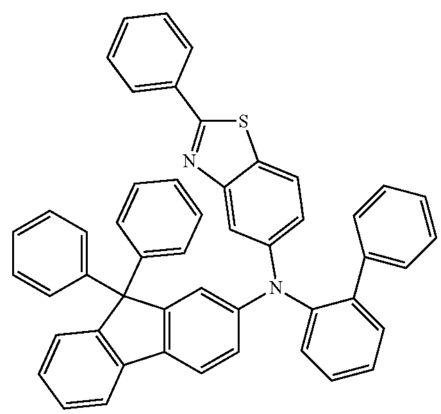

-continued
AZ106
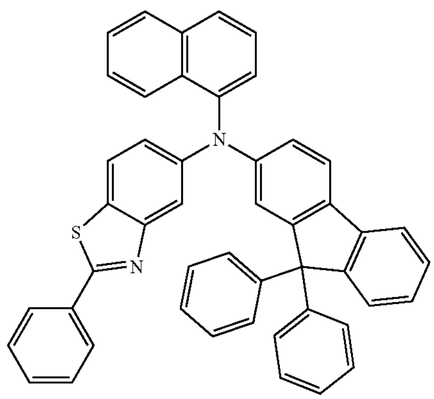
AZ107
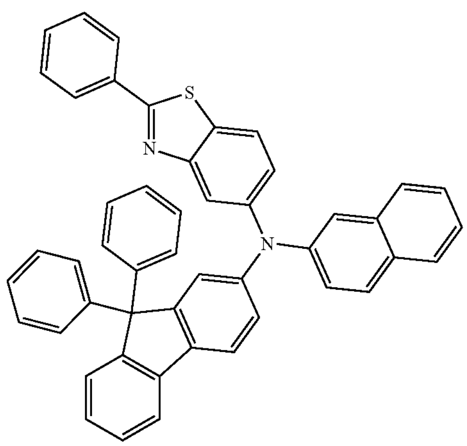
AZ108
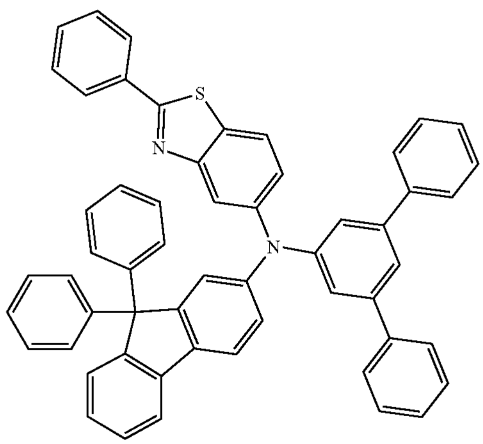
-continued
AZ109
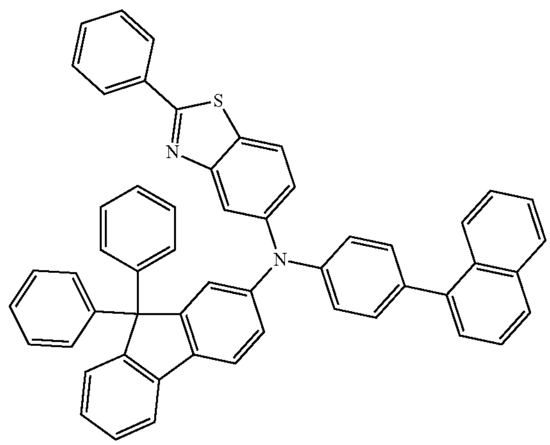
AZ110
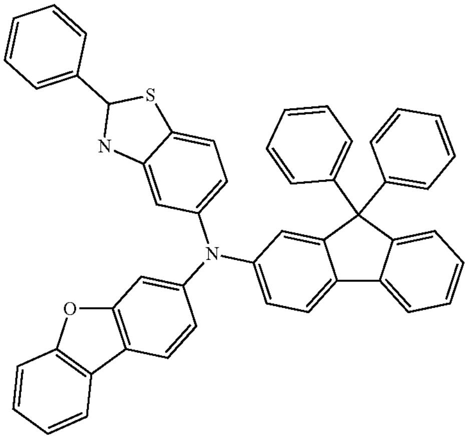
AZ111
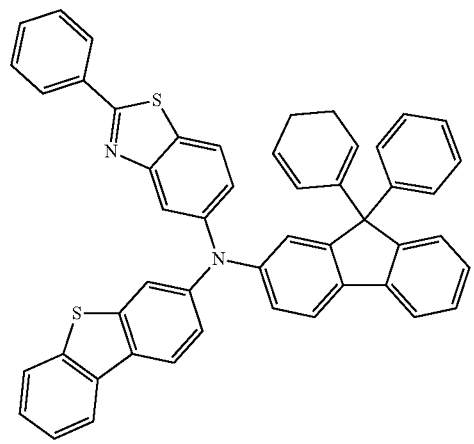

-continued
AZ112
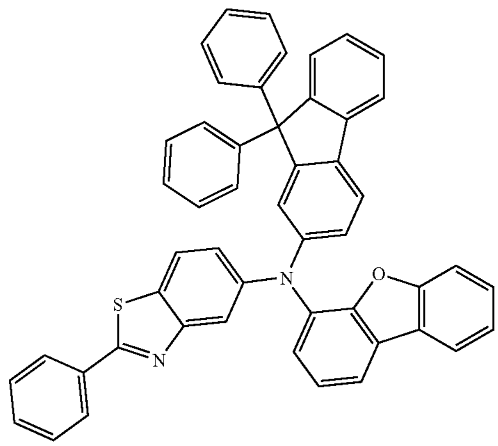
AZ113
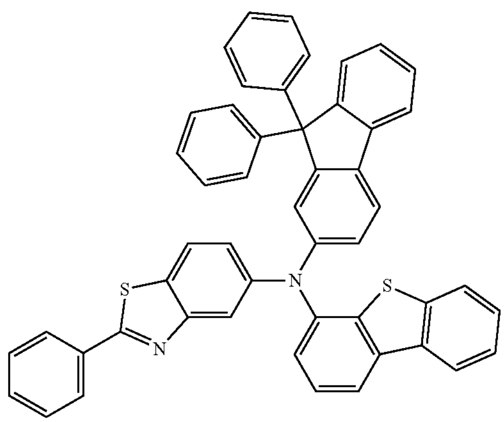
AZ114
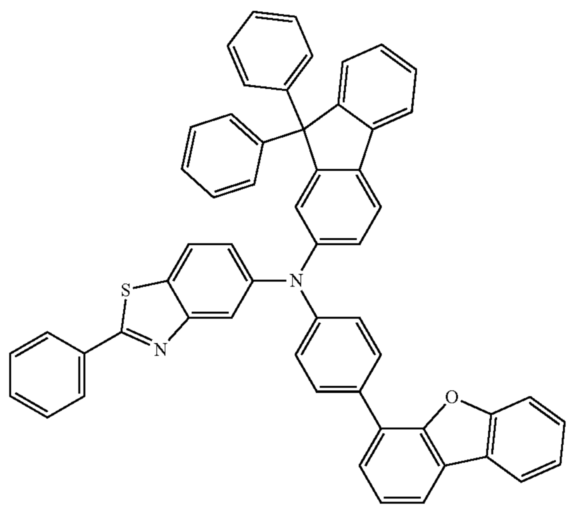
-continued
AZ115
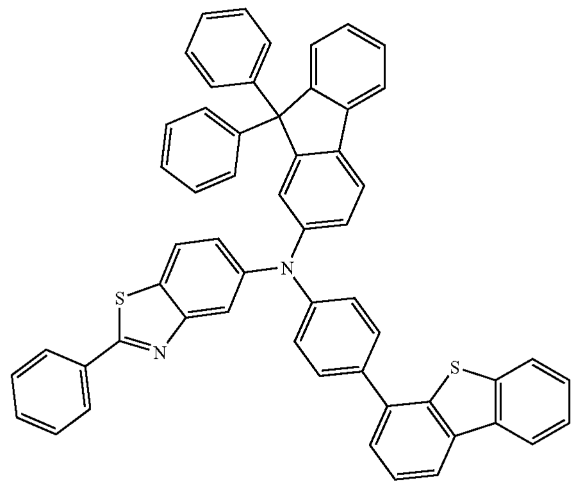
AZ116
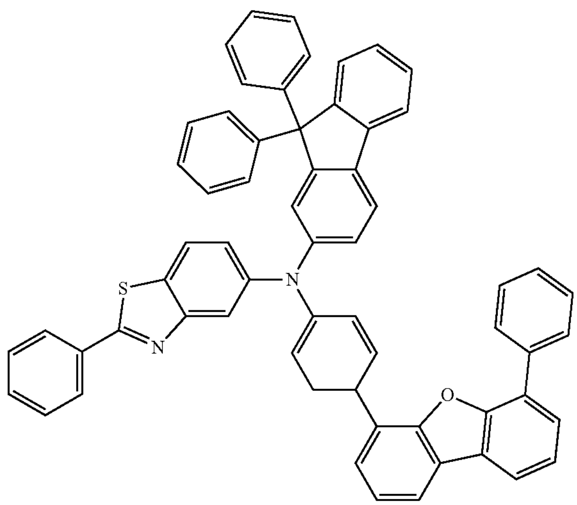
AZ117
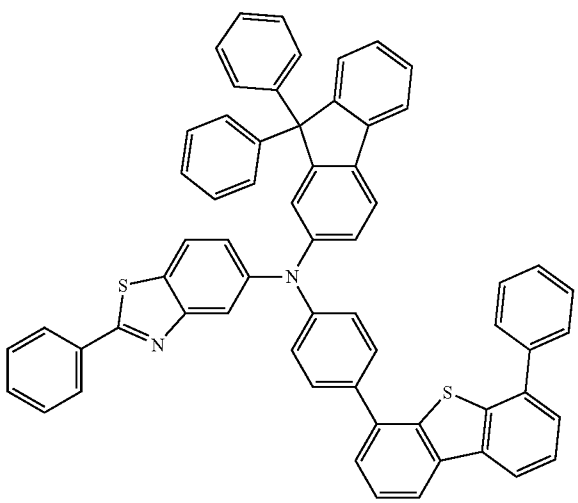

-continued
AZ118
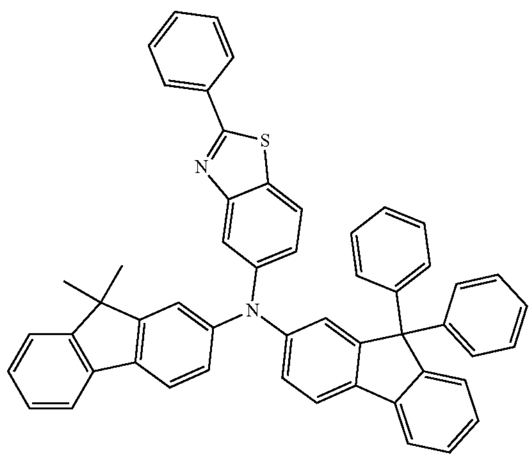
AZ119
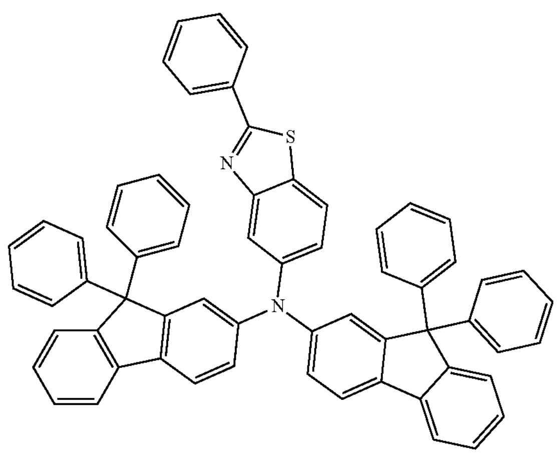
AZ120
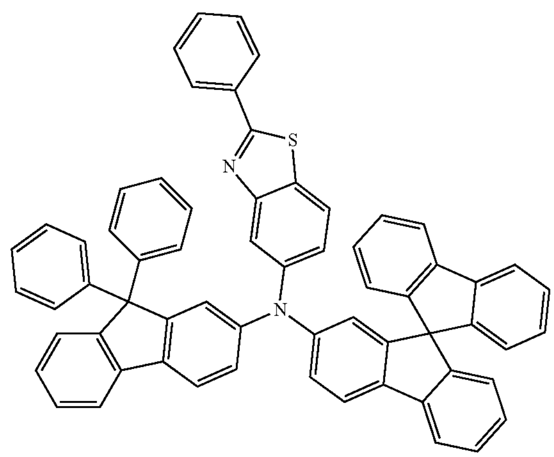
-continued
AZ121
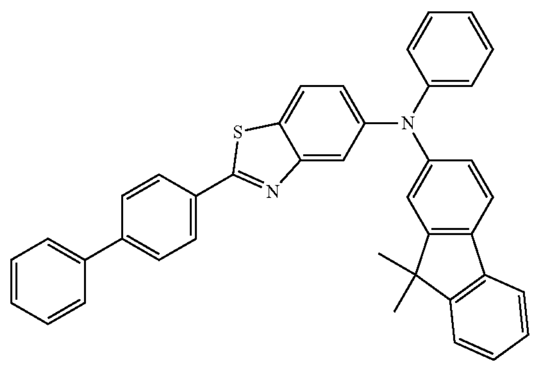
AZ122
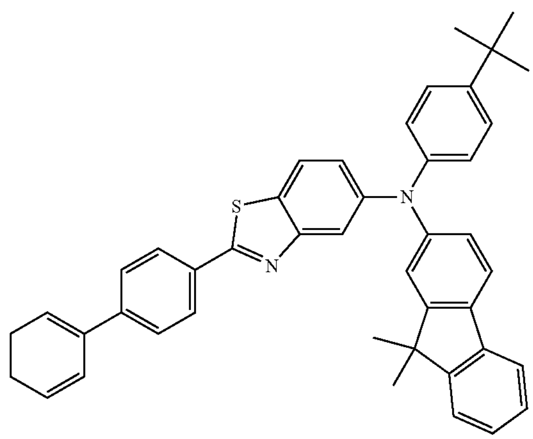
AZ123
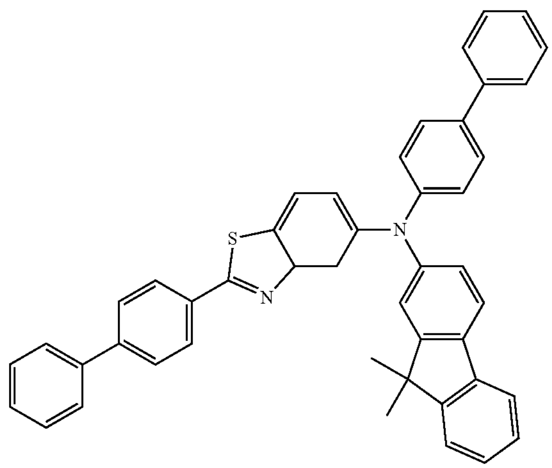

-continued
AZ124
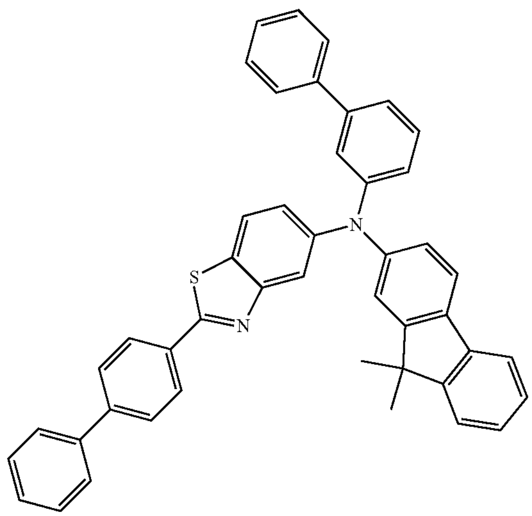
AZ125
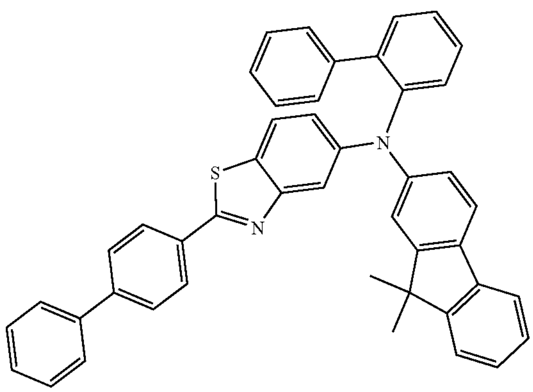
AZ126
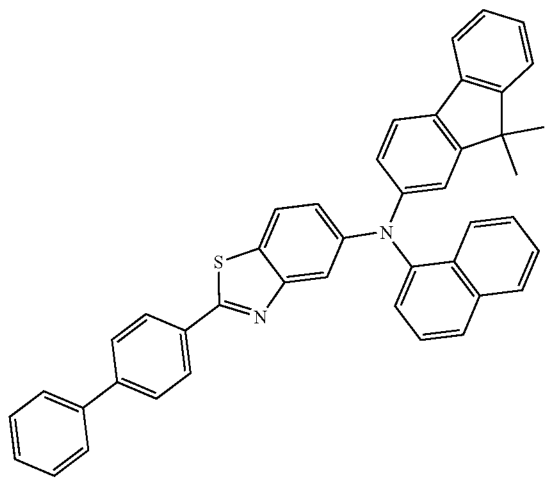
-continued
AZ127
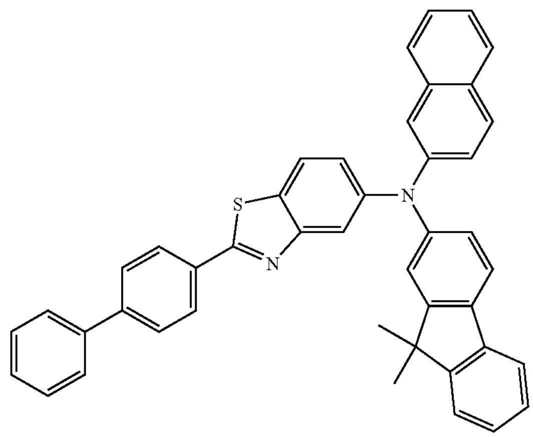
AZ128
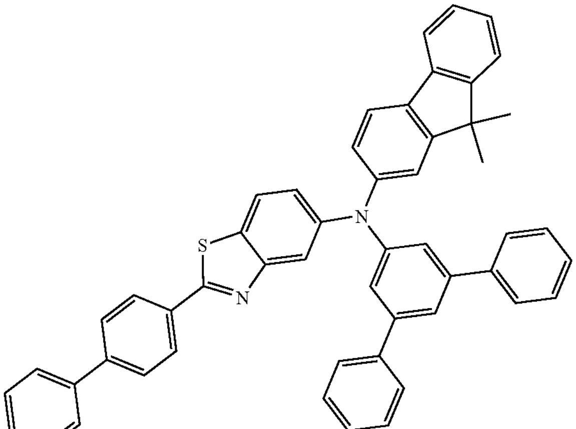
AZ129
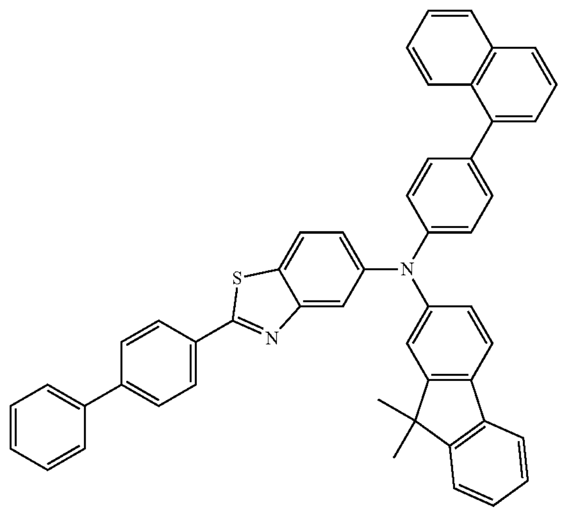

-continued
AZ130
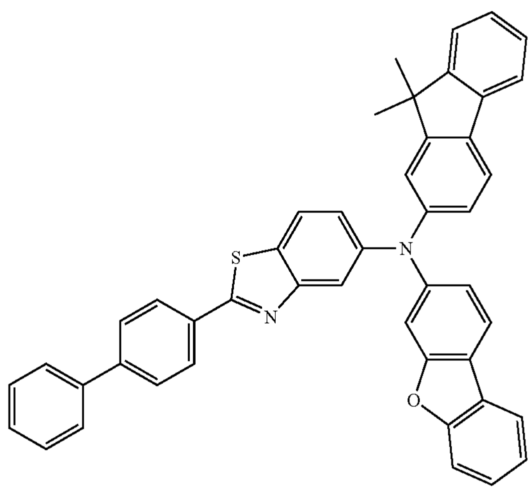
AZ131
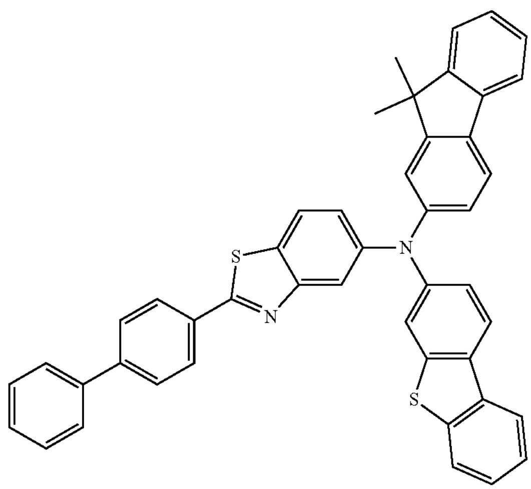
AZ132
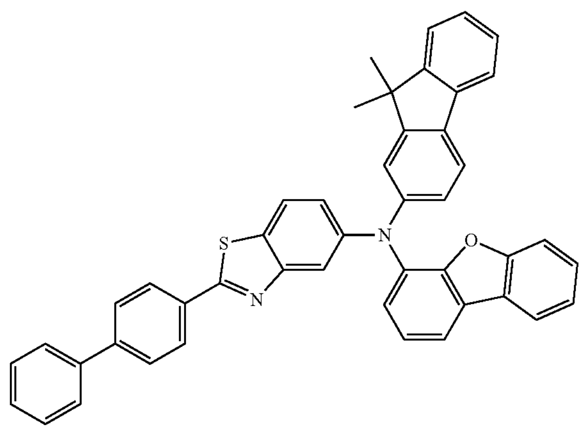
-continued
AZ133
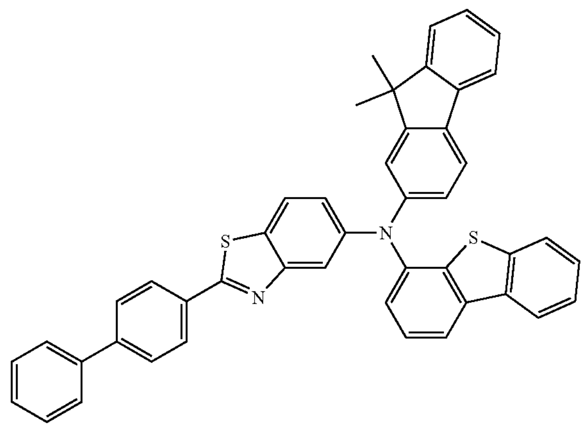
AZ134
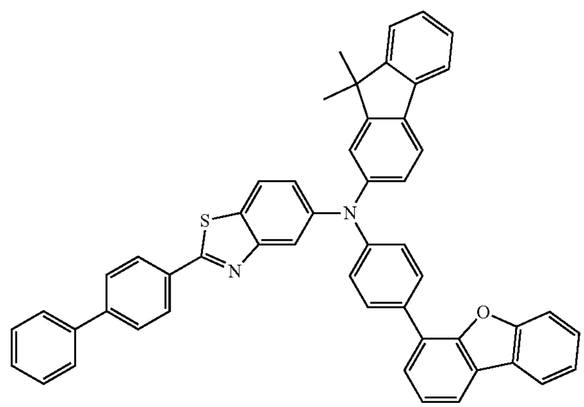
AZ135
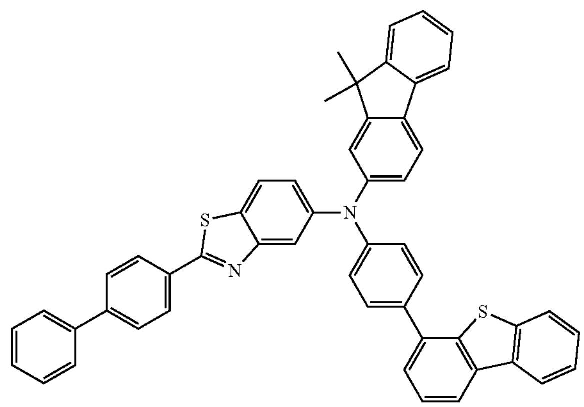

AZ136
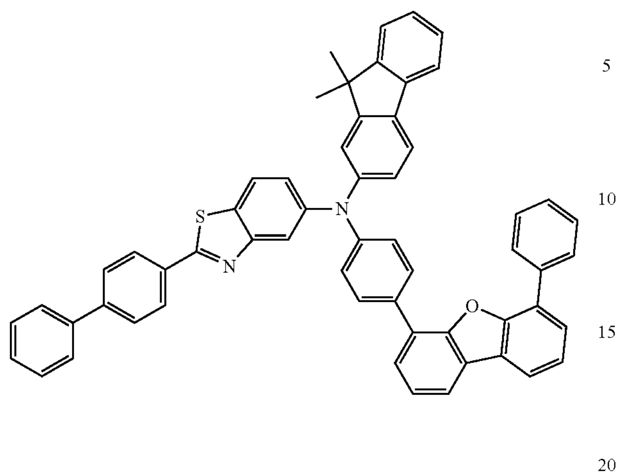
AZ137
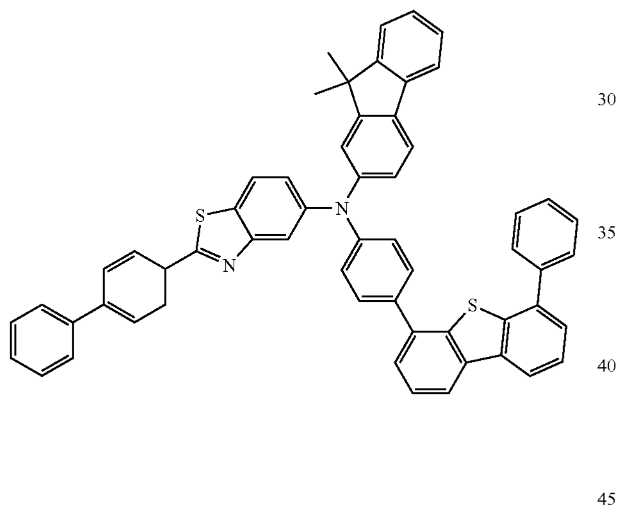
AZ138
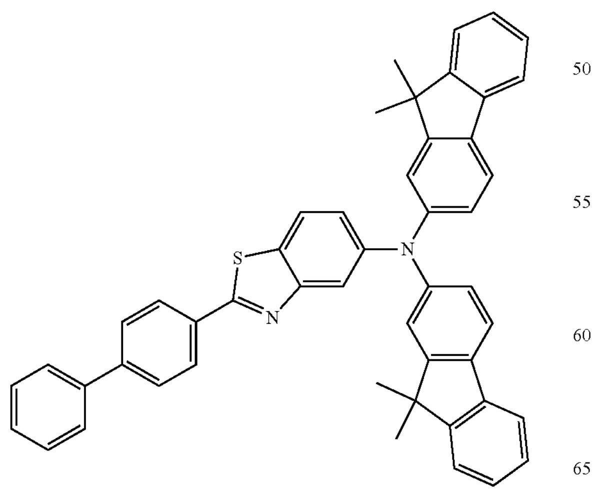
AZ139
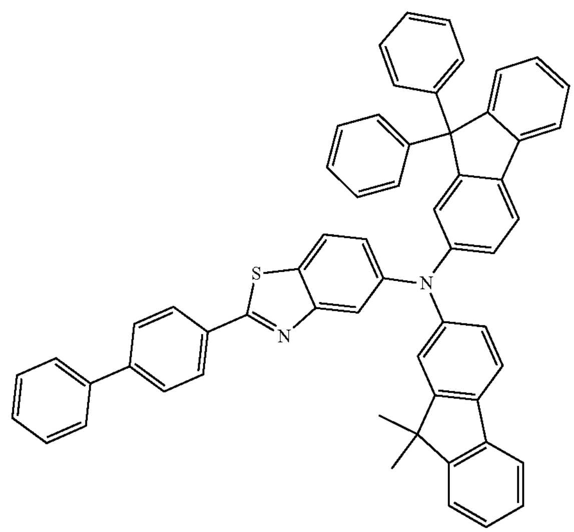
AZ140
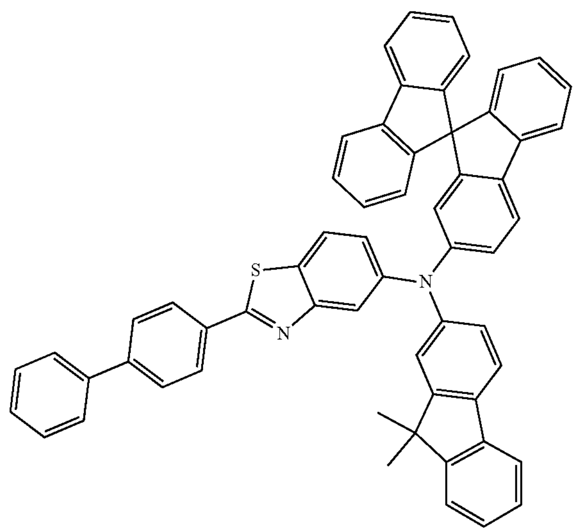
AZ141
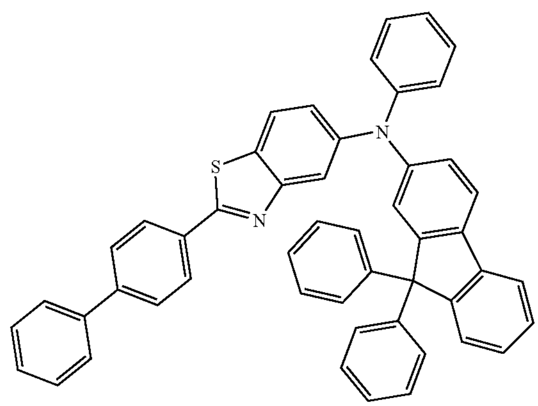

-continued
AZ142
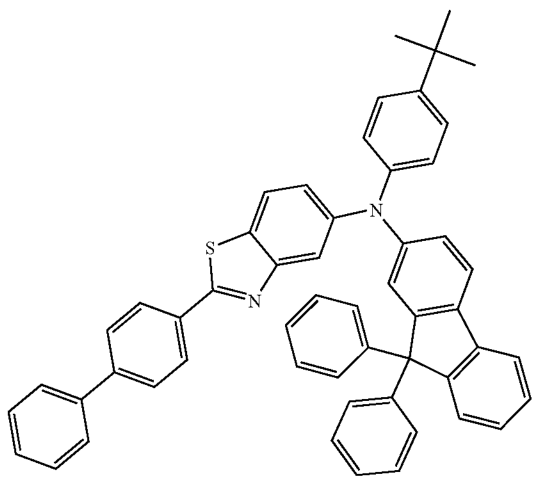
AZ143
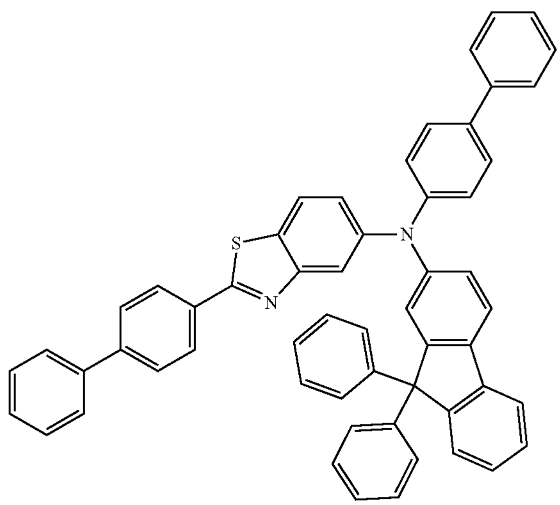
AZ144
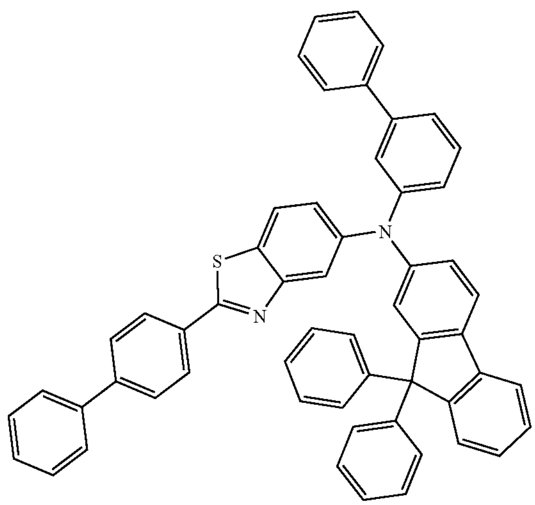
-continued
AZ145
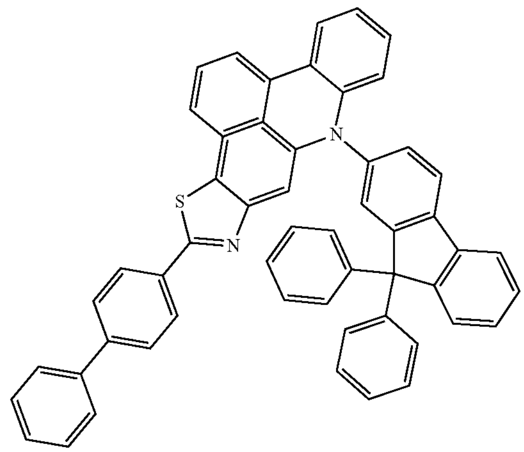
AZ146
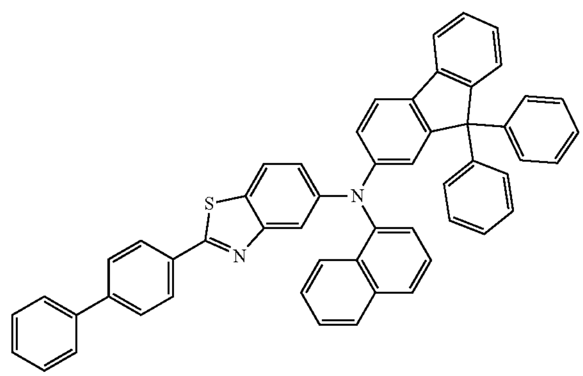
AZ147
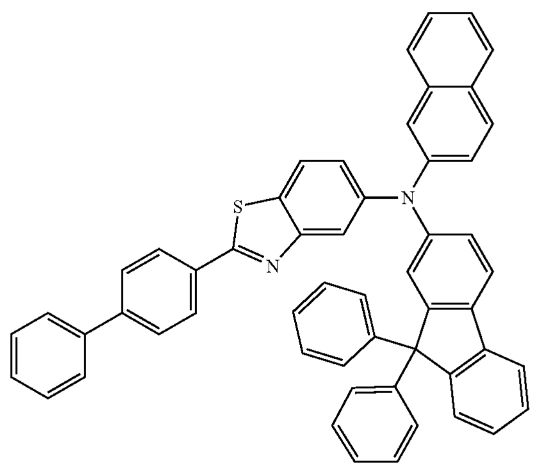

-continued
AZ148
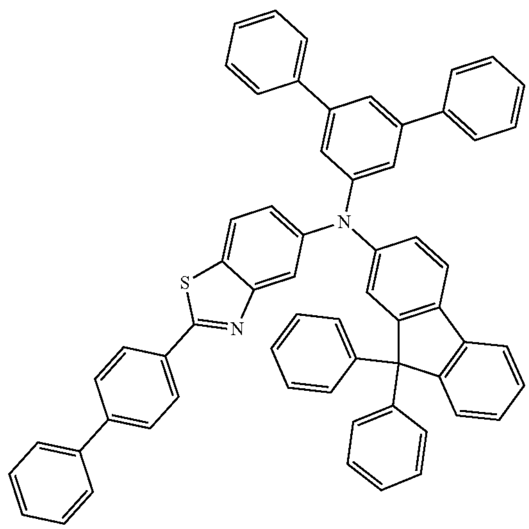
AZ149
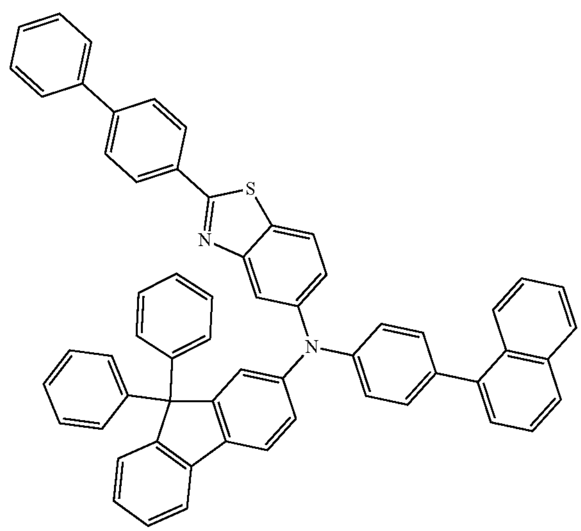
AZ150
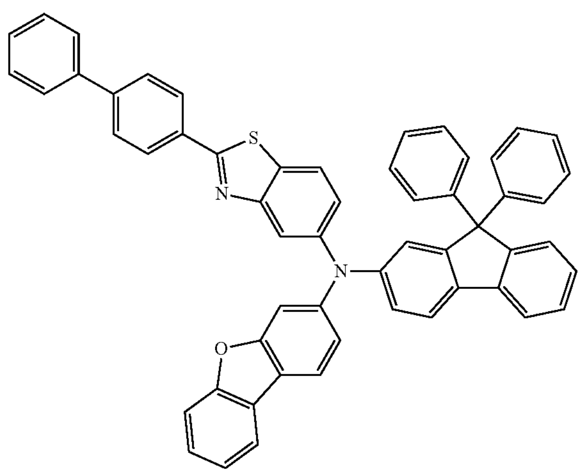
-continued
AZ151
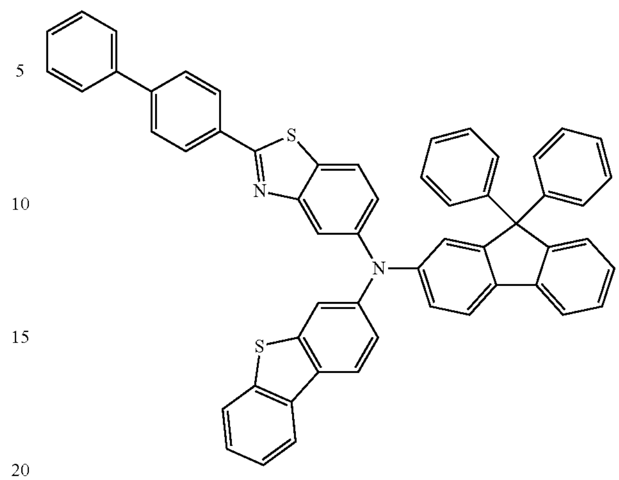
AZ152
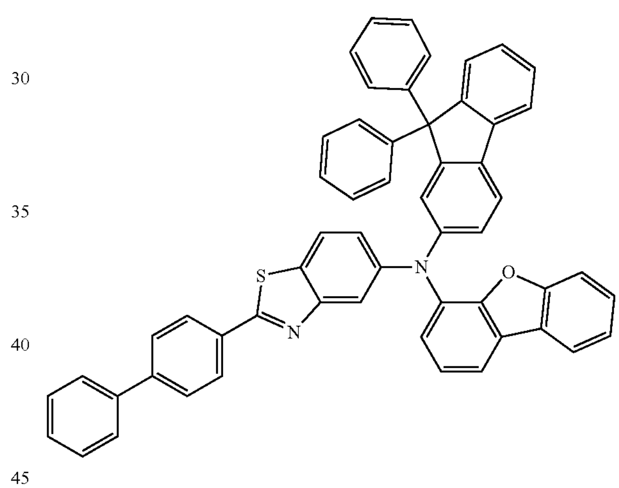
AZ153
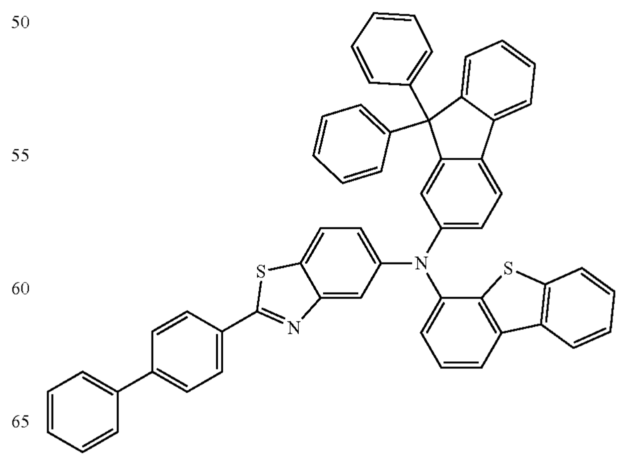

-continued
AZ154
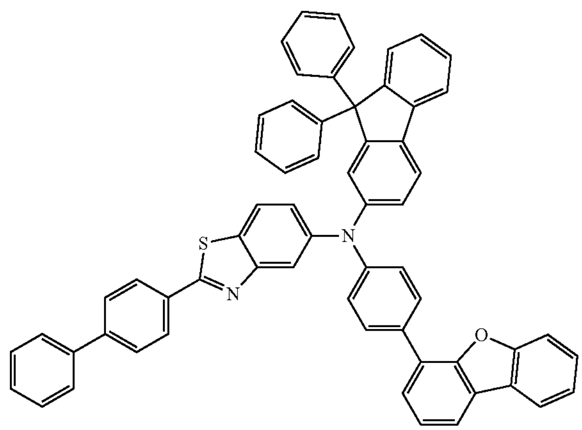
AZ155
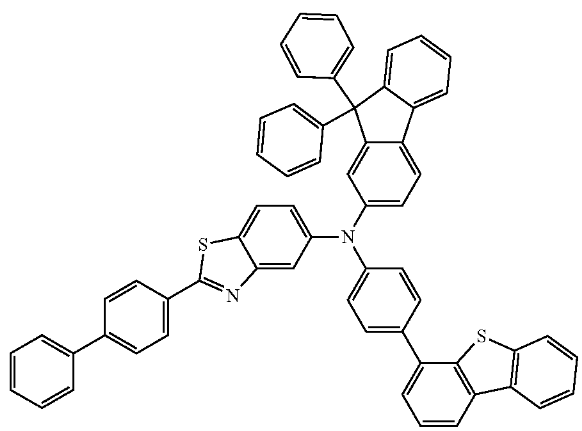
AZ156
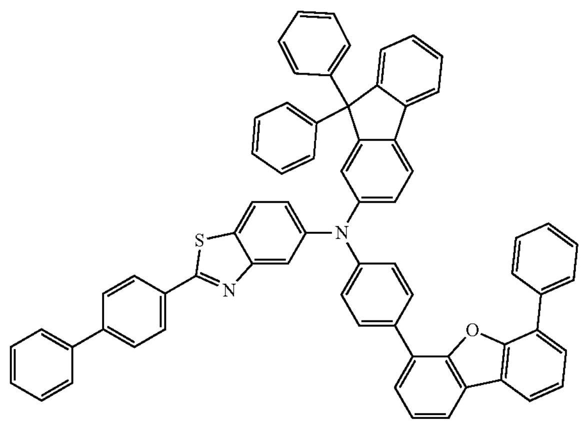
-continued
AZ157
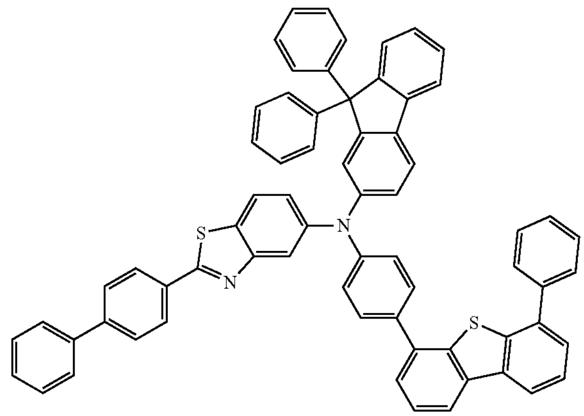
AZ158
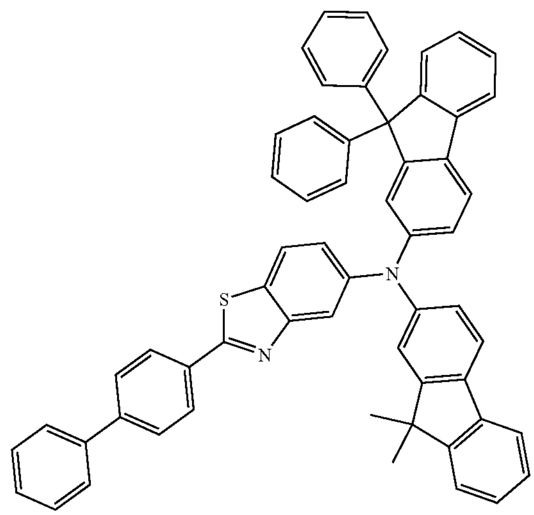
AZ159
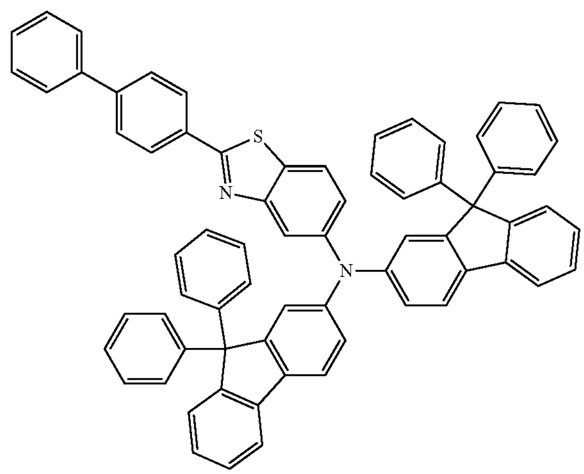

-continued
AZ160
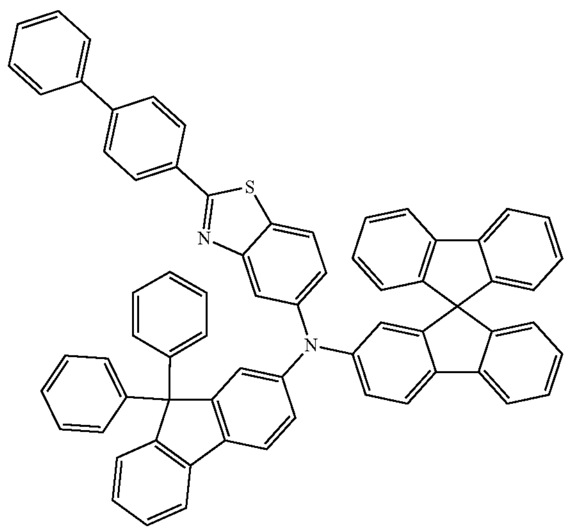
AK1
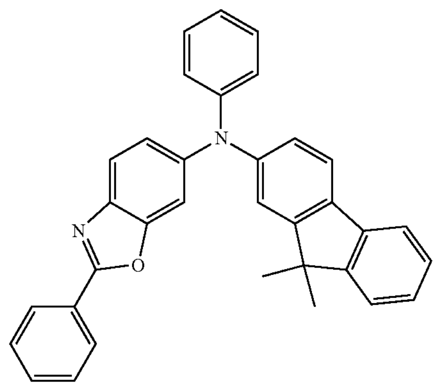
AK2
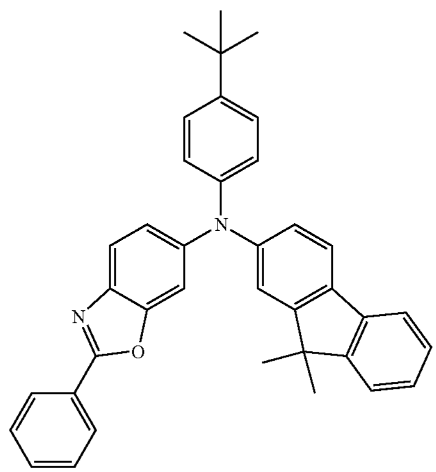
-continued
AK3
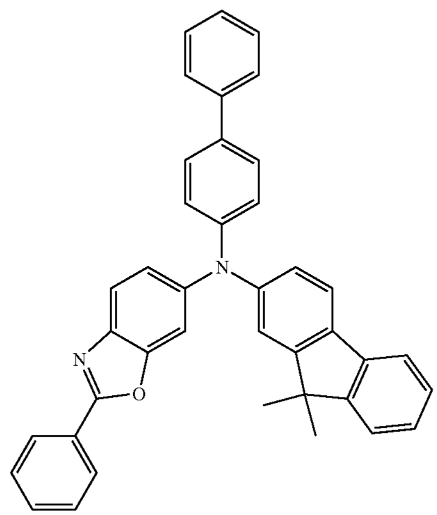
AK4
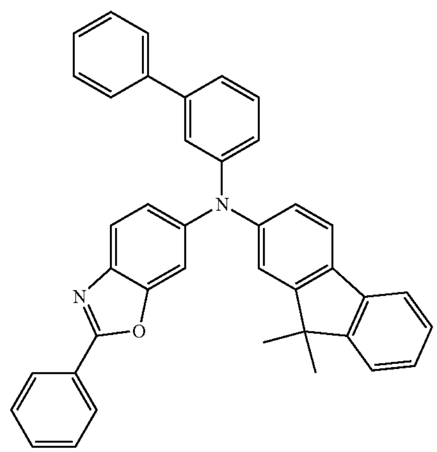
AK5
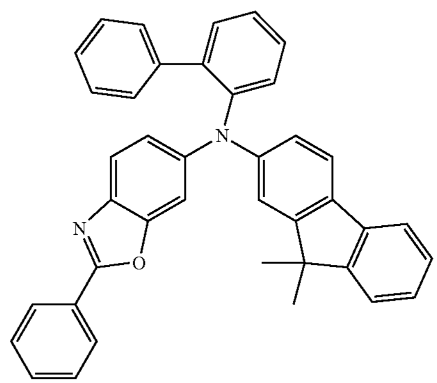

-continued
AK6
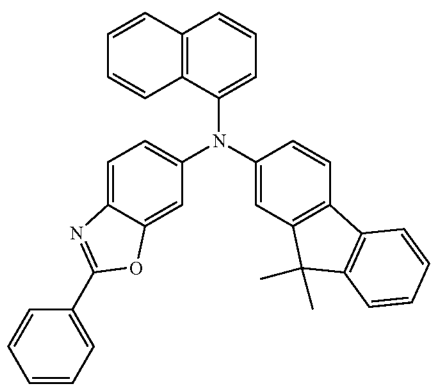
AK7
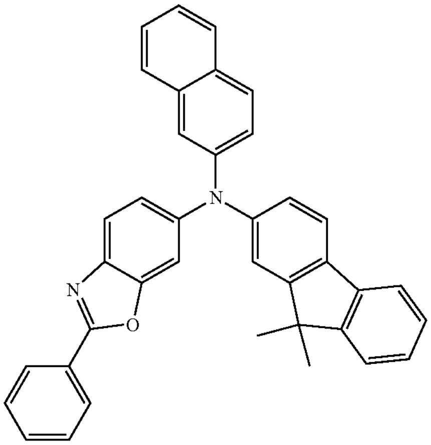
AK8
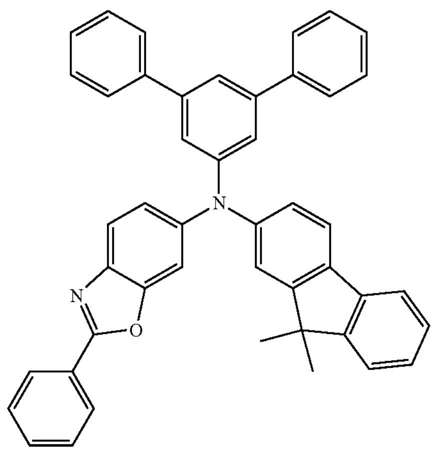
-continued
AK9
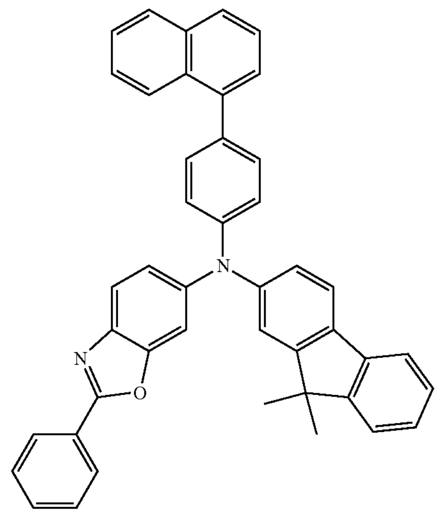
AK10
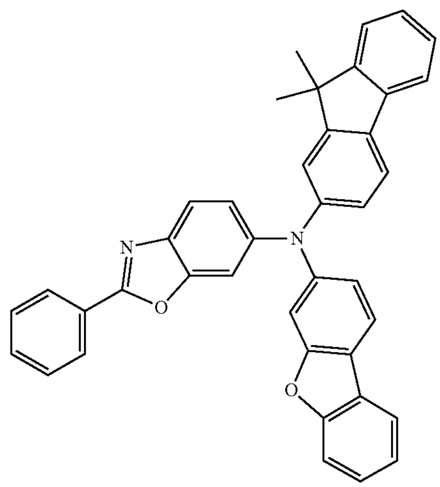
AK11
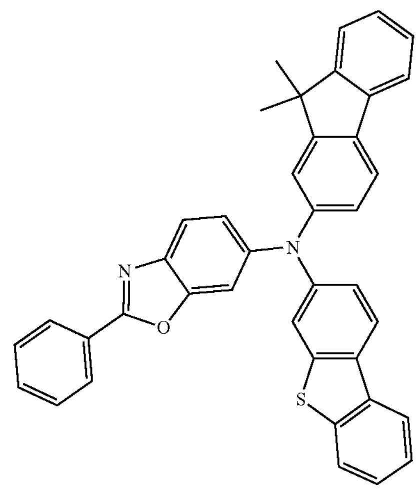

-continued
AK12
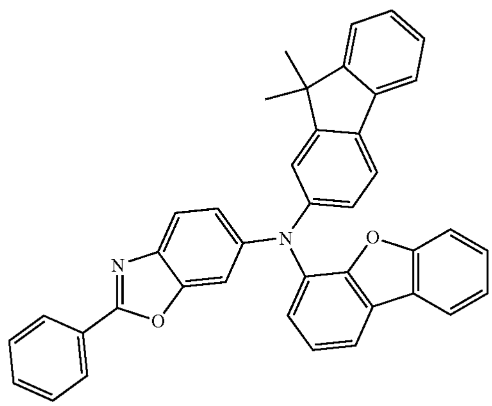
AK13
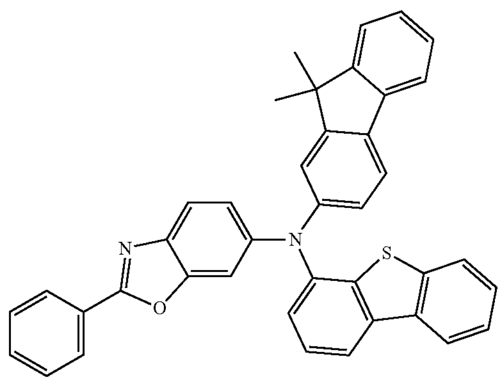
AK14
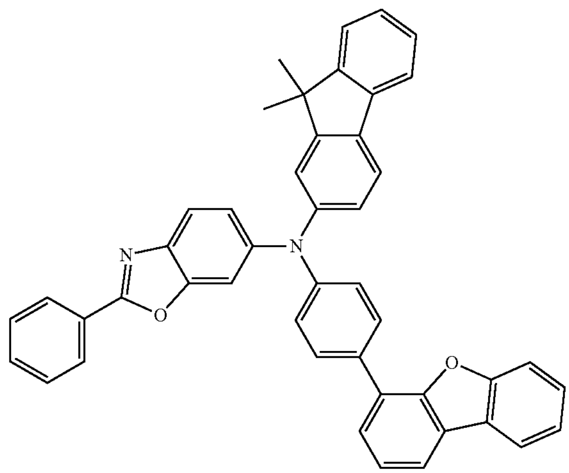
-continued
AK15
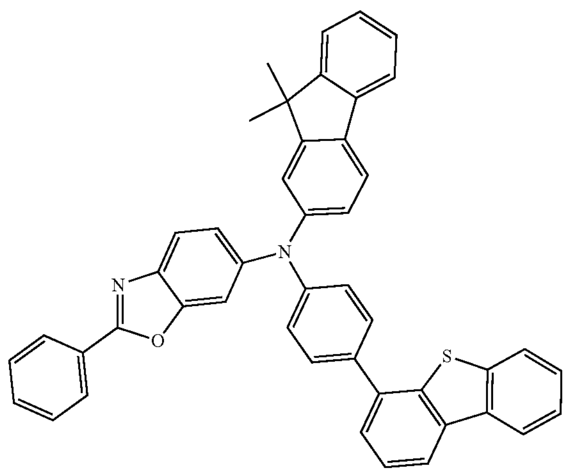
AK16
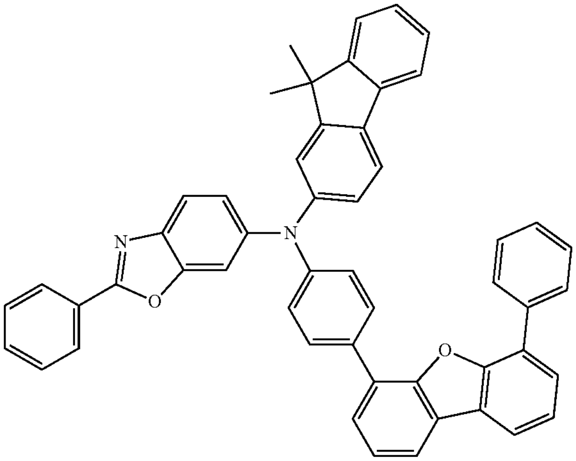
AK17
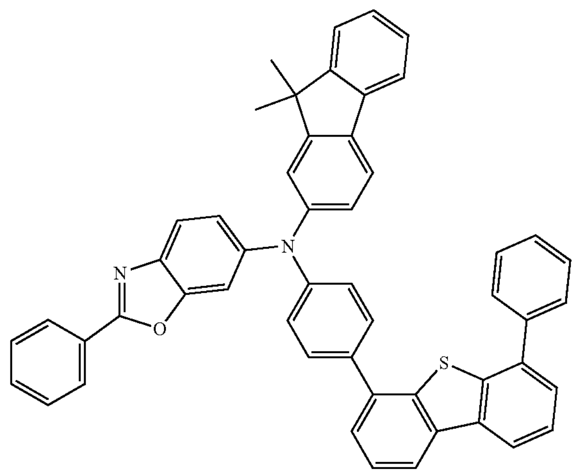

AK18
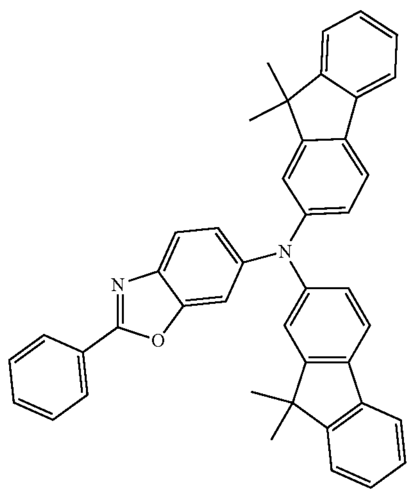
AK19
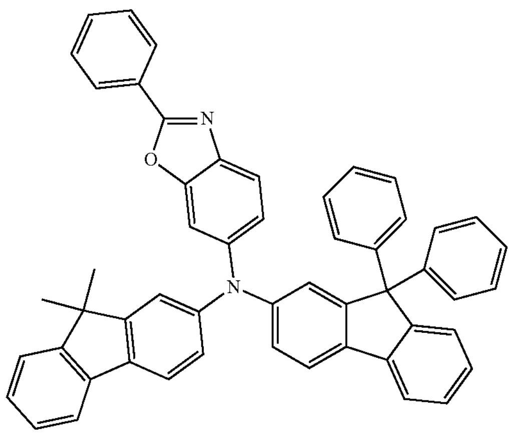
AK20
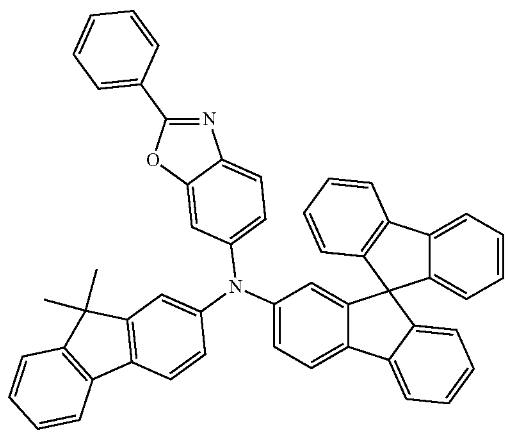
AK21
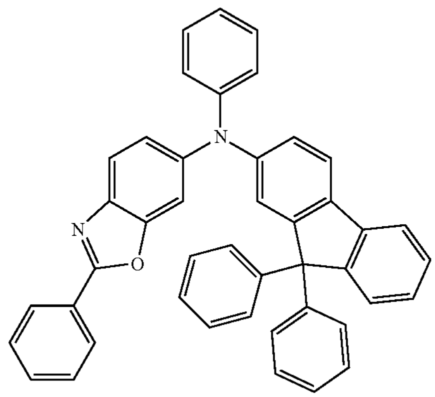
AK22
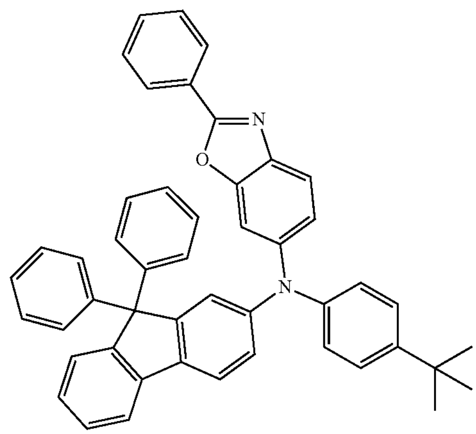
AK23
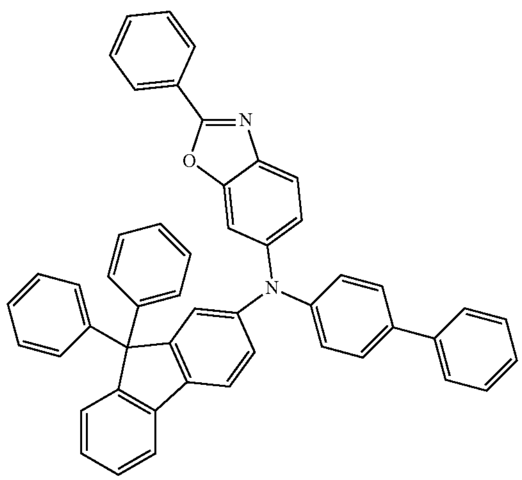

AK24
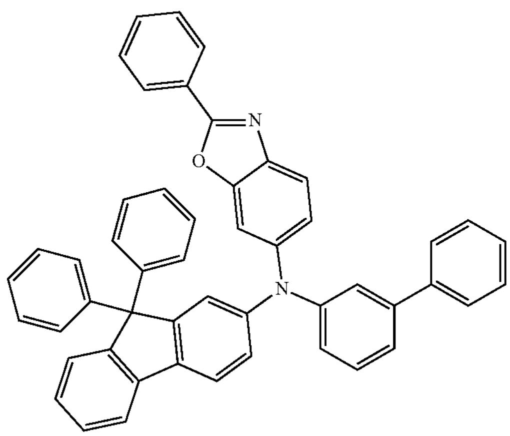
AK25
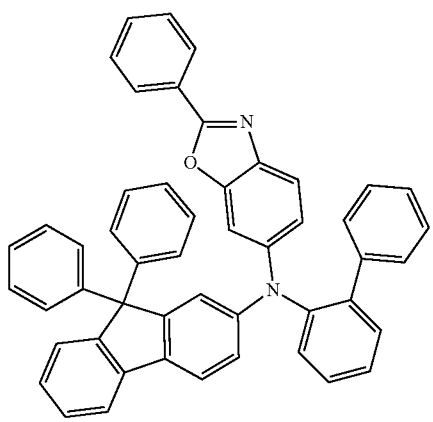
AK26
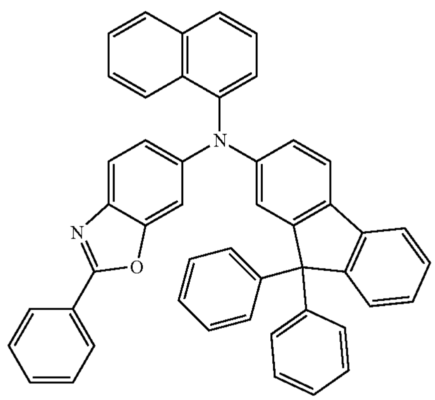
AK27
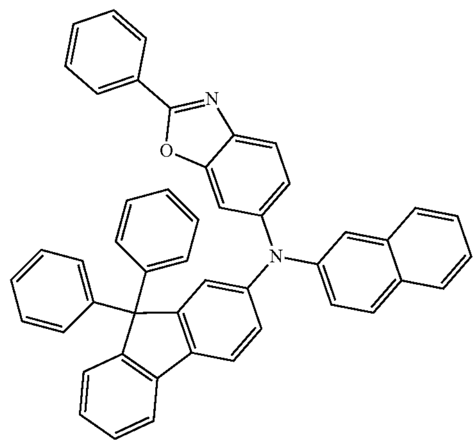
AK28
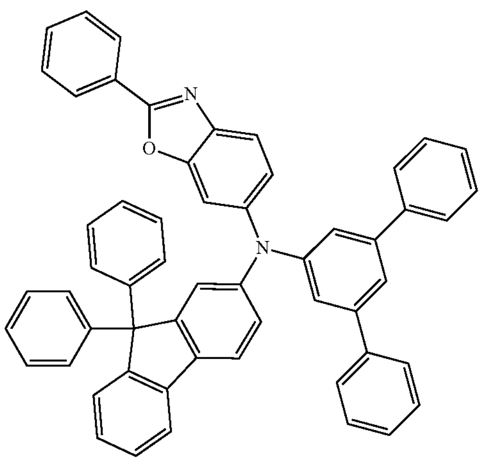
AK29
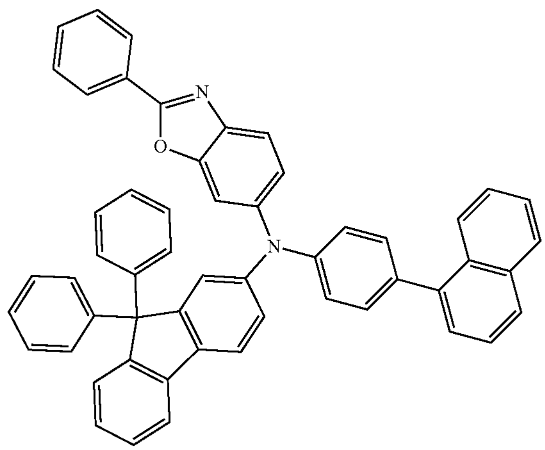

-continued
AK30
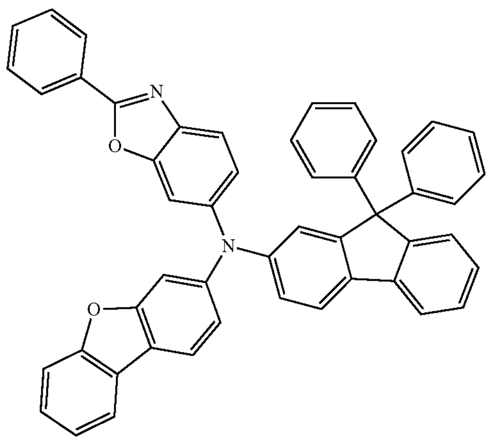
AK31
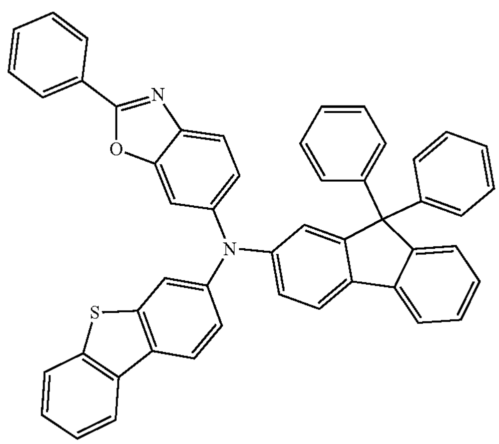
AK32
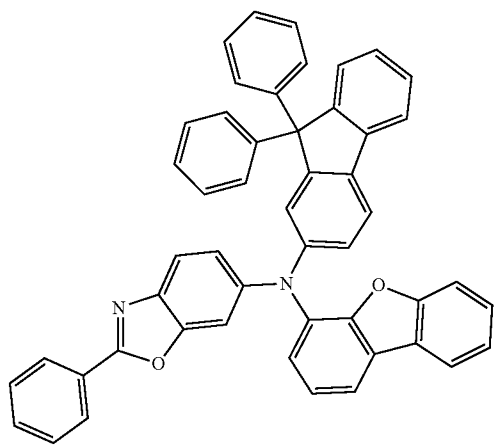
-continued
AK33
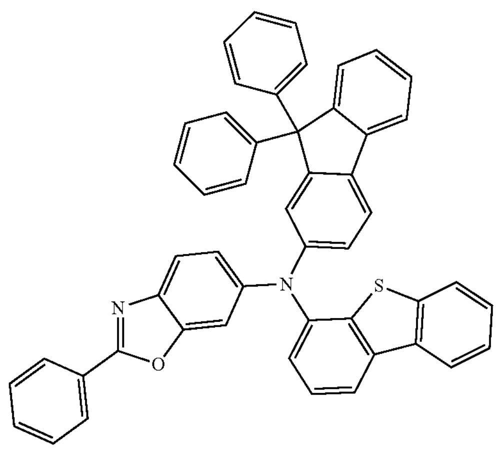
AK34
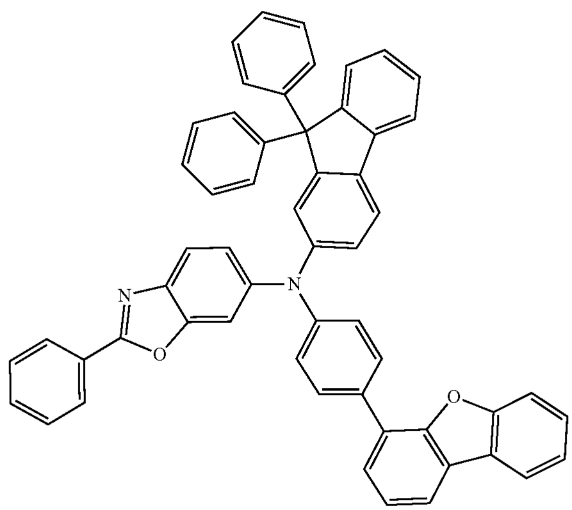
AK35
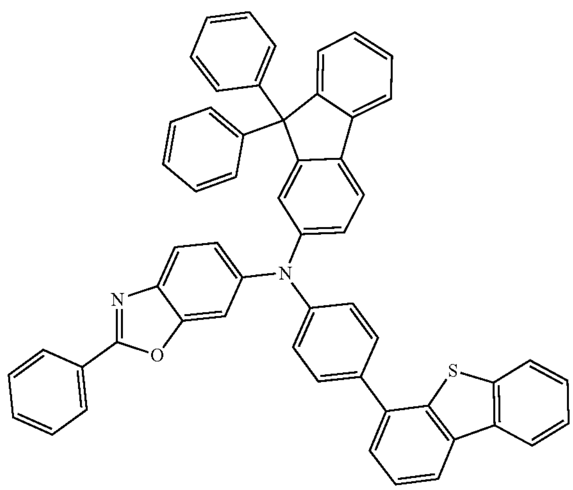

-continued
AK36
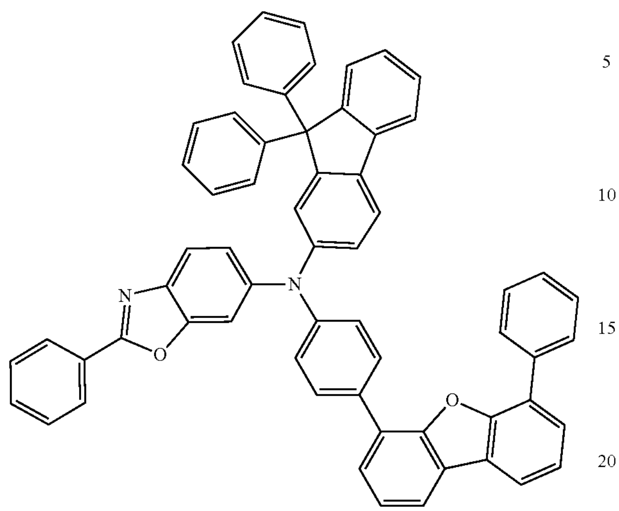
AK37
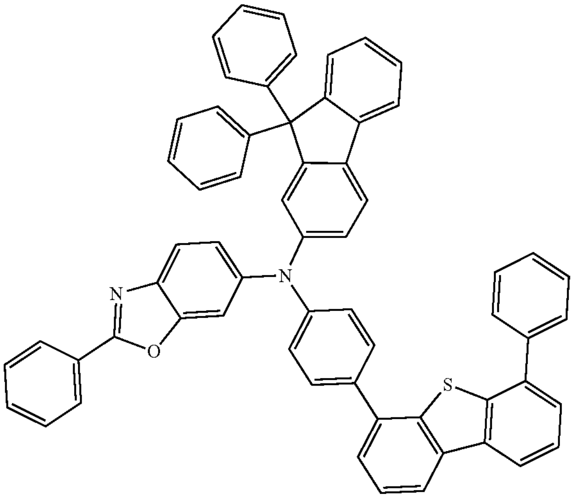
AK38
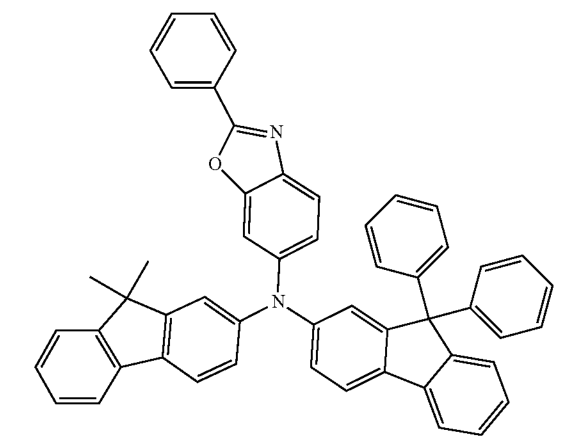
-continued
AK39
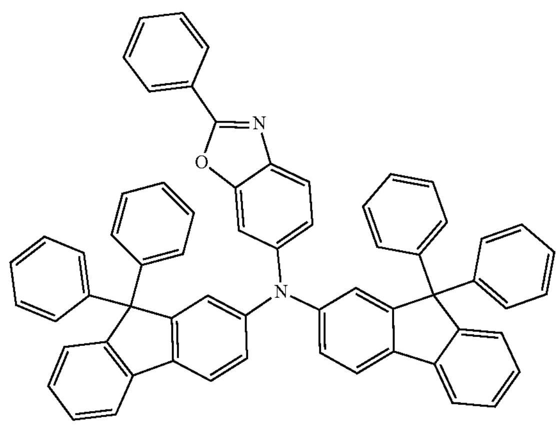
AK40
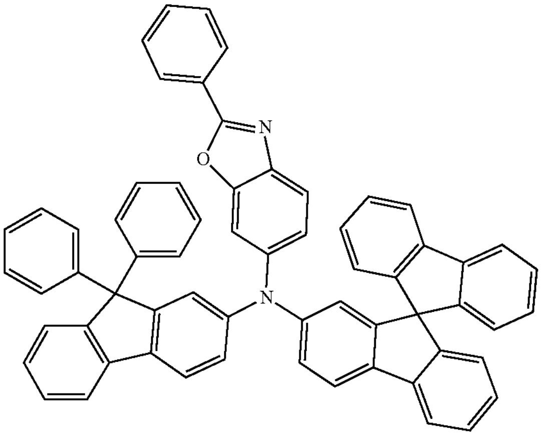
AK41
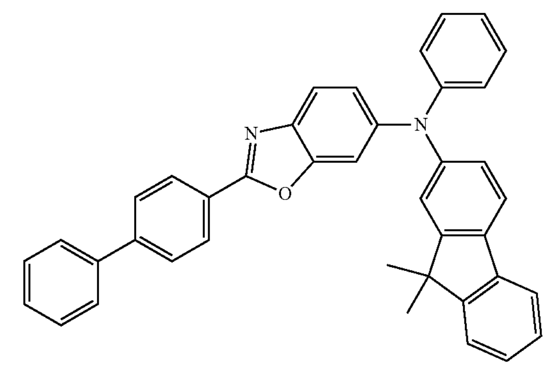

-continued
AK42
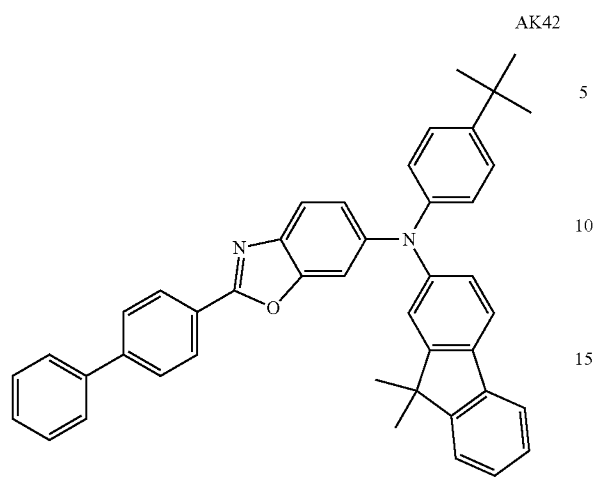
AK43
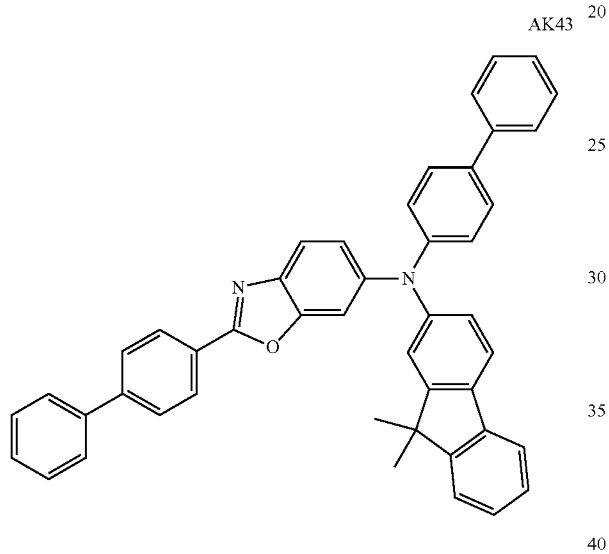
AK44
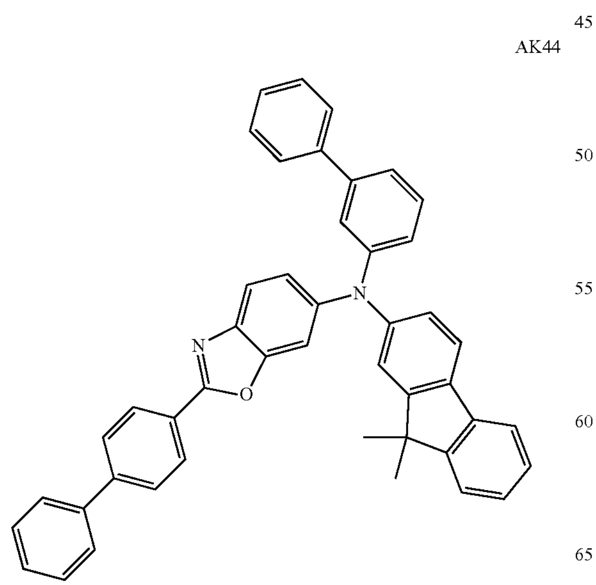
-continued
AK45
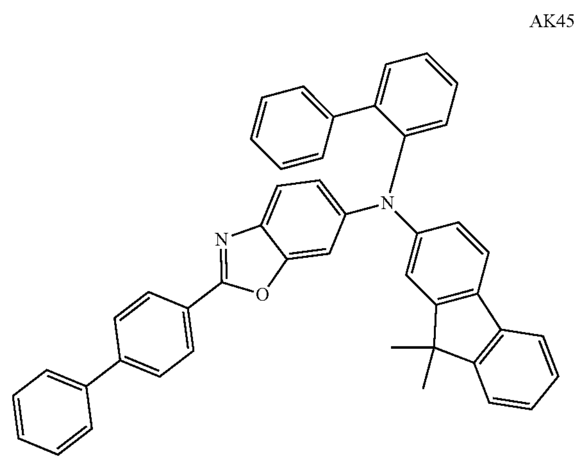
AK46
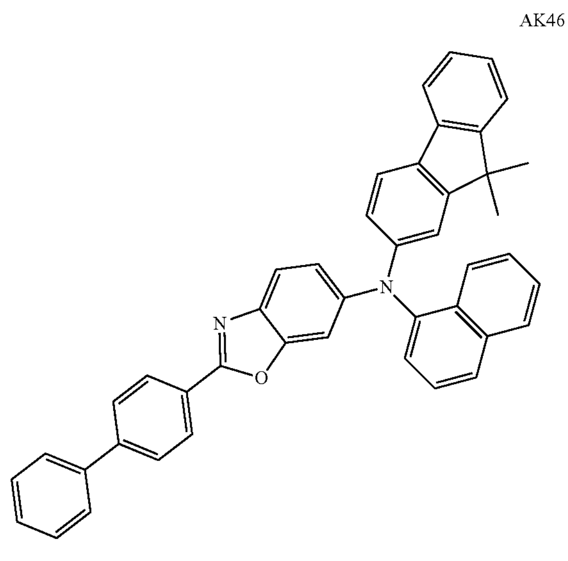
AK47
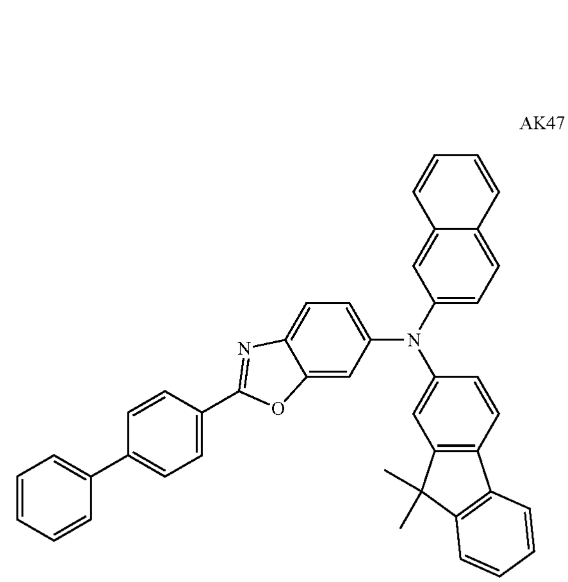

AK48
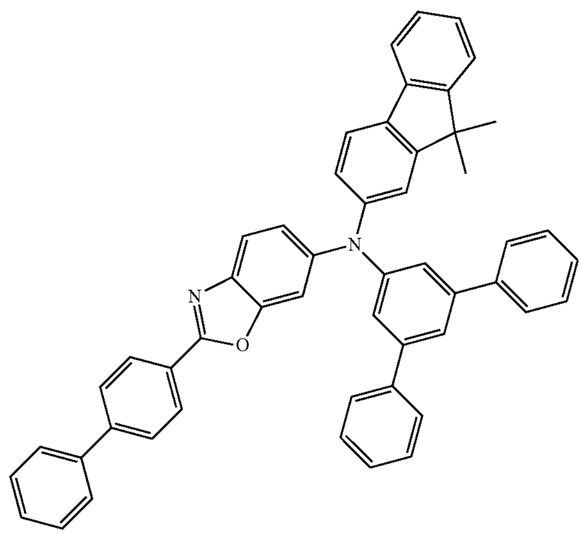
AK49
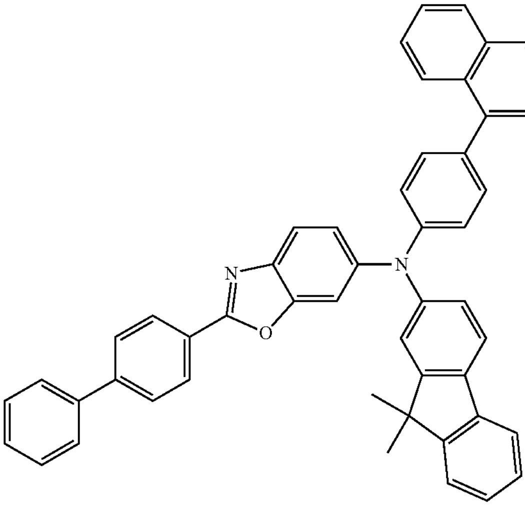
AK50
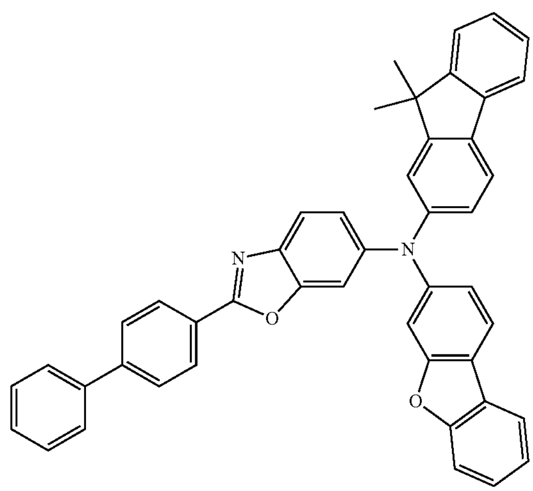
AK51
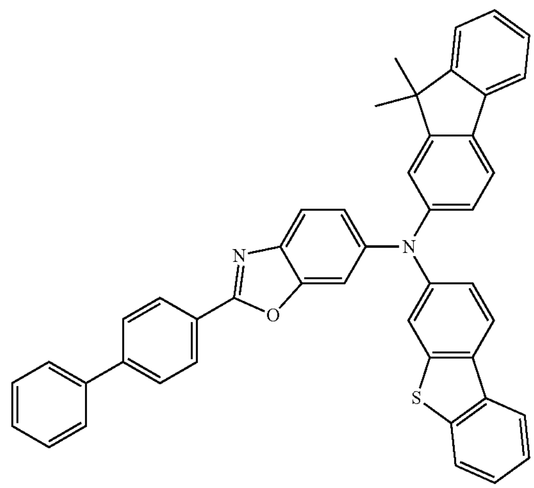
AK52
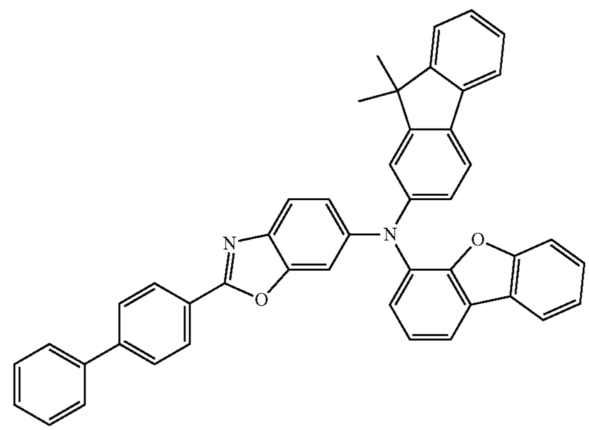
AK53
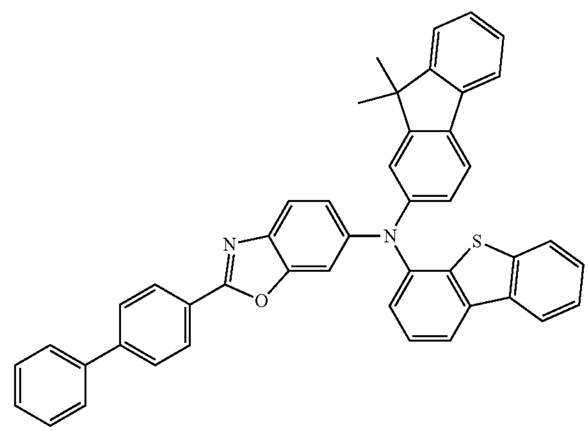

AK54
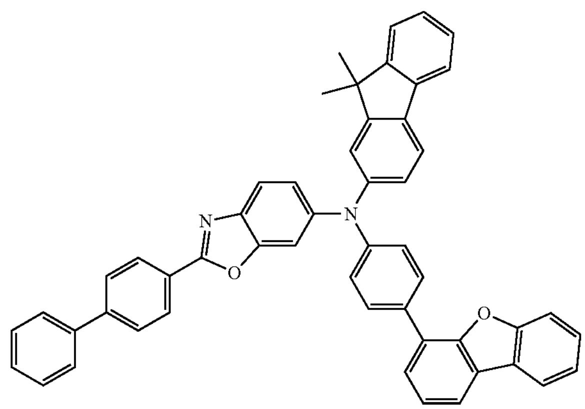
AK55
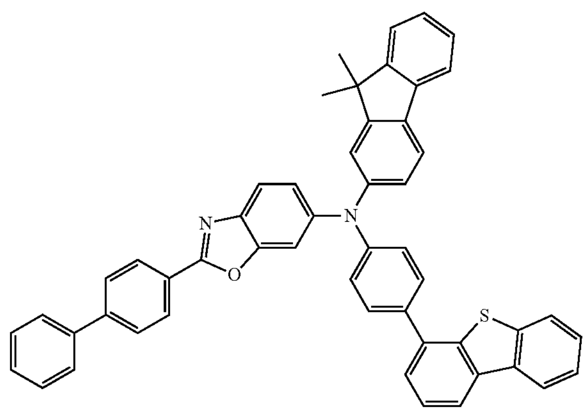
AK56
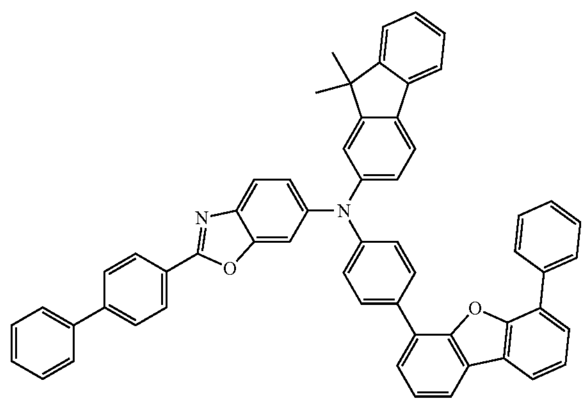
AK57
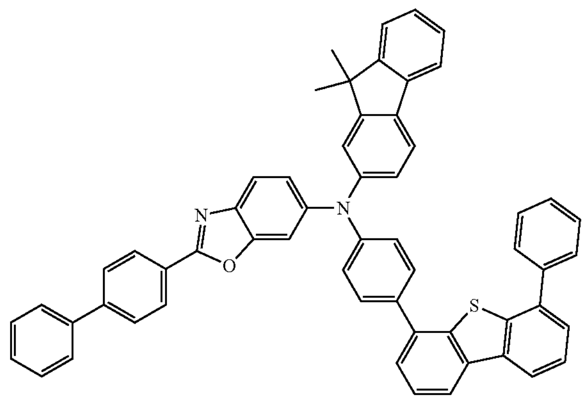
AK58
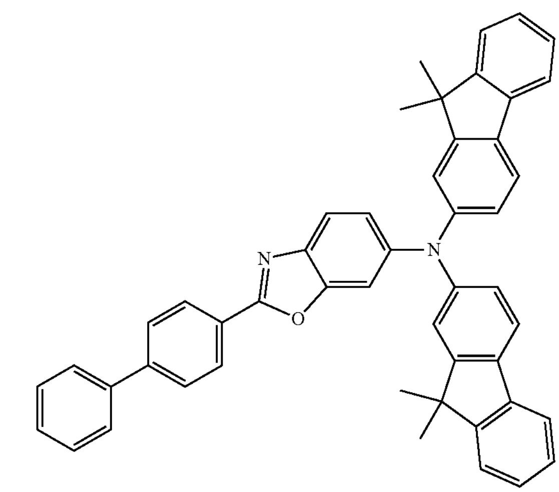
AK59
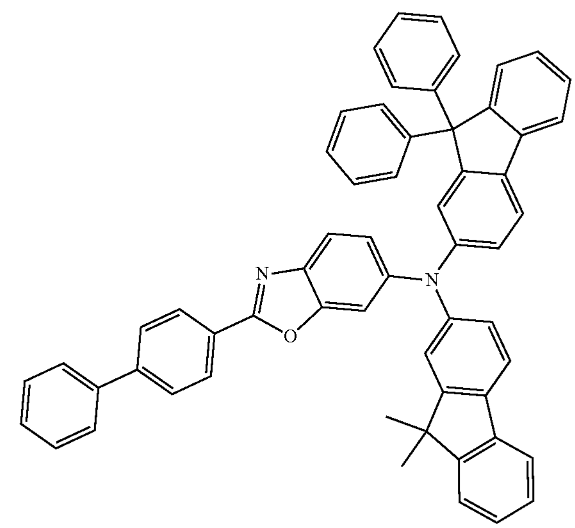

-continued
AK60
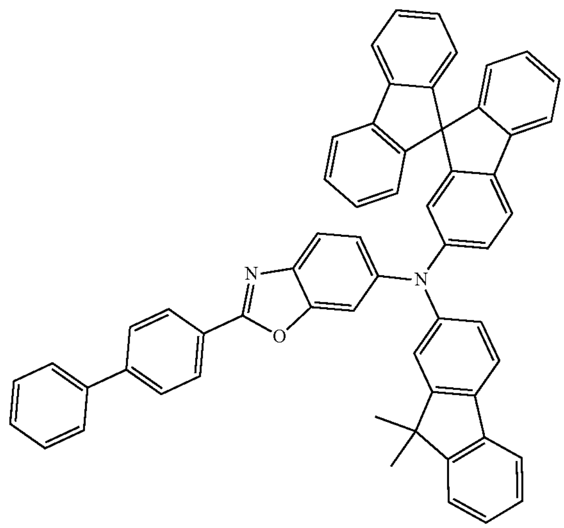
AK61
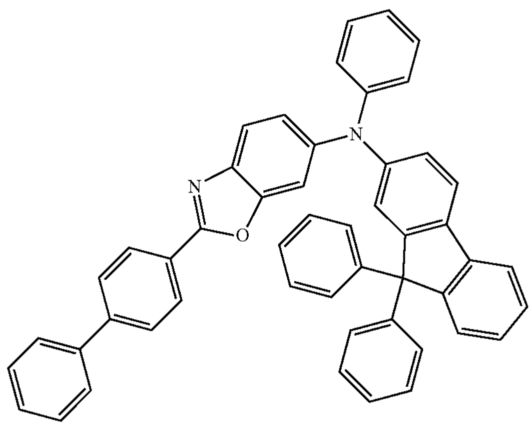
AK62
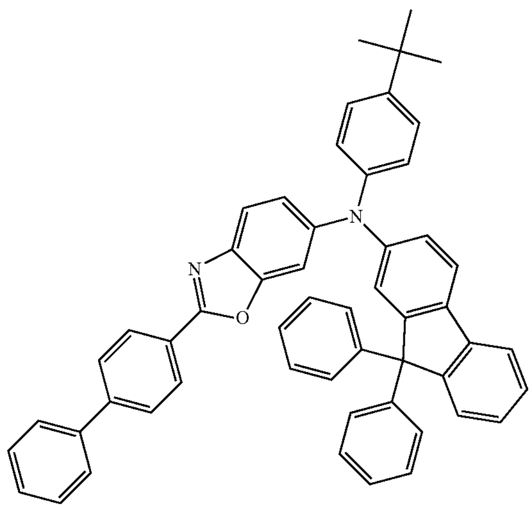
-continued
AK63
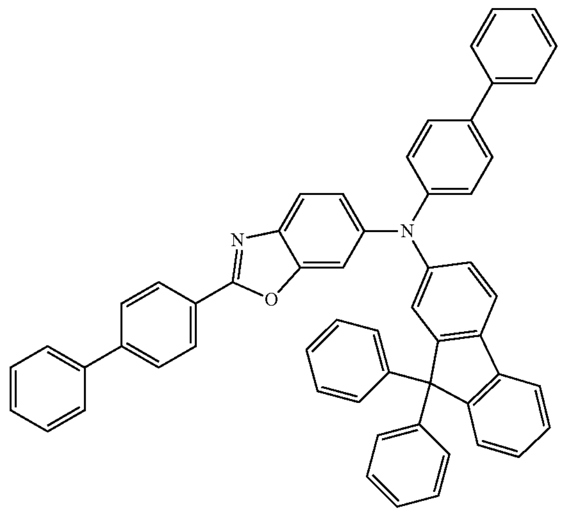
AK64
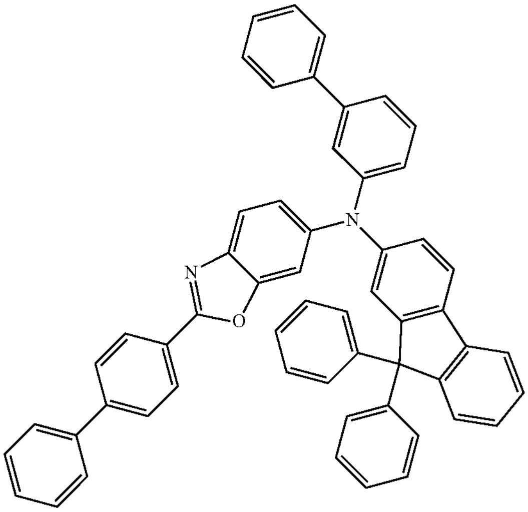
AK65
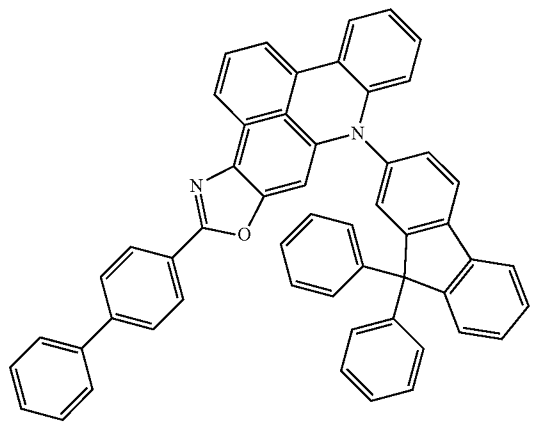

-continued
AK66
AK67
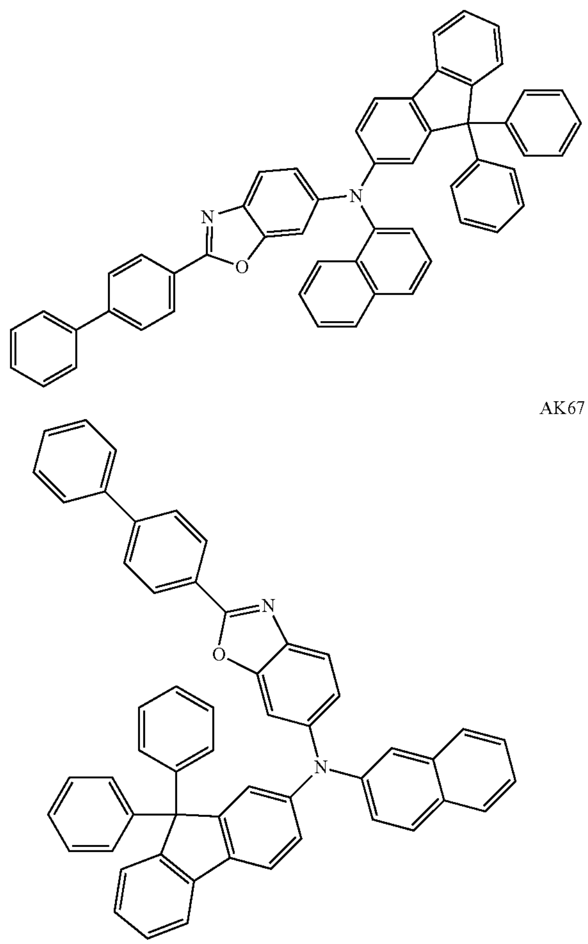
AK68
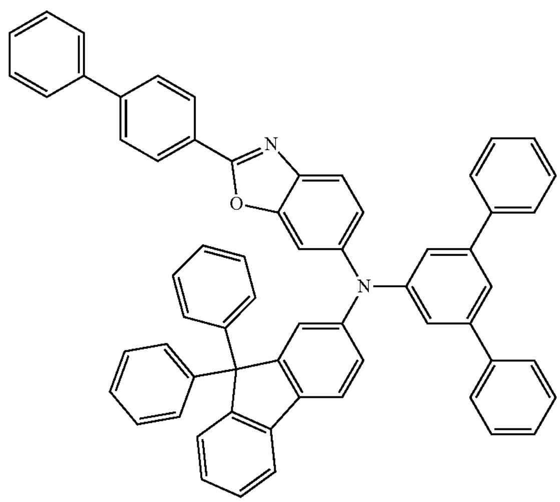
-continued
AK69
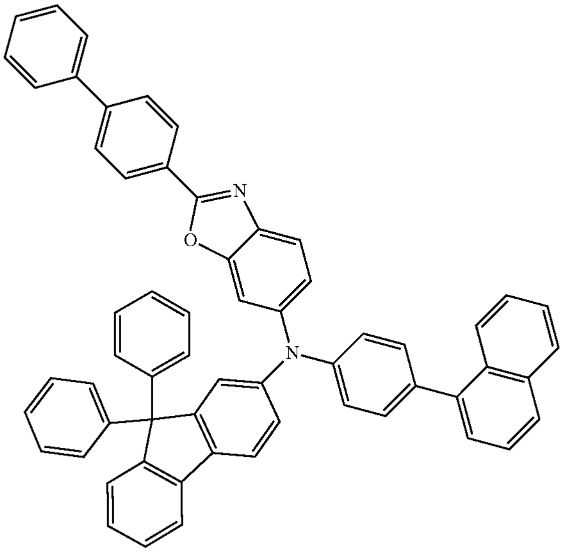
AK70
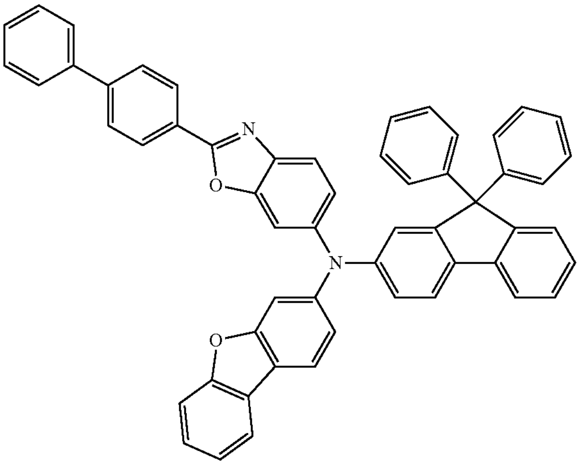
AK71
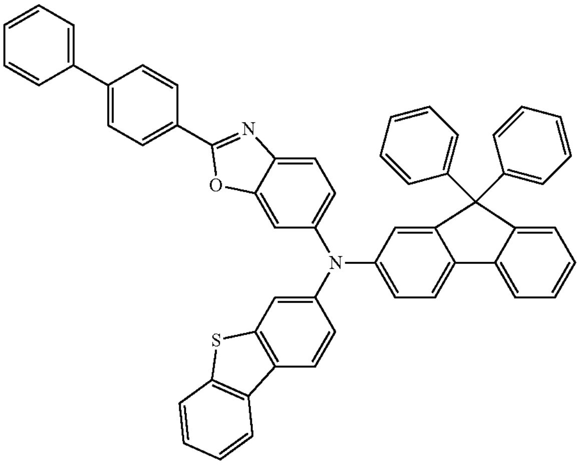

-continued
AK72
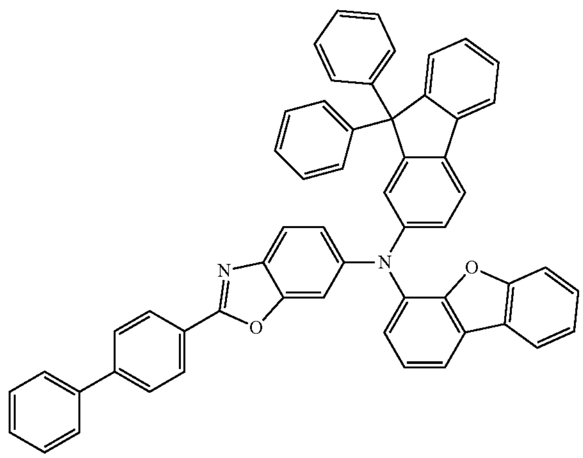
AK73
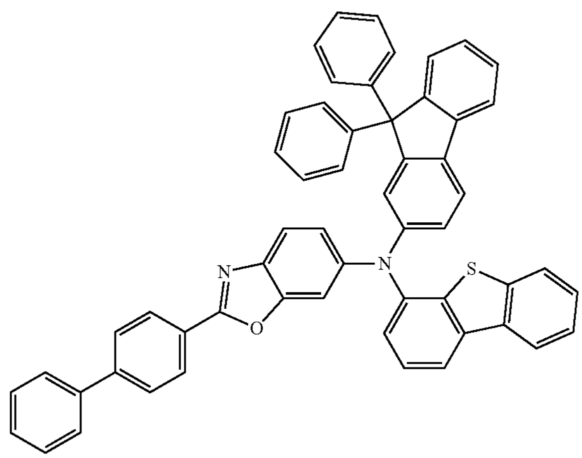
AK74
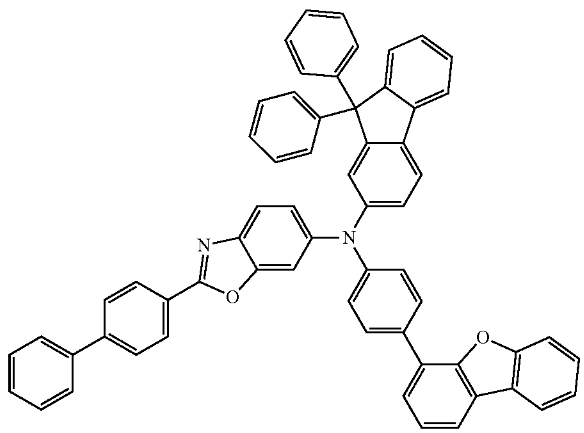
-continued
AK75
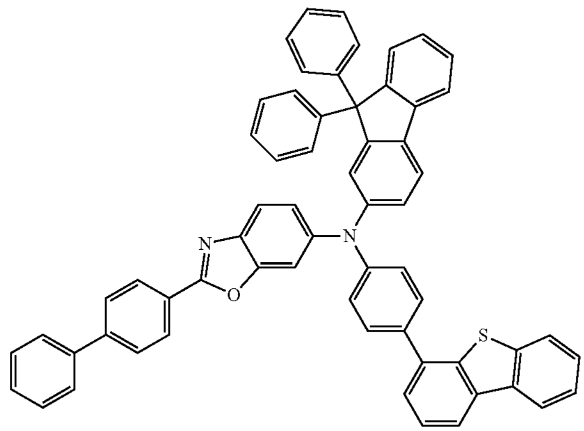
AK76
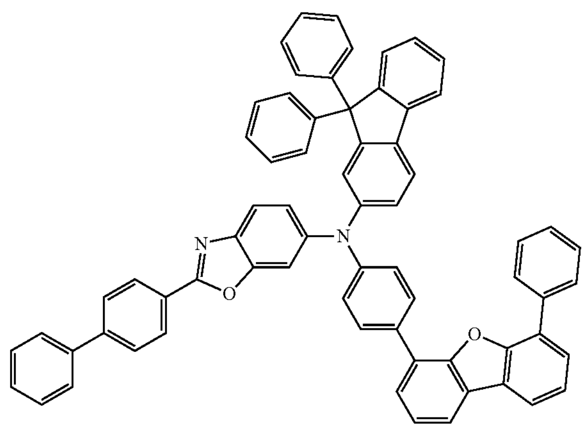
AK77
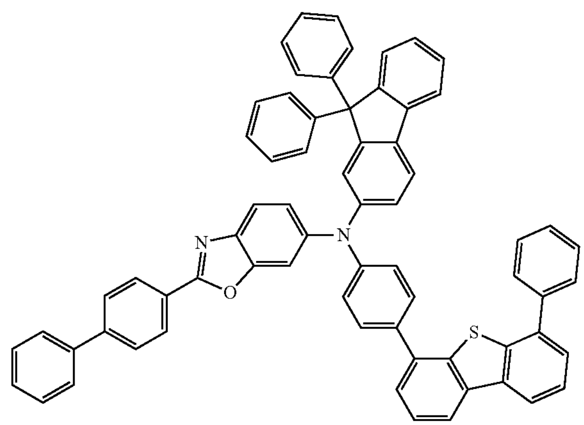

-continued
AK78
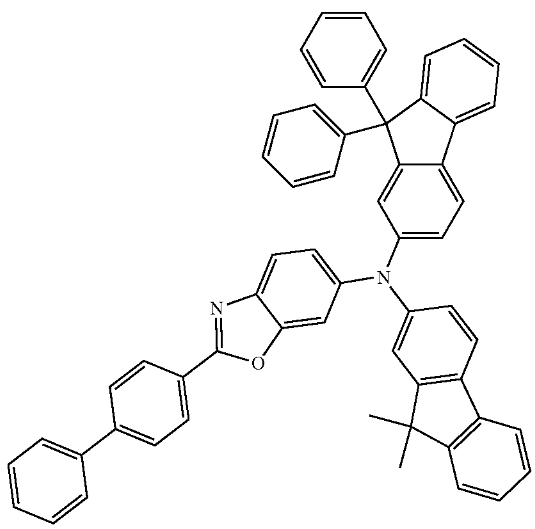
AK79
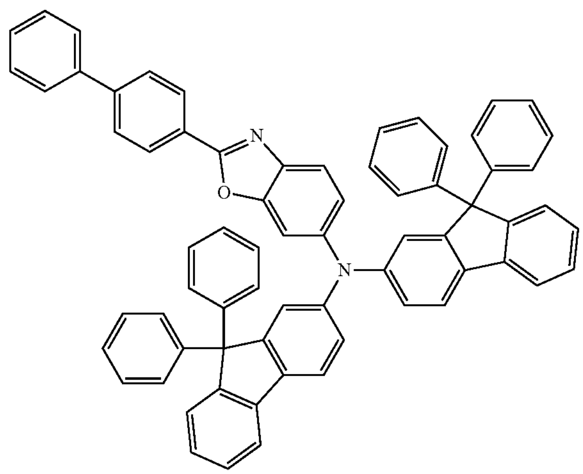
AK80
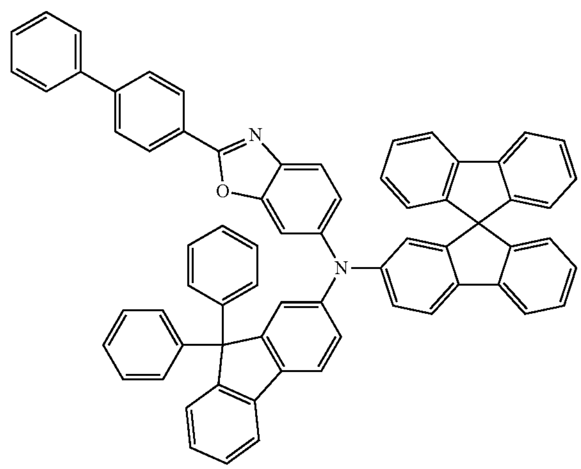
-continued
AK81
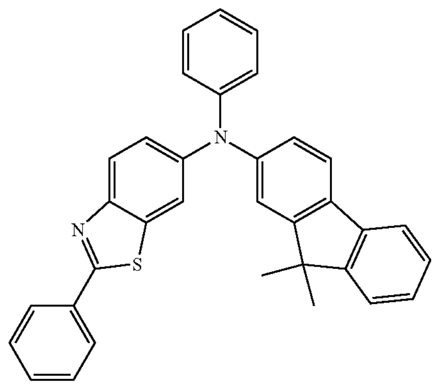
AK82
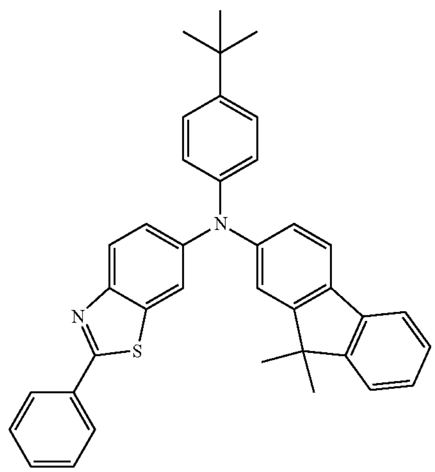
AK83
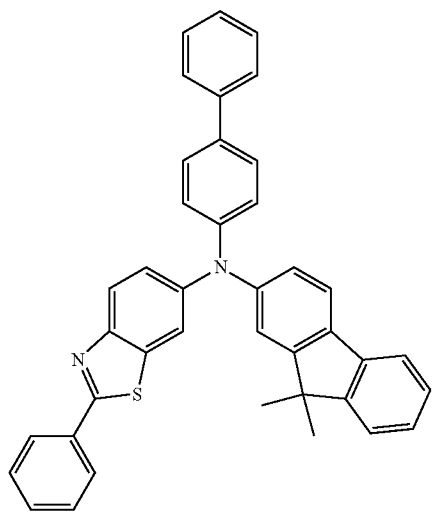

-continued
AK84
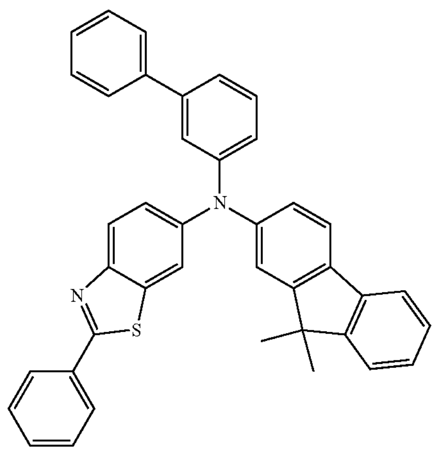
AK85
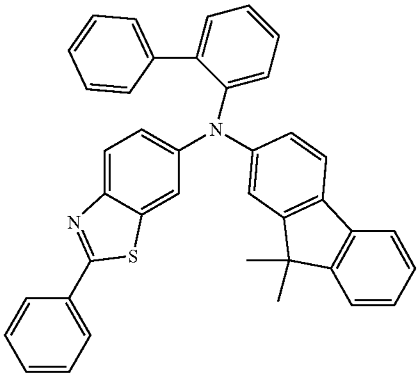
AK86
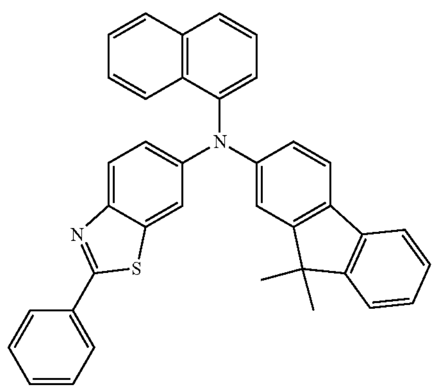
-continued
AK87
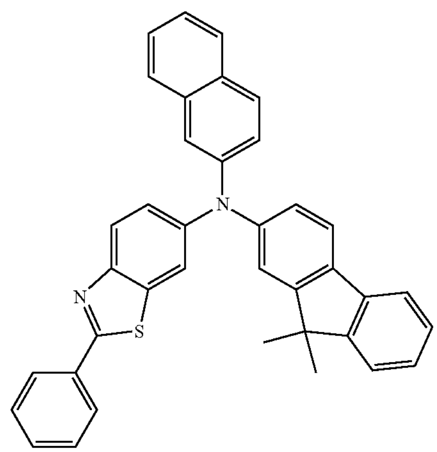
AK88
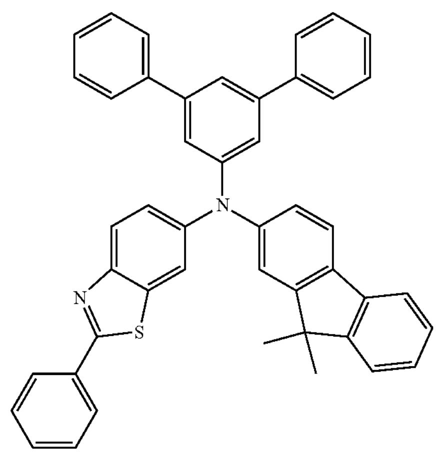
AK89
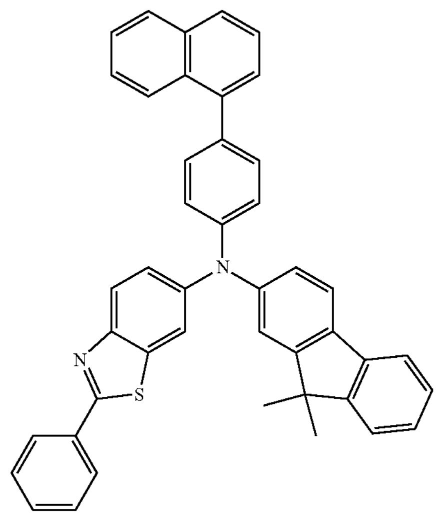

-continued
AK90
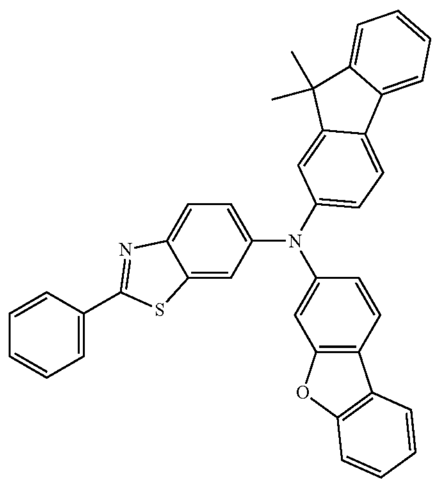
AK91
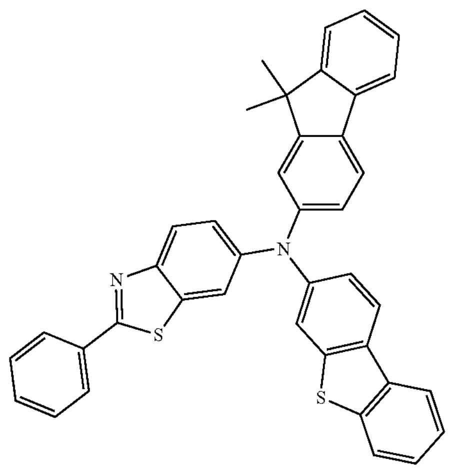
AK92
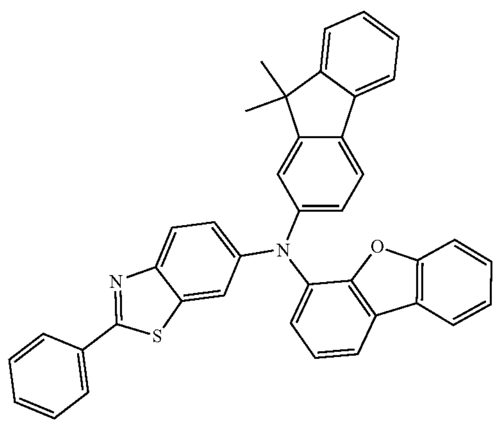
-continued
AK93
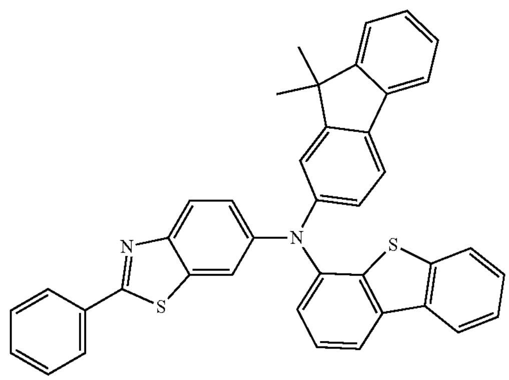
AK94
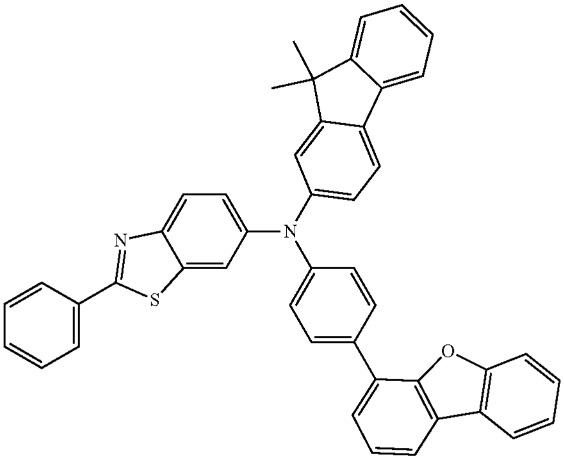
AK95
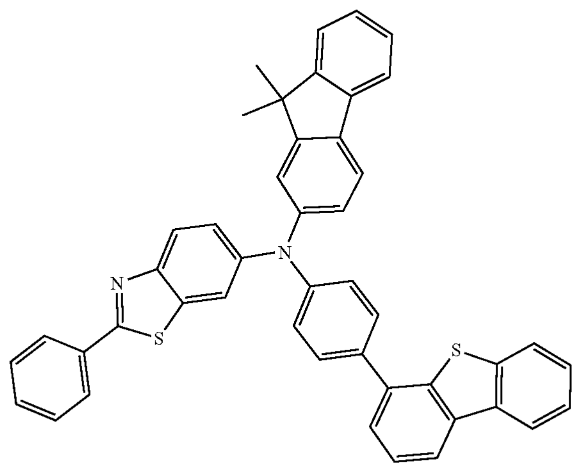

-continued
AK96
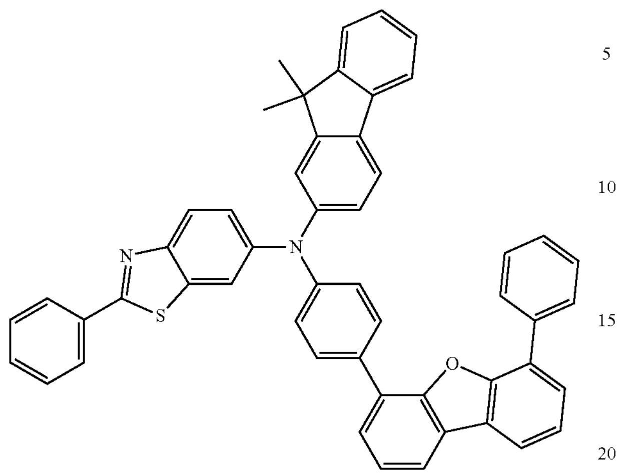
AK97
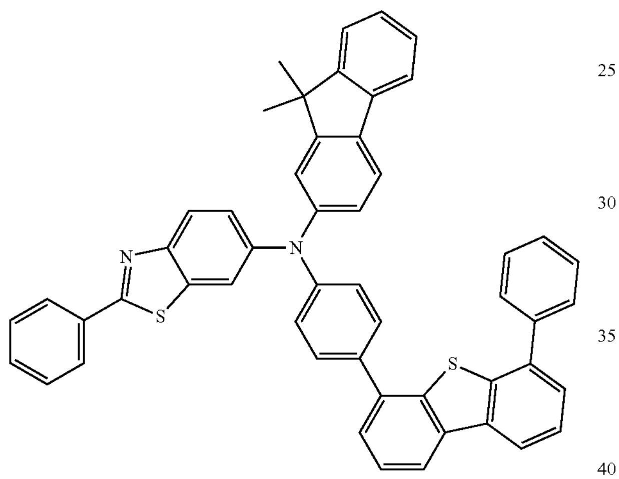
AK98
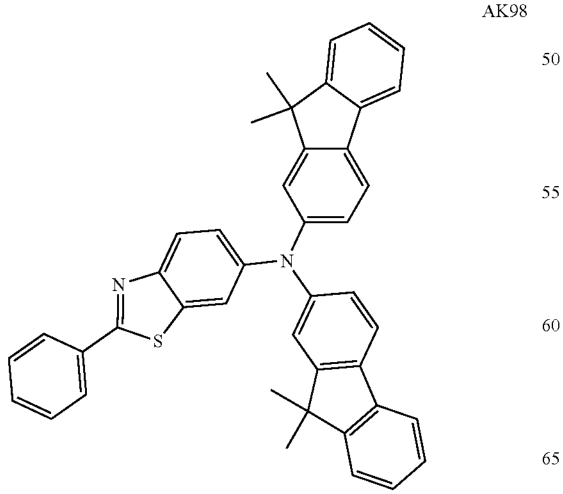
-continued
AK99
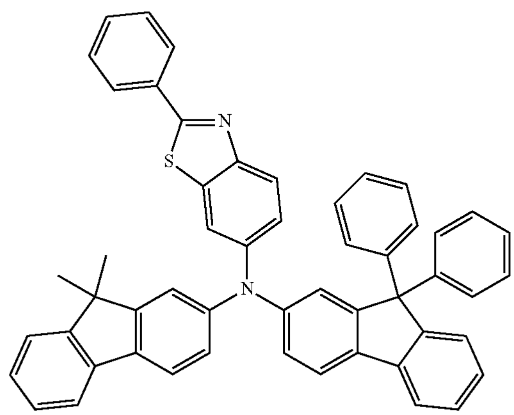
AK100
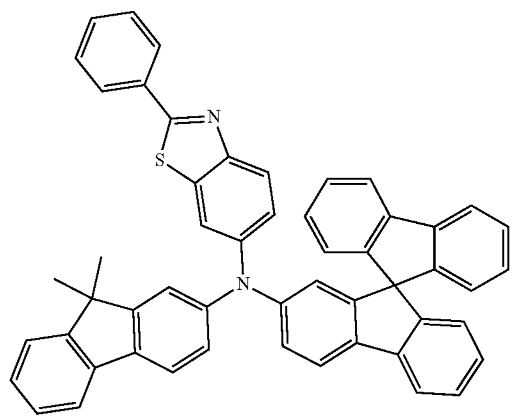
AK101
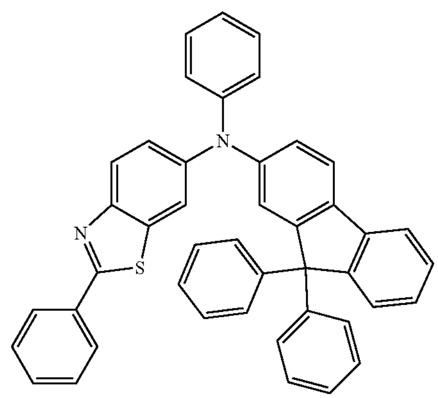

-continued
AK102
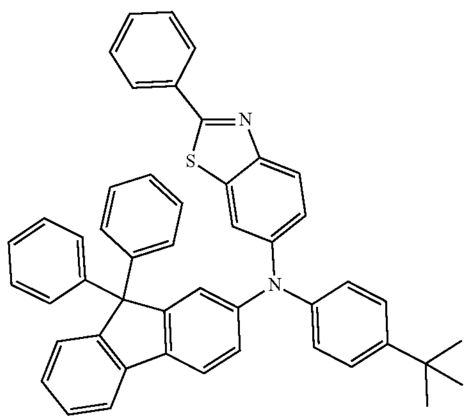
AK103
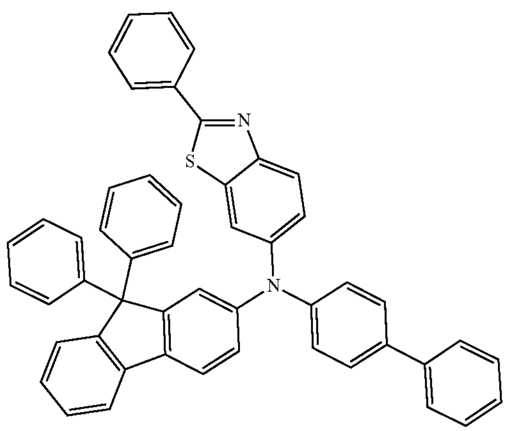
AK104
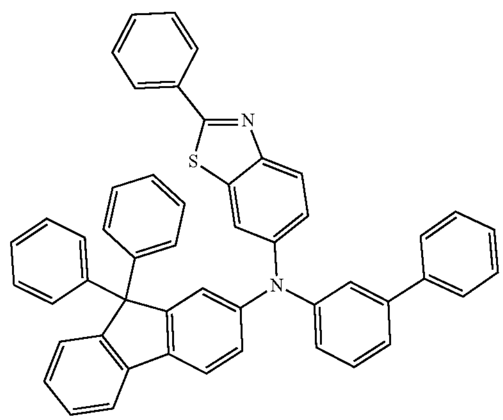
-continued
AK105
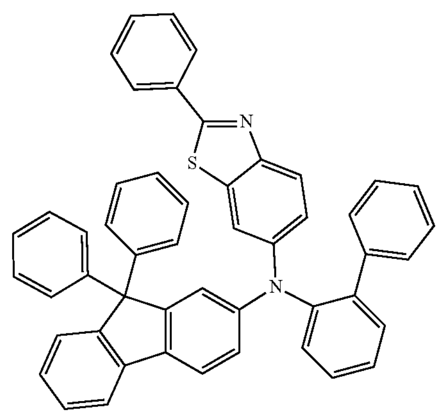
AK106
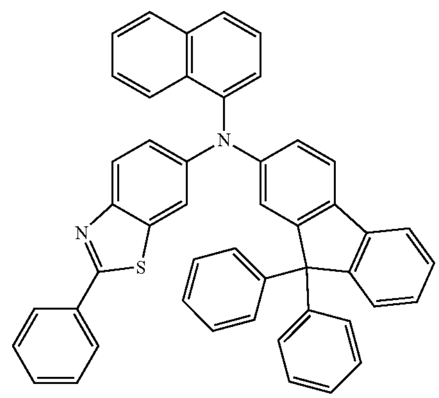
AK107
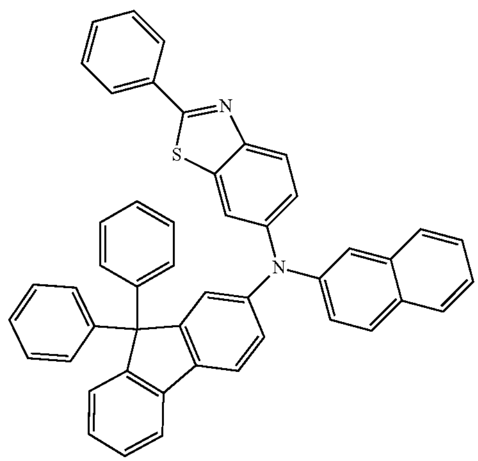

-continued
AK108
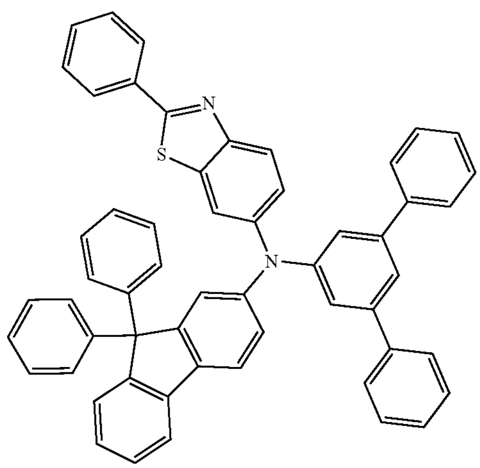
AK109
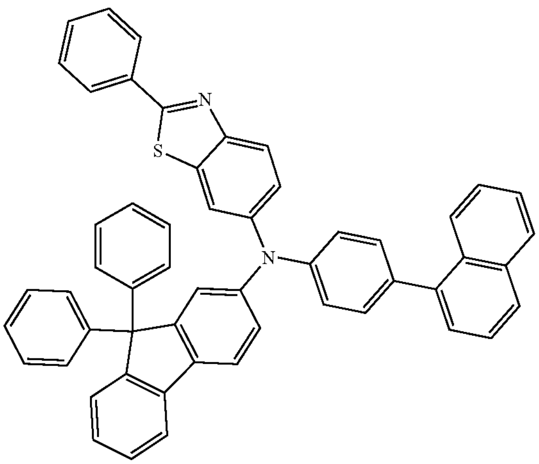
AK110
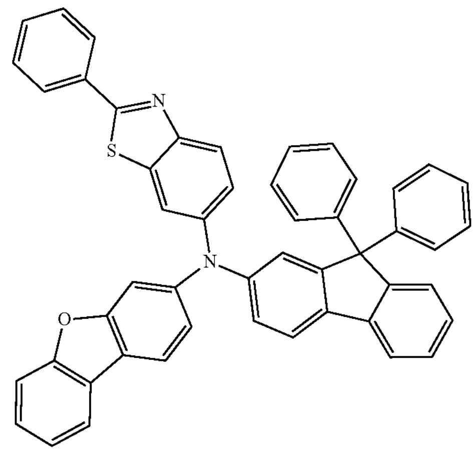
-continued
AK111
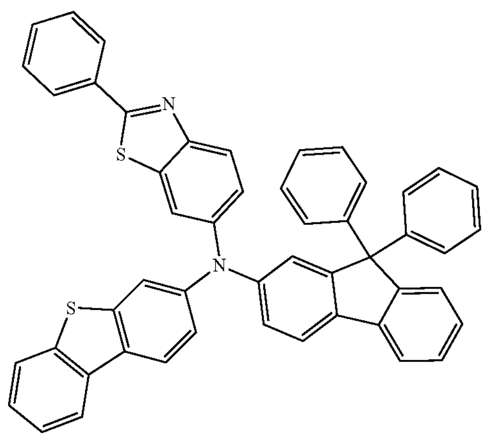
AK112
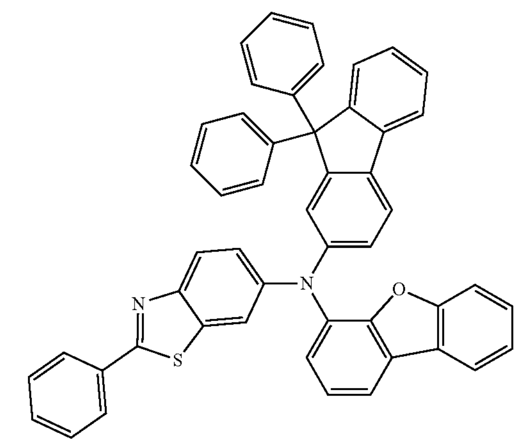
AK113
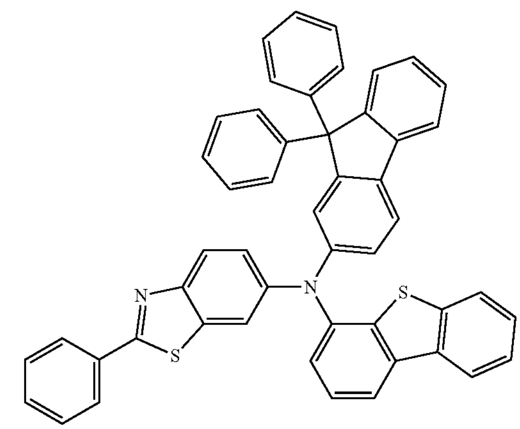

-continued
AK114
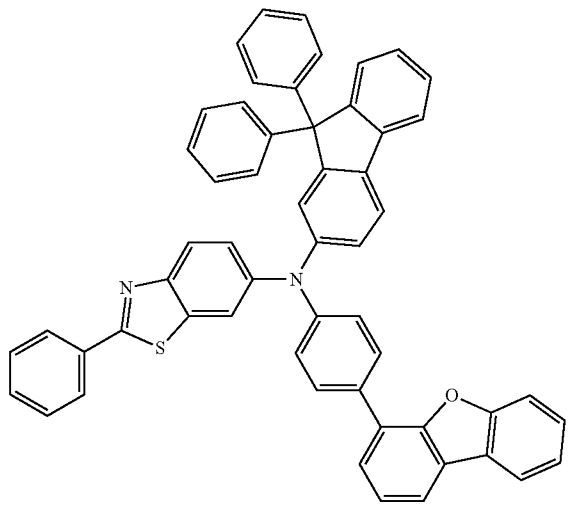
AK115
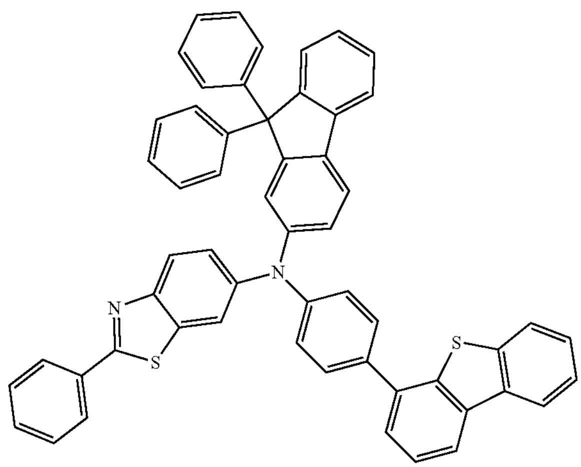
AK116
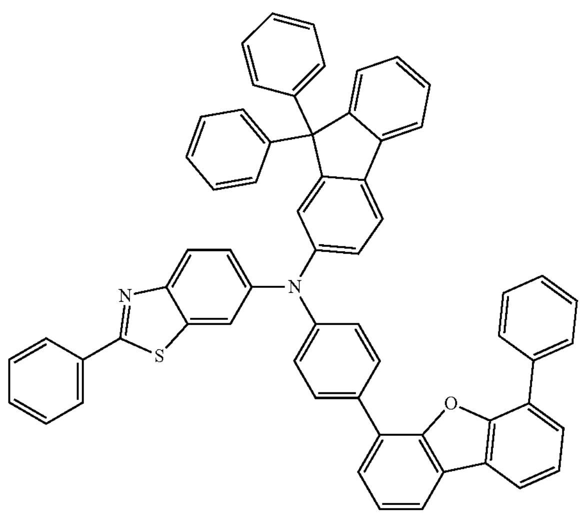
-continued
AK117
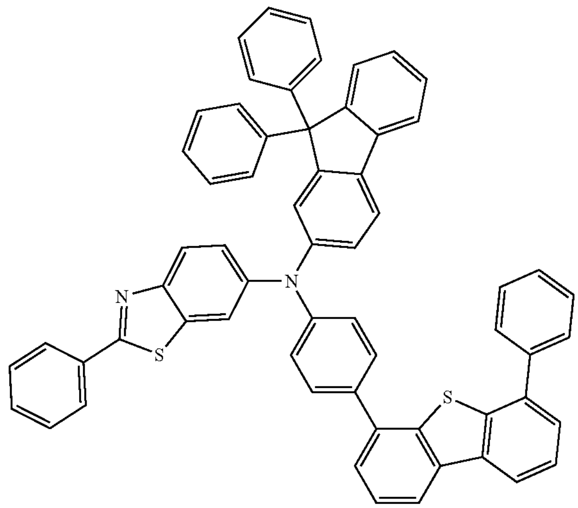
AK118
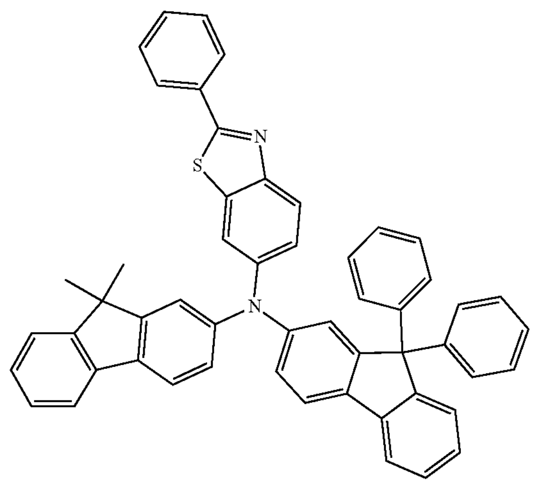
AK119
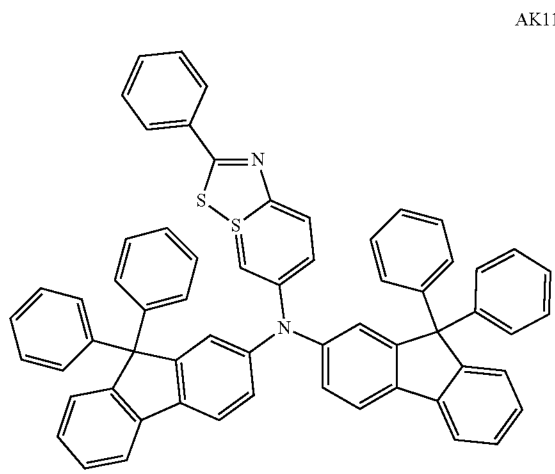

AK120
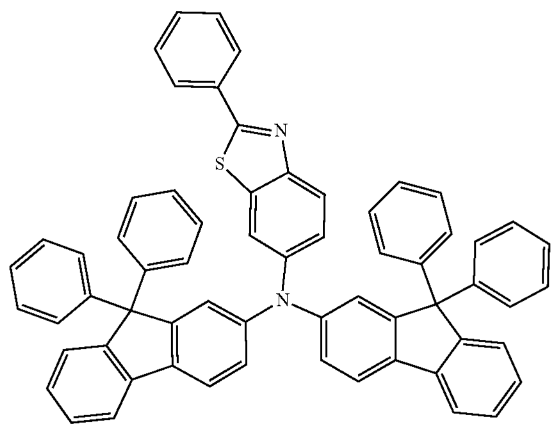
AK121
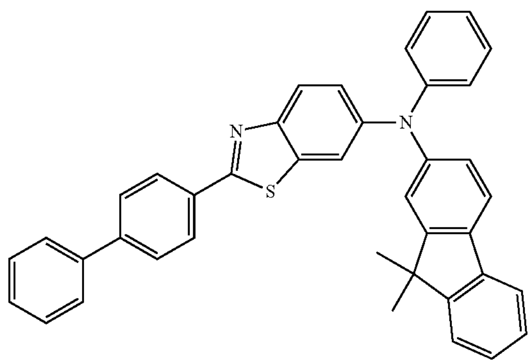
AK122
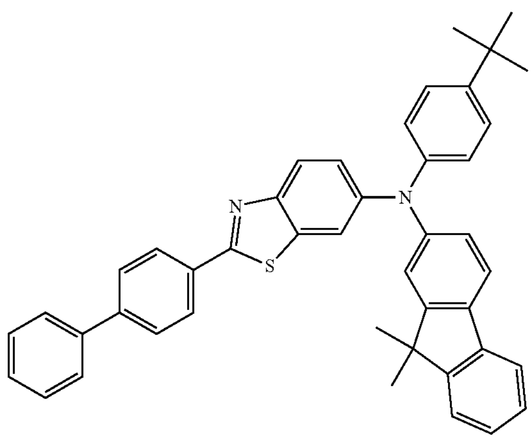
AK123
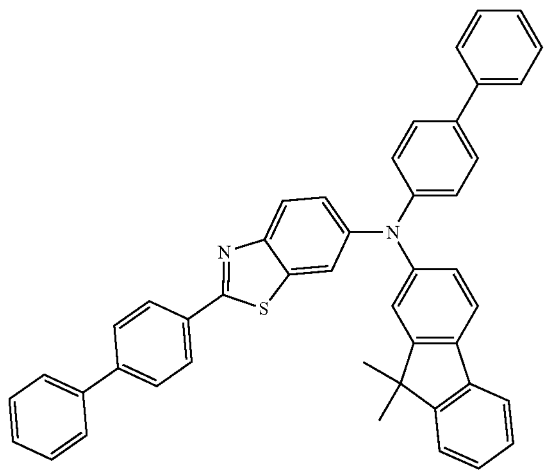
AK124
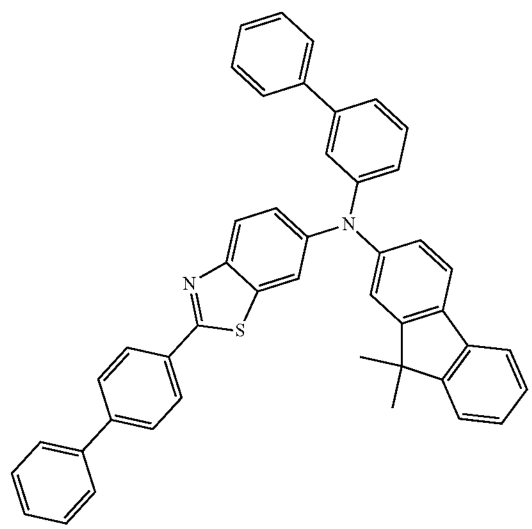
AK125
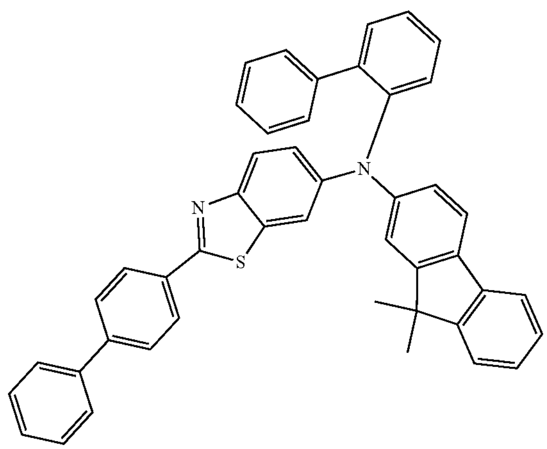

-continued
AK126
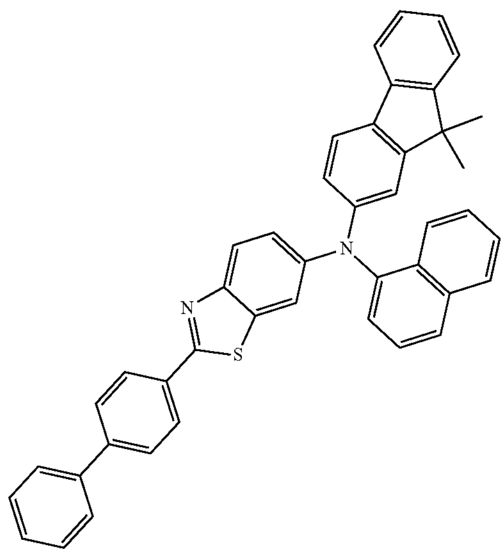
AK127
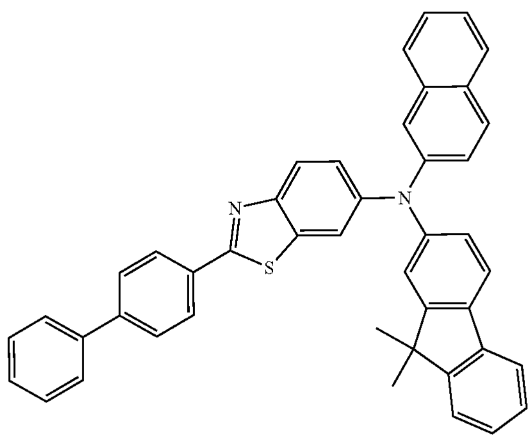
AK128
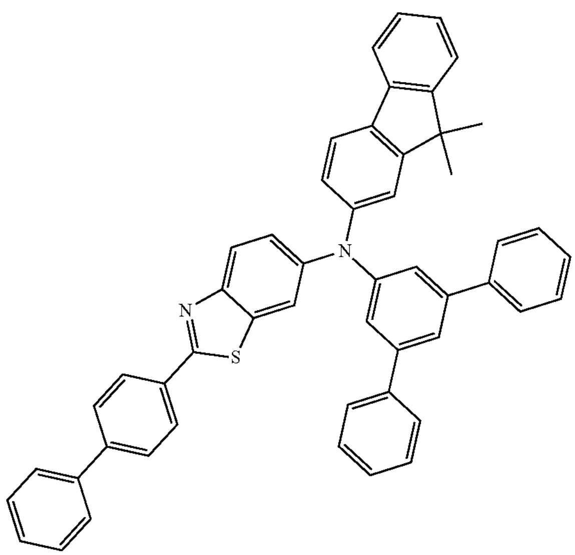
-continued
AK129
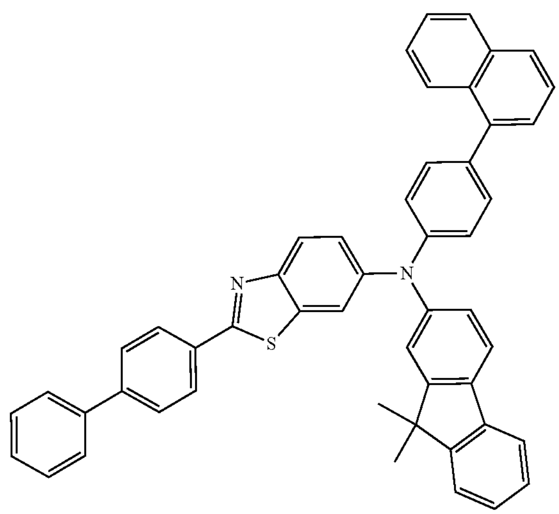
AK130
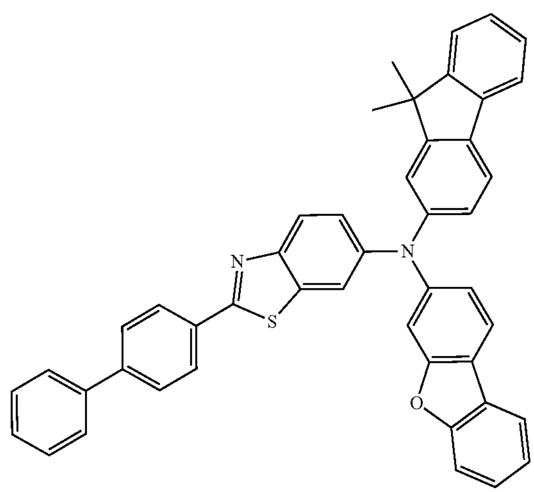
AK131
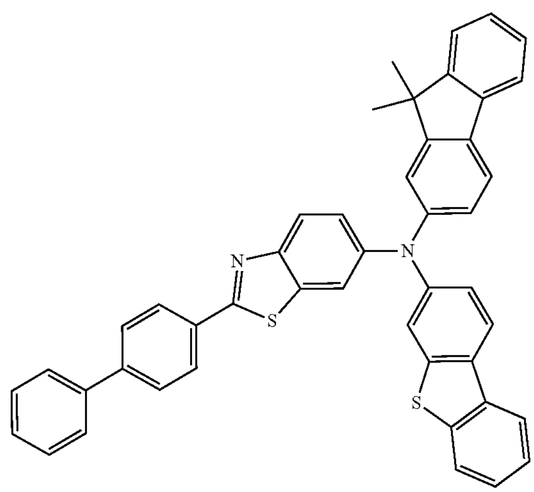

-continued
AK132
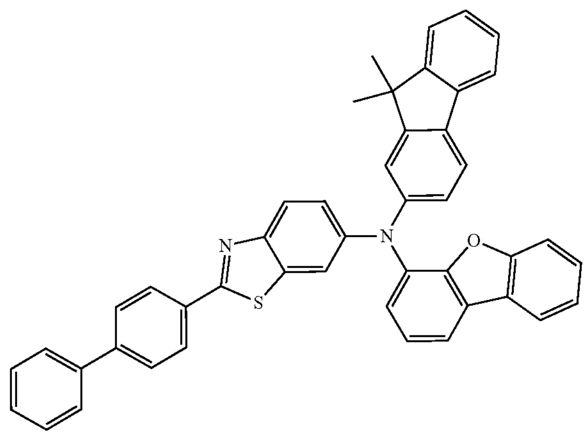
AK133
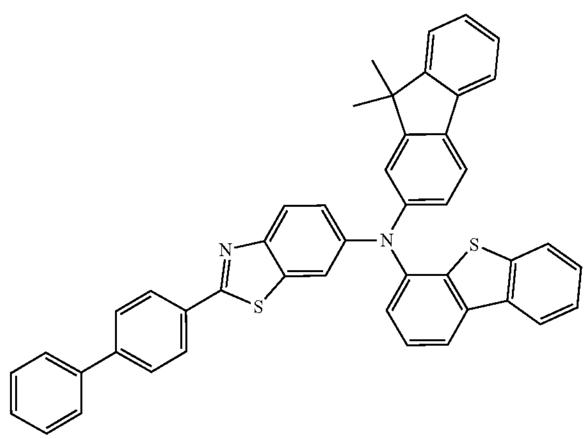
AK134
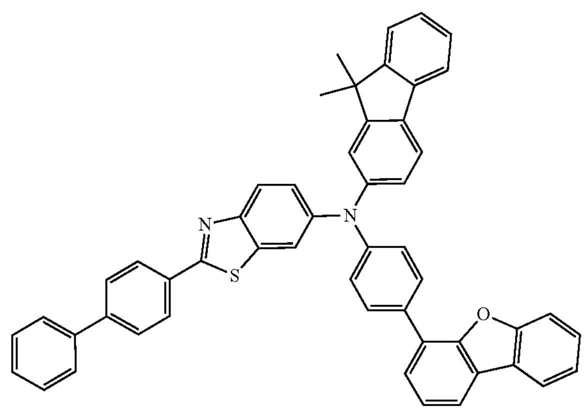
-continued
AK135
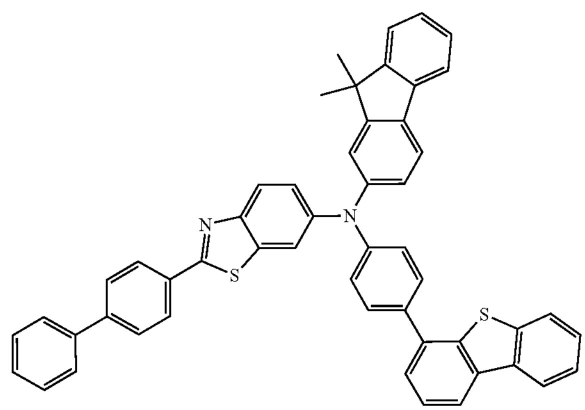
AK136
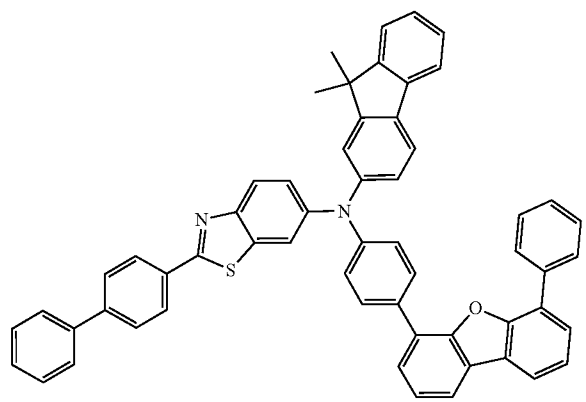
AK137
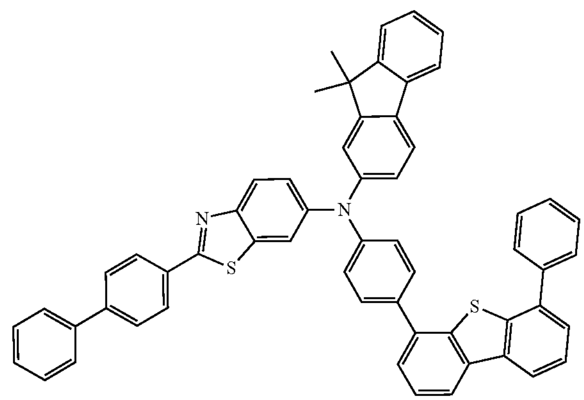

AK138
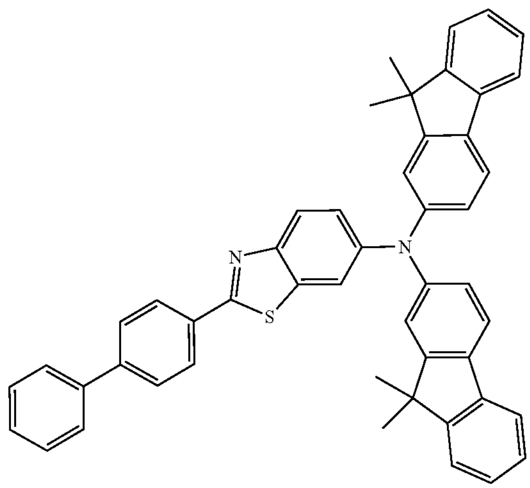
AK139
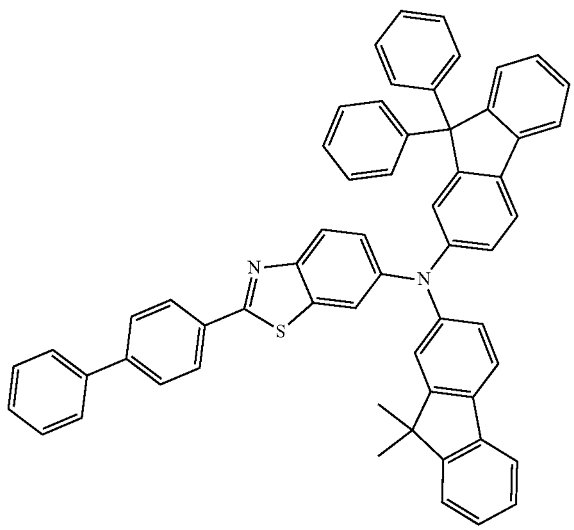
AK140
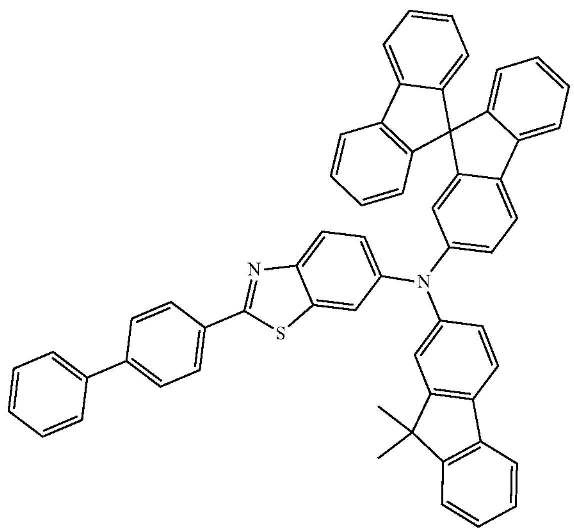
AK141
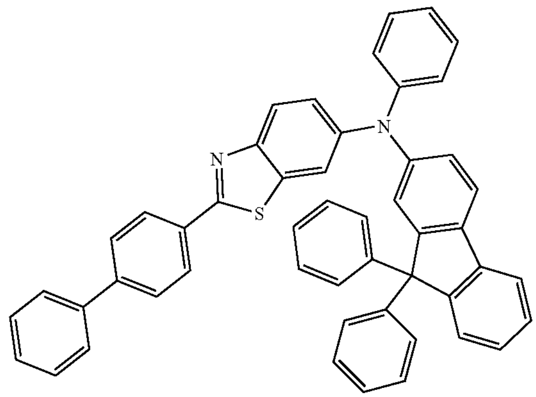
AK142
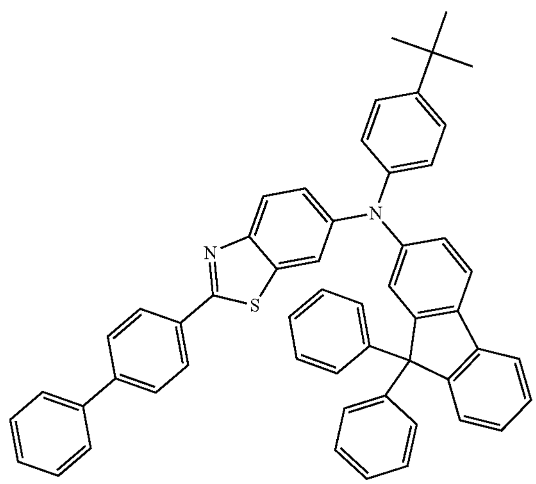
AK143
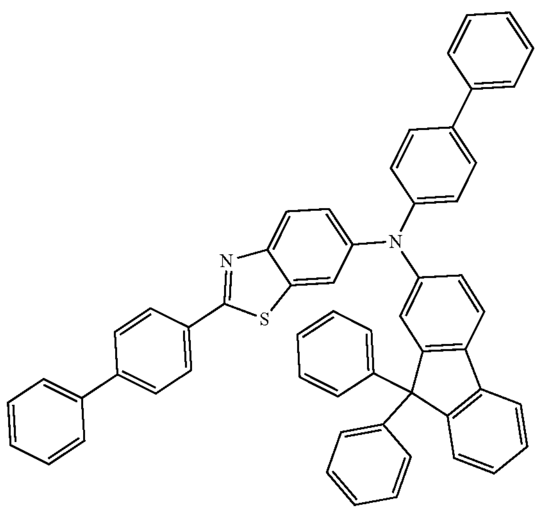

-continued
AK144
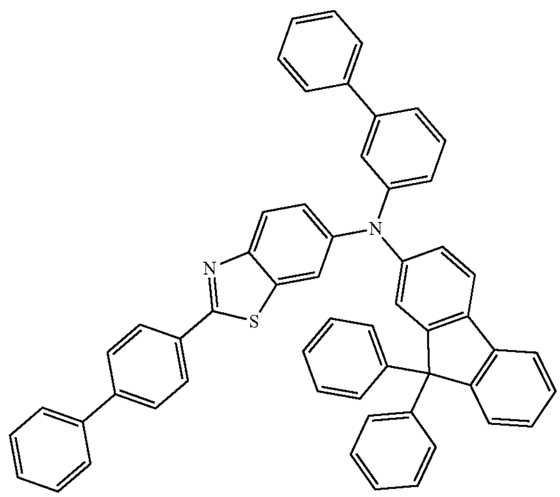
AK145
AK146
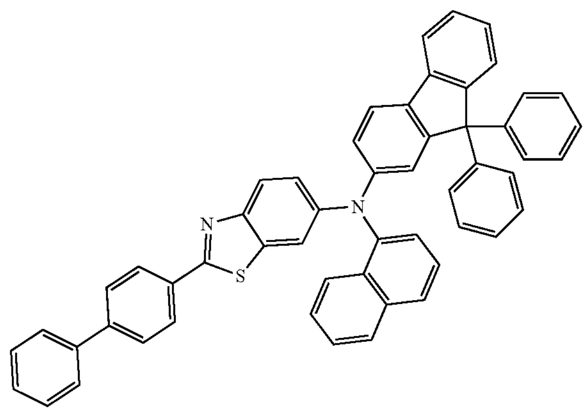
-continued
AK147
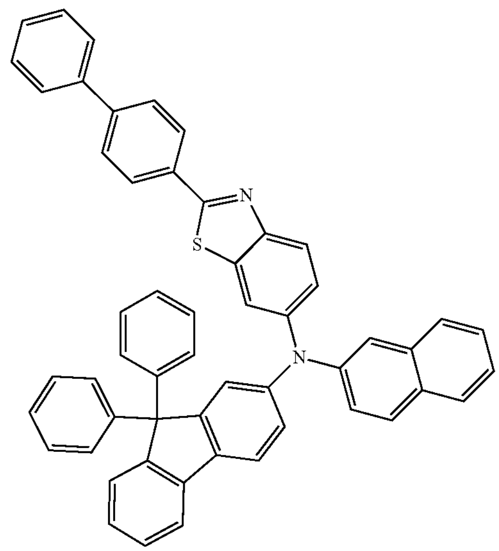
AK148
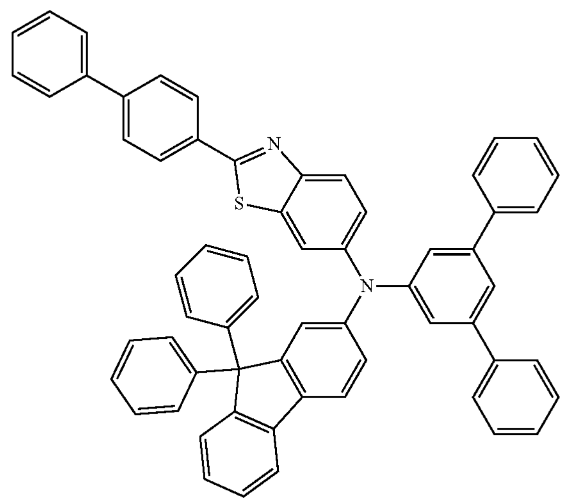
AK149
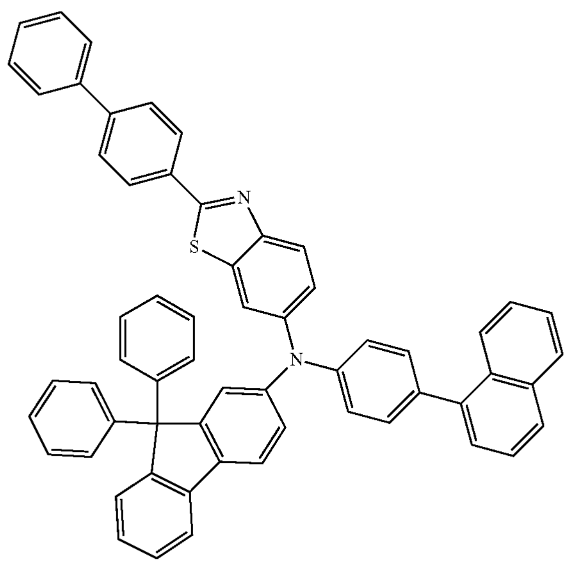

-continued
AK150
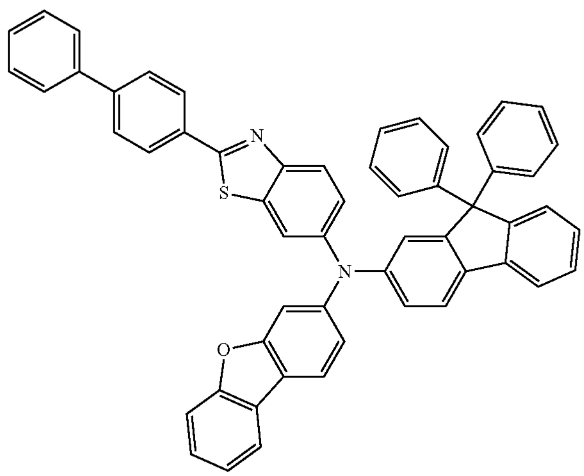
AK151
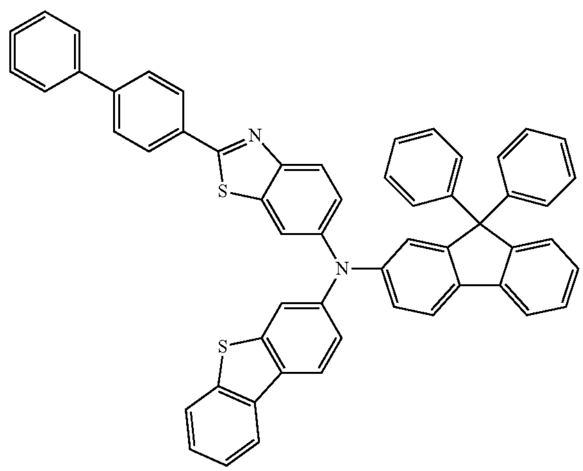
AK152
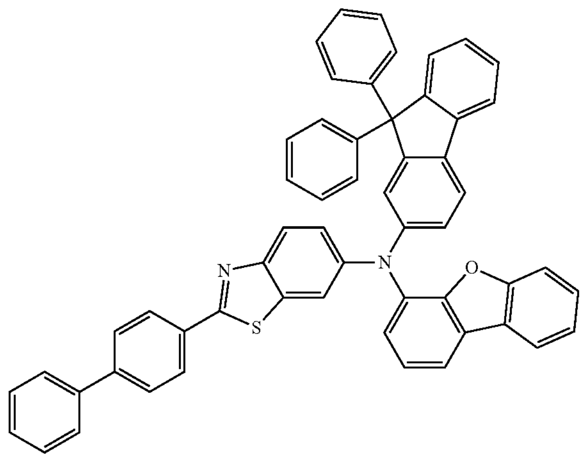
-continued
AK153
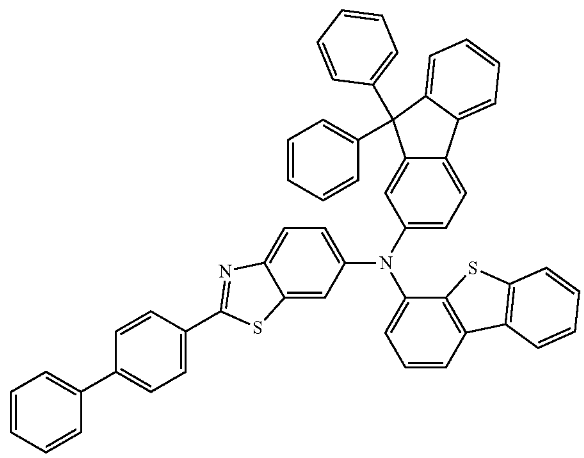
AK154
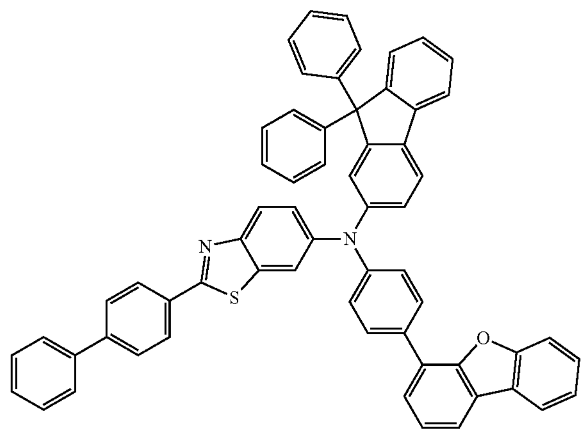
AK155
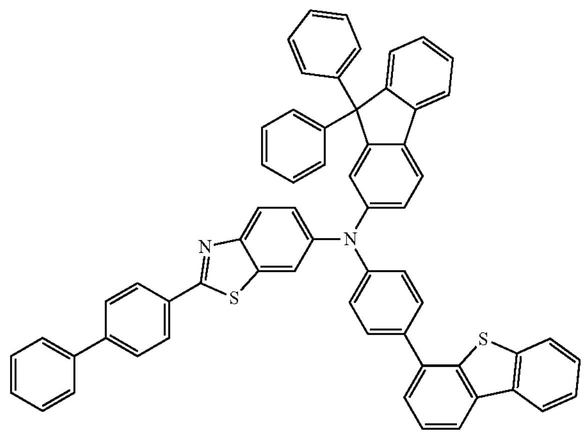

-continued

AK156

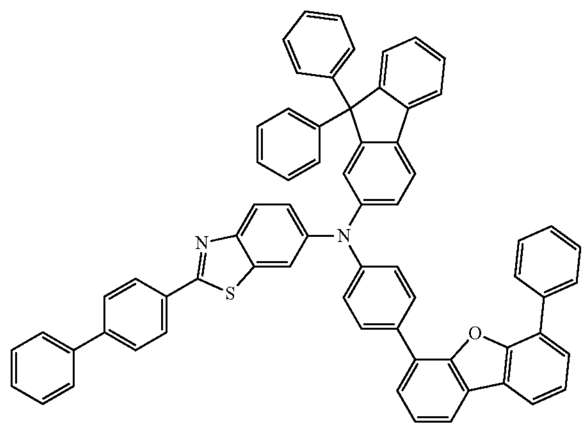

AK157

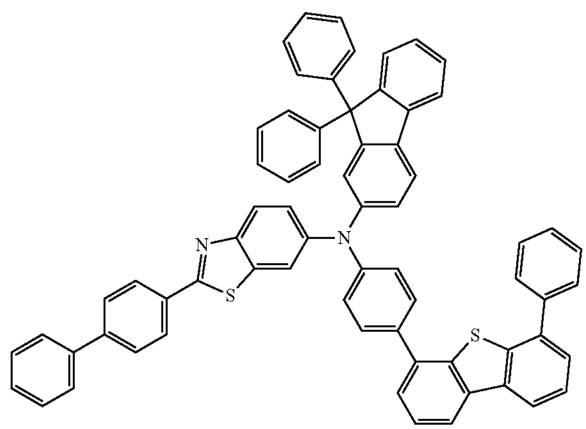

AK158

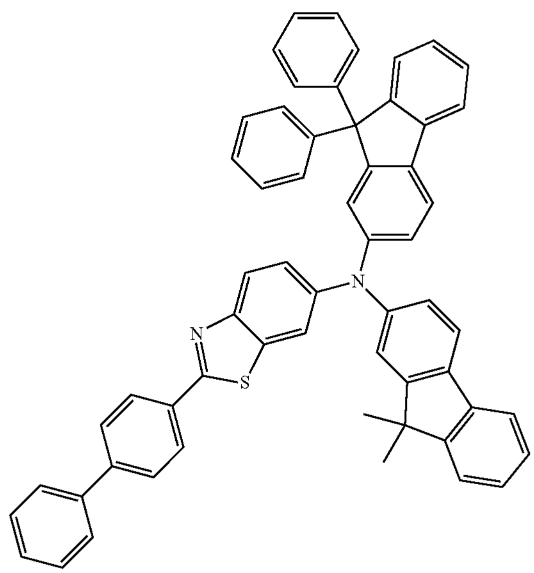

-continued

AK159

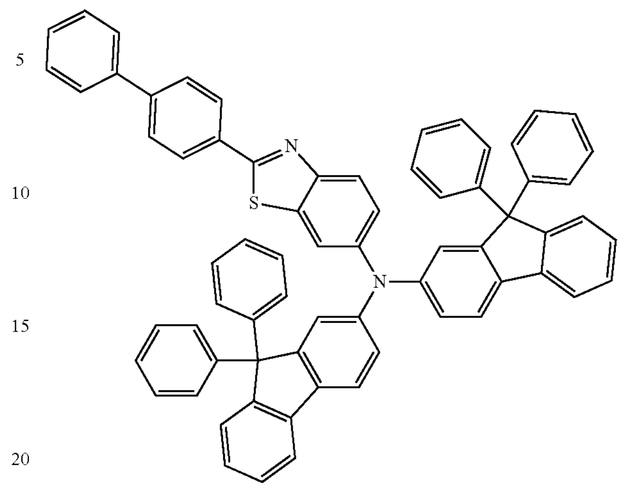

AK160

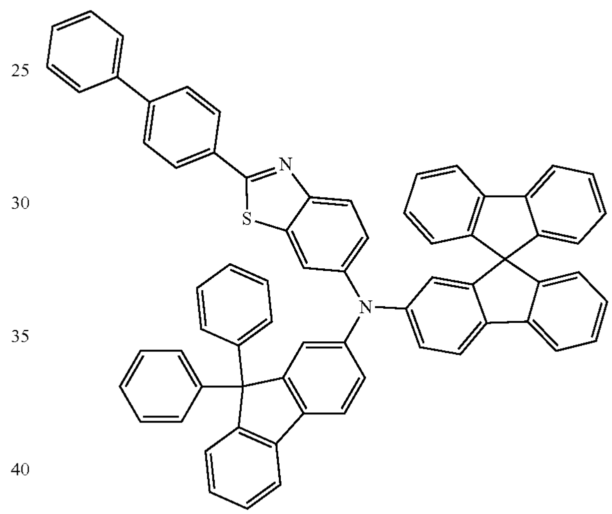

.

4. The organic light emitting element of claim 1, wherein the organic material layer further includes at least one of a hole injection layer, a hole transport layer, an electron transport layer, and an electron injection layer.

5. The organic light emitting element of claim 1, wherein the organic material layer includes a first stack including a first light emitting layer and a second stack including a second light emitting layer.

6. The organic light emitting element of claim 5, wherein the first light emitting layer includes the compound.

7. The organic light emitting element of claim 6, wherein the compound is a host compound of the first light emitting layer.

8. The organic light emitting element of claim 7, wherein the first light emitting layer further includes a host compound different from the compound.

* * * * *